US011482328B2

(12) United States Patent
Felton et al.

(10) Patent No.: US 11,482,328 B2
(45) Date of Patent: Oct. 25, 2022

(54) USER INTERFACES FOR HEALTH APPLICATIONS

(71) Applicant: Apple Inc., Cupertino, CA (US)

(72) Inventors: Nicholas Felton, Sunnyvale, CA (US); Matthew W. Crowley, San Francisco, CA (US); Allison Dryer, San Francisco, CA (US); Eamon Francis Gilravi, San Francisco, CA (US); Kevin Lynch, Woodside, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 17/031,717

(22) Filed: Sep. 24, 2020

(65) Prior Publication Data
US 2021/0373747 A1    Dec. 2, 2021

Related U.S. Application Data

(60) Provisional application No. 63/078,315, filed on Sep. 14, 2020, provisional application No. 63/033,832, (Continued)

(51) Int. Cl.
*G16H 40/67* (2018.01)
*G16H 50/30* (2018.01)
(Continued)

(52) U.S. Cl.
CPC ......... *G16H 40/67* (2018.01); *A61B 5/02444* (2013.01); *A61B 5/7435* (2013.01); (Continued)

(58) Field of Classification Search
CPC .. G06F 3/04842; G06F 3/0482; G06F 3/0488; G16H 40/60; G16H 40/67;
(Continued)

(56) References Cited

U.S. PATENT DOCUMENTS 5,515,344 A    5/1996  Ng
5,642,731 A    7/1997  Kehr
(Continued)

FOREIGN PATENT DOCUMENTS

CA    2815518 A1    5/2012
CN    1585943 A     2/2005
(Continued)

OTHER PUBLICATIONS

Advisory Action received for U.S. Appl. No. 16/144,864, dated Jul. 29, 2019, 6 pages.
(Continued)

*Primary Examiner* — Jeremy L Stanley
(74) *Attorney, Agent, or Firm* — Dentons US LLP

(57) ABSTRACT

The present disclosure generally relates to user interfaces for health applications. In some embodiments, exemplary user interfaces for managing health and safety features on an electronic device are described. In some embodiments, exemplary user interfaces for managing the setup of a health feature on an electronic device are described. In some embodiments, exemplary user interfaces for managing background health measurements on an electronic device are described. In some embodiments, exemplary user interfaces for managing a biometric measurement taken using an electronic device are described. In some embodiments, exemplary user interfaces for providing results for captured health information on an electronic device are described. In some embodiments, exemplary user interfaces for managing background health measurements on an electronic device are described.

42 Claims, 78 Drawing Sheets

Related U.S. Application Data filed on Jun. 3, 2020, provisional application No. 63/033,829, filed on Jun. 2, 2020.

(51) Int. Cl.

| | | |
|---|---|---|
| *G16H 15/00* | (2018.01) | |
| *G16H 10/65* | (2018.01) | |
| *G06F 3/0482* | (2013.01) | |
| *G16H 40/60* | (2018.01) | |
| *G06F 3/04842* | (2022.01) | |
| *A61B 5/024* | (2006.01) | |
| *A61B 5/00* | (2006.01) | |
| *A61B 5/11* | (2006.01) | |
| *A61B 5/332* | (2021.01) | |
| *G16H 20/10* | (2018.01) | |
| *G16H 70/40* | (2018.01) | |
| *G16H 50/20* | (2018.01) | |
| *G16H 50/70* | (2018.01) | |
| *G06F 3/0488* | (2022.01) | |

(52) U.S. Cl.
CPC ........ *G06F 3/0482* (2013.01); *G06F 3/04842* (2013.01); *G16H 10/65* (2018.01); *G16H 15/00* (2018.01); *G16H 20/10* (2018.01); *G16H 40/60* (2018.01); *G16H 50/20* (2018.01); *G16H 50/30* (2018.01); *G16H 50/70* (2018.01); *G16H 70/40* (2018.01); *A61B 5/02438* (2013.01); *A61B 5/1117* (2013.01); *A61B 5/332* (2021.01); *A61B 5/681* (2013.01); *A61B 5/6898* (2013.01); *G06F 3/0488* (2013.01)

(58) Field of Classification Search
CPC ........ G16H 15/00; G16H 50/30; G16H 50/70; G16H 50/20; G16H 70/40; G16H 20/10; G16H 10/65; A61B 5/02444; A61B 5/7435; A61B 5/332; A61B 5/02438; A61B 5/1117; A61B 5/681; A61B 5/6898
See application file for complete search history.

(56) References Cited

U.S. PATENT DOCUMENTS

| | | | |
|---|---|---|---|
| 6,416,471 B1 | 7/2002 | Kumar et al. | |
| 6,600,696 B1 | 7/2003 | Lynn | |
| 6,603,477 B1 | 8/2003 | Tittle | |
| 6,705,972 B1 | 3/2004 | Takano et al. | |
| 6,950,839 B1 | 9/2005 | Green et al. | |
| 7,107,546 B2 | 9/2006 | Coulthard et al. | |
| 7,128,693 B2 | 10/2006 | Brown et al. | |
| 7,166,078 B2 | 1/2007 | Saini et al. | |
| 7,739,148 B2 | 6/2010 | Suzuki et al. | |
| 8,321,006 B1 | 11/2012 | Snyder et al. | |
| 8,475,339 B2 | 7/2013 | Hwang et al. | |
| 8,676,170 B2 | 3/2014 | Porrati et al. | |
| 8,725,527 B1* | 5/2014 | Kahn | G16H 40/63 705/2 |
| 8,758,262 B2 | 6/2014 | Rhee et al. | |
| 8,784,115 B1 | 7/2014 | Chuang | |
| 8,888,707 B2 | 11/2014 | Shirasaki et al. | |
| 9,026,927 B2 | 5/2015 | Brumback et al. | |
| 9,224,291 B2 | 12/2015 | Moll-carrillo et al. | |
| 9,579,060 B1* | 2/2017 | Lisy | A61B 5/0533 |
| 9,589,445 B2 | 3/2017 | White et al. | |
| 9,672,715 B2 | 6/2017 | Roberts et al. | |
| 9,712,629 B2* | 7/2017 | Molettiere | G06F 3/0486 |
| 9,721,066 B1* | 8/2017 | Funaro | G16H 50/30 |
| 9,730,621 B2* | 8/2017 | Cohen | A61B 5/0022 |
| 9,801,562 B1 | 10/2017 | Host-madsen | |
| 9,808,206 B1 | 11/2017 | Zhao et al. | |
| 9,813,642 B1 | 11/2017 | Chen et al. | |
| 9,940,682 B2* | 4/2018 | Hoffman | A63B 24/0059 |
| 10,175,781 B2 | 1/2019 | Karagozler et al. | |
| 10,226,195 B2 | 3/2019 | Briante et al. | |
| 10,254,911 B2 | 4/2019 | Yang | |
| 10,339,830 B2* | 7/2019 | Han | G09B 5/062 |
| 10,576,327 B2 | 3/2020 | Kim et al. | |
| 10,602,964 B2 | 3/2020 | Kerber | |
| 10,635,267 B2 | 4/2020 | Williams | |
| 10,674,942 B2 | 6/2020 | Williams et al. | |
| 10,762,990 B1* | 9/2020 | Schilling | G16B 40/30 |
| 10,764,700 B1 | 9/2020 | Felton | |
| 10,777,314 B1 | 9/2020 | Williams et al. | |
| 10,796,549 B2 | 10/2020 | Roberts et al. | |
| 11,107,580 B1 | 8/2021 | Felton et al. | |
| 2002/0095292 A1 | 7/2002 | Mittal et al. | |
| 2003/0181291 A1 | 9/2003 | Ogawa | |
| 2003/0191609 A1 | 10/2003 | Bernardi et al. | |
| 2003/0200483 A1 | 10/2003 | Sutton | |
| 2003/0216971 A1 | 11/2003 | Sick et al. | |
| 2003/0226695 A1 | 12/2003 | Mault | |
| 2004/0017300 A1 | 1/2004 | Kotzin et al. | |
| 2004/0034288 A1 | 2/2004 | Hennessy et al. | |
| 2004/0077958 A1* | 4/2004 | Kato | A61B 5/1071 600/490 |
| 2004/0190729 A1 | 9/2004 | Yonovitz et al. | |
| 2004/0193069 A1 | 9/2004 | Takehara | |
| 2004/0236189 A1 | 11/2004 | Hawthorne et al. | |
| 2005/0010117 A1 | 1/2005 | Agutter et al. | |
| 2005/0027208 A1 | 2/2005 | Shiraishi et al. | |
| 2005/0075214 A1 | 4/2005 | Brown et al. | |
| 2005/0079905 A1 | 4/2005 | Martens | |
| 2005/0149362 A1 | 7/2005 | Peterson et al. | |
| 2005/0165627 A1 | 7/2005 | Fotsch et al. | |
| 2005/0228735 A1 | 10/2005 | Duquette | |
| 2005/0244013 A1 | 11/2005 | Battenberg et al. | |
| 2005/0272564 A1 | 12/2005 | Pyles et al. | |
| 2006/0094969 A1* | 5/2006 | Nissila | A61B 5/02438 600/509 |
| 2006/0098109 A1 | 5/2006 | Ooki | |
| 2006/0106741 A1 | 5/2006 | Janarthanan | |
| 2006/0136173 A1* | 6/2006 | Case | A63B 24/0062 702/182 |
| 2006/0149144 A1 | 7/2006 | Lynn et al. | |
| 2006/0152372 A1 | 7/2006 | Stout | |
| 2006/0182287 A1 | 8/2006 | Schulein et al. | |
| 2006/0205564 A1 | 9/2006 | Peterson | |
| 2006/0235319 A1 | 10/2006 | Belohlavek et al. | |
| 2006/0274908 A1 | 12/2006 | Choi | |
| 2007/0016440 A1 | 1/2007 | Stroup | |
| 2007/0056727 A1 | 3/2007 | Newman | |
| 2008/0012701 A1 | 1/2008 | Kass et al. | |
| 2008/0058626 A1 | 3/2008 | Miyata et al. | |
| 2008/0146892 A1* | 6/2008 | LeBoeuf | G06Q 30/0251 600/300 |
| 2008/0159547 A1 | 7/2008 | Schuler et al. | |
| 2008/0200312 A1 | 8/2008 | Tagliabue | |
| 2008/0205660 A1 | 8/2008 | Goldstein | |
| 2008/0228045 A1* | 9/2008 | Gao | A61B 5/0022 600/301 |
| 2008/0240519 A1 | 10/2008 | Nagamitsu | |
| 2008/0300110 A1 | 12/2008 | Smith et al. | |
| 2009/0007596 A1 | 1/2009 | Goldstein et al. | |
| 2009/0052677 A1 | 2/2009 | Smith | |
| 2009/0054743 A1 | 2/2009 | Stewart | |
| 2009/0065578 A1 | 3/2009 | Peterson et al. | |
| 2009/0118100 A1 | 5/2009 | Oliver et al. | |
| 2009/0180631 A1 | 7/2009 | Michael et al. | |
| 2009/0192823 A1 | 7/2009 | Hawkins et al. | |
| 2009/0210078 A1 | 8/2009 | Crowley | |
| 2009/0216556 A1 | 8/2009 | Martin et al. | |
| 2009/0245537 A1 | 10/2009 | Morin | |
| 2009/0259134 A1 | 10/2009 | Levine | |
| 2009/0262088 A1 | 10/2009 | Moll-carrillo et al. | |
| 2009/0287103 A1 | 11/2009 | Pillai | |
| 2009/0287327 A1 | 11/2009 | Hsu et al. | |
| 2009/0290721 A1 | 11/2009 | Goldstein et al. | |
| 2009/0307105 A1 | 12/2009 | Lemay et al. | |
| 2009/0319243 A1 | 12/2009 | Suarez-rivera et al. | |
| 2010/0003951 A1 | 1/2010 | Ray et al. | |

(56) References Cited

U.S. PATENT DOCUMENTS

| | | |
|---|---|---|
| 2010/0010832 A1 | 1/2010 | Boute et al. |
| 2010/0017489 A1 | 1/2010 | Birnbaum et al. |
| 2010/0027807 A1 | 2/2010 | Jeon |
| 2010/0042949 A1 | 2/2010 | Chen |
| 2010/0046767 A1 | 2/2010 | Bayley et al. |
| 2010/0062905 A1 | 3/2010 | Rottler et al. |
| 2010/0076331 A1 | 3/2010 | Chan et al. |
| 2010/0094658 A1 | 4/2010 | Mok et al. |
| 2010/0099539 A1* | 4/2010 | Haataja ............... A63B 71/0622 482/8 |
| 2010/0119093 A1 | 5/2010 | Uzuanis et al. |
| 2010/0121700 A1 | 5/2010 | Wigder et al. |
| 2010/0150378 A1 | 6/2010 | Lee et al. |
| 2010/0179832 A1 | 7/2010 | Van et al. |
| 2010/0222645 A1 | 9/2010 | Nadler et al. |
| 2010/0292600 A1 | 11/2010 | Dibenedetto et al. |
| 2010/0305965 A1 | 12/2010 | Benjamin et al. |
| 2010/0312138 A1 | 12/2010 | Regas |
| 2011/0066051 A1 | 3/2011 | Moon et al. |
| 2011/0093481 A1 | 4/2011 | Hussam |
| 2011/0098928 A1 | 4/2011 | Hoffman et al. |
| 2011/0106553 A1 | 5/2011 | Tanaka et al. |
| 2011/0137678 A1 | 6/2011 | Williams |
| 2011/0152656 A1 | 6/2011 | Weinert et al. |
| 2011/0166631 A1 | 7/2011 | Breining |
| 2011/0195383 A1 | 8/2011 | Weiss |
| 2011/0201911 A1 | 8/2011 | Johnson et al. |
| 2011/0214162 A1 | 9/2011 | Brakensiek et al. |
| 2011/0218407 A1 | 9/2011 | Haberman et al. |
| 2011/0245623 A1 | 10/2011 | Chutani et al. |
| 2011/0306389 A1 | 12/2011 | Nagayama |
| 2011/0307821 A1 | 12/2011 | Martens |
| 2012/0002510 A1 | 1/2012 | Berman |
| 2012/0029303 A1 | 2/2012 | Shaya |
| 2012/0038651 A1 | 2/2012 | Case et al. |
| 2012/0041767 A1 | 2/2012 | Hoffman et al. |
| 2012/0059664 A1* | 3/2012 | Georgiev ............... A61B 5/02 705/2 |
| 2012/0065480 A1 | 3/2012 | Badilini et al. |
| 2012/0071770 A1 | 3/2012 | Grey et al. |
| 2012/0112908 A1 | 5/2012 | Prykaeri et al. |
| 2012/0116550 A1 | 5/2012 | Hoffman et al. |
| 2012/0203124 A1 | 8/2012 | Lim |
| 2012/0215115 A1 | 8/2012 | Takahashi |
| 2012/0232929 A1 | 9/2012 | Experton |
| 2012/0245447 A1* | 9/2012 | Karan ................... G16H 40/63 600/365 |
| 2012/0272186 A1 | 10/2012 | Kraut |
| 2012/0283524 A1 | 11/2012 | Kiani et al. |
| 2012/0283587 A1 | 11/2012 | Gosh et al. |
| 2012/0283855 A1 | 11/2012 | Hoffman et al. |
| 2012/0302840 A1 | 11/2012 | Kubo |
| 2012/0302843 A1 | 11/2012 | Otsubo et al. |
| 2012/0317167 A1 | 12/2012 | Rahman et al. |
| 2012/0321094 A1 | 12/2012 | Schiller et al. |
| 2013/0002425 A1 | 1/2013 | Hatch et al. |
| 2013/0011819 A1* | 1/2013 | Horseman ............... A61B 5/72 434/257 |
| 2013/0012788 A1* | 1/2013 | Horseman ............... G16H 50/30 600/301 |
| 2013/0013331 A1* | 1/2013 | Horseman ............... G16H 40/67 705/2 |
| 2013/0033376 A1 | 2/2013 | Seyed et al. |
| 2013/0054150 A1 | 2/2013 | Sacks et al. |
| 2013/0065569 A1 | 3/2013 | Leipzig et al. |
| 2013/0072765 A1 | 3/2013 | Kahn et al. |
| 2013/0073960 A1 | 3/2013 | Eppolito et al. |
| 2013/0095459 A1* | 4/2013 | Tran ...................... G09B 19/00 434/247 |
| 2013/0106603 A1 | 5/2013 | Weast et al. |
| 2013/0106684 A1 | 5/2013 | Weast et al. |
| 2013/0110264 A1 | 5/2013 | Weast et al. |
| 2013/0114100 A1 | 5/2013 | Torii et al. |
| 2013/0115583 A1 | 5/2013 | Gordon et al. |
| 2013/0141233 A1 | 6/2013 | Jacobs et al. |
| 2013/0144653 A1 | 6/2013 | Poe et al. |
| 2013/0151285 A1 | 6/2013 | Mclaren et al. |
| 2013/0158367 A1 | 6/2013 | Pacione et al. |
| 2013/0158416 A1 | 6/2013 | Hatlestad et al. |
| 2013/0187923 A1 | 7/2013 | Yoshimoto et al. |
| 2013/0191647 A1 | 7/2013 | Ferrara et al. |
| 2013/0197679 A1 | 8/2013 | Balakrishnan et al. |
| 2013/0202121 A1 | 8/2013 | Georgiou et al. |
| 2013/0215042 A1 | 8/2013 | Messerschmidt et al. |
| 2013/0231575 A1 | 9/2013 | Erkkila et al. |
| 2013/0231947 A1 | 9/2013 | Shusterman |
| 2013/0262155 A1 | 10/2013 | Hinkamp |
| 2013/0268398 A1 | 10/2013 | Agami et al. |
| 2013/0274628 A1 | 10/2013 | Fausti et al. |
| 2013/0304616 A1 | 11/2013 | Raleigh et al. |
| 2013/0317380 A1 | 11/2013 | Liley et al. |
| 2013/0325396 A1* | 12/2013 | Yuen ..................... A61B 5/222 702/160 |
| 2013/0332286 A1 | 12/2013 | Medelius et al. |
| 2014/0019162 A1 | 1/2014 | Skowronski et al. |
| 2014/0037107 A1 | 2/2014 | Marino et al. |
| 2014/0038781 A1 | 2/2014 | Foley et al. |
| 2014/0073486 A1* | 3/2014 | Ahmed ............... A61B 5/02438 482/9 |
| 2014/0081118 A1 | 3/2014 | Reinhold et al. |
| 2014/0088995 A1* | 3/2014 | Damani ................. G06Q 10/10 705/2 |
| 2014/0100885 A1 | 4/2014 | Stern |
| 2014/0127996 A1 | 5/2014 | Park et al. |
| 2014/0129007 A1 | 5/2014 | Utter |
| 2014/0129243 A1* | 5/2014 | Utter, II ............... G16H 20/60 705/2 |
| 2014/0135592 A1 | 5/2014 | Ohnemus et al. |
| 2014/0142403 A1* | 5/2014 | Brumback ............ A61B 5/681 600/324 |
| 2014/0143678 A1 | 5/2014 | Mistry et al. |
| 2014/0164611 A1* | 6/2014 | Molettiere ............ A61B 5/1112 709/224 |
| 2014/0176335 A1 | 6/2014 | Brumback et al. |
| 2014/0176475 A1 | 6/2014 | Myers et al. |
| 2014/0180595 A1* | 6/2014 | Brumback ............ G06F 1/1694 702/19 |
| 2014/0184422 A1 | 7/2014 | Mensinger et al. |
| 2014/0189510 A1 | 7/2014 | Ozcan |
| 2014/0197946 A1* | 7/2014 | Park ...................... G08B 5/22 340/539.11 |
| 2014/0200426 A1* | 7/2014 | Taub ..................... A61B 5/14532 600/347 |
| 2014/0222446 A1 | 8/2014 | Ash et al. |
| 2014/0240122 A1 | 8/2014 | Roberts et al. |
| 2014/0240349 A1 | 8/2014 | Tuukkanen |
| 2014/0266776 A1 | 9/2014 | Miller et al. |
| 2014/0275852 A1 | 9/2014 | Hong et al. |
| 2014/0275856 A1 | 9/2014 | Kohlrausch et al. |
| 2014/0278220 A1* | 9/2014 | Yuen ..................... A61B 5/02427 702/150 |
| 2014/0297217 A1 | 10/2014 | Yuen |
| 2014/0310643 A1 | 10/2014 | Karmanenko et al. |
| 2014/0327527 A1 | 11/2014 | Goldstein et al. |
| 2014/0336796 A1 | 11/2014 | Agnew |
| 2014/0344687 A1* | 11/2014 | Durham ............... G06F 1/1694 715/716 |
| 2014/0354494 A1* | 12/2014 | Katz ..................... H01Q 9/42 343/718 |
| 2014/0358012 A1 | 12/2014 | Richards et al. |
| 2014/0358584 A1 | 12/2014 | Worden et al. |
| 2014/0371887 A1 | 12/2014 | Hoffman et al. |
| 2015/0081210 A1 | 3/2015 | Yeh et al. |
| 2015/0089536 A1 | 3/2015 | Byerley |
| 2015/0099991 A1 | 4/2015 | Yamaguchi et al. |
| 2015/0100245 A1 | 4/2015 | Huang et al. |
| 2015/0106025 A1 | 4/2015 | Keller et al. |
| 2015/0110277 A1 | 4/2015 | Pidgeon et al. |
| 2015/0110279 A1 | 4/2015 | Tejerina |
| 2015/0120633 A1* | 4/2015 | Norlander ............ G16H 20/70 706/46 |
| 2015/0124067 A1 | 5/2015 | Bala et al. |

(56) References Cited

U.S. PATENT DOCUMENTS

| | | | |
|---|---|---|---|
| 2015/0125832 A1* | 5/2015 | Tran | G09B 19/0092 |
| | | | 434/127 |
| 2015/0127365 A1 | 5/2015 | Rizvi et al. | |
| 2015/0142689 A1 | 5/2015 | Squires | |
| 2015/0164349 A1 | 6/2015 | Gopalakrishnan et al. | |
| 2015/0179186 A1 | 6/2015 | Swierk et al. | |
| 2015/0181314 A1 | 6/2015 | Swanson | |
| 2015/0182843 A1* | 7/2015 | Esposito | G06K 9/00342 |
| | | | 700/91 |
| 2015/0185967 A1 | 7/2015 | Ly et al. | |
| 2015/0186602 A1 | 7/2015 | Pipke et al. | |
| 2015/0193217 A1 | 7/2015 | Xiang et al. | |
| 2015/0196804 A1 | 7/2015 | Koduri et al. | |
| 2015/0205930 A1 | 7/2015 | Shaanan et al. | |
| 2015/0205947 A1* | 7/2015 | Berman | A61B 5/14532 |
| | | | 726/16 |
| 2015/0216448 A1 | 8/2015 | Lotan et al. | |
| 2015/0217163 A1 | 8/2015 | Amis et al. | |
| 2015/0220883 A1 | 8/2015 | Bfar et al. | |
| 2015/0230717 A1* | 8/2015 | Wan | G16H 40/40 |
| | | | 702/19 |
| 2015/0262499 A1 | 9/2015 | Wicka et al. | |
| 2015/0286800 A1* | 10/2015 | Kanagala | G16H 10/20 |
| | | | 705/2 |
| 2015/0287421 A1 | 10/2015 | Benway et al. | |
| 2015/0288797 A1 | 10/2015 | Vincent | |
| 2015/0288944 A1 | 10/2015 | Nistico et al. | |
| 2015/0289823 A1* | 10/2015 | Rack-Gomer | G16H 20/30 |
| | | | 600/365 |
| 2015/0297134 A1 | 10/2015 | Albert et al. | |
| 2015/0324751 A1 | 11/2015 | Orenstein et al. | |
| 2015/0343709 A1 | 12/2015 | Gerstle et al. | |
| 2015/0347690 A1 | 12/2015 | Keen et al. | |
| 2015/0347711 A1* | 12/2015 | Soli | G16H 40/67 |
| | | | 705/3 |
| 2015/0350799 A1 | 12/2015 | Schnaare et al. | |
| 2015/0350861 A1 | 12/2015 | Soli et al. | |
| 2016/0000379 A1 | 1/2016 | Pougatchev et al. | |
| 2016/0019360 A1 | 1/2016 | Pahwa et al. | |
| 2016/0027282 A1 | 1/2016 | Lee | |
| 2016/0055420 A1* | 2/2016 | Karanam | A61B 5/165 |
| | | | 700/52 |
| 2016/0058313 A1 | 3/2016 | Sato | |
| 2016/0058336 A1 | 3/2016 | Blahnik et al. | |
| 2016/0058337 A1 | 3/2016 | Blahnik et al. | |
| 2016/0062582 A1 | 3/2016 | Wilson et al. | |
| 2016/0063215 A1 | 3/2016 | Zamer | |
| 2016/0078778 A1 | 3/2016 | Holland | |
| 2016/0085937 A1 | 3/2016 | Dettinger et al. | |
| 2016/0086500 A1* | 3/2016 | Kaleal, III | G06Q 10/10 |
| | | | 434/257 |
| 2016/0098522 A1 | 4/2016 | Weinstein | |
| 2016/0106398 A1 | 4/2016 | Kuppuswami | |
| 2016/0107031 A1 | 4/2016 | Palatsi et al. | |
| 2016/0109961 A1 | 4/2016 | Parshionikar | |
| 2016/0132046 A1 | 5/2016 | Beoughter et al. | |
| 2016/0135719 A1 | 5/2016 | Von Kraus et al. | |
| 2016/0135731 A1 | 5/2016 | Drennan | |
| 2016/0150978 A1 | 6/2016 | Yuen et al. | |
| 2016/0166181 A1 | 6/2016 | Shennib | |
| 2016/0166195 A1 | 6/2016 | Radecka et al. | |
| 2016/0174857 A1 | 6/2016 | Eggers et al. | |
| 2016/0180026 A1 | 6/2016 | Kim et al. | |
| 2016/0189051 A1 | 6/2016 | Mahmood | |
| 2016/0196635 A1 | 7/2016 | Cho et al. | |
| 2016/0210099 A1 | 7/2016 | Hampapuram et al. | |
| 2016/0210434 A1 | 7/2016 | Al-sharif | |
| 2016/0235325 A1 | 8/2016 | Chou | |
| 2016/0235374 A1* | 8/2016 | Miller | A61B 5/0537 |
| 2016/0249857 A1 | 9/2016 | Choi et al. | |
| 2016/0250517 A1 | 9/2016 | Tilvis et al. | |
| 2016/0256082 A1 | 9/2016 | Ely et al. | |
| 2016/0256741 A1 | 9/2016 | Holma et al. | |
| 2016/0263435 A1 | 9/2016 | Venkatraman et al. | |
| 2016/0270717 A1 | 9/2016 | Luna et al. | |
| 2016/0275990 A1 | 9/2016 | Vassort | |
| 2016/0285985 A1 | 9/2016 | Molettiere et al. | |
| 2016/0287177 A1* | 10/2016 | Huppert | A61B 5/0006 |
| 2016/0292373 A1 | 10/2016 | Spors et al. | |
| 2016/0299769 A1 | 10/2016 | Hunter et al. | |
| 2016/0301761 A1 | 10/2016 | Sanchez-sandoval et al. | |
| 2016/0301794 A1 | 10/2016 | Schlakman et al. | |
| 2016/0302666 A1 | 10/2016 | Shaya | |
| 2016/0314670 A1 | 10/2016 | Roberts et al. | |
| 2016/0314683 A1 | 10/2016 | Felch et al. | |
| 2016/0317341 A1* | 11/2016 | Galvan | A61F 5/028 |
| 2016/0324457 A1 | 11/2016 | Dagum | |
| 2016/0324488 A1* | 11/2016 | Olsen | A61B 5/14552 |
| 2016/0328991 A1 | 11/2016 | Simpson et al. | |
| 2016/0332025 A1 | 11/2016 | Repka | |
| 2016/0346607 A1 | 12/2016 | Rapfogel | |
| 2016/0360100 A1 | 12/2016 | Kim et al. | |
| 2016/0360972 A1 | 12/2016 | Kusakabe et al. | |
| 2016/0379511 A1 | 12/2016 | Dawson et al. | |
| 2017/0000348 A1* | 1/2017 | Karsten | A61B 5/0048 |
| 2017/0000359 A1 | 1/2017 | Kohli et al. | |
| 2017/0007159 A1 | 1/2017 | Dieffenderfer et al. | |
| 2017/0007167 A1 | 1/2017 | Kostic et al. | |
| 2017/0032168 A1 | 2/2017 | Kim | |
| 2017/0039327 A1 | 2/2017 | Bitran et al. | |
| 2017/0043214 A1* | 2/2017 | Higashi | A61B 5/746 |
| 2017/0046024 A1 | 2/2017 | Dascola et al. | |
| 2017/0053542 A1 | 2/2017 | Wilson et al. | |
| 2017/0071551 A1* | 3/2017 | Jain | A61B 5/02438 |
| 2017/0075551 A1 | 3/2017 | Robinson et al. | |
| 2017/0084196 A1 | 3/2017 | Nusbaum et al. | |
| 2017/0086693 A1 | 3/2017 | Peterson et al. | |
| 2017/0127997 A1 | 5/2017 | Hyde et al. | |
| 2017/0132395 A1* | 5/2017 | Futch | G06Q 40/08 |
| 2017/0136297 A1* | 5/2017 | Penie | A61B 5/746 |
| 2017/0147197 A1 | 5/2017 | Yang et al. | |
| 2017/0150917 A1 | 6/2017 | Brief et al. | |
| 2017/0156593 A1* | 6/2017 | Ferber | A61B 5/117 |
| 2017/0161014 A1 | 6/2017 | Kikugawa et al. | |
| 2017/0172522 A1 | 6/2017 | Insler et al. | |
| 2017/0177797 A1 | 6/2017 | Kurniawan et al. | |
| 2017/0181645 A1* | 6/2017 | Mahalingam | A61B 5/14532 |
| 2017/0181678 A1 | 6/2017 | Newberry | |
| 2017/0188841 A1 | 7/2017 | Ma et al. | |
| 2017/0188893 A1 | 7/2017 | Venkatraman et al. | |
| 2017/0188979 A1 | 7/2017 | Volpe | |
| 2017/0202496 A1 | 7/2017 | Ramanathan | |
| 2017/0215811 A1 | 8/2017 | Newberry | |
| 2017/0235443 A1 | 8/2017 | Suzuki | |
| 2017/0237694 A1 | 8/2017 | Choudhary et al. | |
| 2017/0243508 A1 | 8/2017 | Cheng et al. | |
| 2017/0258455 A1 | 9/2017 | Qi | |
| 2017/0274149 A1 | 9/2017 | Aeschlimann | |
| 2017/0274267 A1 | 9/2017 | Blahnik | |
| 2017/0281057 A1 | 10/2017 | Blahnik et al. | |
| 2017/0293727 A1 | 10/2017 | Klaassen et al. | |
| 2017/0294174 A1 | 10/2017 | Albadawi et al. | |
| 2017/0300186 A1 | 10/2017 | Kuhar et al. | |
| 2017/0303844 A1 | 10/2017 | Baker et al. | |
| 2017/0319184 A1 | 11/2017 | Sano | |
| 2017/0330297 A1 | 11/2017 | Cronin et al. | |
| 2017/0348562 A1 | 12/2017 | Jung et al. | |
| 2017/0354845 A1 | 12/2017 | Williams et al. | |
| 2017/0357329 A1 | 12/2017 | Park et al. | |
| 2017/0357520 A1 | 12/2017 | De Vries et al. | |
| 2017/0364637 A1 | 12/2017 | Kshepakaran et al. | |
| 2018/0000426 A1 | 1/2018 | Li | |
| 2018/0001184 A1 | 1/2018 | Tran et al. | |
| 2018/0011686 A1 | 1/2018 | Zhao et al. | |
| 2018/0032234 A1 | 2/2018 | Michalske | |
| 2018/0042559 A1* | 2/2018 | Cabrera, Jr. | G06F 3/04847 |
| 2018/0047277 A1 | 2/2018 | Thyroff | |
| 2018/0049659 A1 | 2/2018 | Briante et al. | |
| 2018/0049696 A1 | 2/2018 | Eom et al. | |
| 2018/0055490 A1 | 3/2018 | Lee et al. | |
| 2018/0060522 A1 | 3/2018 | Petterson et al. | |
| 2018/0064356 A1 | 3/2018 | Mendenhall et al. | |
| 2018/0064388 A1* | 3/2018 | Heneghan | A61B 5/11 |

(56) References Cited

U.S. PATENT DOCUMENTS

| | | |
|---|---|---|
| 2018/0065025 A1 | 3/2018 | Toda et al. |
| 2018/0070861 A1* | 3/2018 | Eastman .............. G06T 11/206 |
| 2018/0074462 A1 | 3/2018 | Helder et al. |
| 2018/0074464 A1 | 3/2018 | Essery et al. |
| 2018/0081918 A1 | 3/2018 | Gravenites et al. |
| 2018/0096739 A1 | 4/2018 | Sano |
| 2018/0107962 A1* | 4/2018 | Lundin ................. G06N 20/00 |
| 2018/0117414 A1* | 5/2018 | Miyasaka ............. G16H 40/67 |
| 2018/0120985 A1 | 5/2018 | Wallace et al. |
| 2018/0132768 A1* | 5/2018 | Sasahara ................ A61B 5/222 |
| 2018/0137937 A1 | 5/2018 | Gass et al. |
| 2018/0140211 A1* | 5/2018 | Nakazawa ................ A61B 5/11 |
| 2018/0140927 A1* | 5/2018 | Kito ...................... G06F 1/163 |
| 2018/0154212 A1* | 6/2018 | Park .................... G06F 3/04847 |
| 2018/0189077 A1 | 7/2018 | Gupta et al. |
| 2018/0211020 A1 | 7/2018 | Fukuda |
| 2018/0226150 A1 | 8/2018 | Hayter et al. |
| 2018/0232494 A1 | 8/2018 | Leppala et al. |
| 2018/0239869 A1* | 8/2018 | Laing ..................... G16H 50/30 |
| 2018/0255159 A1 | 9/2018 | Cohen et al. |
| 2018/0256036 A1* | 9/2018 | Kogure ................. A61B 5/746 |
| 2018/0256078 A1 | 9/2018 | Vaterlaus |
| 2018/0256095 A1* | 9/2018 | Arnold ................. A61B 5/4815 |
| 2018/0263510 A1 | 9/2018 | Cronin et al. |
| 2018/0263517 A1* | 9/2018 | Kubo ................. A61B 5/02225 |
| 2018/0279885 A1* | 10/2018 | Bulut .................... A61B 5/7275 |
| 2018/0294053 A1 | 10/2018 | Runyon et al. |
| 2018/0336530 A1* | 11/2018 | Johnson ............. G06Q 10/1093 |
| 2018/0345078 A1 | 12/2018 | Blahnik et al. |
| 2018/0350451 A1 | 12/2018 | Ohnemus et al. |
| 2018/0350453 A1 | 12/2018 | Nag et al. |
| 2018/0368814 A1 | 12/2018 | R. Kudtarkar |
| 2018/0376107 A1* | 12/2018 | Shibaev ................. G06F 3/0488 |
| 2019/0012898 A1 | 1/2019 | Wittrup |
| 2019/0014205 A1 | 1/2019 | Miloseski et al. |
| 2019/0034050 A1 | 1/2019 | Williams et al. |
| 2019/0034494 A1* | 1/2019 | Bradley ............. G06F 16/2457 |
| 2019/0043337 A1 | 2/2019 | Liu et al. |
| 2019/0073618 A1 | 3/2019 | Kanukurthy et al. |
| 2019/0090800 A1* | 3/2019 | Bosworth ................ B64C 13/02 |
| 2019/0090816 A1* | 3/2019 | Horseman ............ A61B 5/4872 |
| 2019/0104951 A1 | 4/2019 | Valys et al. |
| 2019/0122523 A1 | 4/2019 | Roberts et al. |
| 2019/0138696 A1* | 5/2019 | Carpenter ............... G16H 20/30 |
| 2019/0150854 A1* | 5/2019 | Chung ................... A61B 5/318 |
| 2019/0192086 A1* | 6/2019 | Menon ................... G16H 40/67 |
| 2019/0206538 A1 | 7/2019 | Xing et al. |
| 2019/0223843 A1 | 7/2019 | Vitti |
| 2019/0228179 A1 | 7/2019 | Rakshit et al. |
| 2019/0228640 A1 | 7/2019 | Freedman et al. |
| 2019/0228847 A1 | 7/2019 | Soli |
| 2019/0240534 A1 | 8/2019 | Black |
| 2019/0252054 A1 | 8/2019 | Dirani et al. |
| 2019/0274562 A1 | 9/2019 | Soli et al. |
| 2019/0274563 A1 | 9/2019 | Soli et al. |
| 2019/0274564 A1 | 9/2019 | Soli et al. |
| 2019/0274565 A1 | 9/2019 | Soli et al. |
| 2019/0278556 A1 | 9/2019 | Usher et al. |
| 2019/0298230 A1 | 10/2019 | Nicholson et al. |
| 2019/0336044 A1 | 11/2019 | Williams et al. |
| 2019/0336045 A1 | 11/2019 | Williams et al. |
| 2019/0339849 A1 | 11/2019 | Williams et al. |
| 2019/0365332 A1* | 12/2019 | Fedichev ............... G16H 20/60 |
| 2019/0380624 A1 | 12/2019 | Ota et al. |
| 2019/0385708 A1 | 12/2019 | Hong et al. |
| 2020/0000441 A1 | 1/2020 | Lafon et al. |
| 2020/0069258 A1* | 3/2020 | Grinberg ................ G16H 15/00 |
| 2020/0100693 A1 | 4/2020 | Velo |
| 2020/0126673 A1* | 4/2020 | Tanabe ...................... A61B 5/02 |
| 2020/0203012 A1 | 6/2020 | Kamath et al. |
| 2020/0245928 A1 | 8/2020 | Kang et al. |
| 2020/0261011 A1* | 8/2020 | Seppanen ............... A61B 5/024 |
| 2020/0273566 A1 | 8/2020 | Bhowmik et al. |
| 2020/0297249 A1 | 9/2020 | Williams et al. |
| 2020/0315544 A1 | 10/2020 | Levine |
| 2020/0356687 A1 | 11/2020 | Salzman et al. |
| 2020/0357522 A1 | 11/2020 | Pahwa et al. |
| 2020/0374682 A1 | 11/2020 | Newman et al. |
| 2020/0379611 A1 | 12/2020 | Dryer et al. |
| 2020/0381099 A1 | 12/2020 | Crowley et al. |
| 2020/0381100 A1 | 12/2020 | Williams et al. |
| 2020/0381123 A1 | 12/2020 | Dryer et al. |
| 2020/0382866 A1 | 12/2020 | Felton |
| 2020/0382867 A1 | 12/2020 | Felton |
| 2020/0384314 A1 | 12/2020 | Lee et al. |
| 2021/0068714 A1 | 3/2021 | Crowley et al. |
| 2021/0113137 A1 | 4/2021 | Soli et al. |
| 2021/0210182 A1 | 7/2021 | Nag et al. |
| 2021/0225482 A1 | 7/2021 | Crowley et al. |
| 2021/0369130 A1 | 12/2021 | Felton et al. |
| 2021/0373746 A1 | 12/2021 | Felton et al. |
| 2021/0373748 A1 | 12/2021 | Felton et al. |
| 2021/0375157 A1 | 12/2021 | Sundstrom et al. |
| 2021/0375450 A1 | 12/2021 | Felton et al. |
| 2022/0047212 A1 | 2/2022 | Balsamo et al. |
| 2022/0066902 A1 | 3/2022 | Narra et al. |
| 2022/0109932 A1 | 4/2022 | Felton et al. |
| 2022/0142515 A1 | 5/2022 | Crowley |
| 2022/0160258 A1 | 5/2022 | Williams et al. |

FOREIGN PATENT DOCUMENTS

| | | |
|---|---|---|
| CN | 101150810 A | 3/2008 |
| CN | 101651870 A | 2/2010 |
| CN | 102339201 A | 2/2012 |
| CN | 102448555 | 5/2012 |
| CN | 103191557 A | 7/2013 |
| CN | 103370924 A | 10/2013 |
| CN | 103403627 A | 11/2013 |
| CN | 103561640 A | 2/2014 |
| CN | 104720765 A | 6/2015 |
| CN | 105260078 A | 1/2016 |
| CN | 105388998 A | 3/2016 |
| CN | 105721667 A | 6/2016 |
| CN | 106164808 A | 11/2016 |
| CN | 106537397 A | 3/2017 |
| CN | 106709235 A | 5/2017 |
| CN | 106725384 A | 5/2017 |
| CN | 107278138 A | 10/2017 |
| CN | 107361755 A | 11/2017 |
| CN | 107454831 A | 12/2017 |
| CN | 107591211 A | 1/2018 |
| CN | 107713981 A | 2/2018 |
| EP | 2391004 A1 | 11/2011 |
| EP | 2568409 A1 | 3/2013 |
| EP | 2921899 A2 | 9/2015 |
| EP | 3042606 A1 | 7/2016 |
| EP | 3096235 A1 | 11/2016 |
| EP | 3101882 A2 | 12/2016 |
| EP | 3557590 A1 | 10/2019 |
| JP | 6-187118 A | 7/1994 |
| JP | 2001-76078 A | 3/2001 |
| JP | 2003-337863 A | 11/2003 |
| JP | 2004-102609 A | 4/2004 |
| JP | 2004-113466 A | 4/2004 |
| JP | 2005-79814 A | 3/2005 |
| JP | 2006-107134 A | 4/2006 |
| JP | 2006-230679 A | 9/2006 |
| JP | 2008-11865 A | 1/2008 |
| JP | 2008-183339 A | 8/2008 |
| JP | 2010-12335 A | 1/2010 |
| JP | 2010-517725 A | 5/2010 |
| JP | 2010-162297 A | 7/2010 |
| JP | 2010-181280 A | 8/2010 |
| JP | 2011-125633 A | 6/2011 |
| JP | 2011-183101 A | 9/2011 |
| JP | 2011-192126 A | 9/2011 |
| JP | 2011-200575 A | 10/2011 |
| JP | 2011-259253 A | 12/2011 |
| JP | 2012-59264 A | 3/2012 |
| JP | 2012-524640 A | 10/2012 |
| JP | 2012-239808 A | 12/2012 |
| JP | 2013-117690 A | 6/2013 |
| JP | 2013-544140 A | 12/2013 |

(56) References Cited

FOREIGN PATENT DOCUMENTS

| | | |
|---|---|---|
| JP | 2015-213686 A | 12/2015 |
| JP | 2016-502875 A | 2/2016 |
| JP | 2016-528016 A | 9/2016 |
| JP | 2016-177151 A | 10/2016 |
| JP | 2016-202751 A | 12/2016 |
| JP | 2017-134689 A | 8/2017 |
| JP | 2017-526073 A | 9/2017 |
| JP | 2017-182393 A | 10/2017 |
| JP | 2017-529880 A | 10/2017 |
| JP | 2017-211994 A | 11/2017 |
| JP | 2017-532069 A | 11/2017 |
| JP | 2018-523554 A | 8/2018 |
| JP | 2018-191122 A | 11/2018 |
| KR | 10-2002-0060421 A | 7/2002 |
| KR | 10-2006-0117570 A | 11/2006 |
| KR | 10-2008-0051460 A | 6/2008 |
| KR | 10-2011-0017076 A | 2/2011 |
| KR | 10-2012-0023657 A | 3/2012 |
| KR | 10-2012-0076559 A | 7/2012 |
| KR | 10-2013-0043698 A | 5/2013 |
| KR | 10-2013-0111569 A | 10/2013 |
| KR | 10-2013-0111570 A | 10/2013 |
| KR | 10-2013-0135282 A | 12/2013 |
| KR | 10-2015-0115385 A | 10/2015 |
| KR | 10-1594486 B1 | 2/2016 |
| KR | 10-2016-0028351 A | 3/2016 |
| KR | 10-2016-0076264 A | 6/2016 |
| KR | 10-2017-0003608 A | 1/2017 |
| KR | 10-2017-0029014 A | 3/2017 |
| KR | 10-2019-0094795 A | 8/2019 |
| WO | 1999/41682 A2 | 8/1999 |
| WO | 2002/27530 A2 | 4/2002 |
| WO | 2003/067202 A2 | 8/2003 |
| WO | 2006/046648 A1 | 5/2006 |
| WO | 2008/073359 A2 | 6/2008 |
| WO | 2009/095908 A2 | 8/2009 |
| WO | 2010/126825 A1 | 11/2010 |
| WO | 2012/060588 A2 | 5/2012 |
| WO | 2012/061438 A2 | 5/2012 |
| WO | 2012/061440 A2 | 5/2012 |
| WO | 2012/078079 A2 | 6/2012 |
| WO | 2012/086910 A1 | 6/2012 |
| WO | 2013/052789 A1 | 4/2013 |
| WO | 2013/103570 A1 | 7/2013 |
| WO | 2013/109916 A1 | 7/2013 |
| WO | 2014/006862 A1 | 1/2014 |
| WO | 2014/015378 A1 | 1/2014 |
| WO | 2014/207875 A1 | 12/2014 |
| WO | 2015/027133 A1 | 2/2015 |
| WO | 2015/153803 A1 | 10/2015 |
| WO | 2015/183828 A1 | 12/2015 |
| WO | 2015/187799 A1 | 12/2015 |
| WO | 2015/198488 A1 | 12/2015 |
| WO | 2016/036472 A1 | 3/2016 |
| WO | 2016/036582 A2 | 3/2016 |
| WO | 2016/151479 A1 | 9/2016 |
| WO | 2016/161152 A1 | 10/2016 |
| WO | 2016/164475 A1 | 10/2016 |
| WO | 2016/179559 A2 | 11/2016 |
| WO | 2016/207745 A1 | 12/2016 |
| WO | 2017/003045 A1 | 1/2017 |
| WO | 2017/037242 A1 | 3/2017 |
| WO | 2017/062621 A1 | 4/2017 |
| WO | 2017/087642 A1 | 5/2017 |
| WO | 2017/090810 A1 | 6/2017 |
| WO | 2017/215203 A1 | 12/2017 |
| WO | 2018/132507 A1 | 7/2018 |
| WO | 2018/148356 A1 | 8/2018 |
| WO | 2018/222313 A1 | 12/2018 |
| WO | 2019/017508 A1 | 1/2019 |
| WO | 2019/020977 A1 | 1/2019 |
| WO | 2019/168956 A1 | 9/2019 |

OTHER PUBLICATIONS

Advisory Action received for U.S. Appl. No. 14/732,773, dated Aug. 23, 2019, 6 pages.
Advisory Action received for U.S. Appl. No. 14/732,773, dated Nov. 9, 2018, 6 pages.
Advisory Action received for U.S. Appl. No. 16/143,909, dated Nov. 7, 2019, 5 pages.
Advisory Action received for U.S. Appl. No. 16/143,997, dated Dec. 26, 2019, 7 pages.
Advisory Action received for U.S. Appl. No. 16/144,849, dated Aug. 12, 2019, 5 pages.
Advisory Action received for U.S. Appl. No. 16/144,864, dated Jul. 6, 2020, 6 pages.
Applicant Initiated Interview Summary received for U.S. Appl. No. 16/143,997, dated Aug. 13, 2020, 3 pages.
Applicant Initiated Interview Summary received for U.S. Appl. No. 16/144,849, dated Jan. 21, 2020, 6 pages.
Applicant Initiated Interview Summary received for U.S. Appl. No. 16/144,864, dated Apr. 29, 2020, 4 pages.
Applicant-Initiated Interview Summary received for U.S. Appl. No. 16/138,809, dated Jun. 9, 2020, 4 pages.
Applicant-Initiated Interview Summary received for U.S. Appl. No. 16/144,864, dated Jun. 22, 2020, 3 pages.
Applicant-Initiated Interview Summary received for U.S. Appl. No. 16/584,186, dated Feb. 3, 2020, 4 pages.
Casella Cel Casella, "The Casella dBadge2—World's First Truly Wireless Noise Dosimeter and Airwave App!", Retrieved from URL: <https://www.youtube.com/watch?v=Xvy2fl3cgYo>, May 27, 2015, 3 pages.
Certificate of Examination received for Australian Patent Application No. 2019100222, dated Aug. 29, 2019, 2 pages.
Cho H.S., "Satisfactory Innovative Smart-watch (fitbit force) . . . review after seven days of use, such as the amount of sleep and movement (improving sleep is the object of X-Blue", Online Available at: <https://x-blueuv.blogspot.com/2013/12/fitbit-force.html>, Dec. 3, 2013, 8 pages (2 pages of English Translation and 6 pages of Official Copy).
CNET, "Google Fit's automatic activity tracking is getting smarter on Android Wear", Available online at: https://www.youtube.com/watch?v=lttzlCid_d8, May 18, 2016, 1 page.
Corrected Notice of Allowance received for U.S. Appl. No. 14/732,773, dated Feb. 10, 2020, 3 pages.
Corrected Notice of Allowance received for U.S. Appl. No. 14/732,773, dated Mar. 24, 2020, 3 pages.
Corrected Notice of Allowance received for U.S. Appl. No. 16/143,909, dated Feb. 20, 2020, 3 pages.
Corrected Notice of Allowance received for U.S. Appl. No. 16/143,909, dated Mar. 18, 2020, 3 pages.
Corrected Notice of Allowance received for U.S. Appl. No. 16/143,959, dated Dec. 13, 2019, 2 pages.
Corrected Notice of Allowance received for U.S. Appl. No. 16/584,186, dated Jul. 31, 2020, 2 pages.
Cyclespeed Tours, "The Most Useful Data Fields to Display on Your Garmin", Online Available at: https://www.youtube.com/watch?v=AN0Eo50yxdg, Nov. 16, 2016, 3 pages.
DC Rainmaker, "Garmin Fenix3 New Auto Climb Functionality", Available online at: https://www.youtube.com/watch?v=iuavOSNpVRc, Feb. 19, 2015, 1 page.
Decision to Grant received for Danish Patent Application No. PA201870379, dated Jul. 5, 2019, 2 pages.
Decision to Grant received for Danish Patent Application No. PA201870600, dated Oct. 17, 2019, 2 pages.
Decision to Grant received for Danish Patent Application No. PA201870601, dated Aug. 17, 2020, 2 pages.
Decision to Grant received for Danish Patent Application No. PA201870602, dated Aug. 18, 2020, 2 pages.
Decision to Refuse received for European Patent Application No. 13811085.3, dated Sep. 11, 2018, 21 pages.
Extended European Search Report received for European Patent Application No. 20180581.9, dated Aug. 12, 2020, 9 pages.
Extended European Search Report received for European Patent Application No. 20180592.6, dated Aug. 11, 2020, 10 pages.

(56) References Cited

OTHER PUBLICATIONS

Epstein et al., "Examining Menstrual Tracking to Inform the Design of Personal Informatics Tools", Proceedings of the 2017 CHI Conference on Human Factors in Computing Systems, CHI '17, ACM Press, Denver, CO, USA, May 6-11, 2017, pp. 6876-6888.
Evergreen et al., "Bar Chart", Better Evaluation, Available Online at: https://www.betterevaluation.org/en/evaluation-options/BarChart, Oct. 31, 2014, 8 pages.
Final Office Action received for U.S. Appl. No. 14/732,773, dated Jul. 13, 2018, 48 pages.
Final Office Action received for U.S. Appl. No. 14/732,773, dated Jun. 21, 2019, 32 pages.
Final Office Action received for U.S. Appl. No. 16/138,809, dated Aug. 27, 2020, 24 pages.
Final Office Action received for U.S. Appl. No. 16/143,909, dated Aug. 28, 2019, 20 pages.
Final Office Action received for U.S. Appl. No. 16/143,997, dated Sep. 30, 2019, 16 pages.
Final Office Action received for U.S. Appl. No. 16/144,030, dated Feb. 13, 2020, 11 pages.
Final Office Action received for U.S. Appl. No. 16/144,030, dated Oct. 1, 2019, 13 pages.
Final Office Action received for U.S. Appl. No. 16/144,849, dated Jun. 7, 2019, 29 pages.
Final Office Action received for U.S. Appl. No. 16/144,864, dated May 17, 2019, 24 pages.
Final Office Action received for U.S. Appl. No. 16/144,864, dated May 28, 2020, 29 pages.
"Fitbit App", Available online at: <http://web.archive.org/web/20180114083150/https://www.fitbit.com/au/app>, Jan. 14, 2018, 8 pages.
Garmin, "Fenix 5x Owner's Manual", Online Available at :—https://web.archive.org/web/20180127170640/https://static.garmin.com/pumac/fenix5x_OM_EN.pdf, Jan. 27, 2018, 42 pages.
"Graphs and Charts", Online available at: <https://www.teachervision.com/lesson-planning/graph-chart-teacher-resources, retrieved on Dec. 12, 2018, 4 pages.
Intention to Grant received for Danish Patent Application No. PA201870379, dated May 2, 2019, 2 pages.
Intention to Grant received for Danish Patent Application No. PA201870600, dated Jul. 10, 2019, 2 pages.
Intention to Grant received for Danish Patent Application No. PA201870601, dated Apr. 24, 2020, 2 pages.
Intention to Grant received for Danish Patent Application No. PA201870602, dated Apr. 24, 2020, 2 pages.
International Preliminary Report on Patentability received for PCT Patent Application No. PCT/US2013/073195, dated Jun. 16, 2016, 10 pages.
International Preliminary Report on Patentability received for PCT Patent Application No. PCT/US2019/014215, dated Aug. 6, 2020, 14 pages.
International Preliminary Report on Patentability received for PCT Patent Application No. PCT/US2019/019694, dated Sep. 24, 2020, 12 pages.
International Search Report and Written Opinion received for PCT Patent Application No. PCT/US2019/014215, dated Jun. 4, 2019, 17 pages.
International Search Report and Written Opinion received for PCT Patent Application No. PCT/US2019/019694, dated Sep. 2, 2019, 17 pages.
International Search Report and Written Opinion received for PCT Patent Application No. PCT/US2019/024570, dated Aug. 8, 2019, 18 pages.
International Search Report and written Opinion received for PCT Patent Application No. PCT/US2020/025768, dated Aug. 10, 2020, 11 pages.
International Search Report and written Opinion received for PCT Patent Application No. PCT/US2020/025997, dated Jul. 1, 2020, 16 pages.
International Search Report and Written Opinion received for PCT Patent Application No. PCT/US2020/025997, dated Jul. 14, 2020, 15 pages.
International Search Report received for PCT Patent Application No. PCT/US2013/073195, dated Jun. 23, 2014, 3 pages.
International Written Opinion received for PCT Patent Application No. PCT/US2013/073195, dated Jun. 23, 2014, 8 pages.
Invitation to Pay Addition Fees and Partial International Search Report received for PCT Patent Application No. PCT/US2019/014215, dated Apr. 12, 2019, 13 pages.
Invitation to Pay Additional Fees received for PCT Patent Application No. PCT/US2019/019694, dated Jul. 10, 2019, 12 pages.
Invitation to Pay Search Fees received for European Patent Application No. 19726205.8, dated Feb. 14, 2020, 5 pages.
JenBSJourney, "Wondering About a Fitbit?", Available at: https://jenbsjourney.blogspot.kr/2013/08/wondering-about-fitbit.html, Aug. 6, 2013, 12 pages.
Megadepot, "Casella dBadge2 Noise Dosimeter", Retrieved from URL: <https://www.youtube.com/watch?v=pHiHLiYCD08>, Jun. 12, 2018, 3 pages.
Minutes of Oral Proceedings received for European Patent Application No. 13811085.3, dated Sep. 11, 2018, 3 pages.
Moglia et al., "Evaluation of Smartphone Menstrual Cycle Tracking Applications Using an Adapted Applications Scoring System", Obstetrics and Gynecology, vol. 127. No. 6, Jun. 2016, pp. 1153-1160.
"Multi-Set Bar Chart", The Data Visualization Catalogue, Available Online at: https://datavizcatalogue.com/methods/multiset_barchart.html, Feb. 8, 2014, 3 pages.
Myflo App, "Functional Medicine Period Tracker and Hormone Balancing App", Available online at <https://web.archive.org/web/20170127104125/https://myflotracker.com/>, Jan. 2017, 14 pages.
Myflo Tutorial, "How to change the start date of your current period", Available online at <https://www.youtube.com/watch?v=uQQ-odlBJB4>, Jan. 23, 2017, 3 pages.
Myflo Tutorial, "Setting and changing the end date of your period", Available online at <https://www.youtube.com/watch?v=UvAA4OgqL3E>, Jan. 23, 2017, 3 pages.
Non-Final Office Action received for U.S. Appl. No. 16/144,864, dated Dec. 18, 2018, 19 pages.
Non-Final Office Action received for U.S. Appl. No. 14/732,773, dated Feb. 8, 2019, 32 pages.
Non-Final Office Action received for U.S. Appl. No. 14/732,773, dated Jan. 19, 2018., 45 pages.
Non-Final Office Action received for U.S. Appl. No. 16/138,809, dated Feb. 28, 2020, 22 pages.
Non-Final Office Action received for U.S. Appl. No. 16/143,909, dated Apr. 19, 2019, 16 pages.
Non-Final Office Action received for U.S. Appl. No. 16/143,959, dated Apr. 17, 2019, 15 pages.
Non-Final Office Action received for U.S. Appl. No. 16/143,997, dated Jul. 27, 2020, 15 pages.
Non-Final Office Action received for U.S. Appl. No. 16/143,997, dated May 21, 2019, 15 pages.
Non-Final Office Action received for U.S. Appl. No. 16/144,030, dated Apr. 12, 2019, 8 pages.
Non-Final Office Action received for U.S. Appl. No. 16/144,849, dated Dec. 31, 2018, 28 pages.
Non-Final Office Action received for U.S. Appl. No. 16/144,849, dated Sep. 17, 2019, 9 pages.
Non-Final Office Action received for U.S. Appl. No. 16/144,864, dated Jan. 31, 2020, 29 pages.
Non-Final Office Action received for U.S. Appl. No. 16/584,186, dated Dec. 6, 2019, 13 pages.
Non-Final Office Action received for U.S. Appl. No. 16/880,552, dated Jul. 23, 2020, 19 pages.
Non-Final Office Action received for U.S. Appl. No. 16/907,261, dated Sep. 30, 2020, 22 pages.
Notice of Acceptance received for Australian Patent Application No. 2019222943, dated May 5, 2020, 3 pages.
Notice of Acceptance received for Australian Patent Application No. 2020204153, dated Jul. 6, 2020, 3 pages.

(56) References Cited

OTHER PUBLICATIONS

Notice of Allowance received for Chinese Patent Application No. 201910972529.2, dated Sep. 14, 2020, 6 pages (3 pages of English Translation and 3 pages of Official Copy).
Notice of Allowance received for Japanese Patent Application No. 2016-535045, dated Mar. 2, 2018, 4 pages (1 page of English Translation and 3 pages of Official Copy).
Notice of Allowance received for Japanese Patent Application No. 2018-068846, dated Dec. 9, 2019, 4 pages (1 page of English Translation and 3 pages of Official Copy).
Notice of Allowance received for Korean Patent Application No. 10-2016-7014577, dated May 30, 2019, 5 pages (2 pages of English Translation and 3 pages of Official Copy).
Notice of Allowance received for U.S. Appl. No. 14/732,773, dated Dec. 18, 2019, 21 pages.
Notice of Allowance received for U.S. Appl. No. 16/143,909, dated Jan. 21, 2020, 9 pages.
Notice of Allowance received for U.S. Appl. No. 16/143,959, dated Oct. 31, 2019, 10 pages.
Notice of Allowance received for U.S. Appl. No. 16/144,849, dated Apr. 17, 2020, 2 pages.
Notice of Allowance received for U.S. Appl. No. 16/144,849, dated Mar. 6, 2020, 9 pages.
Notice of Allowance received for U.S. Appl. No. 16/144,864, dated Jul. 28, 2020, 27 pages.
Notice of Allowance received for U.S. Appl. No. 16/144,864, dated Sep. 10, 2020, 3 pages.
Notice of Allowance received for U.S. Appl. No. 16/144,864, dated Sep. 16, 2020, 2 pages.
Notice of Allowance received for U.S. Appl. No. 16/144,864, dated Sep. 29, 2020, 2 pages.
Notice of Allowance received for U.S. Appl. No. 16/584,186, dated Mar. 24, 2020, 10 pages.
Notice of Allowance received for U.S. Appl. No. 16/588,950, dated Feb. 10, 2020, 9 pages.
Notice of Allowance received for U.S. Appl. No. 16/588,950, dated May 5, 2020, 9 pages.
Office Action received for Australian Patent Application No. 2019100222, dated May 24, 2019, 6 pages.
Office Action received for Australian Patent Application No. 2019100495, dated Mar. 6, 2020, 3 pages.
Office Action received for Australian Patent Application No. 2019100495, dated Mar. 16, 2020, 3 pages.
Office Action received for Australian Patent Application No. 2019100495, dated Sep. 17, 2019, 7 pages.
Office Action received for Australian Patent Application No. 2019222943, dated Oct. 3, 2019, 3 pages.
Office Action received for Chinese Patent Application No. 201380081349.6, dated Feb. 26, 2019, 12 pages (6 pages of English Translation and 6 pages of Official Copy).
Office Action received for Chinese Patent Application No. 201380081349.6, dated Jan. 16, 2020, 11 pages (6 pages of English Translation and 5 pages of Official Copy).
Office Action received for Chinese Patent Application No. 201380081349.6, dated Jul. 15, 2019, 10 pages (5 pages of English Translation and 5 pages of Official copy).
Office Action received for Chinese Patent Application No. 201380081349.6, dated Jul. 15, 2020, 9 pages (4 pages of English Translation and 5 pages of Official Copy).
Office Action received for Chinese Patent Application No. 201910858933.7, dated Aug. 18, 2020, 14 pages (7 pages of English Translation and 7 pages of Official Copy).
Office Action received for Chinese Patent Application No. 201910972529.2, dated Jun. 28, 2020, 8 pages (1 page of English Translation and 7 pages of Official Copy).
Office Action received for Danish Patent Application No. PA201870378, dated Feb. 25, 2019, 3 pages.
Office Action received for Danish Patent Application No. PA201870378, dated Jan. 6, 2020, 3 pages.
Office Action received for Danish Patent Application No. PA201870379, dated Feb. 28, 2019, 3 pages.
Office Action received for Danish Patent Application No. PA201870380, dated Mar. 5, 2020, 2 pages.
Office Action received for Danish Patent Application No. PA201870380, dated Mar. 27, 2019, 4 pages.
Office Action received for Danish Patent Application No. PA201870380, dated Sep. 11, 2018, 9 pages.
Office Action received for Danish Patent Application No. PA201870599, dated Dec. 20, 2019, 5 pages.
Office Action received for Danish Patent Application No. PA201870600, dated May 8, 2019, 3 pages.
Office Action received for Danish Patent Application No. PA201870601, dated Dec. 13, 2018, 8 pages.
Office Action received for Danish Patent Application No. PA201870601, dated Jan. 14, 2020, 3 pages.
Office Action received for Danish Patent Application No. PA201870601, dated Jun. 25, 2019, 3 pages.
Office Action received for Danish Patent Application No. PA201870602, dated Feb. 5, 2020, 3 pages.
Office Action received for Danish Patent Application No. PA201870602, dated Jun. 26, 2019, 3 Pages.
Office Action received for Danish Patent Application No. PA201970532, dated May 29, 2020, 3 pages.
Office Action received for Danish Patent Application No. PA201970534, dated Jun. 29, 2020, 2 pages.
Office Action received for European Patent Application No. 13811085.3, dated Apr. 20, 2018, 15 pages.
Office Action received for European Patent Application No. 19721883.7, dated Jan. 10, 2020, 4 pages.
Office Action received for European Patent Application No. 19721883.7, dated May 28, 2020, 11 pages.
Office Action received for European Patent Application No. 19726205.8, dated Jun. 26, 2020, 9 pages.
Office Action received for Japanese Patent Application No. 2016-535045, dated May 12, 2017, 10 pages (5 pages of English Translation and 5 pages of Official Copy).
Office Action received for Japanese Patent Application No. 2018-068846, dated Jan. 8, 2019, 6 pages (3 pages of English Translation and 3 pages of Official copy).
Office Action received for Japanese Patent Application No. 2019-162293, dated Jan. 31, 2020, 8 pages (4 pages of English Translation and 4 pages of Official Copy).
Office Action received for Japanese Patent Application No. 2019-162293, dated Jul. 27, 2020, 9 pages (5 pages of English Translation and 4 pages of Official Copy).
Office Action received for Korean Patent Application No. 10-2016-7014577, dated Dec. 26, 2017, 14 pages (6 pages of English Translation and 8 pages of Official Copy).
Office Action received for Korean Patent Application No. 10-2016-7014577, dated Oct. 31, 2018, 11 pages (5 pages of English Translation and 6 pages of Official Copy).
Office Action received for Korean Patent Application No. 10-2019-7025538, dated Aug. 15, 2020, 8 pages (4 pages of English Translation and 4 pages of Official Copy).
Office Action received for Korean Patent Application No. 10-2019-7025538, dated Feb. 17, 2020, 12 pages (6 pages of English Translation and 6 pages of Official Copy).
Office Action received for Korean Patent Application No. 10-2019-7025781, dated Nov. 26, 2019, 10 pages (4 pages of English Translation and 6 pages of Official Copy).
Rizknows, "Tom Tom Multisport Cardio Review", Online available at :—https://www.youtube.com/watch?v=WoVCzLrSN9A, Sep. 4, 2015, 1 page.
Search Report and Opinion received for Danish Patent Application No. PA201870378, dated Sep. 10, 2018, 9 pages.
Search Report and Opinion received for Danish Patent Application No. PA201870379, dated Sep. 14, 2018, 9 pages.
Search Report and Opinion received for Danish Patent Application No. PA201870599, dated Dec. 21, 2018, 9 pages.
Search Report and Opinion received for Danish Patent Application No. PA201870600, dated Jan. 31, 2019, 8 pages.

(56) References Cited

OTHER PUBLICATIONS

Search Report and Opinion received for Danish Patent Application No. PA201870602, dated Dec. 19, 2018, 8 pages.
Search Report and Opinion received for Danish Patent Application No. PA201970532, dated Nov. 8, 2019, 9 pages.
Search Report and Opinion received for Danish Patent Application No. PA201970534, dated Sep. 23, 2019, 6 pages.
Smith, "Garmin Fenix 5 Activity/Smart Watch Review", Online Available at :—https://www.youtube.com/watch?v=6PkQxXQxpoU, Sep. 2, 2017, 1 page.
SportsTechGuides, "Garmin Fenix 5: How to Add Power Data Fields", Online Available at :—https://www.youtube.com/watch?v=ZkPptnnXEiQ, Apr. 29, 2017, 2 pages.
SportsTechGuides, "Garmin Fenix 5: How to Set Up Run Alerts", Online Available at :—https://www.youtube.com/watch?v=gSMwv8vlhB4, May 13, 2017, 2 pages.
StudioSixDigital, "Dosimeter", Retrieved from URL: <https://studiosixdigital.com/audiotools-modules-2/spl-modules/dosimeter.html>, Mar. 3, 2017, 6 pages.
Summons to attend oral proceedings received for European Patent Application No. 13811085.3, dated Jan. 26, 2018., 14 pages.
Supplemental Notice of Allowance received for U.S. Appl. No. 16/144,849, dated Mar. 31, 2020, 2 pages.
Supplemental Notice of Allowance received for U.S. Appl. No. 16/588,950, dated Apr. 1, 2020, 2 pages.
Supplemental Notice of Allowance received for U.S. Appl. No. 16/588,950, dated Jul. 29, 2020, 2 pages.
Supplemental Notice of Allowance received for U.S. Appl. No. 16/588,950, dated Jun. 18, 2020, 2 pages.
"Suunto Spartan Trainer Wrist HR 1.12", Online Available at :—https://web.archive.org/web/20180127155200/https://ns.suunto.com/Manuals/Spartan_Trainer_WristHR/Userguides/Suunto_Spartan_Trainer_WristHR_UserGuide_EN.pdf, Jan. 17, 2018, 47 pages.
Suunto, "Suunto Spartan—Heart Rate Zones", Online Available at :—https://www.youtube.com/watch?v=aixfoCnS0OU, Mar. 19, 2018, 2 page.
Teunmo, "Data field: Visual Pace Alarm", Garmin Forum; Available online at: https://forums.garmin.com/forum/developers/connect-iq/connect-iq-showcase/115996-data-field-visual-pace-alarm, Nov. 17, 2015, 10 pages.
TomTom, "TomTom Runner & Multi-Sport Reference Guide", Online available at :—https://web.archive.org/web/20150908075934/http://download.tomtom.com/open/manuals/Runner_Multi-Sport/refman/TomTom-Runner-Multi-Sport-RG-en-gb.pdf, Sep. 8, 2015, 44 pages.
"Utilization of Galaxy S4—S Health", ChatOn and Samsung Hub, Available at: http://seeit.kr/1263, Jun. 12, 2013, 25 pages (Official Copy only). {See Communication under 37 CFR § 1.98(a) (3)}.
"Visual Pace Alarm app", Available Online at: https://apps.garmin.com/en-US/apps/3940f3a2-4847-4078-a911-d77422966c82, Oct. 19, 2016, 1 page.
Wesley, "Apple Watch Series 1", online available at:—http://toolbox.info/blog/archives/1737-unknown.html, May 28, 2015, 5 pages (Official copy only). {See Communication under 37 CFR § 1.98(a) (3)}.
Youtube, "Apple Watch Series 3", Online available at:—https://www.youtube.com/watch?v=iBPr9gEfkK8, Nov. 21, 2017, 15 pages (Official copy only). {See Communication under 37 CFR § 1.98(a) (3)}.
Zlelik, "Garmin Fenix Open Water Swimming Activity Demo", Online Available at :—https://www.youtube.com/watch?v=iSVhdvw2dcs, Jun. 9, 2017, 1 page.
Applicant-Initiated Interview Summary received for U.S. Appl. No. 16/880,552, dated Oct. 20, 2020, 6 pages.
Chatrzarrin Hanieh, "Feature Extraction for the Differentiation of Dry and Wet Cough Sounds", Carleton University, Sep. 2011, 144 pages.
Haslam Oliver, "Stop Coronavirus in its Tracks by Using This Apple Watch App to Time Hand Washes", Available Online at: https://www.imore.com/stop-coronavirus-its-tracks-using-apple-watch-app-time-hand-washes, Mar. 12, 2020, 12 pages.
Invitation to Pay Additional Fees received for PCT Patent Application No. PCT/US2020/035474, dated Oct. 2, 2020, 11 pages.
Liaqat et al., "Challenges with Real-World Smartwatch based Audio Monitoring", WearSys'18, Munich, Germany, Available Online at: https://doi.org/10.1145/3211960.3211977, Jun. 10, 2018, 6 pages.
Lyles Taylor, "Wear OS Smartwatches are Now Sending Reminders to Wash Your Hands", Available Online at: https://www.theverge.com/2020/4/14/21221294/google-wear-os-smartwatches-reminders-wash-your-hands, Apr. 14, 2020, 2 pages.
Non-Final Office Action received for U.S. Appl. No. 16/894,309, dated Oct. 15, 2020, 24 pages.
Peters Jay, "Samsung's Smartwatches Get a Hand-Washing Reminder and Timer App", Available Online at: https://www.theverge.eom/2020/4/17/21225205/samsung-smartwatch-galaxy-active-hand-washing-timer-reminder-app, Apr. 17, 2020, 2 pages.
Result of Consultation received for European Patent Application No. 19721883.7, dated Oct. 7, 2020, 3 pages.
Schoon Ben, "Wear OS Now Sends a Reminder to Wash Your Hands Every Few Hours", Available Online at: https://9to5google.com/2020/04/14/wear-os-wash-hands-reminder-coronavirus/, Apr. 14, 2020, 7 pages.
Non-Final Office Action received for U.S. Appl. No. 16/586,154, dated Dec. 28, 2020, 26 pages.
Notice of Allowance received for Japanese Patent Application No. 2020-104679, dated Jan. 4, 2021, 4 pages (1 page of English Translation and 3 pages of Official Copy).
European Search Report received for European Patent Application No. 20182116.2, dated Oct. 21, 2020, 4 pages.
Office Action received for Japanese Patent Application No. 2020-104679, dated Sep. 18, 2020, 13 pages (7 pages of English Translation and 6 pages of Official Copy).
Summons to Attend Oral Proceedings received for European Patent Application No. 19726205.8, dated Oct. 29, 2020, 13 pages.
Applicant-Initiated Interview Summary received for U.S. Appl. No. 16/586,154, dated Dec. 11, 2020, 5 pages.
Board Decision received for Chinese Patent Application No. 201380081349.6, dated Nov. 23, 2020, 2 pages (1 page of English Translation and 1 page of Official Copy).
Non-Final Office Action received for U.S. Appl. No. 16/820,383, dated Dec. 14, 2020, 11 pages.
Non-Final Office Action received for U.S. Appl. No. 17/031,704, dated Dec. 10, 2020, 30 pages.
Applicant Initiated Interview Summary received for U.S. Appl. No. 16/894,309, dated Jan. 26, 2021, 3 pages.
Extended European Search Report received for European Patent Application No. 20203526.7, dated Jan. 29, 2021, 13 pages.
International Search Report and Written Opinion received for PCT Patent Application No. PCT/US2020/042439, dated Oct. 9, 2020, 14 pages.
Lovejoy Ben, "Apple Watch blood sugar measurement coming in Series 7, claims report", Available Online at: https://9to5mac.com/2021/01/25/apple-watch-blood-sugar-measurement/, Jan. 25, 2021, 6 pages.
Office Action received for Japanese Patent Application No. 2020-000492, dated Dec. 11, 2020, 6 pages (3 pages English Translation and 3 pages of Official Copy).
Supplemental Notice of Allowance received for U.S. Appl. No. 17/031,727, dated Jan. 15, 2021, 2 pages.
Bagala et al., "Evaluation of Accelerometer-Based Fall Detection Algorithms on Real-World Falls", PLoS One, vol. 7, No. 5, May 16, 2012, 9 pages.
Non-Final Office Action received for U.S. Appl. No. 16/144,030, dated Nov. 5, 2020, 5 pages.
Office Action received for Australian Patent Application No. 2019234289, dated Nov. 2, 2020, 6 pages.
Office Action received for Australian Patent Application No. 2020230340, dated Nov. 2, 2020, 5 pages.
Office Action received for European Patent Application No. 20182116.2, dated Nov. 6, 2020, 9 pages.

(56) References Cited

OTHER PUBLICATIONS

Office Action received for Korean Patent Application No. 10-2019-7025781, dated Oct. 30, 2020, 10 pages (4 pages of English Translation and 6 pages of Official Copy).
Applicant-Initiated Interview Summary received for U.S. Appl. No. 16/138,809, dated Dec. 16, 2020, 7 pages.
Applicant-Initiated Interview Summary received for U.S. Appl. No. 16/880,552, dated Dec. 16, 2020, 6 pages.
Applicant-Initiated Interview Summary received for U.S. Appl. No. 16/907,261, dated Dec. 16, 2020, 6 pages.
Corrected Notice of Allowance received for U.S. Appl. No. 16/880,552, dated Dec. 23, 2020, 2 pages.
Notice of Allowance received for U.S. Appl. No. 17/031,727, dated Dec. 24, 2020, 12 pages.
Search Report and Opinion received for Danish Patent Application No. PA202070620, dated Dec. 11, 2020, 9 pages.
Applicant Initiated Interview Summary received for U.S. Appl. No. 16/586,154, dated Mar. 11, 2020, 4 pages.
Final Office Action received for U.S. Appl. No. 16/586,154, dated Jul. 6, 2020, 27 pages.
International Preliminary Report on Patentability received for PCT Patent Application No. PCT/US2019/024570, dated Nov. 19, 2020, 10 pages.
International Search Report and Written Opinion received for PCT Patent Application No. PCT/US2020/035462, dated Sep. 11, 2020, 17 pages.
International Search Report and Written Opinion received for PCT Patent Application No. PCT/US2020/035474, dated Nov. 26, 2020, 16 pages.
Invitation to Pay Additional Fees and Partial International Search Report received for PCT Patent Application No. PCT/US2020/035164, dated Oct. 16, 2020, 14 pages.
Non-Final Office Action received for U.S. Appl. No. 16/586,154, dated Dec. 9, 2019, 23 pages.
Non-Final Office Action received for U.S. Appl. No. 16/880,714, dated Oct. 28, 2020, 11 pages.
Notice of Allowance received for U.S. Appl. No. 16/880,552, dated Dec. 1, 2020, 7 pages.
Search Report and Opinion received for Danish Patent Application No. PA202070335, dated Nov. 27, 2020, 10 pages.
Search Report and Opinion received for Danish Patent Application No. PA202070395, dated Nov. 24, 2020, 10 pages.
Search Report and Opinion received for Danish Patent Application No. PA202070619, dated Dec. 2, 2020, 11 pages.
Gupta Rajat, "Disable High Volume Warning (no root) in Samsung S7, S8 / Android 7.0", Online available at: https://www.youtube.com/watch?v=9fKwRBtk-x8, Aug. 6, 2017, 1 page.
Kalyani Tech.,"I See Some problems in Honor Band 5", Retrieved from: https://www.youtube.com/watch?v=5XPnYJFqajl, May 19, 2020, 1 page.
Smartwatch Ticks,"SENBONO S10 IP67 Waterproof Multi-Function Blood Pressure Sports Smartwatch: One Minute Overview", Retrieved from: https://www.youtube.com/watch?v=rMxLJvKIVBs, Oct. 30, 2019, 1 page.
Applicant-Initiated Interview Summary received for U.S. Appl. No. 16/249,627, dated Jun. 2, 2021, 5 pages.
Corrected Notice of Allowance received for U.S. Appl. No. 16/143,997, dated Jun. 4, 2021, 2 pages.
FAQ|SleepScore, Available Online at: https://www.sleepscore.com/sleepscore-app/faq/, Retrieved on May 26, 2021, 31 pages.
Office Action received for Australian Patent Application No. 2019210192, dated May 25, 2021, 4 pages.
Office Action received for European Patent Application No. 20182116.2, dated May 25, 2021, 9 pages.
Applicant-Initiated Interview Summary received for U.S. Appl. No. 17/031,704, dated Feb. 9, 2021, 3 pages.
Final Office Action received for U.S. Appl. No. 16/143,997, dated Feb. 9, 2021, 16 pages.
Notice of Allowance received for U.S. Appl. No. 16/144,864, dated Feb. 9, 2021, 13 pages.

Office Action received for Korean Patent Application No. 10-2020-7026391, dated Jan. 27, 2021, 5 pages (2 pages of English Translation and 3 pages of Official Copy).
Office Action received for Korean Patent Application No. 10-2020-7026453, dated Jan. 27, 2021, 5 pages (2 pages of English Translation and 3 pages of Official Copy).
Notice of Allowance received for U.S. Appl. No. 16/880,714, dated Jun. 9, 2021, 6 pages.
Office Action received for Australian Patent Application No. 2020256383, dated Jun. 4, 2021, 3 pages.
Office Action received for Danish Patent Application No. PA202070335, dated Jun. 11, 2021, 4 pages.
Office Action received for European Patent Application No. 19721883.7, dated Jun. 15, 2021, 9 pages.
Applicant-Initiated Interview Summary received for U.S. Appl. No. 16/894,309, dated Jun. 25, 2021, 4 pages.
Applicant-Initiated Interview Summary received for U.S. Appl. No. 17/031,704, dated Jun. 25, 2021, 3 pages.
Corrected Notice of Allowance received for U.S. Appl. No. 16/143,997, dated Jul. 2, 2021, 2 pages.
Corrected Notice of Allowance received for U.S. Appl. No. 16/880,552, dated Jul. 7, 2021, 2 pages.
Notice of Allowance received for U.S. Appl. No. 17/031,727, dated Jun. 25, 2021, 6 pages.
Office Action received for Australian Patent Application No. 2020230340, dated May 27, 2021, 5 pages.
Office Action received for Chinese Patent Application No. 202010606407.4, dated Jun. 2, 2021, 12 pages (5 pages of English Translation and 7 pages of Official Copy).
Office Action received for Chinese Patent Application No. 202011220489.5, dated Jun. 1, 2021, 12 pages (6 pages of English Translation and 6 pages of Official Copy).
Office Action received for Japanese Patent Application No. 2020-153166, dated May 31, 2021, 6 pages (3 pages of English Translation and 3 pages of Official Copy).
Applicant-Initiated Interview Summary received for U.S. Appl. No. 16/143,997, dated May 3, 2021, 4 pages.
Applicant-Initiated Interview Summary received for U.S. Appl. No. 16/586,154, dated Apr. 14, 2021, 4 pages.
Applicant-Initiated Interview Summary received for U.S. Appl. No. 16/820,383, dated Mar. 11, 2021, 2 pages.
Applicant-Initiated Interview Summary received for U.S. Appl. No. 16/880,552, dated Apr. 21, 2021, 3 pages.
Applicant-Initiated Interview Summary received for U.S. Appl. No. 16/880,714, dated Feb. 26, 2021, 5 pages.
Applicant-Initiated Interview Summary received for U.S. Appl. No. 16/907,261, dated Mar. 25, 2021, 2 pages.
Cook, James, "German Period Tracking App Clue Has Over 2.5 Million Active Users—But It's Still Not Sure How It's Going to Make Money", Available online at: https://www.businessinsider.in/tech/german-period-tracking-app-clue-has-over-2-5-million-active-users-but-its-still-not-sure-how-its-going-to-make-money/articleshow/50511307.cms, Jan. 9, 2016, 9 pages.
Decision on Appeal received for Korean Patent Application No. 10-2019-7025538, dated Feb. 24, 2021, 20 pages (4 pages of English Translation and 16 pages of Official Copy).
Final Office Action received for U.S. Appl. No. 16/586,154, dated May 24, 2021, 29 pages.
Final Office Action received for U.S. Appl. No. 16/894,309, dated Feb. 24, 2021, 30 pages.
Final Office Action received for U.S. Appl. No. 16/907,261, dated Mar. 18, 2021, 20 pages.
Final Office Action received for U.S. Appl. No. 17/031,704, dated Apr. 1, 2021, 31 pages.
International Search Report and Written Opinion received for PCT Patent Application No. PCT/US2020/035164, dated Feb. 8, 2021, 26 pages.
International Search Report and Written Opinion received for PCT Patent Application No. PCT/US2020/070280, dated Nov. 30, 2020, 20 pages.
Invitation to Pay Additional Fees received for PCT Patent Application No. PCT/US2020/070280, dated Oct. 7, 2020, 12 pages.

(56) References Cited

OTHER PUBLICATIONS

Non-Final Office Action received for U.S. Appl. No. 16/249,627, dated Mar. 11, 2021, 21 pages.
Non-Final Office Action received for U.S. Appl. No. 16/880,552, dated Feb. 19, 2021, 11 pages.
Non-Final Office Action received for U.S. Appl. No. 16/990,846, dated May 10, 2021, 16 pages.
Notice of Allowance received for Japanese Patent Application No. 2019-162293, dated Apr. 9, 2021, 4 pages (1 page of English Translation and 3 pages of Official Copy).
Notice of Allowance received for Korean Patent Application No. 10-2019-7025538, dated Mar. 10, 2021, 5 pages (2 pages of English Translation and 3 pages of Official Copy).
Notice of Allowance received for Korean Patent Application No. 10-2020-7026391, dated May 11, 2021, 3 pages (1 page of English Translation and 2 pages of Official Copy).
Notice of Allowance received for Korean Patent Application No. 10-2020-7026453, dated May 11, 2021, 3 pages (1 page of English Translation and 2 pages of Official Copy).
Notice of Allowance received for U.S. Appl. No. 16/138,809, dated Apr. 16, 2021, 11 pages.
Notice of Allowance received for U.S. Appl. No. 16/143,997, dated May 13, 2021, 10 pages.
Notice of Allowance received for U.S. Appl. No. 16/144,030, dated Apr. 5, 2021, 8 pages.
Notice of Allowance received for U.S. Appl. No. 16/144,864, dated Mar. 12, 2021, 2 pages.
Notice of Allowance received for U.S. Appl. No. 16/144,864, dated Mar. 30, 2021, 2 pages.
Notice of Allowance received for U.S. Appl. No. 16/820,383, dated Mar. 31, 2021, 11 pages.
Notice of Allowance received for U.S. Appl. No. 16/880,552, dated May 12, 2021, 7 pages.
Notice of Allowance received for U.S. Appl. No. 16/880,714, dated Mar. 19, 2021, 7 pages.
Notice of Allowance received for U.S. Appl. No. 17/031,727, dated Mar. 12, 2021, 7 pages.
Office Action received for Australian Patent Application No. 2019234289, dated Mar. 16, 2021, 8 pages.
Office Action received for Australian Patent Application No. 2020230340, dated Mar. 2, 2021, 6 pages.
Office Action received for Chinese Patent Application No. 201380081349.6, dated Jan. 5, 2021, 16 pages (7 pages of English Translation and 9 pages of Official Copy).
Office Action received for Chinese Patent Application No. 202010606407.4, dated Jan. 27, 2021, 16 pages (7 pages of English Translation and 9 pages of Official Copy).
Office Action received for Chinese Patent Application No. 202010618240.3, dated Mar. 29, 2021, 21 pages (11 pages of English Translation and 10 pages of Official Copy).
Office Action received for Chinese Patent Application No. 202010618569.X, dated Mar. 12, 2021, 14 pages (7 pages of English Translation and 7 pages of Official Copy).
Office Action received for Danish Patent Application No. PA201970534, dated Feb. 16, 2021, 2 pages.
Office Action received for Danish Patent Application No. PA202070620, dated May 10, 2021, 5 pages.
Office Action received for European Patent Application No. 20180581.9, dated Apr. 1, 2021, 11 pages.
Office Action received for European Patent Application No. 20180592.6, dated Apr. 1, 2021, 11 pages.
Office Action received for Japanese Patent Application No. 2018-184532, dated Mar. 1, 2021, 11 pages (6 pages of English Translation and 5 pages of Official Copy).
Office Action received for Japanese Patent Application No. 2020-547369, dated Apr. 9, 2021, 4 pages (2 pages of English Translation and 2 pages of Official Copy).
Office Action received for Korean Patent Application No. 10-2020-7026035, dated Feb. 19, 2021, 13 pages (6 pages of English Translation and 7 pages of Official Copy).
Result of Consultation received for European Patent Application No. 19726205.8, dated Mar. 15, 2021, 19 pages.
Search Report and Opinion received for Danish Patent Application No. PA202070815, dated Mar. 16, 2021, 8 pages.
Corrected Notice of Allowance received for U.S. Appl. No. 16/820,383, dated Aug. 13, 2021, 2 pages.
Corrected Notice of Allowance received for U.S. Appl. No. 16/820,383, dated Aug. 19, 2021, 2 pages.
Notice of Acceptance received for Australian Patent Application No. 2020256383, dated Aug. 3, 2021, 3 pages.
Notice of Allowance received for U.S. Appl. No. 16/907,261, dated Aug. 13, 2021, 8 pages.
Summons to Attend Oral Proceedings received for European Patent Application No. 20180581.9, dated Aug. 18, 2021, 15 pages.
Summons to Attend Oral Proceedings received for European Patent Application No. 20180592.6, dated Aug. 11, 2021, 16 pages.
Applicant-Initiated Interview Summary received for U.S. Appl. No. 16/907,261, dated Jul. 16, 2021, 10 pages.
Notice of Allowance received for Korean Patent Application No. 10-2019-7025781, dated Jun. 29, 2021, 5 pages (2 pages of English Translation and 3 pages of Official Copy).
Notice of Allowance received for U.S. Appl. No. 16/138,809, dated Jul. 20, 2021, 6 pages.
Notice of Allowance received for U.S. Appl. No. 16/820,383, dated Jul. 21, 2021, 11 pages.
Notice of Allowance received for U.S. Appl. No. 17/031,704, dated Jul. 21, 2021, 10 pages.
Office Action received for Chinese Patent Application No. 201380081349.6, dated Jun. 2, 2021, 17 pages (8 pages of English Translation and 9 pages of Official Copy).
Office Action received for Chinese Patent Application No. 201910858933.7, dated Jun. 29, 2021, 8 pages (3 pages of English Translation and 5 pages of Official Copy).
Non-Final Office Action received for U.S. Appl. No. 16/994,352, dated Jul. 30, 2021, 11 pages.
Notice of Allowance received for Japanese Patent Application No. 2020-000492, dated Jul. 16, 2021, 4 pages (1 page of English Translation and 3 pages of Official Copy).
Notice of Allowance received for Japanese Patent Application No. 2020-547369, dated Jul. 16, 2021, 4 pages (1 page of English Translation and 3 pages of Official Copy).
Notice of Allowance received for U.S. Appl. No. 16/880,552, dated Jul. 23, 2021, 5 pages.
Office Action received for Australian Patent Application No. 2019234289, dated Jul. 20, 2021, 4 pages.
Office Action received for Australian Patent Application No. 2020239692, dated Jul. 20, 2021, 5 pages.
Office Action received for Australian Patent Application No. 2020239740, dated Jul. 9, 2021, 4 pages.
Applicant-Initiated Interview Summary received for U.S. Appl. No. 15/978,126, dated Jan. 19, 2021, 4 pages.
Applicant-Initiated Interview Summary received for U.S. Appl. No. 15/978,126, dated Jul. 1, 2020, 6 pages.
Applicant-Initiated Interview Summary received for U.S. Appl. No. 16/249,627, dated Oct. 6, 2021, 4 pages.
Corrected Notice of Allowance received for U.S. Appl. No. 16/820,383, dated Oct. 5, 2021, 2 pages.
Final Office Action received for U.S. Appl. No. 15/978,126, dated Sep. 30, 2020, 23 pages.
International Preliminary Report on Patentability received for PCT Patent Application No. PCT/US2018/023303, dated Dec. 12, 2019, 8 pages.
International Search Report and Written Opinion received for PCT Patent Application No. PCT/US2018/023303, dated Jun. 19, 2018, 10 pages.
Non-Final Office Action received for U.S. Appl. No. 15/978,126, dated Mar. 26, 2020, 16 pages.
Notice of Allowance received for U.S. Appl. No. 15/978,126, dated Feb. 4, 2021, 10 pages.
Notice of Allowance received for U.S. Appl. No. 16/143,997, dated Sep. 30, 2021, 8 pages.
Office Action received for Australian Patent Application No. 2020239740, dated Sep. 28, 2021, 5 pages.

(56) References Cited

OTHER PUBLICATIONS

Applicant-Initiated Interview Summary received for U.S. Appl. No. 16/586,154, dated Sep. 3, 2021, 4 pages.
Non-Final Office Action received for U.S. Appl. No. 16/249,627, dated Aug. 31, 2021, 18 pages.
Notice of Allowance received for Korean Patent Application No. 10-2020-7026035, dated Aug. 23, 2021, 4 pages (2 pages of English Translation and 2 pages of Official Copy).
Notice of Allowance received for U.S. Appl. No. 16/921,312, dated Sep. 14, 2021, 9 pages.
Office Action received for Danish Patent Application No. PA202070619, dated Aug. 27, 2021, 12 pages.
Office Action received for Korean Patent Application No. 10-2021-7026284, dated Aug. 31, 2021, 10 pages (4 pages of English Translation and 6 pages of Official Copy).
Brief Communication Regarding Oral Proceedings received for European Patent Application No. 20180581.9, dated Nov. 30, 2021, 1 page.
Corrected Notice of Allowance received for U.S. Appl. No. 16/880,552, dated Dec. 22, 2021, 2 pages.
Corrected Notice of Allowance received for U.S. Appl. No. 16/921,312, dated Dec. 7, 2021, 2 pages.
Final Office Action received for U.S. Appl. No. 16/994,352, dated Dec. 6, 2021, 14 pages.
International Preliminary Report on Patentability received for PCT Patent Application No. PCT/US2020/035164, dated Dec. 16, 2021, 19 pages.
International Preliminary Report on Patentability received for PCT Patent Application No. PCT/US2020/035462, dated Dec. 16, 2021, 16 pages.
International Preliminary Report on Patentability received for PCT Patent Application No. PCT/US2020/025768, dated Dec. 16, 2021, 8 pages.
International Preliminary Report on Patentability received for PCT Patent Application No. PCT/US2020/035474, dated Dec. 16, 2021, 11 pages.
Notice of Acceptance received for Australian Patent Application No. 2019210192, dated Dec. 2, 2021, 3 pages.
Office Action received for Danish Patent Application No. PA202070395, dated Dec. 15, 2021, 5 pages.
Office Action received for Indian Patent Application No. 202014041484, dated Dec. 8, 2021, 8 pages.
Corrected Notice of Allowance received for U.S. Appl. No. 16/921,312, dated Sep. 24, 2021, 2 pages.
Notice of Allowance received for Japanese Patent Application No. 2020-153166, dated Sep. 13, 2021, 4 pages (1 page of English Translation and 3 pages of Official Copy).
Notice of Allowance received for U.S. Appl. No. 16/907,261, dated Sep. 28, 2021, 6 pages.
Notice of Allowance received for U.S. Appl. No. 16/990,846, dated Sep. 22, 2021, 9 pages.
Office Action received for Australian Patent Application No. 2019210192, dated Sep. 9, 2021, 4 pages.
Office Action received for Chinese Patent Application No. 202010618569.X, dated Sep. 7, 2021, 7 pages (4 pages of English Translation and 3 pages of Official Copy).
Supplemental Notice of Allowance received for U.S. Appl. No. 16/880,714, dated Sep. 16, 2021, 2 pages.
Non-Final Office Action received for U.S. Appl. No. 16/820,383, dated Jan. 10, 2022, 18 pages.
Notice of Acceptance received for Australian Patent Application No. 2020288147, dated Dec. 22, 2021, 3 pages.
Notice of Allowance received for Chinese Patent Application No. 202010618569.X, dated Jan. 7, 2022, 2 pages (1 page of English Translation and 1 page of Official Copy).
Office Action received for Chinese Patent Application No. 202011220489.5, dated Dec. 1, 2021, 19 pages (11 pages of English Translation and 8 pages of Official Copy).
Office Action received for Japanese Patent Application No. 2020-551585, dated Jan. 6, 2022, 11 pages (5 pages of English Translation and 6 pages of Official Copy).
Brief Communication Regarding Oral Proceedings received for European Patent Application No. 20180581.9, dated Jan. 26, 2022, 1 page.
Brief Communication regarding Oral Proceedings received for European Patent Application No. 20180592.6, dated Jan. 26, 2022, 2 pages.
Intention to Grant received for Danish Patent Application No. PA202070619, dated Jan. 17, 2022, 2 pages.
International Preliminary Report on Patentability received for PCT Patent Application No. PCT/US2020/042439, dated Jan. 27, 2022, 10 pages.
Non-Final Office Action received for U.S. Appl. No. 17/031,723, dated Jan. 24, 2022, 17 pages.
Notice of Allowance received for Chinese Patent Application No. 202010606407.4, dated Jan. 24, 2022, 2 pages (1 page of English Translation and 1 page of Official Copy).
Notice of Allowance received for Japanese Patent Application No. 2018-184532, dated Jan. 17, 2022, 4 pages (1 page of English Translation and 3 pages of Official Copy).
Notice of Allowance received for Korean Patent Application No. 10-2021-7042504, dated Jan. 17, 2022, 6 pages (1 page of English Translation and 5 pages of Official Copy).
Notice of Allowance received for U.S. Appl. No. 16/990,846, dated Jan. 20, 2022, 6 pages.
Office Action received for Japanese Patent Application No. 2020-160023, dated Jan. 17, 2022, 11 pages (6 pages of English Translation and 5 pages of Official Copy).
Result of Consultation received for European Patent Application No. 20180581.9, dated Jan. 21, 2022, 14 pages.
Result of Consultation received for European Patent Application No. 20180592.6, dated Jan. 26, 2022, 18 pages.
Supplemental Notice of Allowance received for U.S. Appl. No. 16/894,309, dated Jan. 25, 2022, 2 pages.
Corrected Notice of Allowance received for U.S. Appl. No. 16/143,997, dated Nov. 16, 2021, 2 pages.
International Preliminary Report on Patentability received for PCT Patent Application No. PCT/US2020/025997, dated Nov. 18, 2021, 10 pages.
International Search Report and Written Opinion received for PCT Patent Application No. PCT/US2021/035504, dated Sep. 16, 2021, 12 pages.
Notice of Allowance received for U.S. Appl. No. 16/880,552, dated Nov. 24, 2021, 5 pages.
Notice of Allowance received for U.S. Appl. No. 16/921,312, dated Nov. 29, 2021, 5 pages.
Office Action received for Danish Patent Application No. PA202070335, dated Nov. 17, 2021, 6 pages.
Office Action received for Danish Patent Application No. PA202070620, dated Nov. 19, 2021, 2 pages.
Office Action received for European Patent Application No. 20203526.7, dated Nov. 23, 2021, 9 pages.
Brief Communication regarding Oral Proceedings received for European Patent Application No. 20180592.6, dated Dec. 21, 2021, 1 page.
Notice of Allowance received for Chinese Patent Application No. 201380081349.6, dated Dec. 17, 2021, 2 pages (1 page of English Translation and 1 page of Official Copy).
Notice of Allowance received for Korean Patent Application No. 10-2021-7038005, dated Dec. 14, 2021, 4 pages (2 pages of English Translation and 2 pages of Official Copy).
Office Action received for Chinese Patent Application No. 202010606407.4, dated Nov. 18, 2021, 6 pages (3 pages of English Translation and 3 pages of Official Copy).
Office Action received for Chinese Patent Application No. 202010618240.3, dated Dec. 3, 2021, 23 pages (14 pages of English Translation and 9 pages of Official Copy).
Office Action received for Chinese Patent Application No. 202110363565.6, dated Nov. 16, 2021, 16 pages (9 pages of English Translation and 7 pages of Official Copy).

(56) References Cited

OTHER PUBLICATIONS

Summons to Attend Oral Proceedings received for European Patent Application No. 20182116.2, dated Dec. 21, 2021, 7 pages.
Supplemental Notice of Allowance received for U.S. Appl. No. 16/894,309, dated Dec. 24, 2021, 2 pages.
Applicant Initiated Interview Summary received for U.S. Appl. No. 16/994,352, dated Nov. 2, 2021, 4 pages.
Corrected Notice of Allowance received for U.S. Appl. No. 17/031,704, dated Nov. 2, 2021, 7 pages.
Notice of Allowance received for Japanese Patent Application No. 2020-560883, dated Oct. 29, 2021, 4 pages (1 page of English Translation and 3 pages of Official Copy).
Notice of Allowance received for U.S. Appl. No. 16/894,309, dated Nov. 5, 2021, 12 pages.
Office Action received for Australian Patent Application No. 2019234289, dated Nov. 1, 2021, 4 pages.
Office Action received for European Patent Application No. 20721342.2, dated Nov. 4, 2021, 9 pages.
Corrected Notice of Allowance received for U.S. Appl. No. 16/990,846, dated Feb. 9, 2022, 3 pages.
Final Office Action received for U.S. Appl. No. 16/249,627, dated Feb. 14, 2022, 19 pages.
Non-Final Office Action received for U.S. Appl. No. 17/031,779, dated Feb. 16, 2022, 17 pages.
Office Action received for Australian Patent Application No. 2020239692, dated Jan. 27, 2022, 3 pages.
Office Action received for Korean Patent Application No. 10-2020-7023277, dated Jan. 26, 2022, 11 pages (5 pages of English Translation and 6 pages of Official Copy).
Corrected Notice of Allowance received for U.S. Appl. No. 16/143,997, dated Oct. 21, 2021, 2 pages.
Corrected Notice of Allowance received for U.S. Appl. No. 16/586,154, dated Oct. 27, 2021, 2 pages.
International Search Report and Written Opinion received for PCT Patent Application No. PCT/US2021/035227, dated Oct. 6, 2021, 17 pages.
Notice of Allowance received for U.S. Appl. No. 16/586,154, dated Oct. 15, 2021, 8 pages.
Office Action received for Australian Patent Application No. 2020230340, dated Oct. 11, 2021, 4 pages.
Office Action received for Danish Patent Application No. PA202070619, dated Oct. 14, 2021, 3 pages.
Office Action received for Danish Patent Application No. PA202070815, dated Oct. 18, 2021, 2 pages.
Notice of Acceptance received for Australian Patent application No. 2020239740, dated Feb. 22, 2022., 3 pages.
International Search Report and Written Opinion received for PCT Patent Application No. PCT/US2021/045375, dated Jan. 10, 2022, 21 pages.
Invitation to Pay Additional Fees received for PCT Patent Application No. PCT/US2021/045375, dated Nov. 16, 2021, 12 pages.
International Search Report and Written Opinion received for PCT Patent Application No. PCT/US2021/048568, dated Jan. 7, 2022 14 pages.
Notice of Allowance received for U.S. Appl. No. 16/894,309, dated Feb. 25, 2022, 9 pages.
Notice of Allowance received for U.S. Appl. No. 16/994,352, dated Mar. 2, 2022, 14 pages.

Office Action received for Chinese Patent Application No. 201910858933.7, dated Dec. 30, 2021, 9 pages (4 pages of English Translation and 5 pages of Official Copy).
Notice of Allowance received for Japanese Patent Application No. 2020-160023, dated Apr. 11, 2022, 4 pages (1 page of English Translation and 3 pages of Official Copy).
Applicant-Initiated Interview Summary received for U.S. Appl. No. 16/249,627, dated Mar. 23, 2022, 3 pages.
Applicant-Initiated Interview Summary received for U.S. Appl. No. 16/820,383, dated May 10, 2022, 2 pages.
Applicant-Initiated Interview Summary received for U.S. Appl. No. 17/031,723, dated Mar. 21, 2021, 5 pages.
Applicant-Initiated Interview Summary received for U.S. Appl. No. 17/031,779, dated Mar. 10, 2022, 2 pages.
Brief Communication Regarding Oral Proceedings received for European Patent Application No. 20182116.2, dated Apr. 13, 2022, 3 pages.
Decision to Refuse received for European Patent Application No. 20180581.9, dated Apr. 13, 2022, 16 pages.
"Garmin Edge 520", Owner's Manual, Online available at https://www8.garmin.com/manuals/webhelp/edge520/EN-US/Edge_520_OM_EN-US.pdf, 2015, 24 pages.
Intention to Grant received for European Patent Application No. 20180592.6, dated Apr. 20, 2022, 21 pages.
Intention to Grant received for European Patent Application No. 20182116.2, dated Jun. 2, 2022, 8 pages.
International Preliminary Report on Patentability received for PCT Patent Application No. PCT/US2020/070280, dated Mar. 17, 2022, 15 pages.
Minutes of the Oral Proceedings received for European Patent Application No. 20180581.9, dated Apr. 13, 2022, 10 pages.
Minutes of the Oral Proceedings received for European Patent Application No. 20180592.6, dated Apr. 7, 2022, 10 pages.
Minutes of the Oral Proceedings received for European Patent Application No. 20182116.2, dated May 24, 2022, 7 pages.
Non-Final Office Action received for U.S. Appl. No. 16/851,451, dated May 9, 2022, 26 pages.
Non-Final Office Action received for U.S. Appl. No. 16/888,780, dated Apr. 20, 2022, 22 pages.
Non-Final Office Action received for U.S. Appl. No. 17/041,415, dated Mar. 29, 2022, 11 pages.
Notice of Acceptance received for Australian Patent Application No. 2020239692, dated Apr. 6, 2022, 3 pages.
Notice of Allowance received for Japanese Patent Application No. 2021-571467, dated Apr. 11, 2022, 4 pages (1 page of English Translation and 3 pages of Official Copy).
Notice of Allowance received for Korean Patent Application No. 10-2022-7008569, dated May 19, 2022, 5 pages (2 pages of English Translation and 3 pages of Official Copy).
Notice of Allowance received for U.S. Appl. No. 16/994,352, dated Jun. 3, 2022, 9 pages.
Office Action received for Chinese Patent Application No. 202011220489.5, dated Apr. 25, 2022, 15 pages (9 pages of English Translation and 6 pages of Official Copy).
Summons to Attend Oral Proceedings received for European Patent Application No. 13811085.3, dated Mar. 3, 2022, 3 pages.
Summons to Attend Oral Proceedings received for European Patent Application No. 20721342.2, dated May 20, 2022, 11 pages.
Supplemental Notice of Allowance received for U.S. Appl. No. 16/894,309, dated Apr. 8, 2022, 3 pages.

* cited by examiner

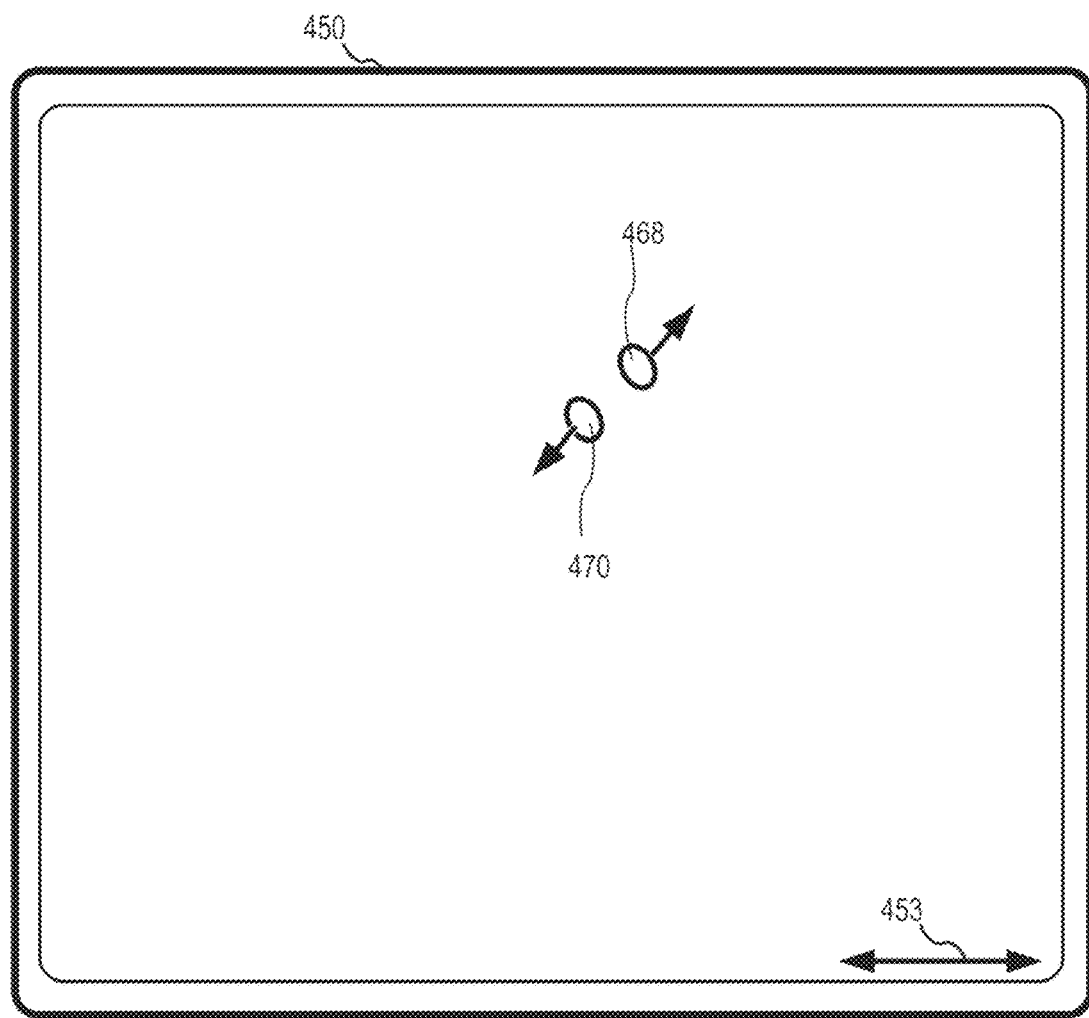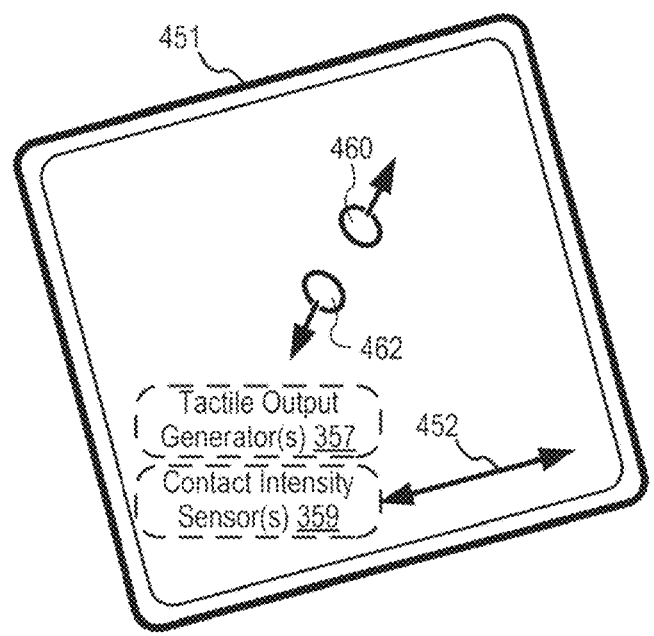
*FIG. 4B*

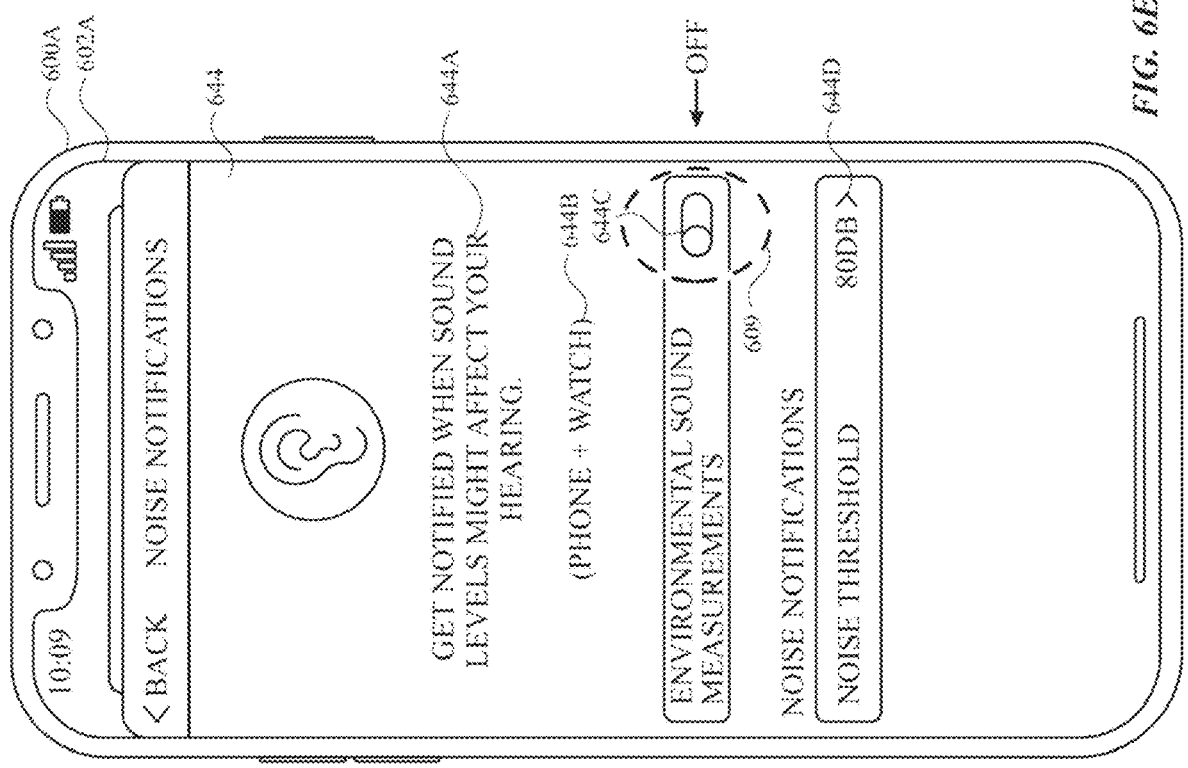

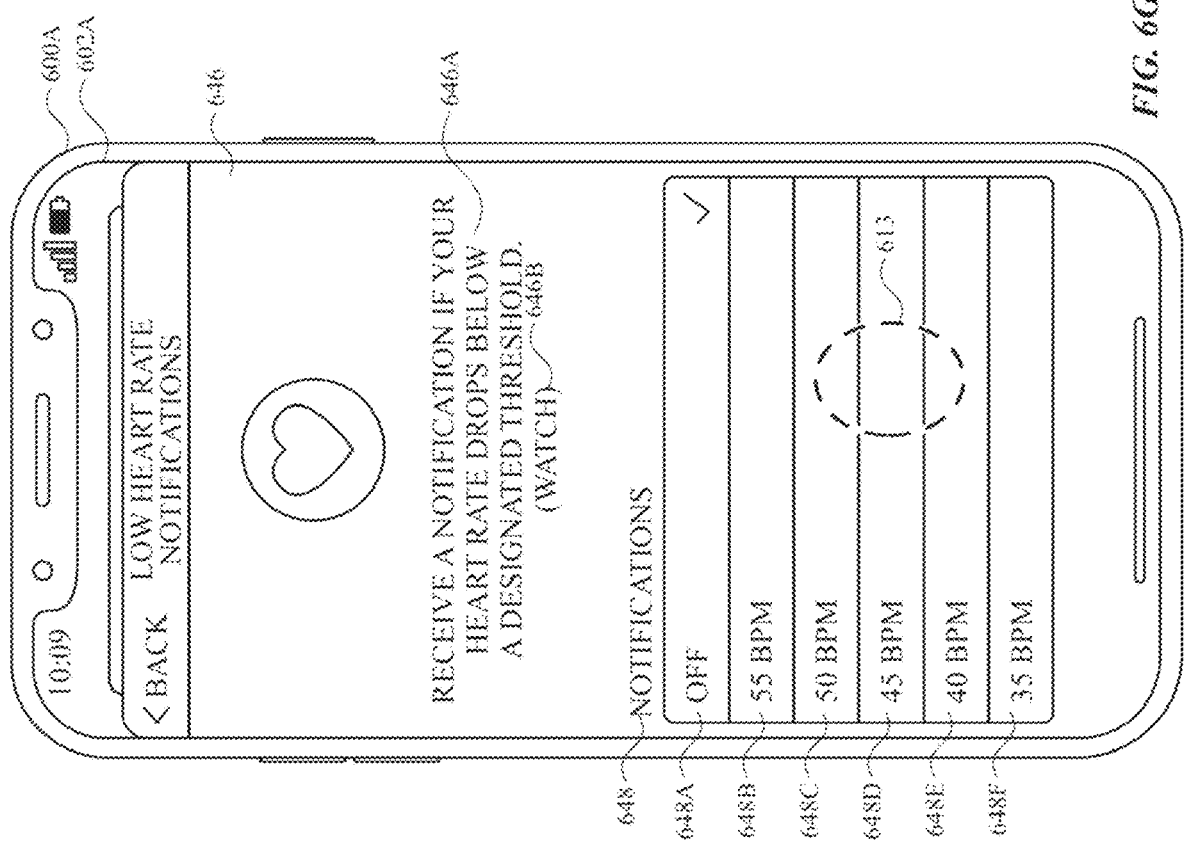

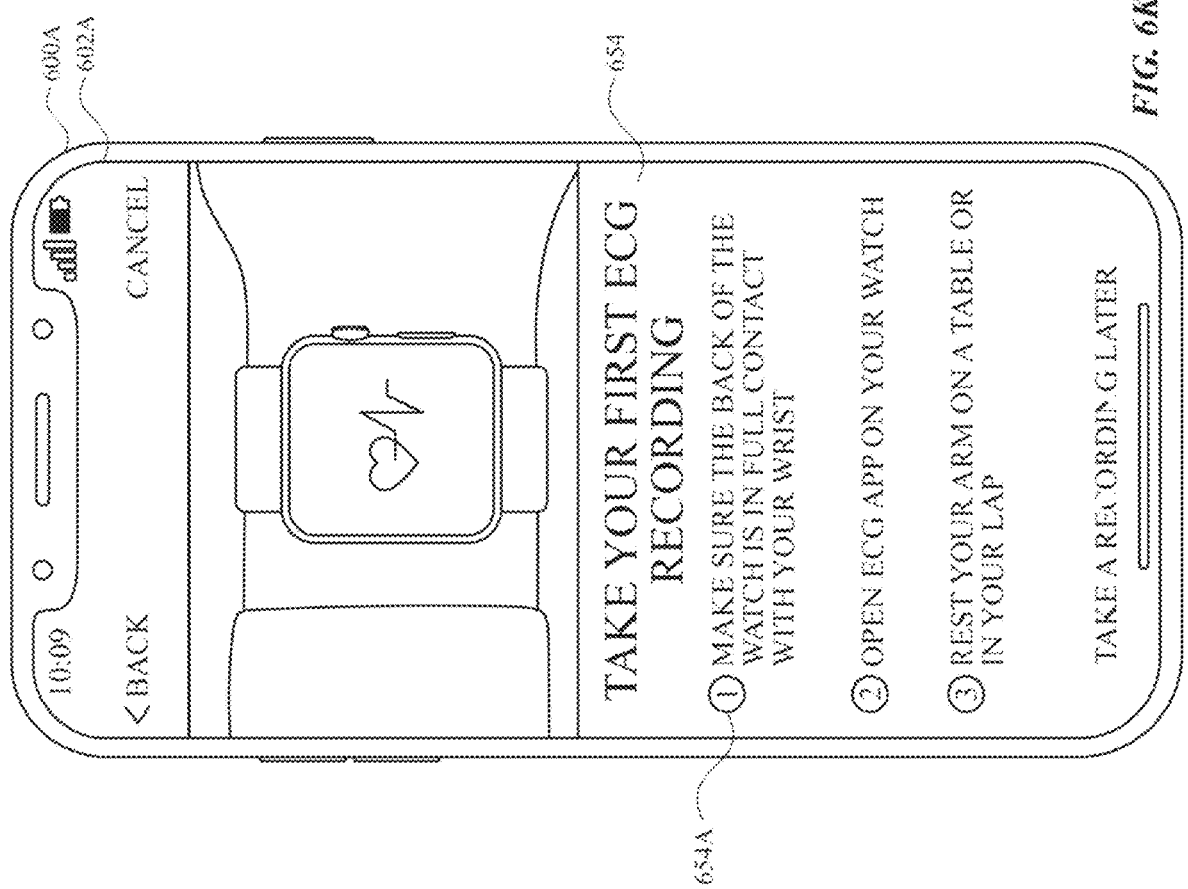

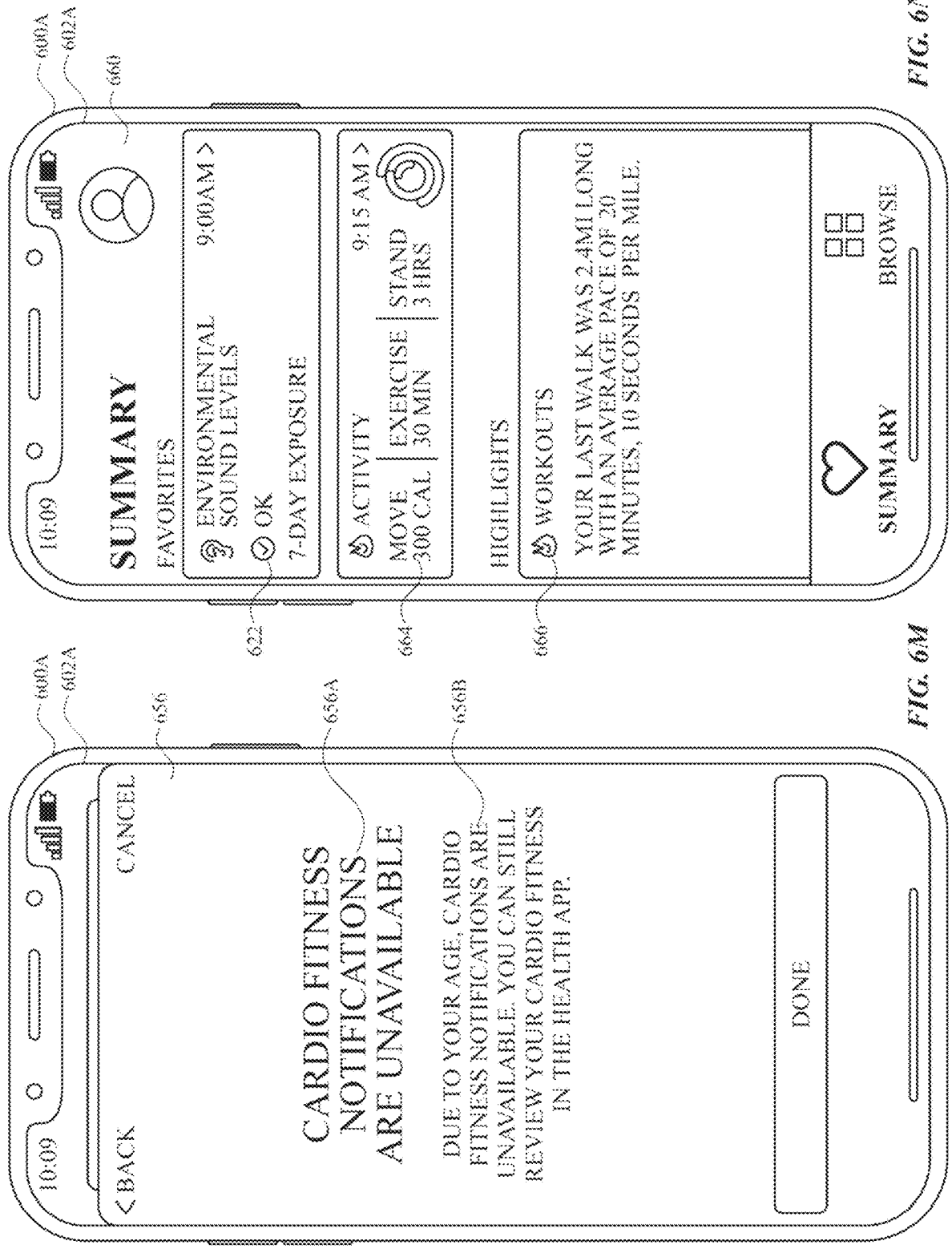

700

702
Display, via the display generation component, a user interface that includes a plurality of user interface objects that corresponds to health-related functions, the plurality of user interface objects including a first user interface object that corresponds to a first health-related function.

704
The first user interface object includes:

706
In accordance with a determination that the first health-related function is currently active, an indication that the first health-related function is active.

708
In accordance with a determination that the first health-related function is currently inactive and available for activation via a set of one or more inputs received at the computer system, an indication that the first health-related function is available for activation.

(A)

710
In accordance with a determination that the first health-related function is currently inactive and not available for activation, an indication that the first health-related function is not available for activation.

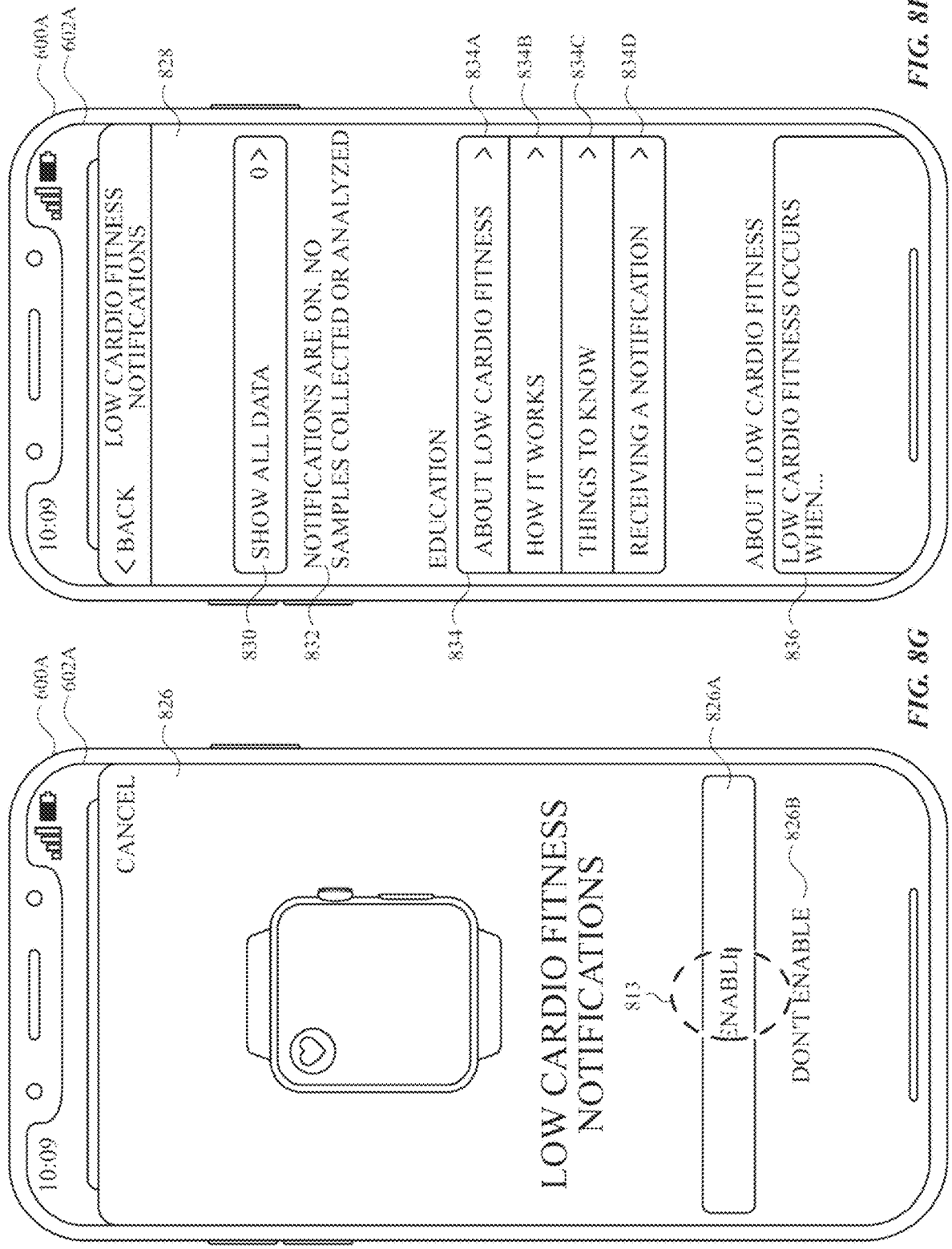

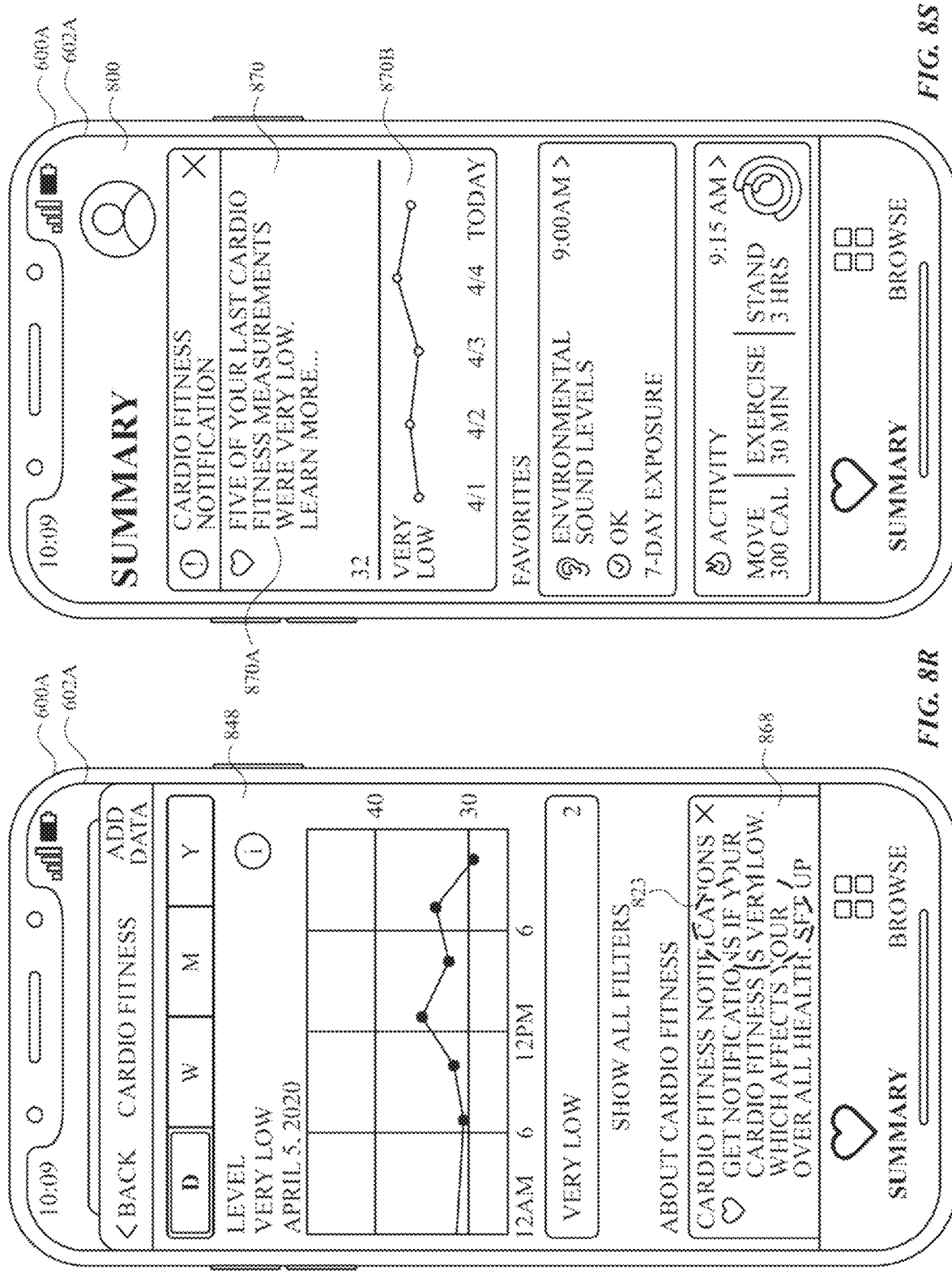

900

902
Display, via the display generation component, a set of one or more user interfaces that corresponds to a first health-related function, wherein the first health-related function is currently inactive.

904
Display the set of one or more user interfaces that correspond to the first health-related function includes:

906
In accordance with a determination that a set of activation-permissibility criteria are satisfied, the set of activation-permissibility criteria including a location-based criterion that is satisfied when a current location of the computer system satisfies a set of location-based criteria, display a first activation user interface of a set of one or more activation user interfaces, the set of one or more activation user interfaces including a first selectable user interface object that, when selected via an input received via the one or more input devices, activates the first health-related function.

(A)

908
In accordance with a determination that the set of activation-permissibility criteria are not satisfied, display a notification interface that includes first information corresponding to the first health-related function and that does not include a selectable user interface object that, when selected via an input received via the one or more input devices, activates the first health related function.

*FIG. 9A*

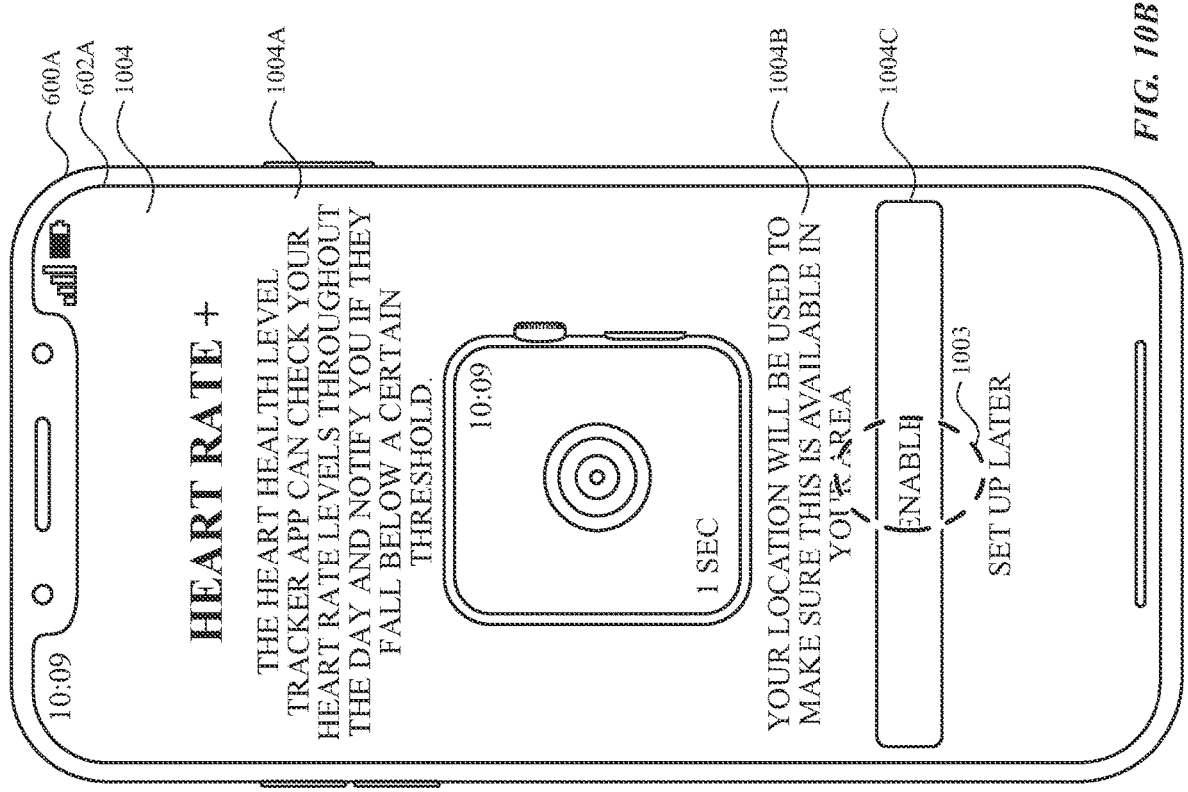
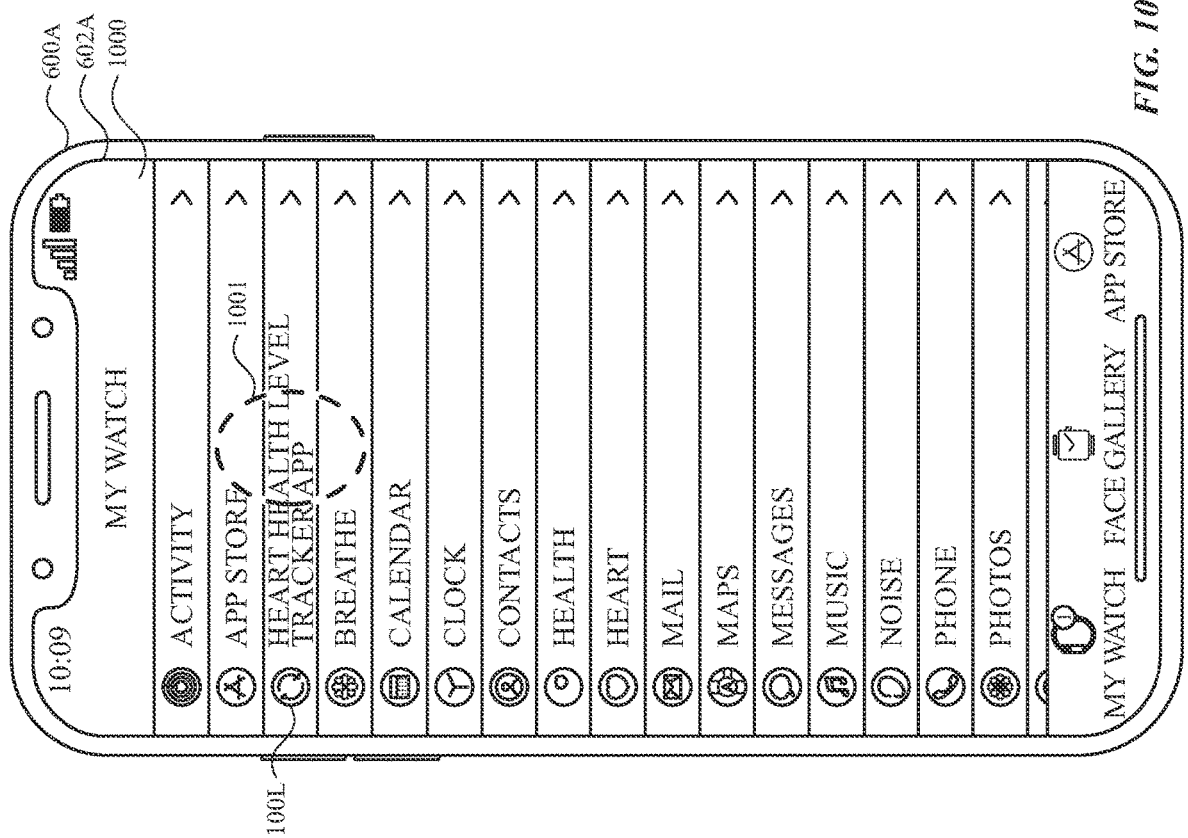

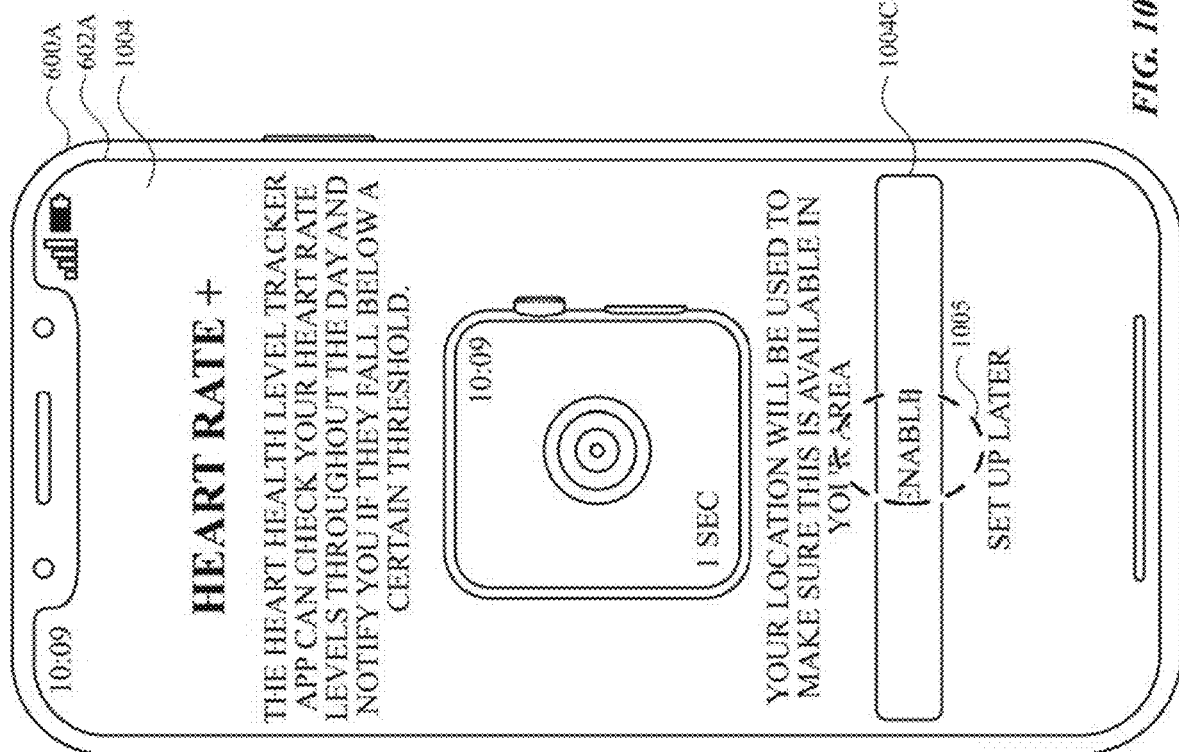
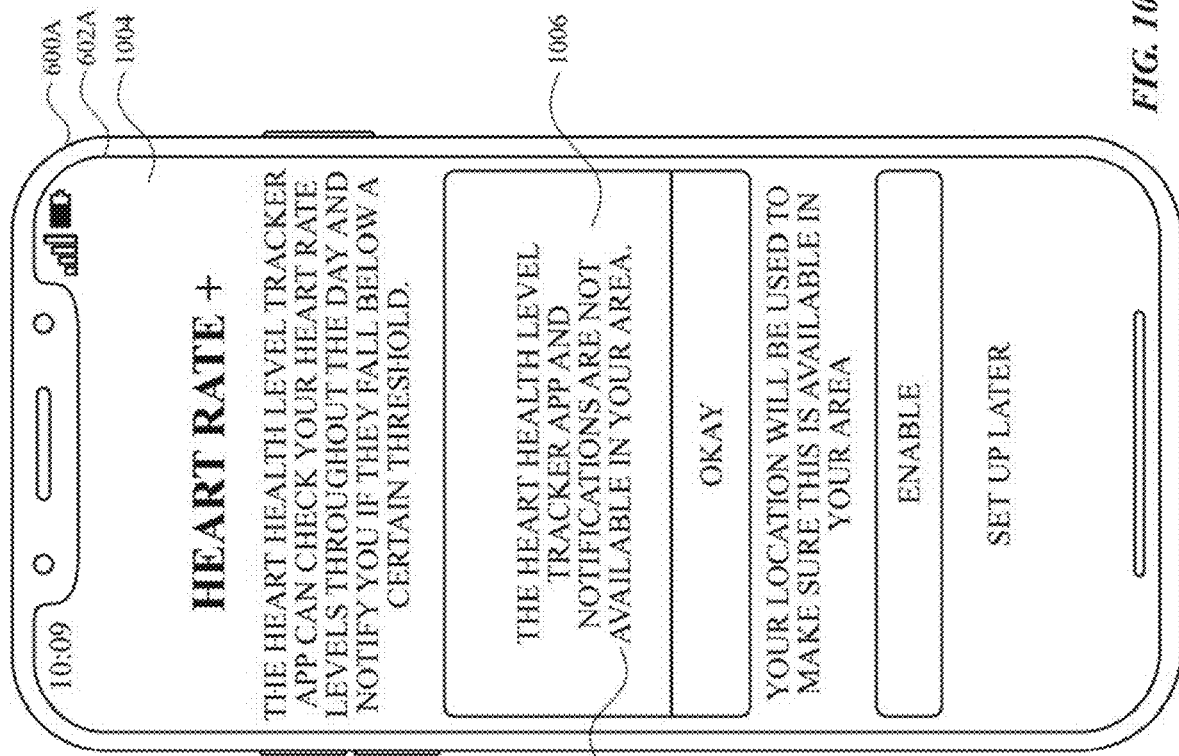

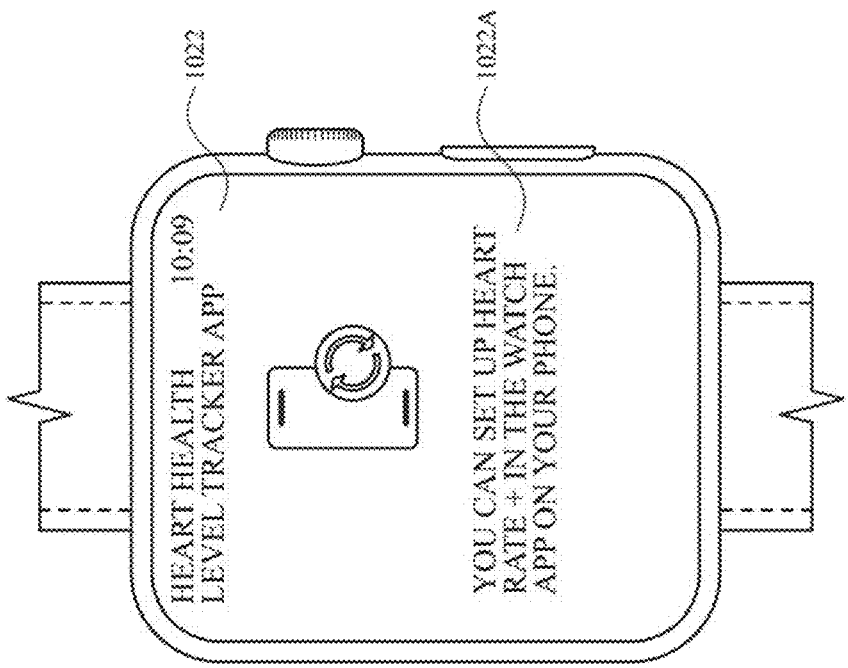
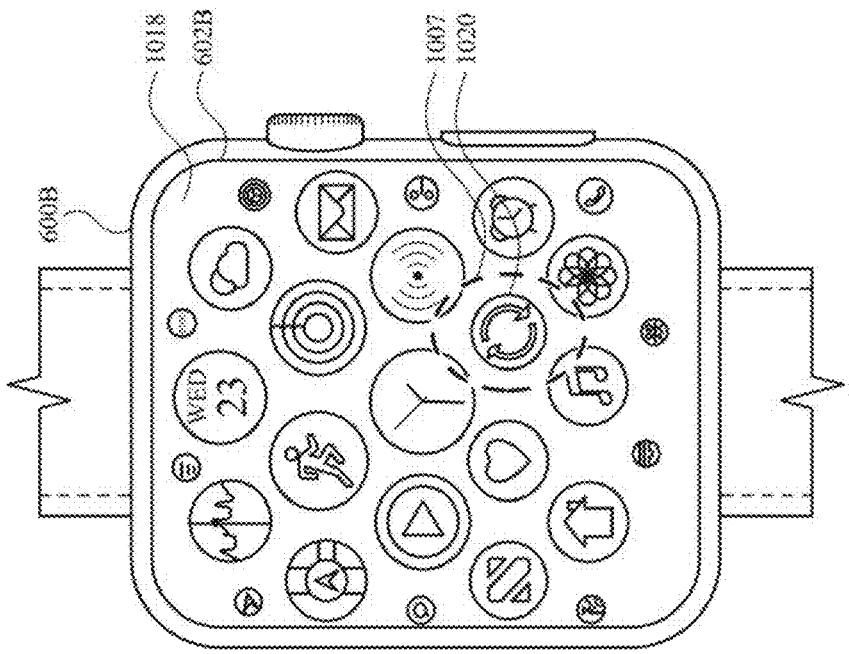
FIG. 10F
FIG. 10G

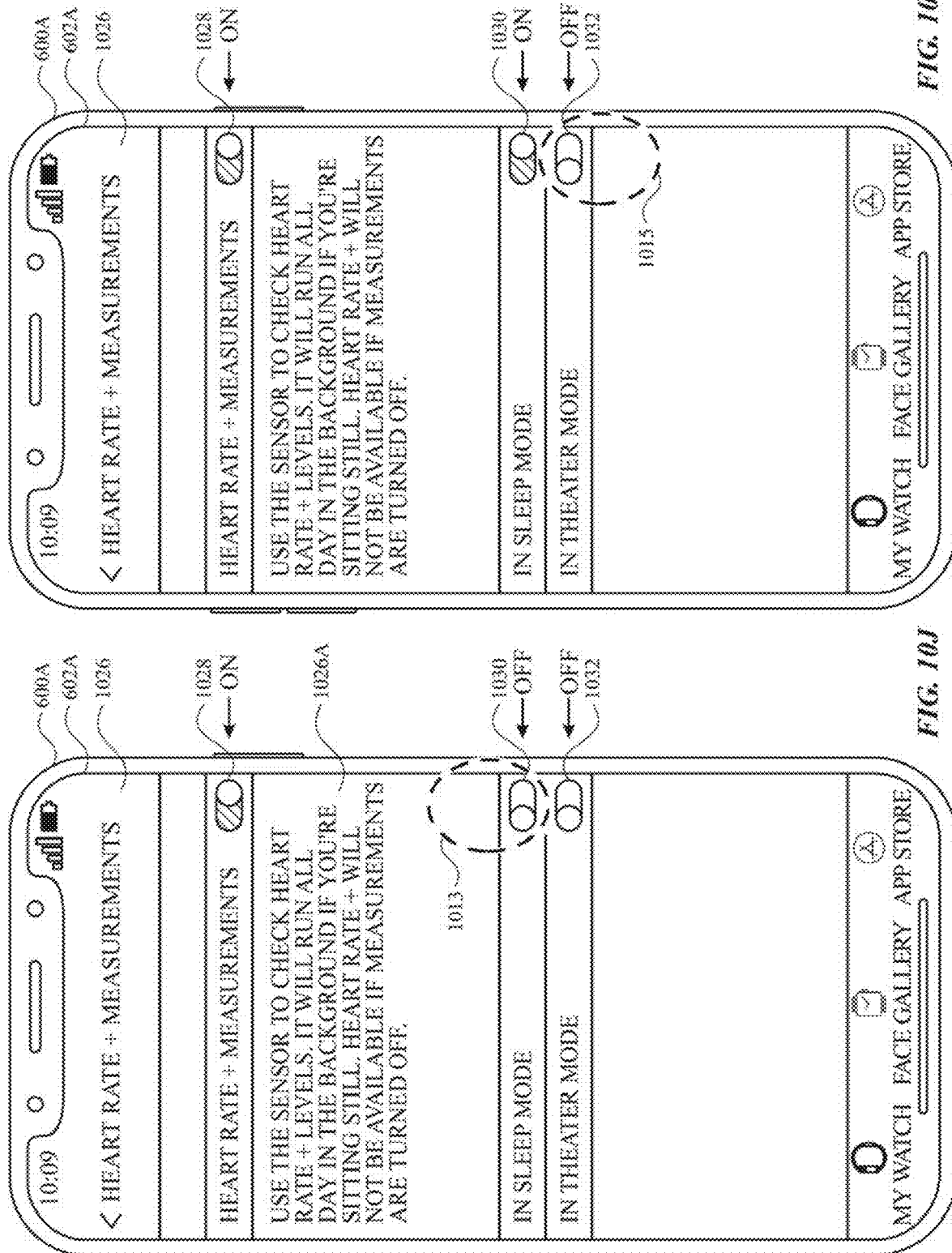

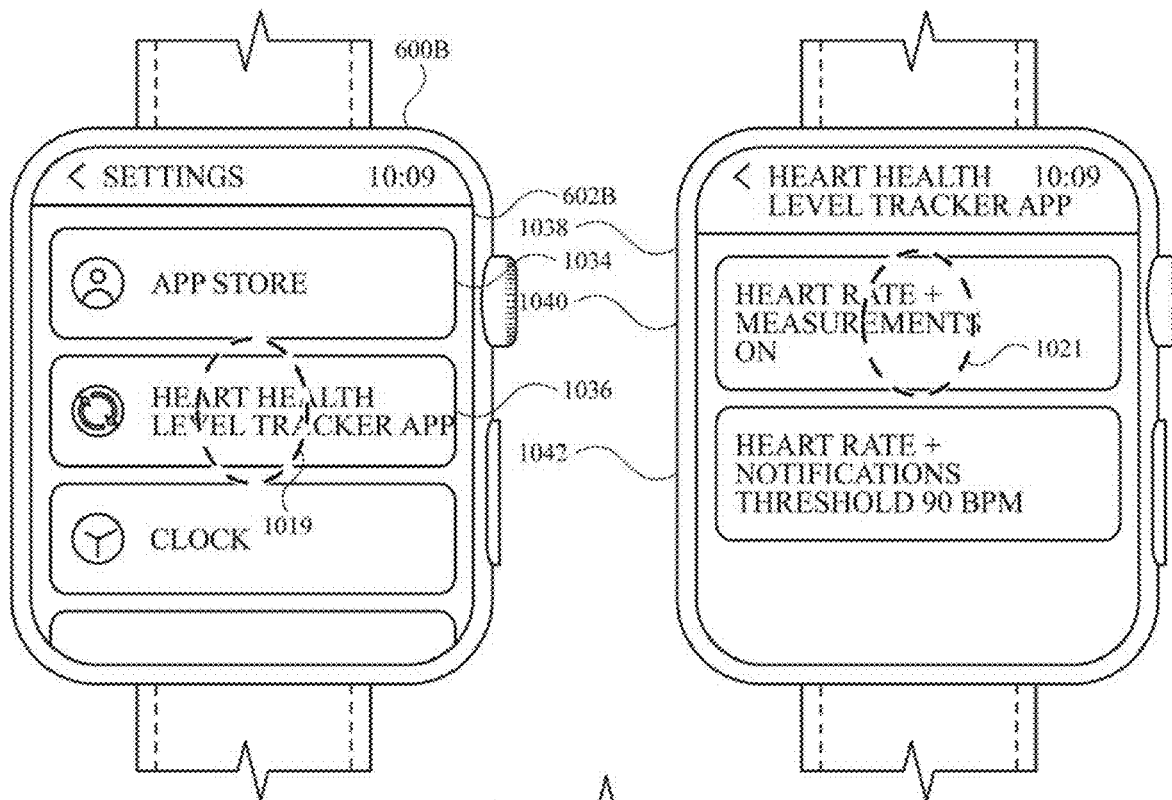
FIG. 10N
FIG. 10O
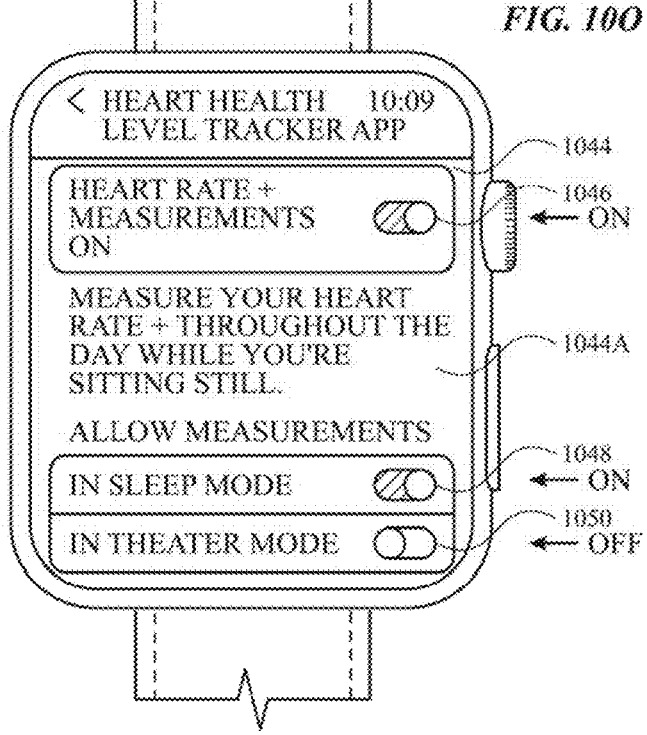
FIG. 10P

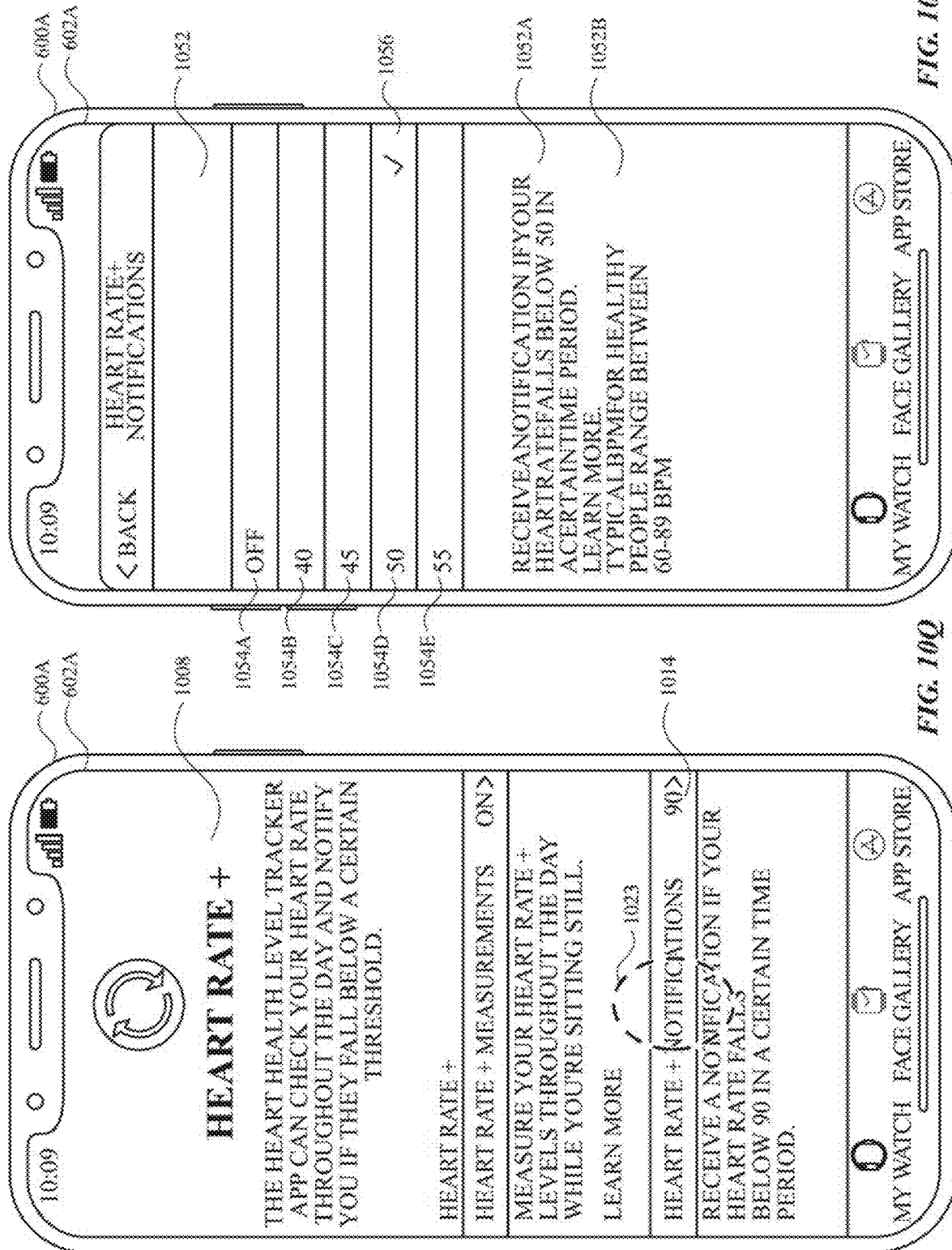

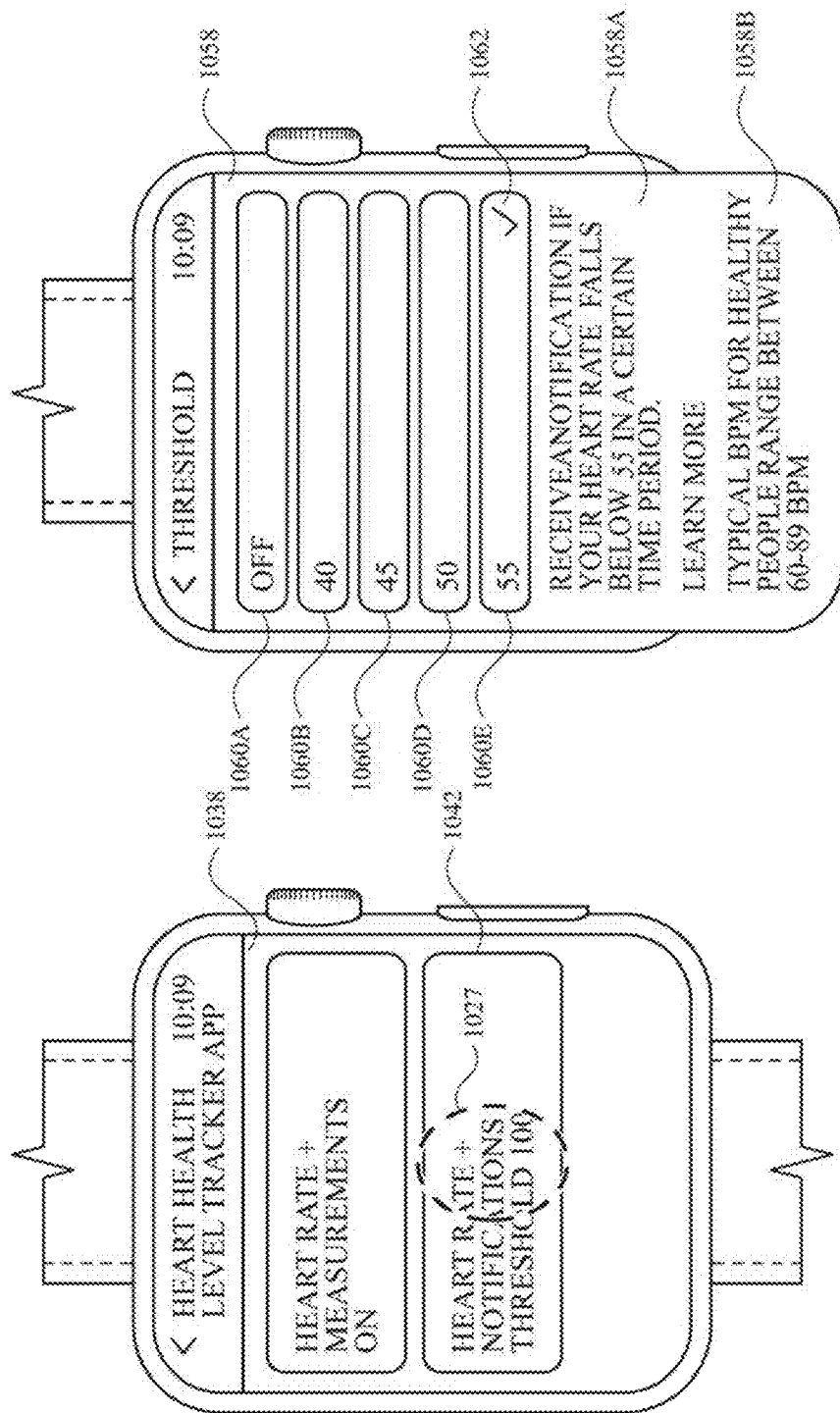

1100

1102
Display, via the display generation component, a first configuration user interface of a set of one or more configuration user interfaces for a first health-related tracking function, wherein the first configuration user interface includes a first selectable user interface object, and wherein the first health-related tracking function is currently configured to track a first set of health-related data while the computer system is in a first mode and a second mode that is different from the first mode.

1104
The set of one or more configuration user interfaces includes a third selectable user interface object that, when selected, configures a threshold value of the first set of health-related data that causes the computer system to issue a perceptual notification when the health-related tracking function detects that the threshold value has been exceeded.

1106
The computer system is in the first mode when the current time corresponds to a predetermined period of time.

1108
Receive a set of one or more inputs, the set of one or more inputs including an input corresponding to the first selectable user interface object.

1110
In response to the set of one or more inputs, configuring the first health-related tracking function to not track the first set of health-related data while the computer system is in the first mode while continuing to track the first set of health-related data while the computer system is in the second mode.

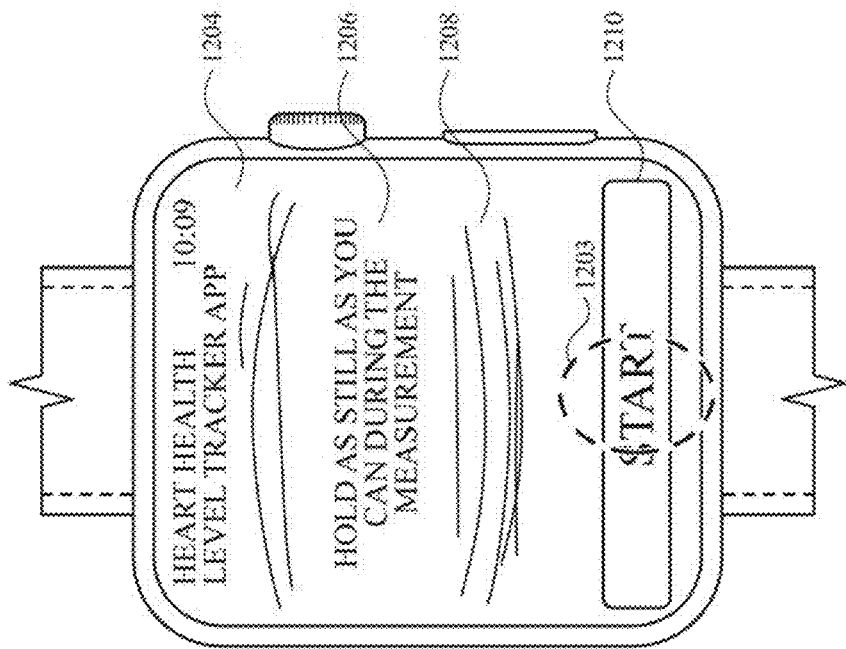
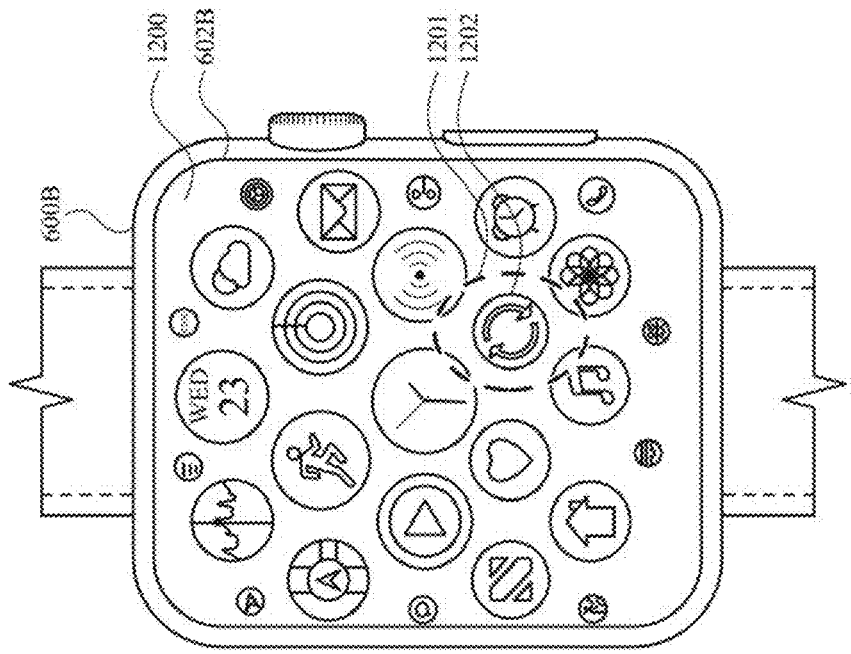
FIG. 12A
FIG. 12B

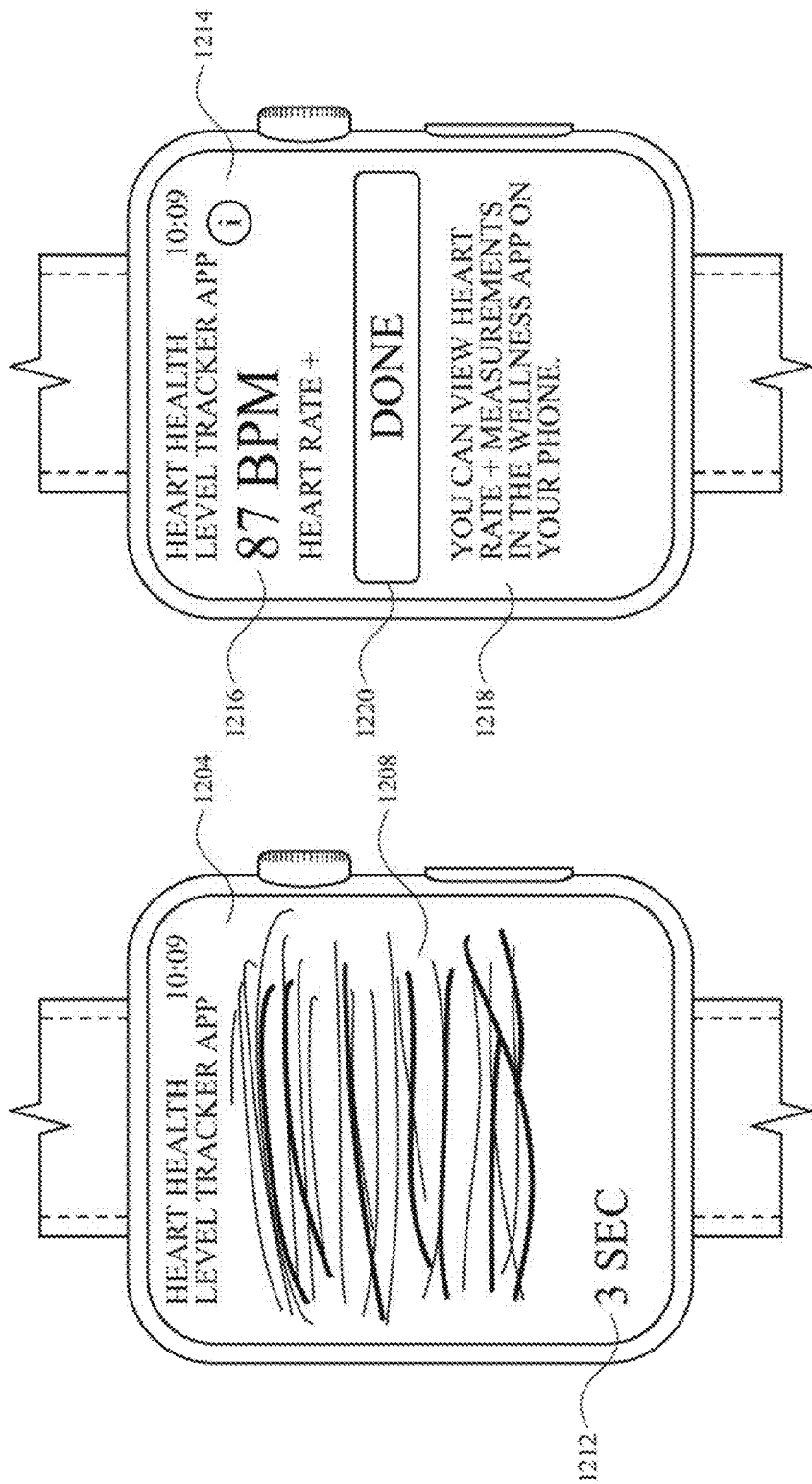

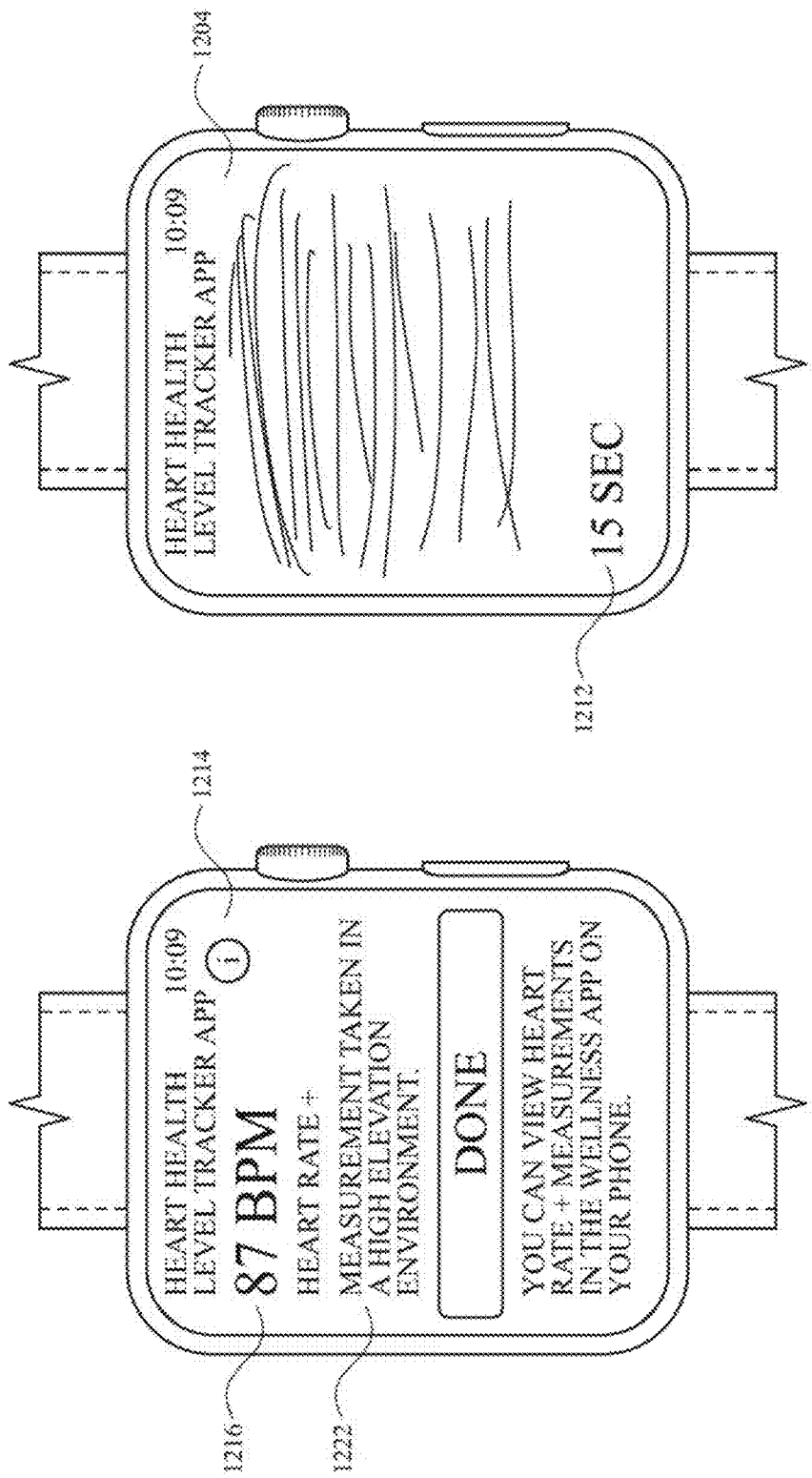

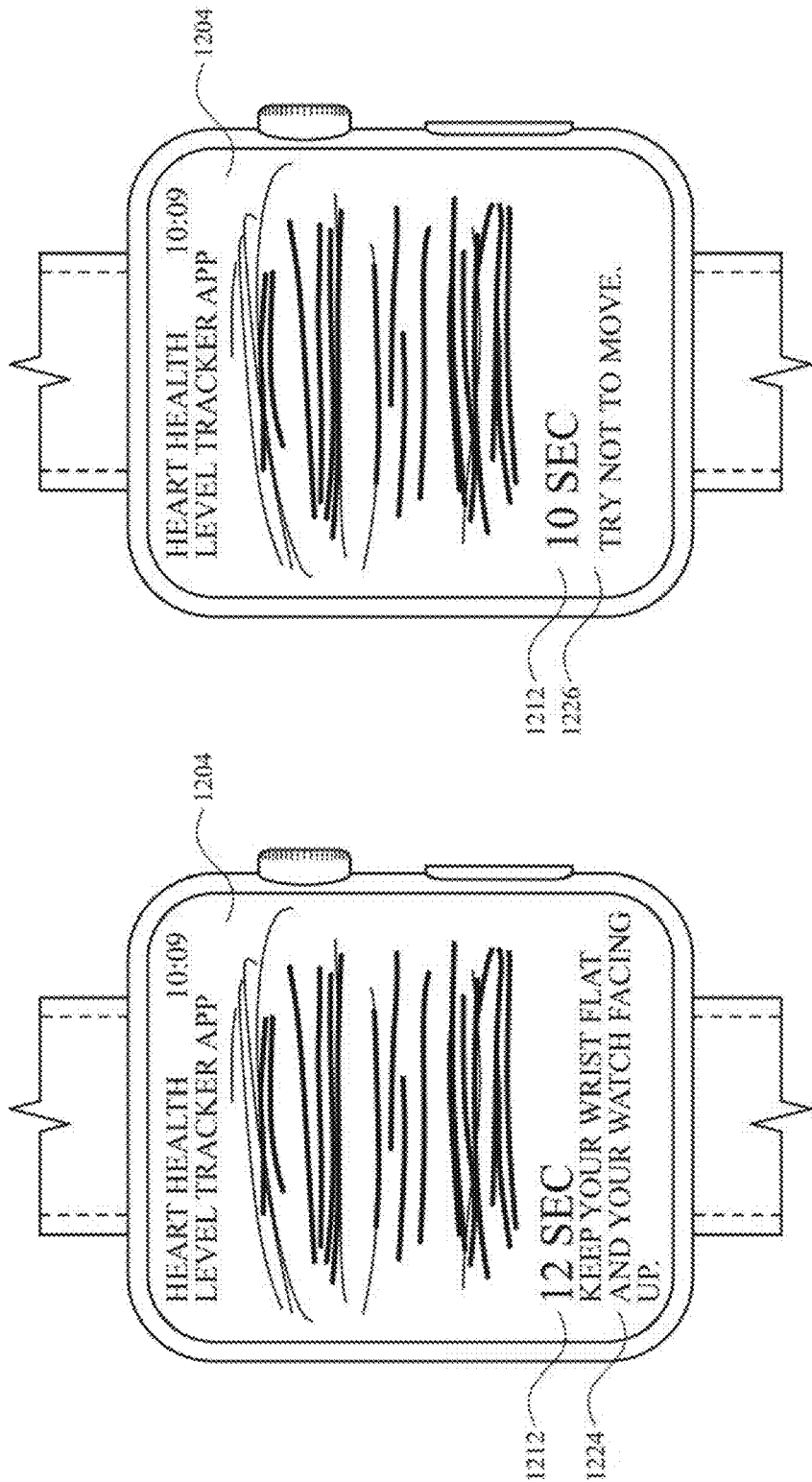

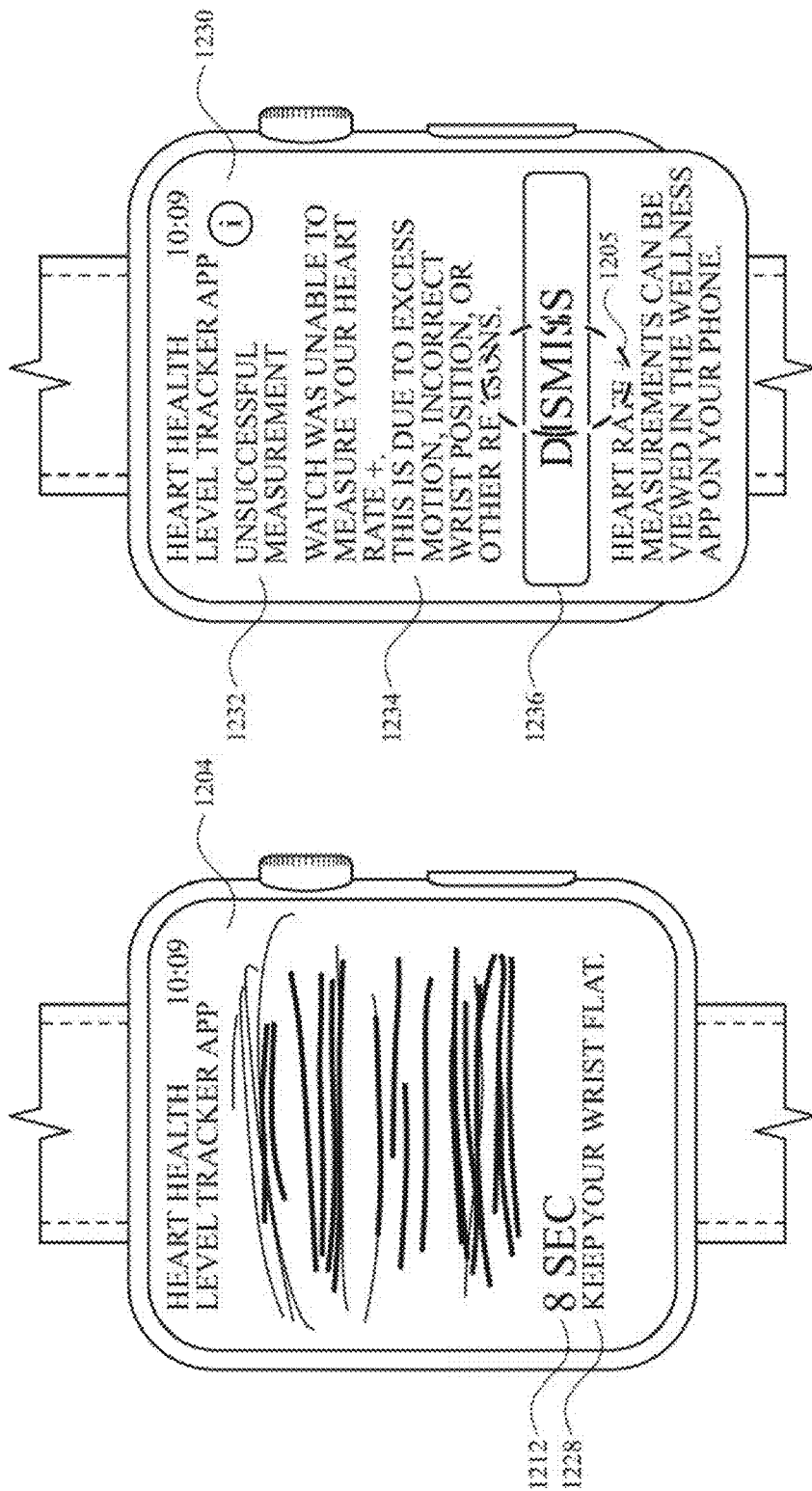

1300

1302
Initiate a biometric analysis process that includes detecting, via the one or more biometric sensors, first biometric data.

1304
The set of one or more sensors includes at least a first sensor configured to detect a position or movement of the computer system.

1306
During the biometric analysis process:

1308
Detect, via the set of one or more sensors, a first set of sensor data.

1310
In response to detecting the first set of sensor data:

1312
In accordance with a determination that the first set of sensor data satisfies a first set of cessation criteria, cease the biometric analysis process.

1314
Detect, via the set of one or more sensors, a second set of sensor data indicative of a position of the computer system or movement of the computer system.

1316
In response to detecting the second set of sensor data:

1318
In accordance with a determination that the second set of sensor data satisfies a first set of prompting criteria, display, via the display generation component, a first prompt to change a position of the computer system or to limit changes in position of the computer system.

1320
The first prompt includes guidance on how to have a proper position of the computer system or limit motion of the computer system.

1322
The first prompt to change a position of the computer system or to limit changes in position of the computer system includes:

1324
In accordance with a determination that the second set of sensor data satisfies a first set of position criteria, the first set of position criteria including a criterion that is satisfied when the position of the computer system matches a first predetermined position of a set of one or more predetermined positions, a prompt to change the position of the computer system.

1326
In accordance with a determination that the second set of sensor data satisfies a first set of movement criteria, the first set of movement criteria including a criterion that is satisfied when a degree of movement of the computer system exceeds a threshold value, a prompt to limit movement of the computer system.

1328
After displaying the first prompt:

1330
Continue with the biometric analysis process.

1332
Detect, via the set of one or more sensors, a third set of sensor data indicative of a position of the computer system or a movement of the computer system that satisfies the first set of criteria.

1334
In response to detecting the third set of sensor data, replace the first prompt with a second prompt to change a position of the computer system or to limit changes in position of the computer system, wherein the second prompt is different from the first prompt.

*FIG. 13B*

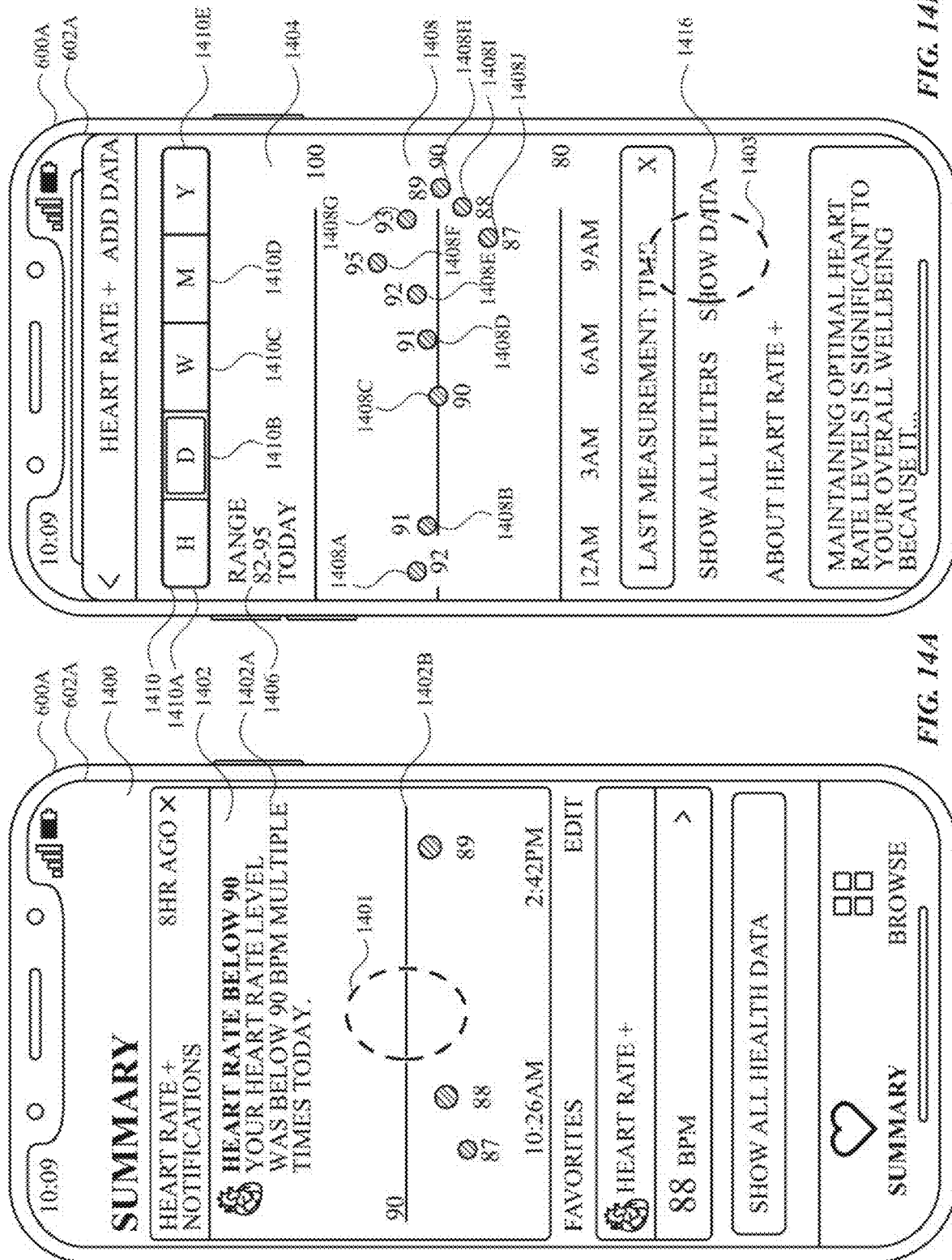

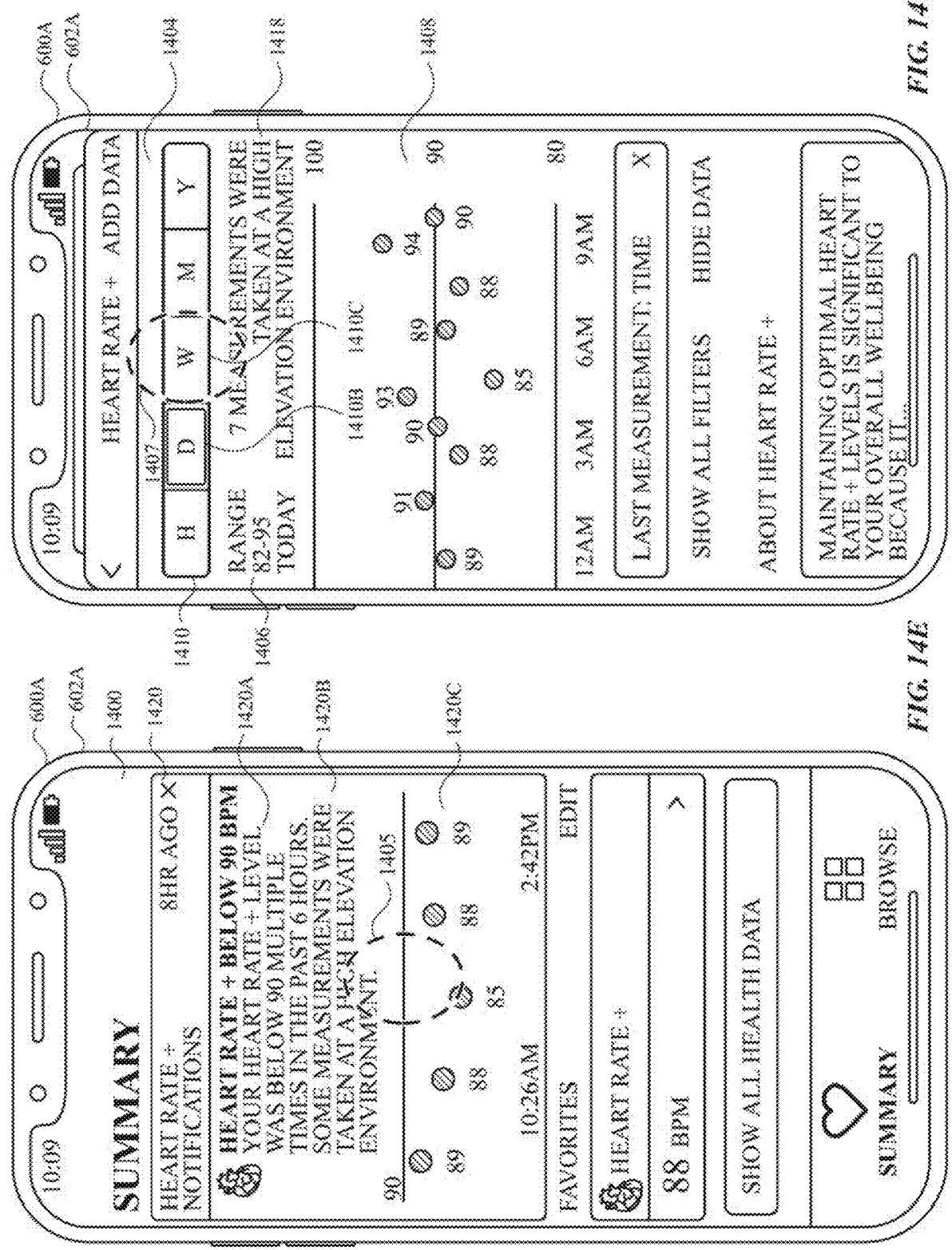

1502
Display, via the display generation component, a summary user interface of a first health-related tracking function.

1504
The summary user interface includes a set of one or more user interface objects that correspond to tracking data gathered by the first health-related tracking function.

1506
The set of one or more user interface objects includes:

1508
A first user interface object that corresponds to first datum gathered via the first health-related tracking function.

1510
A plurality of user interface objects that correspond to tracking data gathered by the first health-related tracking function.

1512
The summary user interface includes:

1514
In accordance with a determination that the first datum was gathered under one or more conditions of a first type, displaying the first user interface object with an indication that indicates that at least some of the tracking data gathered by the first health-related tracking function was gathered under the one or more conditions of the first type.

1516
The one or more conditions of the first type includes an altitude that exceeds a threshold value.

1518
The summary user interface includes:

1520
In accordance with a determination that the tracking data gathered by the first health-related tracking function indicates that a biometric parameter of a user of the computer system has been below a threshold value for at least a predetermined period of time, displaying an indication that the biometric parameter of the user has been below the threshold value for at least the predetermined period of time.

*FIG. 15B*

| 24-HOUR PERIOD | DEVICE MODE | MEASUREMENT TAKEN? |
|---|---|---|
| 12:00 AM | Sleep mode | NO |
| 1:00 AM | Sleep mode | NO |
| 2:00 AM | Sleep mode | NO |
| 3:00 AM | Sleep mode | NO |
| 4:00 AM | Sleep mode | NO |
| 5:00 AM | Sleep mode | NO |
| 6:00 AM | Sleep mode | NO |
| 7:00 AM | Normal mode | YES |
| 8:00 AM | Normal mode | YES |
| 9:00 AM | Normal mode | YES |
| 10:00 AM | Normal mode | YES |
| 11:00 AM | Theater mode | NO |
| 12:00 PM | Normal mode | YES |
| 1:00 PM | Normal mode | YES |
| 2:00 PM | Theater mode | NO |
| 3:00 PM | Theater mode | NO |
| 4:00 PM | Theater mode | NO |
| 5:00 PM | Normal mode | YES |
| 6:00 PM | Normal mode | YES |
| 7:00 PM | Normal mode | YES |
| 8:00 PM | Normal mode | YES |
| 9:00 PM | Normal mode | YES |
| 10:00 PM | Sleep mode | NO |
| 11:00 PM | Sleep mode | NO |

1702
Detect that a first set of health measurement criteria are satisfied.

1704
The computer system includes:

1706
An outer housing.

1708
A light generation component configured to illuminate a volume outside the outer housing.

1710
In response to detecting that the set of health measurement criteria are satisfied:

1712
In accordance with a determination that the computer system is in a first mode, measure, via the set of one or more biometric sensors, a value of a biometric parameter.

1714
Activate a sensor that is visible from a viewing perspective outside the outer housing.

1716
Activate the light generation component and increase the brightness of the volume outside the outer housing.

1718
In accordance with a determination that the computer system is in a second mode, different from the first mode, forgo measuring the biometric parameter.

//USER INTERFACES FOR HEALTH APPLICATIONS

CROSS-REFERENCE TO RELATED APPLICATIONS

This application claims priority to U.S. Provisional Patent Application Nos. 63/033,829, "USER INTERFACES FOR HEALTH APPLICATIONS," filed Jun. 2, 2020; 63/033,832, "USER INTERFACES FOR HEALTH APPLICATIONS," filed Jun. 3, 2020; 63/078,315, "USER INTERFACES FOR HEALTH APPLICATIONS," filed Sep. 14, 2020. All of these applications are incorporated by reference herein in their entirety.

FIELD

The present disclosure relates generally to computer user interfaces, and more specifically to techniques for managing and/or presenting health data.

BACKGROUND

Measuring and managing health information using health applications on electronic devices is a convenient and effective method of providing and maintaining awareness of one's health. Using electronic devices enable a user to quickly and easily capture health information and manage and monitor the health information.

BRIEF SUMMARY

Some techniques for managing health data using electronic devices, are generally cumbersome and inefficient. For example, some techniques use a complex and time-consuming user interface, which may include multiple key presses or keystrokes. Such techniques require more time than necessary, wasting user time and device energy. This latter consideration is particularly important in battery-operated devices.

Accordingly, the present techniques provide electronic devices with faster, more efficient methods and interfaces for managing and/or presenting health data. Such methods and interfaces optionally complement or replace other methods for managing and/or presenting health data. Such methods and interfaces reduce the cognitive burden on a user and produce a more efficient human-machine interface. For battery-operated computing devices, such methods and interfaces conserve power and increase the time between battery charges. Such methods and interfaces also enable a user to quickly and easily capture health information, thereby incentivizing the user to frequently monitor his or her health. Such methods and interfaces also enable a user to conveniently view and manage recorded health information, thereby raising awareness to the user of the user's current health status.

In accordance with some embodiments, a method performed at a computer system that is in communication with a display generation component and one or more input devices is described. The method comprises: displaying, via the display generation component, a user interface that includes a plurality of user interface objects that correspond to health-related functions, the plurality of user interface objects including a first user interface object that corresponds to a first health-related function, wherein the first user interface object includes: in accordance with a determination that the first health-related function is currently active, an indication that the first health-related function is active; in accordance with a determination that the first health-related function is currently inactive and available for activation via a set of one or more inputs received at the computer system, an indication that the first health-related function is available for activation; and in accordance with a determination that the first health-related function is currently inactive and not available for activation, an indication that the first health-related function is not available for activation.

In accordance with some embodiments, a non-transitory computer-readable storage medium storing one or more programs configured to be executed by one or more processors of a computer system that is in communication with a display generation component and one or more input devices is described. The one or more programs include instructions for: displaying, via the display generation component, a user interface that includes a plurality of user interface objects that correspond to health-related functions, the plurality of user interface objects including a first user interface object that corresponds to a first health-related function, wherein the first user interface object includes: in accordance with a determination that the first health-related function is currently active, an indication that the first health-related function is active; in accordance with a determination that the first health-related function is currently inactive and available for activation via a set of one or more inputs received at the computer system, an indication that the first health-related function is available for activation; and in accordance with a determination that the first health-related function is currently inactive and not available for activation, an indication that the first health-related function is not available for activation.

In accordance with some embodiments, a transitory computer-readable storage medium storing one or more programs configured to be executed by one or more processors of a computer system that is in communication with a display generation component and one or more input devices is described. The one or more programs include instructions for: displaying, via the display generation component, a user interface that includes a plurality of user interface objects that correspond to health-related functions, the plurality of user interface objects including a first user interface object that corresponds to a first health-related function, wherein the first user interface object includes: in accordance with a determination that the first health-related function is currently active, an indication that the first health-related function is active; in accordance with a determination that the first health-related function is currently inactive and available for activation via a set of one or more inputs received at the computer system, an indication that the first health-related function is available for activation; and in accordance with a determination that the first health-related function is currently inactive and not available for activation, an indication that the first health-related function is not available for activation.

In accordance with some embodiments, a computer system comprising a display generation component, one or more input devices, one or more processors, and memory storing one or more programs configured to be executed by the one or more processors is described. The one or more programs include instructions for: displaying, via the display generation component, a user interface that includes a plurality of user interface objects that correspond to health-related functions, the plurality of user interface objects including a first user interface object that corresponds to a first health-related function, wherein the first user interface object includes: in accordance with a determination that the first health-related function is currently active, an indication that the first health-related function is active; in accordance with a determination that the first health-related function is currently inactive and available for activation via a set of one or more inputs received at the computer system, an indication that the first health-related function is available for activation; and in accordance with a determination that the first health-related function is currently inactive and not available for activation, an indication that the first health-related function is not available for activation.

In accordance with some embodiments, a computer system is described. The computer system comprises: a display generation component; one or more input devices; means for displaying, via the display generation component, a user interface that includes a plurality of user interface objects that correspond to health-related functions, the plurality of user interface objects including a first user interface object that corresponds to a first health-related function, wherein the first user interface object includes: in accordance with a determination that the first health-related function is currently active, an indication that the first health-related function is active; in accordance with a determination that the first health-related function is currently inactive and available for activation via a set of one or more inputs received at the computer system, an indication that the first health-related function is available for activation; and in accordance with a determination that the first health-related function is currently inactive and not available for activation, an indication that the first health-related function is not available for activation.

In accordance with some embodiments, a method performed at a computer system that is in communication with a display generation component and one or more input devices is described. The method comprises: displaying, via the display generation component, a set of one or more user interfaces that corresponds to a first health-related function, wherein the first health-related function is currently inactive and wherein displaying the set of one or more user interfaces that correspond to the first health-related function includes: in accordance with a determination that a set of activation-permissibility criteria are satisfied, the set of activation-permissibility criteria including a location-based criterion that is satisfied when a current location of the computer system satisfies a set of location-based criteria, displaying a first activation user interface of a set of one or more activation user interfaces, the set of one or more activation user interfaces including a first selectable user interface object that, when selected via an input received via the one or more input devices, activates the first health-related function; and in accordance with a determination that the set of activation-permissibility criteria are not satisfied, displaying a notification interface that includes first information corresponding to the first health-related function and that does not include a selectable user interface object that, when selected via an input received via the one or more input devices, activates the first health related function.

In accordance with some embodiments, a non-transitory computer-readable storage medium storing one or more programs configured to be executed by one or more processors of a computer system that is in communication with a display generation component and one or more input devices is described. The one or more programs include instructions for: displaying, via the display generation component, a set of one or more user interfaces that corresponds to a first health-related function, wherein the first health-related function is currently inactive and wherein displaying the set of one or more user interfaces that correspond to the first health-related function includes: in accordance with a determination that a set of activation-permissibility criteria are satisfied, the set of activation-permissibility criteria including a location-based criterion that is satisfied when a current location of the computer system satisfies a set of location-based criteria, displaying a first activation user interface of a set of one or more activation user interfaces, the set of one or more activation user interfaces including a first selectable user interface object that, when selected via an input received via the one or more input devices, activates the first health-related function; and in accordance with a determination that the set of activation-permissibility criteria are not satisfied, displaying a notification interface that includes first information corresponding to the first health-related function and that does not include a selectable user interface object that, when selected via an input received via the one or more input devices, activates the first health related function.

In accordance with some embodiments, a transitory computer-readable storage medium storing one or more programs configured to be executed by one or more processors of a computer system that is in communication with a display generation component and one or more input devices is described. The one or more programs include instructions for: displaying, via the display generation component, a set of one or more user interfaces that corresponds to a first health-related function, wherein the first health-related function is currently inactive and wherein displaying the set of one or more user interfaces that correspond to the first health-related function includes: in accordance with a determination that a set of activation-permissibility criteria are satisfied, the set of activation-permissibility criteria including a location-based criterion that is satisfied when a current location of the computer system satisfies a set of location-based criteria, displaying a first activation user interface of a set of one or more activation user interfaces, the set of one or more activation user interfaces including a first selectable user interface object that, when selected via an input received via the one or more input devices, activates the first health-related function; and in accordance with a determination that the set of activation-permissibility criteria are not satisfied, displaying a notification interface that includes first information corresponding to the first health-related function and that does not include a selectable user interface object that, when selected via an input received via the one or more input devices, activates the first health related function.

In accordance with some embodiments, a computer system comprising a display generation component, one or more input devices, one or more processors, and memory storing one or more programs configured to be executed by the one or more processors is described. The one or more programs include instructions for: displaying, via the display generation component, a set of one or more user interfaces that corresponds to a first health-related function, wherein the first health-related function is currently inactive and wherein displaying the set of one or more user interfaces that correspond to the first health-related function includes: in accordance with a determination that a set of activation-permissibility criteria are satisfied, the set of activation-permissibility criteria including a location-based criterion that is satisfied when a current location of the computer system satisfies a set of location-based criteria, displaying a first activation user interface of a set of one or more activation user interfaces, the set of one or more activation user interfaces including a first selectable user interface object that, when selected via an input received via the one or more input devices, activates the first health-related function; and in accordance with a determination that the set of activation-permissibility criteria are not satisfied, displaying a notification interface that includes first information corresponding to the first health-related function and that does not include a selectable user interface object that, when selected via an input received via the one or more input devices, activates the first health related function.

In accordance with some embodiments, a computer system is described. The computer system comprises: a display generation component; one or more input devices; means for displaying, via the display generation component, a set of one or more user interfaces that corresponds to a first health-related function, wherein the first health-related function is currently inactive and wherein displaying the set of one or more user interfaces that correspond to the first health-related function includes: in accordance with a determination that a set of activation-permissibility criteria are satisfied, the set of activation-permissibility criteria including a location-based criterion that is satisfied when a current location of the computer system satisfies a set of location-based criteria, displaying a first activation user interface of a set of one or more activation user interfaces, the set of one or more activation user interfaces including a first selectable user interface object that, when selected via an input received via the one or more input devices, activates the first health-related function; and in accordance with a determination that the set of activation-permissibility criteria are not satisfied, displaying a notification interface that includes first information corresponding to the first health-related function and that does not include a selectable user interface object that, when selected via an input received via the one or more input devices, activates the first health related function.

In accordance with some embodiments, a method performed at a computer system that is in communication with a display generation component and one or more input devices is described. The method comprises: displaying, via the display generation component, a first configuration user interface of a set of one or more configuration user interfaces for a first health-related tracking function, wherein the first configuration user interface includes a first selectable user interface object, and wherein the first health-related tracking function is currently configured to track a first set of health-related data while the computer system is in a first mode and a second mode that is different from the first mode; receiving a set of one or more inputs, the set of one or more inputs including an input corresponding to the first selectable user interface object; and in response to the set of one or more inputs, configuring the first health-related tracking function to not track the first set of health-related data while the computer system is in the first mode while continuing to track the first set of health-related data while the computer system is in the second mode.

In accordance with some embodiments, a non-transitory computer-readable storage medium storing one or more programs configured to be executed by one or more processors of a computer system that is in communication with a display generation component and one or more input devices is described. The one or more programs include instructions for: displaying, via the display generation component, a first configuration user interface of a set of one or more configuration user interfaces for a first health-related tracking function, wherein the first configuration user interface includes a first selectable user interface object, and wherein the first health-related tracking function is currently configured to track a first set of health-related data while the computer system is in a first mode and a second mode that is different from the first mode; receiving a set of one or more inputs, the set of one or more inputs including an input corresponding to the first selectable user interface object; and in response to the set of one or more inputs, configuring the first health-related tracking function to not track the first set of health-related data while the computer system is in the first mode while continuing to track the first set of health-related data while the computer system is in the second mode.

In accordance with some embodiments, a transitory computer-readable storage medium storing one or more programs configured to be executed by one or more processors of a computer system that is in communication with a display generation component and one or more input devices is described. The one or more programs include instructions for: displaying, via the display generation component, a first configuration user interface of a set of one or more configuration user interfaces for a first health-related tracking function, wherein the first configuration user interface includes a first selectable user interface object, and wherein the first health-related tracking function is currently configured to track a first set of health-related data while the computer system is in a first mode and a second mode that is different from the first mode; receiving a set of one or more inputs, the set of one or more inputs including an input corresponding to the first selectable user interface object; and in response to the set of one or more inputs, configuring the first health-related tracking function to not track the first set of health-related data while the computer system is in the first mode while continuing to track the first set of health-related data while the computer system is in the second mode.

In accordance with some embodiments, a computer system comprising a display generation component, one or more input devices, one or more processors, and memory storing one or more programs configured to be executed by the one or more processors is described. The one or more programs include instructions for: displaying, via the display generation component, a first configuration user interface of a set of one or more configuration user interfaces for a first health-related tracking function, wherein the first configuration user interface includes a first selectable user interface object, and wherein the first health-related tracking function is currently configured to track a first set of health-related data while the computer system is in a first mode and a second mode that is different from the first mode; receiving a set of one or more inputs, the set of one or more inputs including an input corresponding to the first selectable user interface object; and in response to the set of one or more inputs, configuring the first health-related tracking function to not track the first set of health-related data while the computer system is in the first mode while continuing to track the first set of health-related data while the computer system is in the second mode.

In accordance with some embodiments, a computer system is described. The computer system comprises: a display generation component; one or more input devices; means for displaying, via the display generation component, a first configuration user interface of a set of one or more configuration user interfaces for a first health-related tracking function, wherein the first configuration user interface includes a first selectable user interface object, and wherein the first health-related tracking function is currently configured to track a first set of health-related data while the computer system is in a first mode and a second mode that is different from the first mode; means for receiving a set of one or more inputs, the set of one or more inputs including an input corresponding to the first selectable user interface object; and means for, in response to the set of one or more inputs, configuring the first health-related tracking function to not track the first set of health-related data while the computer system is in the first mode while continuing to track the first set of health-related data while the computer system is in the second mode.

In accordance with some embodiments, a method performed at a computer system that is in communication with a display generation component, a set of one or more biometric sensors, and a set of one or more sensors is described. The method comprises: initiating a biometric analysis process that includes detecting, via the one or more biometric sensors, first biometric data; during the biometric analysis process: detecting, via the set of one or more sensors, a first set of sensor data; and in response to detecting the first set of sensor data: in accordance with a determination that the first set of sensor data satisfies a first set of cessation criteria, ceasing the biometric analysis process.

In accordance with some embodiments, a non-transitory computer-readable storage medium storing one or more programs configured to be executed by one or more processors of a computer system that is in communication with a display generation component, a set of one or more biometric sensors, and a set of one or more sensors is described. The one or more programs include instructions for: initiating a biometric analysis process that includes detecting, via the one or more biometric sensors, first biometric data; during the biometric analysis process: detecting, via the set of one or more sensors, a first set of sensor data; and in response to detecting the first set of sensor data: in accordance with a determination that the first set of sensor data satisfies a first set of cessation criteria, ceasing the biometric analysis process.

In accordance with some embodiments, a transitory computer-readable storage medium storing one or more programs configured to be executed by one or more processors of a computer system that is in communication with a display generation component, a set of one or more biometric sensors, and a set of one or more sensors is described. The one or more programs include instructions for: initiating a biometric analysis process that includes detecting, via the one or more biometric sensors, first biometric data; during the biometric analysis process: detecting, via the set of one or more sensors, a first set of sensor data; and in response to detecting the first set of sensor data: in accordance with a determination that the first set of sensor data satisfies a first set of cessation criteria, ceasing the biometric analysis process.

In accordance with some embodiments, a computer system comprising a display generation component, a set of one or more biometric sensors, a set of one or more sensors, one or more processors, and memory storing one or more programs configured to be executed by the one or more processors is described. The one or more programs include instructions for: initiating a biometric analysis process that includes detecting, via the one or more biometric sensors, first biometric data; during the biometric analysis process: detecting, via the set of one or more sensors, a first set of sensor data; and in response to detecting the first set of sensor data: in accordance with a determination that the first set of sensor data satisfies a first set of cessation criteria, ceasing the biometric analysis process.

In accordance with some embodiments, a computer system is described. The computer system comprises: a display generation component; a set of one or more biometric sensors; a set of one or more sensors; means for initiating a biometric analysis process that includes detecting, via the one or more biometric sensors, first biometric data; means for, during the biometric analysis process: detecting, via the set of one or more sensors, a first set of sensor data; and in response to detecting the first set of sensor data: in accordance with a determination that the first set of sensor data satisfies a first set of cessation criteria, ceasing the biometric analysis process.

In accordance with some embodiments, a method performed at a computer system that is in communication with a display generation component and one or more input devices is described. The method comprises: displaying, via the display generation component, a summary user interface of a first health-related tracking function, wherein: the summary user interface includes a set of one or more user interface objects that correspond to tracking data gathered by the first health-related tracking function, the set of one or more user interface objects includes a first user interface object that corresponds to first datum gathered via the first health-related tracking function, and displaying the summary user interface includes: in accordance with a determination that the first datum was gathered under one or more conditions of a first type, displaying the first user interface object with an indication that indicates that at least some of the tracking data gathered by the first health-related tracking function was gathered under the one or more conditions of the first type.

In accordance with some embodiments, a non-transitory computer-readable storage medium storing one or more programs configured to be executed by one or more processors of a computer system that is in communication with a display generation component and one or more input devices is described. The one or more programs include instructions for: displaying, via the display generation component, a summary user interface of a first health-related tracking function, wherein: the summary user interface includes a set of one or more user interface objects that correspond to tracking data gathered by the first health-related tracking function, the set of one or more user interface objects includes a first user interface object that corresponds to first datum gathered via the first health-related tracking function, and displaying the summary user interface includes: in accordance with a determination that the first datum was gathered under one or more conditions of a first type, displaying the first user interface object with an indication that indicates that at least some of the tracking data gathered by the first health-related tracking function was gathered under the one or more conditions of the first type.

In accordance with some embodiments, a transitory computer-readable storage medium storing one or more programs configured to be executed by one or more processors of a computer system that is in communication with a display generation component and one or more input devices is described. The one or more programs include instructions for: displaying, via the display generation component, a summary user interface of a first health-related tracking function, wherein: the summary user interface includes a set of one or more user interface objects that correspond to tracking data gathered by the first health-related tracking function, the set of one or more user interface objects includes a first user interface object that corresponds to first datum gathered via the first health-related tracking function, and displaying the summary user interface includes: in accordance with a determination that the first datum was gathered under one or more conditions of a first type, displaying the first user interface object with an indication that indicates that at least some of the tracking data gathered by the first health-related tracking function was gathered under the one or more conditions of the first type.

In accordance with some embodiments, a computer system comprising a display generation component, one or more input devices, one or more processors, and memory storing one or more programs configured to be executed by the one or more processors is described. The one or more programs include instructions for: displaying, via the display generation component, a summary user interface of a first health-related tracking function, wherein: the summary user interface includes a set of one or more user interface objects that correspond to tracking data gathered by the first health-related tracking function, the set of one or more user interface objects includes a first user interface object that corresponds to first datum gathered via the first health-related tracking function, and displaying the summary user interface includes: in accordance with a determination that the first datum was gathered under one or more conditions of a first type, displaying the first user interface object with an indication that indicates that at least some of the tracking data gathered by the first health-related tracking function was gathered under the one or more conditions of the first type.

In accordance with some embodiments, a computer system is described. The computer system comprises: a display generation component; one or more input devices; means for displaying, via the display generation component, a summary user interface of a first health-related tracking function, wherein: the summary user interface includes a set of one or more user interface objects that correspond to tracking data gathered by the first health-related tracking function, the set of one or more user interface objects includes a first user interface object that corresponds to first datum gathered via the first health-related tracking function, and displaying the summary user interface includes: in accordance with a determination that the first datum was gathered under one or more conditions of a first type, displaying the first user interface object with an indication that indicates that at least some of the tracking data gathered by the first health-related tracking function was gathered under the one or more conditions of the first type.

In accordance with some embodiments, a method performed at a computer system that is in communication with a set of one or more biometric sensors is described. The method comprises: detecting that a first set of health measurement criteria are satisfied; and in response to detecting that the set of health measurement criteria are satisfied: in accordance with a determination that the computer system is in a first mode, measuring, via the set of one or more biometric sensors, a value of a biometric parameter; and in accordance with a determination that the computer system is in a second mode, different from the first mode, forgoing measuring the biometric parameter.

In accordance with some embodiments, a non-transitory computer-readable storage medium storing one or more programs configured to be executed by one or more processors of a computer system that is in communication with a set of one or more biometric sensors is described. The one or more programs include instructions for: detecting that a first set of health measurement criteria are satisfied; and in response to detecting that the set of health measurement criteria are satisfied: in accordance with a determination that the computer system is in a first mode, measuring, via the set of one or more biometric sensors, a value of a biometric parameter; and in accordance with a determination that the computer system is in a second mode, different from the first mode, forgoing measuring the biometric parameter.

In accordance with some embodiments, a transitory computer-readable storage medium storing one or more programs configured to be executed by one or more processors of a computer system that is in communication with a set of one or more biometric sensors is described. The one or more programs include instructions for: detecting that a first set of health measurement criteria are satisfied; and in response to detecting that the set of health measurement criteria are satisfied: in accordance with a determination that the computer system is in a first mode, measuring, via the set of one or more biometric sensors, a value of a biometric parameter; and in accordance with a determination that the computer system is in a second mode, different from the first mode, forgoing measuring the biometric parameter.

In accordance with some embodiments, a computer system comprising a set of one or more biometric sensors, one or more processors, and memory storing one or more programs configured to be executed by the one or more processors is described. The one or more programs include instructions for: detecting that a first set of health measurement criteria are satisfied; and in response to detecting that the set of health measurement criteria are satisfied: in accordance with a determination that the computer system is in a first mode, measuring, via the set of one or more biometric sensors, a value of a biometric parameter; and in accordance with a determination that the computer system is in a second mode, different from the first mode, forgoing measuring the biometric parameter.

In accordance with some embodiments, a computer system is described. The computer system comprises: a set of one or more biometric sensors; means for detecting that a first set of health measurement criteria are satisfied; and means for, in response to detecting that the set of health measurement criteria are satisfied: in accordance with a determination that the computer system is in a first mode, measuring, via the set of one or more biometric sensors, a value of a biometric parameter; and in accordance with a determination that the computer system is in a second mode, different from the first mode, forgoing measuring the biometric parameter.

Executable instructions for performing these functions are, optionally, included in a non-transitory computer-readable storage medium or other computer program product configured for execution by one or more processors. Executable instructions for performing these functions are, optionally, included in a transitory computer-readable storage medium or other computer program product configured for execution by one or more processors.

Thus, devices are provided with faster, more efficient methods and interfaces for managing and/or presenting health data, thereby increasing the effectiveness, efficiency, and user satisfaction with such devices. Such methods and interfaces may complement or replace other methods for managing and/or presenting health data.

DESCRIPTION OF THE FIGURES

For a better understanding of the various described embodiments, reference should be made to the Description of Embodiments below, in conjunction with the following drawings in which like reference numerals refer to corresponding parts throughout the figures.

FIG. 4B illustrates an exemplary user interface for a multifunction device with a touch-sensitive surface that is separate from the display in accordance with some embodiments.

FIGS. 7A-7C are a flow diagram illustrating a method for managing health and safety features on an electronic device, in accordance with some embodiments.

FIGS. 9A-9C are a flow diagram illustrating a method for managing the setup of a health feature on an electronic device, in accordance with some embodiments.

FIGS. 11A-11B are a flow diagram illustrating a method for managing background health measurements on an electronic device, in accordance with some embodiments.

FIGS. 13A-13B are a flow diagram illustrating a method for managing a biometric measurement taken using an electronic device, in accordance with some embodiments.

FIGS. 14A-14I illustrate exemplary user interfaces for providing results for captured health information on an electronic device, in accordance with some embodiments.

FIGS. 15A-15B are a flow diagram illustrating a method for providing results for captured health information on an electronic device, in accordance with some embodiments.

FIGS. 16A-16C illustrate exemplary user interfaces for managing background health measurements on an electronic device, in accordance with some embodiments.

FIGS. 17A-17B are a flow diagram illustrating a method for managing background health measurements on an electronic device, in accordance with some embodiments.

DESCRIPTION OF EMBODIMENTS

The following description sets forth exemplary methods, parameters, and the like. It should be recognized, however, that such description is not intended as a limitation on the scope of the present disclosure but is instead provided as a description of exemplary embodiments.

There is a need for electronic devices that provide efficient methods and interfaces for managing and/or presenting health data. For example, there is a need for electronic devices that enable a user to quickly and easily measure health information to enable the user to conveniently monitor his or her health. For another example, there is a need for electronic devices that enable a user to conveniently and efficiently manage and monitor captured health information such that the user can easily understand and properly respond to the results. For another example, there is a need for electronic devices that enable a user to conveniently view and manage various health and safety features in order for the user to use the electronic device to assess his or her health in an efficient and effective manner. Such techniques can reduce the cognitive burden on a user who accesses health data on an electronic device, thereby enhancing productivity. Further, such techniques can reduce processor and battery power otherwise wasted on redundant user inputs.

Figure 6A:
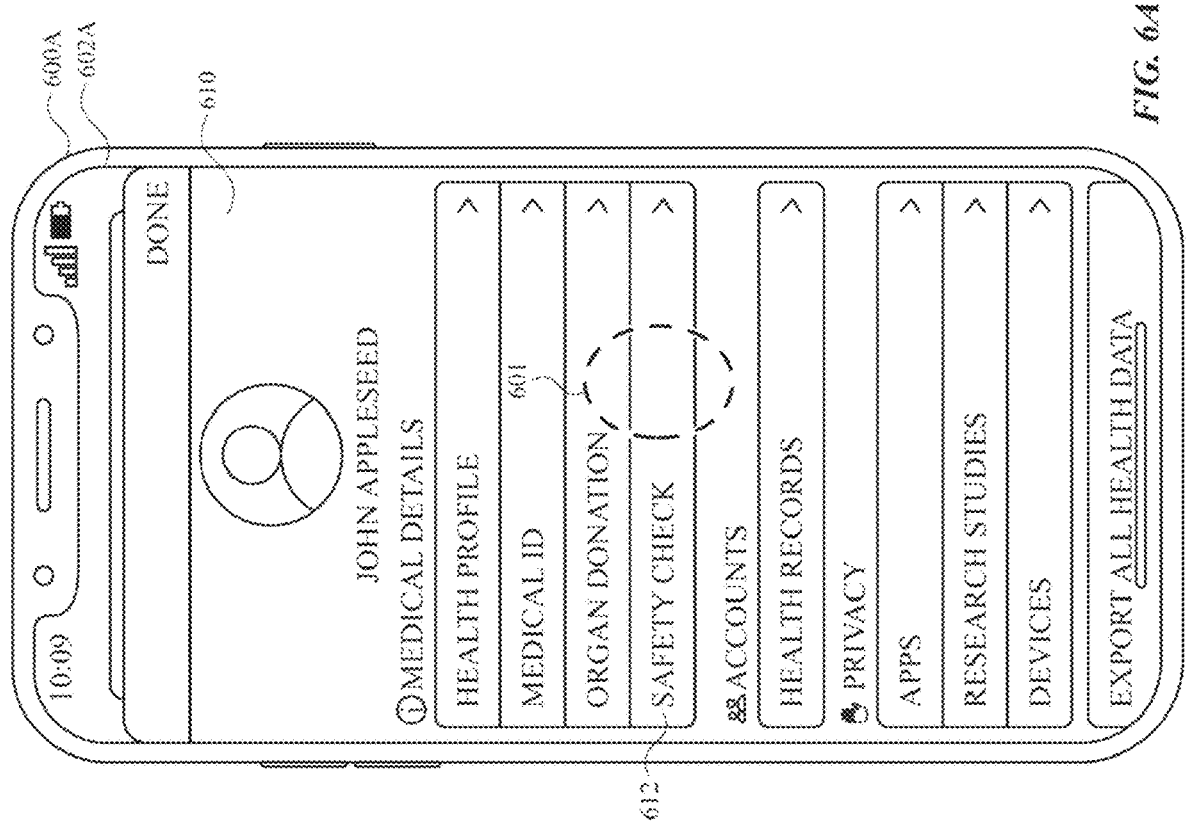
FIGS. 6A-6O illustrate exemplary user interfaces for managing health and safety features on an electronic device, in accordance with some embodiments.
Figure 7B:
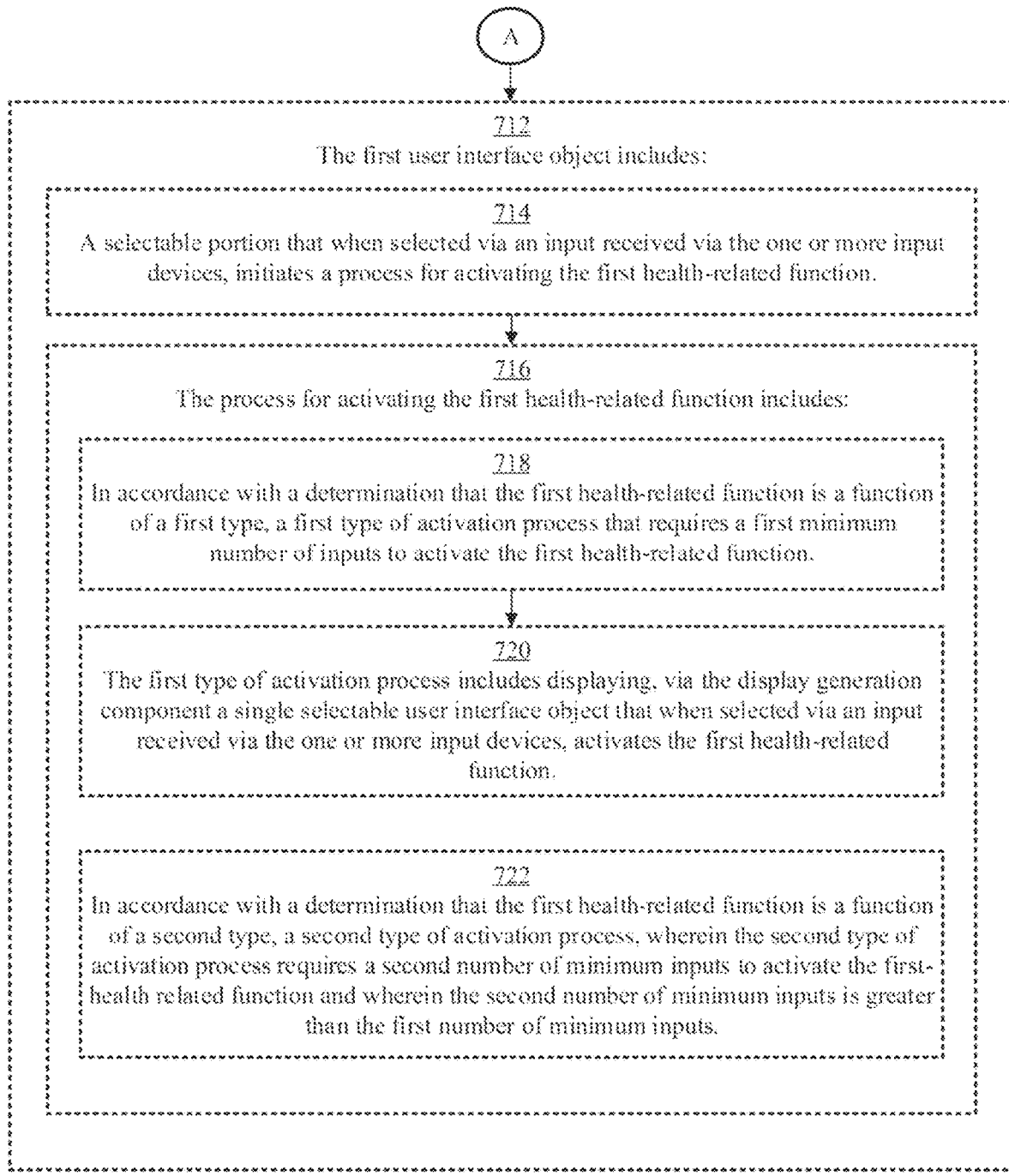
Figure 7C:
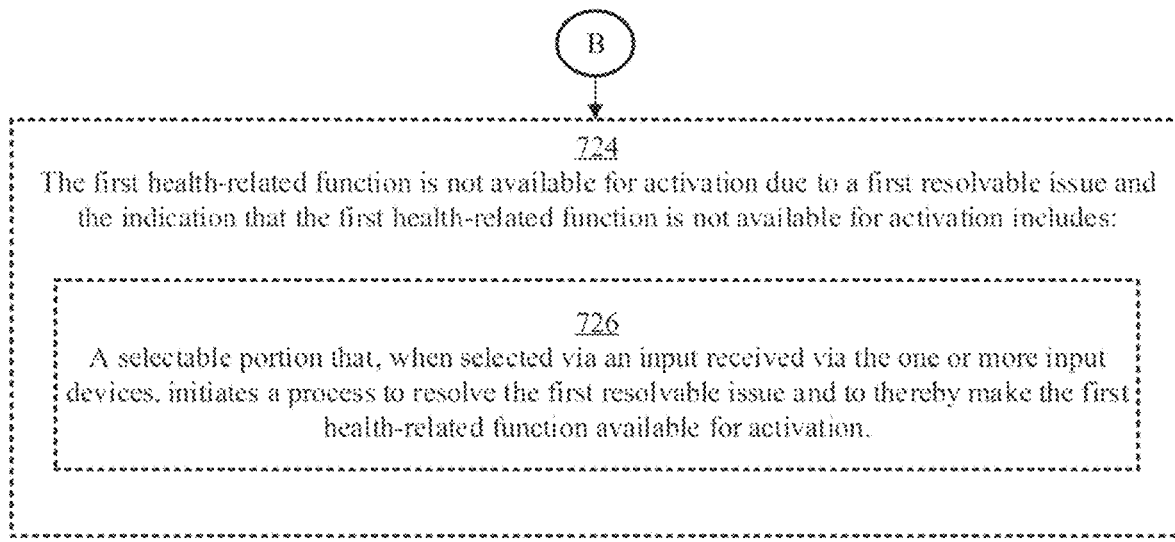
Figure 8A:
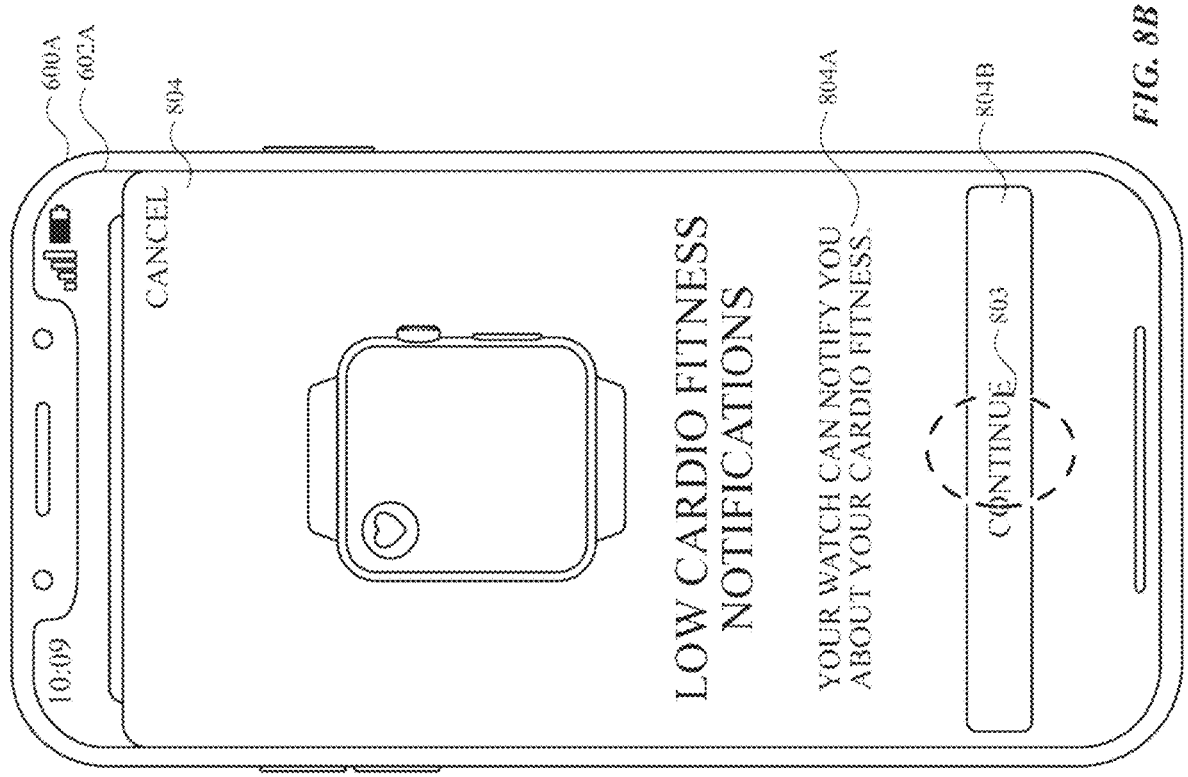
FIGS. 8A-8S illustrate exemplary user interfaces for managing the setup of a health feature on an electronic device, in accordance with some embodiments.
Figure 9B:
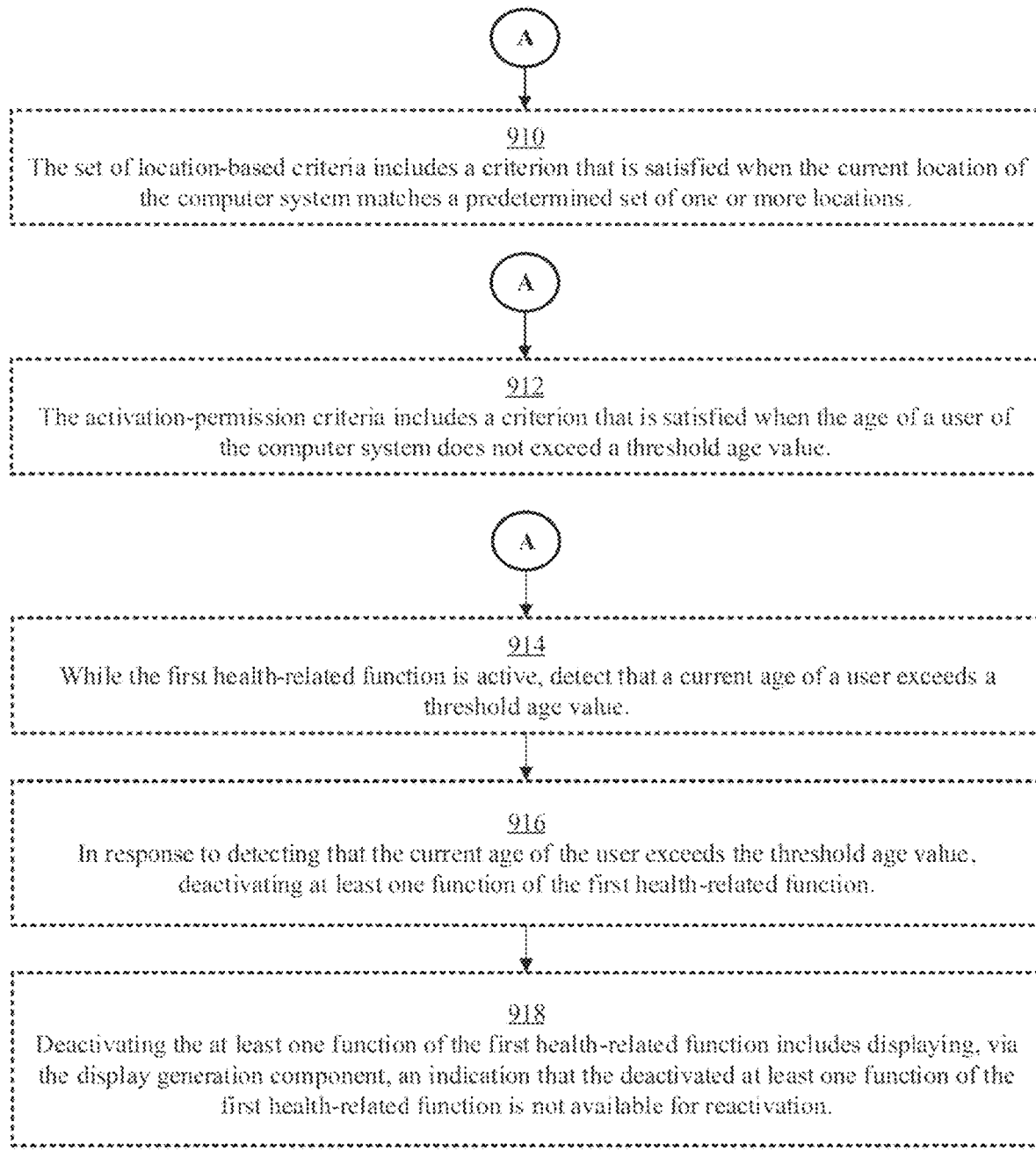
Figure 9C:
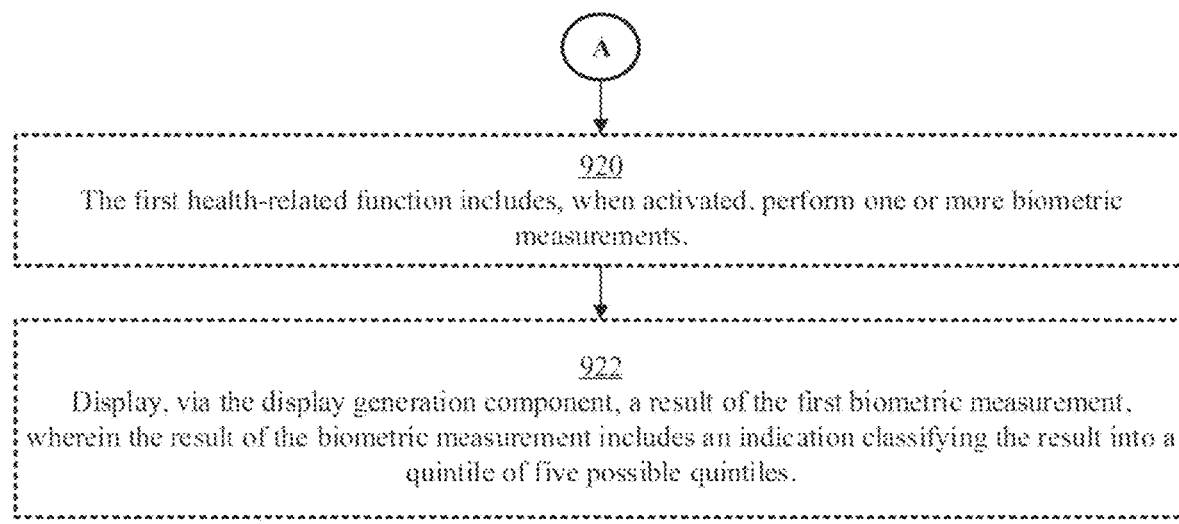
Figure 11B:
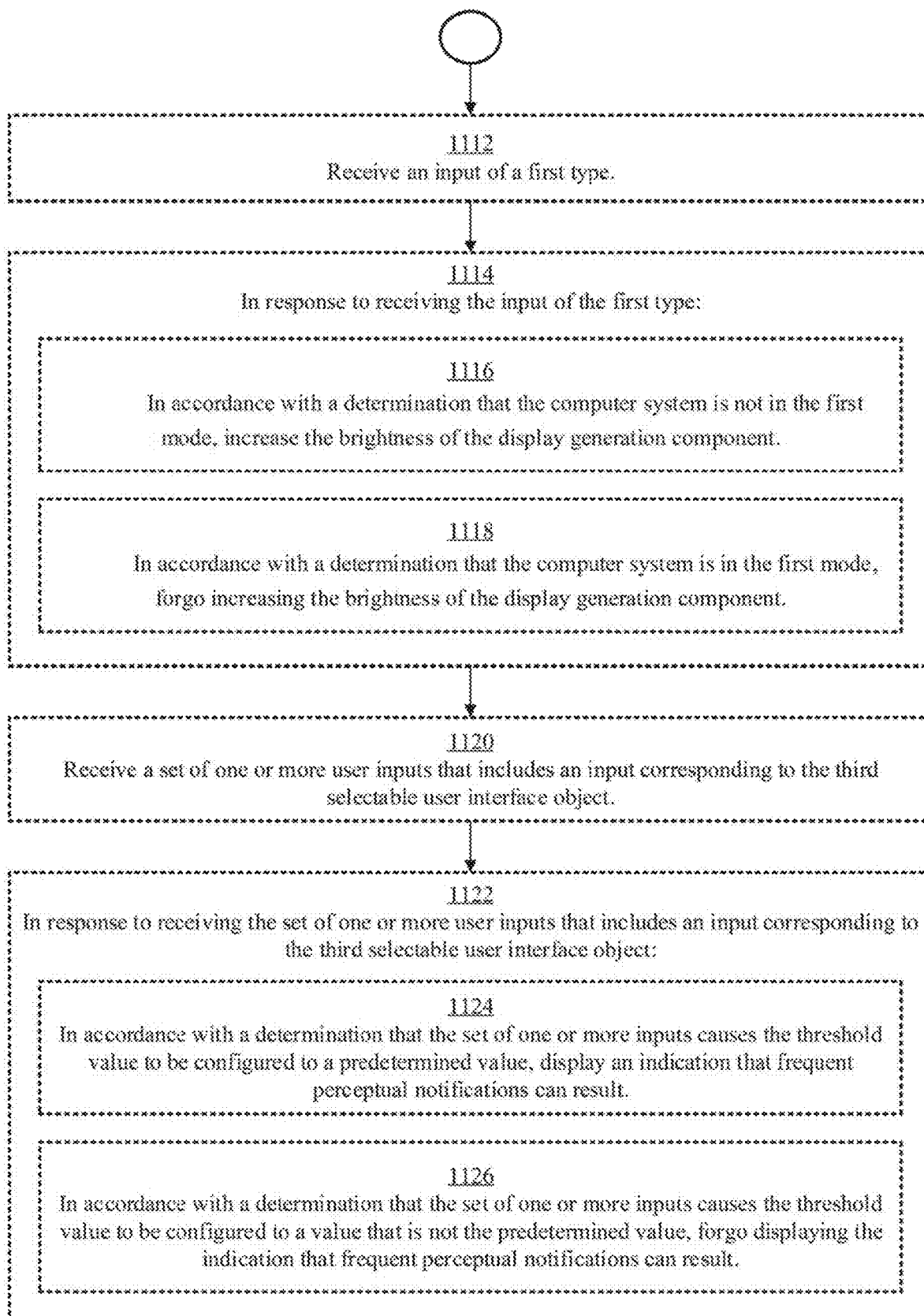
Figure 12D:
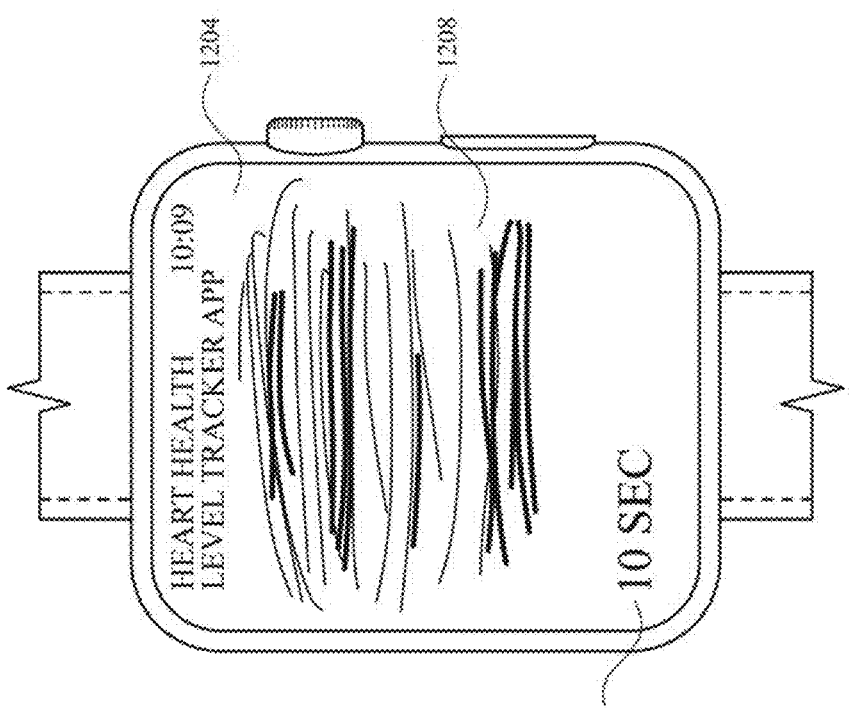
FIGS. 12A-12N and 12Q-12AG illustrate exemplary user interfaces for managing a biometric measurement taken using an electronic device, in accordance with some embodiments.
FIGS. 12O and 12P are flow diagrams illustrating methods for managing prompts and measurements based on position and movement data, respectively.
Figure 12C:
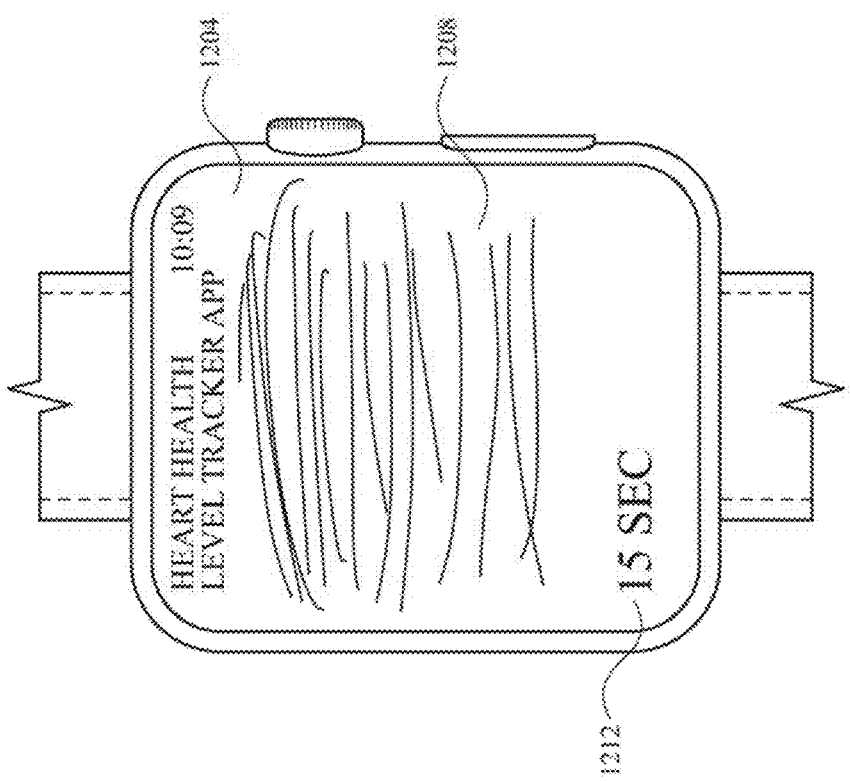
Figure 12N:
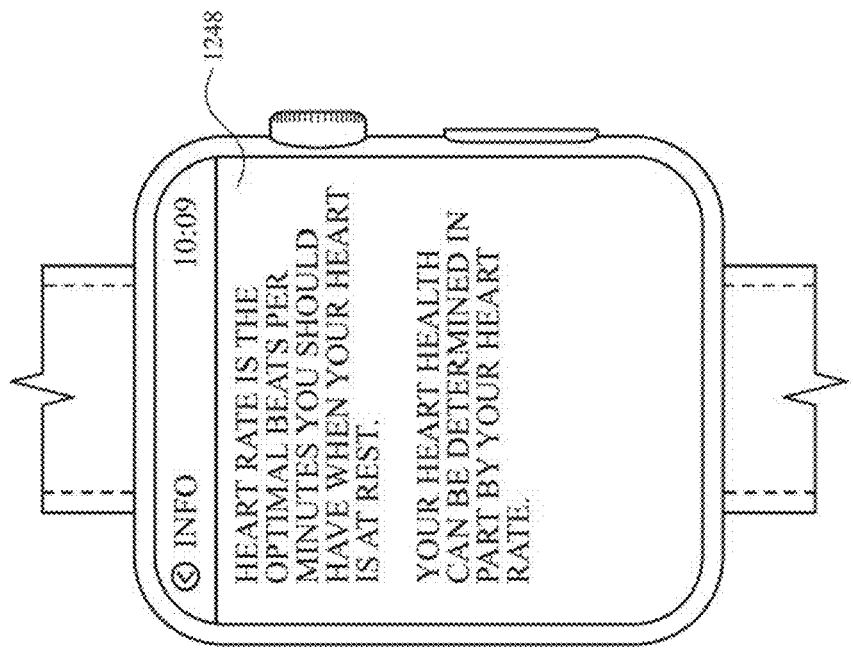
Figure 16B:
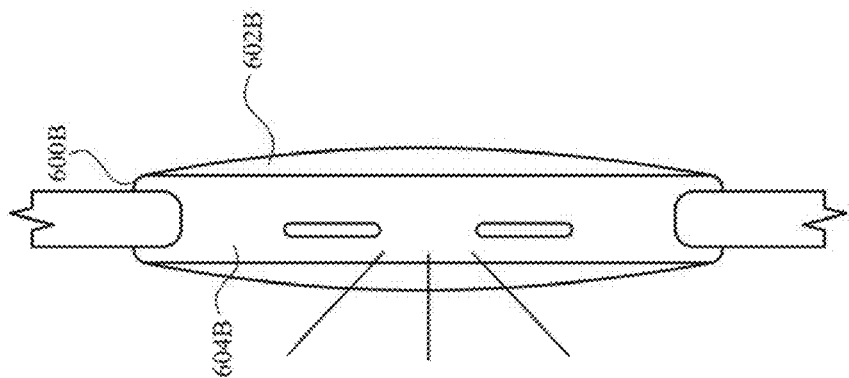
Figure 16A:
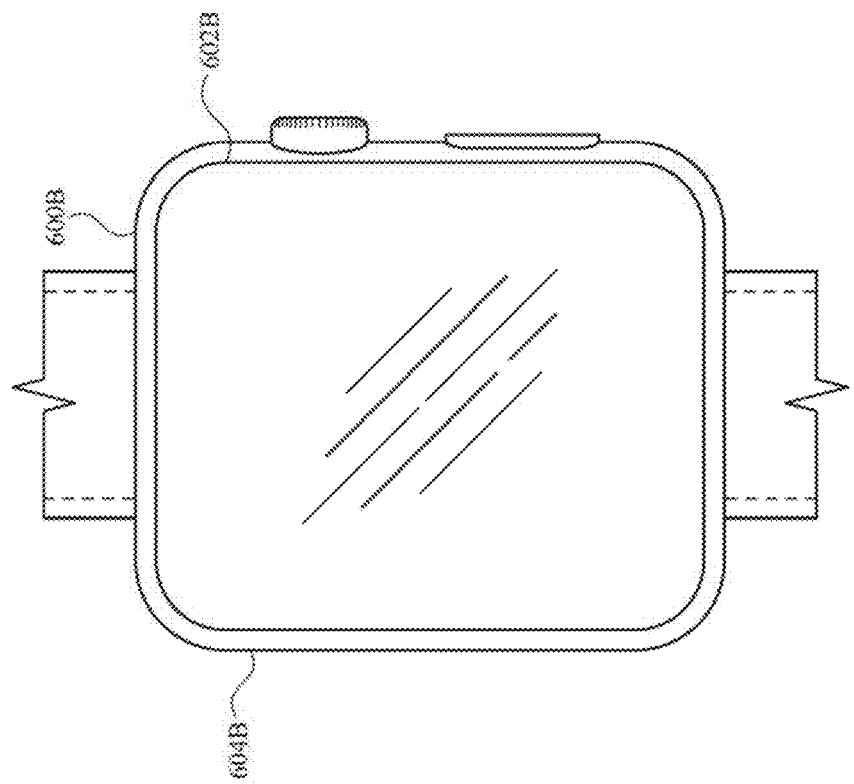
Figure 17B:
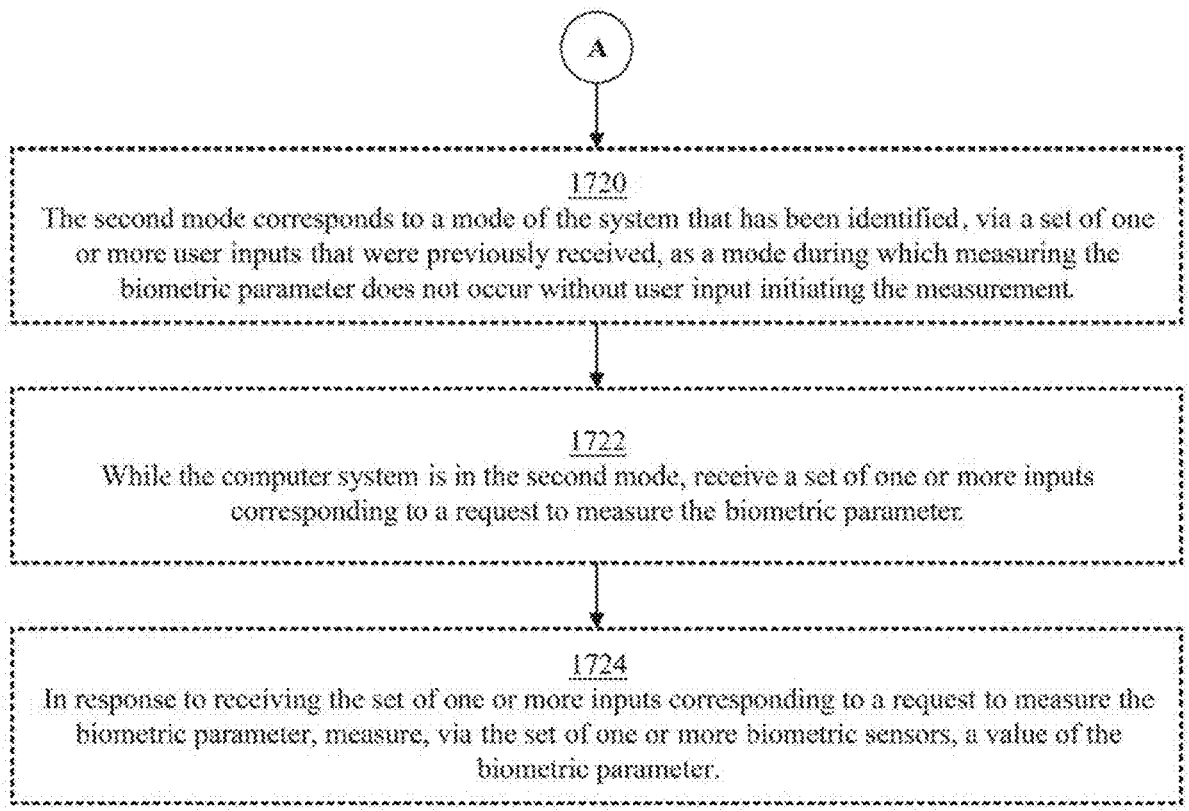

Below, FIGS. 1A-1B, 2, 3, 4A-4B, and 5A-5B provide a description of exemplary devices for performing the techniques for managing and/or presenting health data. FIGS. 6A-6O illustrate exemplary user interfaces for managing health and safety features on an electronic device, in accordance with some embodiments. FIGS. 7A-7C are a flow diagram illustrating a method for managing health and safety features on an electronic device, in accordance with some embodiments. The user interfaces in FIGS. 6A-6O are used to illustrate the processes described below, including the processes in FIGS. 7A-7C. FIGS. 8A-8S illustrate exemplary user interfaces for managing the setup of a health feature on an electronic device, in accordance with some embodiments. FIGS. 9A-9C are a flow diagram illustrating a method for managing the setup of a health feature on an electronic device, in accordance with some embodiments. The user interfaces in FIGS. 8A-8S are used to illustrate the processes described below, including the processes in FIGS. 9A-9C. FIGS. 10A-10V illustrate exemplary user interfaces for managing background health measurements on an electronic device, in accordance with some embodiments. FIGS. 11A-11B are a flow diagram illustrating a method for managing background health measurements on an electronic device, in accordance with some embodiments. The user interfaces in FIGS. 10A-10V are used to illustrate the processes described below, including the processes in FIGS. 11A-11B. FIGS. 12A-12N and 12Q-12AG illustrate exemplary user interfaces for managing a biometric measurement taken using an electronic device, in accordance with some embodiments. FIGS. 12O and 12P are flow diagrams illustrating methods for managing prompts and measurements based on position and movement data, respectively. FIGS. 13A-13B are a flow diagram illustrating a method for managing a biometric measurement taken using an electronic device, in accordance with some embodiments. The user interfaces in FIGS. 12A-12N and 12Q-12AG are used to illustrate the processes described below, including the processes in FIGS. 12O-12P and 13A-13B. FIGS. 14A-14I illustrate exemplary user interfaces for providing results for captured health information on an electronic device, in accordance with some embodiments. FIGS. 15A-15B are a flow diagram illustrating a method for providing results for captured health information on an electronic device, in accordance with some embodiments. The user interfaces in FIGS. 14A-14I are used to illustrate the processes described below, including the processes in FIGS. 15A-15B. FIGS. 16A-16C illustrate exemplary user interfaces for managing background health measurements on an electronic device, in accordance with some embodiments. FIGS. 17A-17B are a flow diagram illustrating a method for managing background health measurements on an electronic device, in accordance with some embodiments. The user interfaces in FIGS. 16A-16C are used to illustrate the processes described below, including the processes in FIGS. 17A-17B.

Although the following description uses terms "first," "second," etc. to describe various elements, these elements should not be limited by the terms. These terms are only used to distinguish one element from another. For example, a first touch could be termed a second touch, and, similarly, a second touch could be termed a first touch, without departing from the scope of the various described embodiments. The first touch and the second touch are both touches, but they are not the same touch.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

Embodiments of electronic devices, user interfaces for such devices, and associated processes for using such devices are described. In some embodiments, the device is a portable communications device, such as a mobile telephone, that also contains other functions, such as PDA and/or music player functions. Exemplary embodiments of portable multifunction devices include, without limitation, the iPhone®, iPod Touch®, and iPad® devices from Apple Inc. of Cupertino, Calif. Other portable electronic devices, such as laptops or tablet computers with touch-sensitive surfaces (e.g., touch screen displays and/or touchpads), are, optionally, used. It should also be understood that, in some embodiments, the device is not a portable communications device, but is a desktop computer with a touch-sensitive surface (e.g., a touch screen display and/or a touchpad). In some embodiments, the electronic device is a computer system that is in communication (e.g., via wireless communication, via wired communication) with a display generation component. The display generation component is configured to provide visual output, such as display via a CRT display, display via an LED display, or display via image projection. In some embodiments, the display generation component is integrated with the computer system. In some embodiments, the display generation component is separate from the computer system. As used herein, "displaying" content includes causing to display the content (e.g., video data rendered or decoded by display controller 156) by transmitting, via a wired or wireless connection, data (e.g., image data or video data) to an integrated or external display generation component to visually produce the content.

In the discussion that follows, an electronic device that includes a display and a touch-sensitive surface is described. It should be understood, however, that the electronic device optionally includes one or more other physical user-interface devices, such as a physical keyboard, a mouse, and/or a joystick.

The device typically supports a variety of applications, such as one or more of the following: a drawing application, a presentation application, a word processing application, a website creation application, a disk authoring application, a spreadsheet application, a gaming application, a telephone application, a video conferencing application, an e-mail application, an instant messaging application, a workout support application, a photo management application, a digital camera application, a digital video camera application, a web browsing application, a digital music player application, and/or a digital video player application.

The various applications that are executed on the device optionally use at least one common physical user-interface device, such as the touch-sensitive surface. One or more functions of the touch-sensitive surface as well as corresponding information displayed on the device are, optionally, adjusted and/or varied from one application to the next and/or within a respective application. In this way, a common physical architecture (such as the touch-sensitive surface) of the device optionally supports the variety of applications with user interfaces that are intuitive and transparent to the user.

Figure 1A:
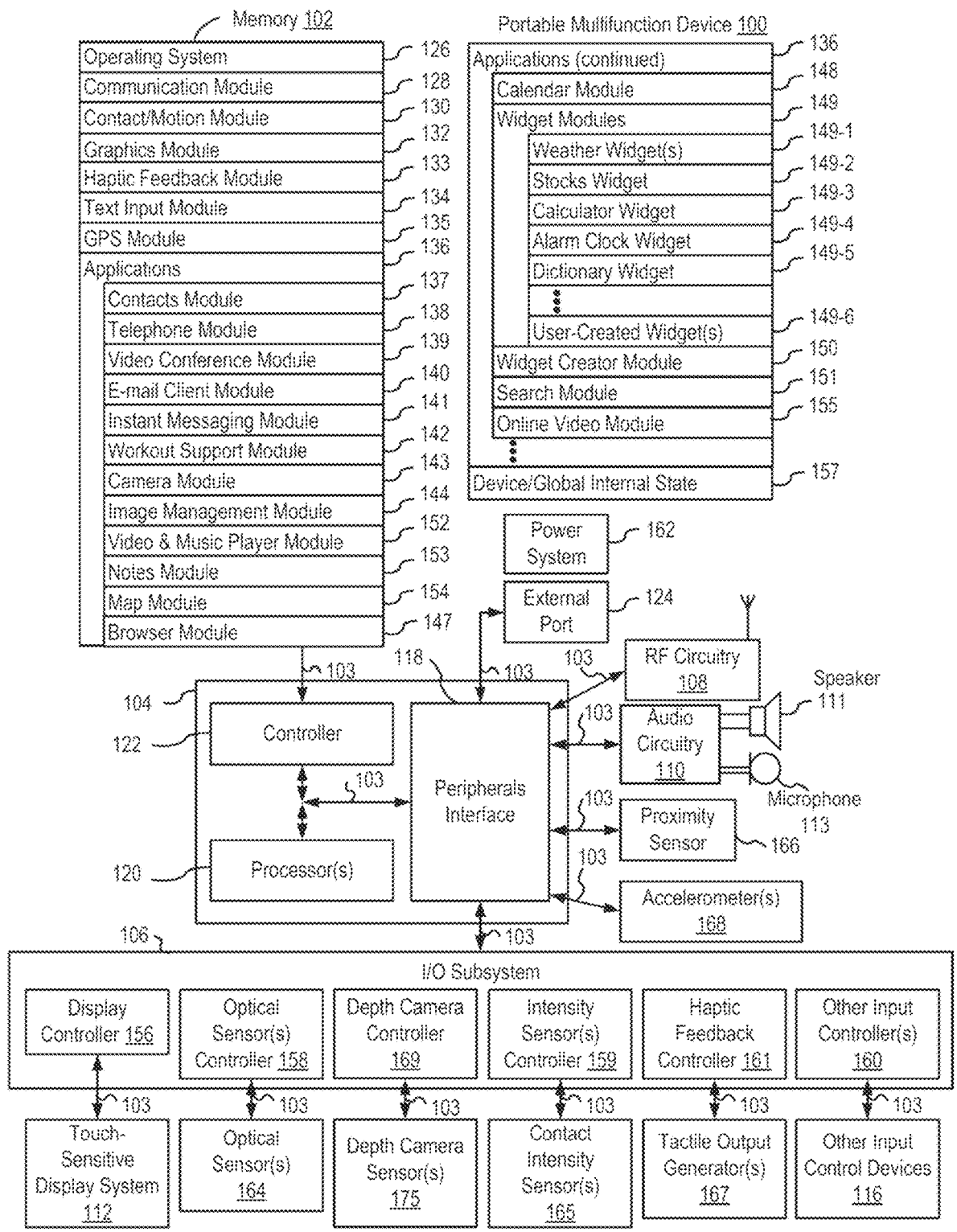
FIG. 1A is a block diagram illustrating a portable multifunction device with a touch-sensitive display in accordance with some embodiments.

Attention is now directed toward embodiments of portable devices with touch-sensitive displays. FIG. 1A is a block diagram illustrating portable multifunction device 100 with touch-sensitive display system 112 in accordance with some embodiments. Touch-sensitive display 112 is sometimes called a "touch screen" for convenience and is sometimes known as or called a "touch-sensitive display system." Device 100 includes memory 102 (which optionally includes one or more computer-readable storage mediums), memory controller 122, one or more processing units (CPUs) 120, peripherals interface 118, RF circuitry 108, audio circuitry 110, speaker 111, microphone 113, input/output (I/O) subsystem 106, other input control devices 116, and external port 124. Device 100 optionally includes one or more optical sensors 164. Device 100 optionally includes one or more contact intensity sensors 165 for detecting intensity of contacts on device 100 (e.g., a touch-sensitive surface such as touch-sensitive display system 112 of device 100). Device 100 optionally includes one or more tactile output generators 167 for generating tactile outputs on device 100 (e.g., generating tactile outputs on a touch-sensitive surface such as touch-sensitive display system 112 of device 100 or touchpad 355 of device 300). These components optionally communicate over one or more communication buses or signal lines 103.

As used in the specification and claims, the term "intensity" of a contact on a touch-sensitive surface refers to the force or pressure (force per unit area) of a contact (e.g., a finger contact) on the touch-sensitive surface, or to a substitute (proxy) for the force or pressure of a contact on the touch-sensitive surface. The intensity of a contact has a range of values that includes at least four distinct values and more typically includes hundreds of distinct values (e.g., at least 256). Intensity of a contact is, optionally, determined (or measured) using various approaches and various sensors or combinations of sensors. For example, one or more force sensors underneath or adjacent to the touch-sensitive surface are, optionally, used to measure force at various points on the touch-sensitive surface. In some implementations, force measurements from multiple force sensors are combined (e.g., a weighted average) to determine an estimated force of a contact. Similarly, a pressure-sensitive tip of a stylus is, optionally, used to determine a pressure of the stylus on the touch-sensitive surface. Alternatively, the size of the contact area detected on the touch-sensitive surface and/or changes thereto, the capacitance of the touch-sensitive surface proximate to the contact and/or changes thereto, and/or the resistance of the touch-sensitive surface proximate to the contact and/or changes thereto are, optionally, used as a substitute for the force or pressure of the contact on the touch-sensitive surface. In some implementations, the substitute measurements for contact force or pressure are used directly to determine whether an intensity threshold has been exceeded (e.g., the intensity threshold is described in units corresponding to the substitute measurements). In some implementations, the substitute measurements for contact force or pressure are converted to an estimated force or pressure, and the estimated force or pressure is used to determine whether an intensity threshold has been exceeded (e.g., the intensity threshold is a pressure threshold measured in units of pressure). Using the intensity of a contact as an attribute of a user input allows for user access to additional device functionality that may otherwise not be accessible by the user on a reduced-size device with limited real estate for displaying affordances (e.g., on a touch-sensitive display) and/or receiving user input (e.g., via a touch-sensitive display, a touch-sensitive surface, or a physical/mechanical control such as a knob or a button).

As used in the specification and claims, the term "tactile output" refers to physical displacement of a device relative to a previous position of the device, physical displacement of a component (e.g., a touch-sensitive surface) of a device relative to another component (e.g., housing) of the device, or displacement of the component relative to a center of mass of the device that will be detected by a user with the user's sense of touch. For example, in situations where the device or the component of the device is in contact with a surface of a user that is sensitive to touch (e.g., a finger, palm, or other part of a user's hand), the tactile output generated by the physical displacement will be interpreted by the user as a tactile sensation corresponding to a perceived change in physical characteristics of the device or the component of the device. For example, movement of a touch-sensitive surface (e.g., a touch-sensitive display or trackpad) is, optionally, interpreted by the user as a "down click" or "up click" of a physical actuator button. In some cases, a user will feel a tactile sensation such as an "down click" or "up click" even when there is no movement of a physical actuator button associated with the touch-sensitive surface that is physically pressed (e.g., displaced) by the user's movements. As another example, movement of the touch-sensitive surface is, optionally, interpreted or sensed by the user as "roughness" of the touch-sensitive surface, even when there is no change in smoothness of the touch-sensitive surface. While such interpretations of touch by a user will be subject to the individualized sensory perceptions of the user, there are many sensory perceptions of touch that are common to a large majority of users. Thus, when a tactile output is described as corresponding to a particular sensory perception of a user (e.g., an "up click," a "down click," "roughness"), unless otherwise stated, the generated tactile output corresponds to physical displacement of the device or a component thereof that will generate the described sensory perception for a typical (or average) user.

It should be appreciated that device 100 is only one example of a portable multifunction device, and that device 100 optionally has more or fewer components than shown, optionally combines two or more components, or optionally has a different configuration or arrangement of the components. The various components shown in FIG. 1A are implemented in hardware, software, or a combination of both hardware and software, including one or more signal processing and/or application-specific integrated circuits.

Memory 102 optionally includes high-speed random access memory and optionally also includes non-volatile memory, such as one or more magnetic disk storage devices, flash memory devices, or other non-volatile solid-state memory devices. Memory controller 122 optionally controls access to memory 102 by other components of device 100.

Peripherals interface 118 can be used to couple input and output peripherals of the device to CPU 120 and memory 102. The one or more processors 120 run or execute various software programs and/or sets of instructions stored in memory 102 to perform various functions for device 100 and to process data. In some embodiments, peripherals interface 118, CPU 120, and memory controller 122 are, optionally, implemented on a single chip, such as chip 104. In some other embodiments, they are, optionally, implemented on separate chips.

RF (radio frequency) circuitry 108 receives and sends RF signals, also called electromagnetic signals. RF circuitry 108 converts electrical signals to/from electromagnetic signals and communicates with communications networks and other communications devices via the electromagnetic signals. RF circuitry 108 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 108 optionally communicates with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The RF circuitry 108 optionally includes well-known circuitry for detecting near field communication (NFC) fields, such as by a short-range communication radio. The wireless communication optionally uses any of a plurality of communications standards, protocols, and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Bluetooth Low Energy (BTLE), Wireless Fidelity (Wi-Fi) (e.g., IEEE 802.11a, IEEE 802.11b, IEEE 802.11g, IEEE 802.11n, and/or IEEE 802.11ac), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

Audio circuitry 110, speaker 111, and microphone 113 provide an audio interface between a user and device 100. Audio circuitry 110 receives audio data from peripherals interface 118, converts the audio data to an electrical signal, and transmits the electrical signal to speaker 111. Speaker 111 converts the electrical signal to human-audible sound waves. Audio circuitry 110 also receives electrical signals converted by microphone 113 from sound waves. Audio circuitry 110 converts the electrical signal to audio data and transmits the audio data to peripherals interface 118 for processing. Audio data is, optionally, retrieved from and/or transmitted to memory 102 and/or RF circuitry 108 by peripherals interface 118. In some embodiments, audio circuitry 110 also includes a headset jack (e.g., 212, FIG. 2). The headset jack provides an interface between audio circuitry 110 and removable audio input/output peripherals, such as output-only headphones or a headset with both output (e.g., a headphone for one or both ears) and input (e.g., a microphone).

I/O subsystem 106 couples input/output peripherals on device 100, such as touch screen 112 and other input control devices 116, to peripherals interface 118. I/O subsystem 106 optionally includes display controller 156, optical sensor controller 158, depth camera controller 169, intensity sensor controller 159, haptic feedback controller 161, and one or more input controllers 160 for other input or control devices. The one or more input controllers 160 receive/send electrical signals from/to other input control devices 116. The other input control devices 116 optionally include physical buttons (e.g., push buttons, rocker buttons, etc.), dials, slider switches, joysticks, click wheels, and so forth. In some embodiments, input controller(s) 160 are, optionally, coupled to any (or none) of the following: a keyboard, an infrared port, a USB port, and a pointer device such as a mouse. The one or more buttons (e.g., 208, FIG. 2) optionally include an up/down button for volume control of speaker 111 and/or microphone 113. The one or more buttons optionally include a push button (e.g., 206, FIG. 2). In some embodiments, the electronic device is a computer system that is in communication (e.g., via wireless communication, via wired communication) with one or more input devices. In some embodiments, the one or more input devices include a touch-sensitive surface (e.g., a trackpad, as part of a touch-sensitive display). In some embodiments, the one or more input devices include one or more camera sensors (e.g., one or more optical sensors 164 and/or one or more depth camera sensors 175), such as for tracking a user's gestures (e.g., hand gestures) as input. In some embodiments, the one or more input devices are integrated with the computer system. In some embodiments, the one or more input devices are separate from the computer system.

A quick press of the push button optionally disengages a lock of touch screen 112 or optionally begins a process that uses gestures on the touch screen to unlock the device, as described in U.S. patent application Ser. No. 11/322,549, "Unlocking a Device by Performing Gestures on an Unlock Image," filed Dec. 23, 2005, U.S. Pat. No. 7,657,849, which is hereby incorporated by reference in its entirety. A longer press of the push button (e.g., 206) optionally turns power to device 100 on or off. The functionality of one or more of the buttons are, optionally, user-customizable. Touch screen 112 is used to implement virtual or soft buttons and one or more soft keyboards.

Touch-sensitive display 112 provides an input interface and an output interface between the device and a user. Display controller 156 receives and/or sends electrical signals from/to touch screen 112. Touch screen 112 displays visual output to the user. The visual output optionally includes graphics, text, icons, video, and any combination thereof (collectively termed "graphics"). In some embodiments, some or all of the visual output optionally corresponds to user-interface objects.

Touch screen 112 has a touch-sensitive surface, sensor, or set of sensors that accepts input from the user based on haptic and/or tactile contact. Touch screen 112 and display controller 156 (along with any associated modules and/or sets of instructions in memory 102) detect contact (and any movement or breaking of the contact) on touch screen 112 and convert the detected contact into interaction with user-interface objects (e.g., one or more soft keys, icons, web pages, or images) that are displayed on touch screen 112. In an exemplary embodiment, a point of contact between touch screen 112 and the user corresponds to a finger of the user.

Touch screen 112 optionally uses LCD (liquid crystal display) technology, LPD (light emitting polymer display) technology, or LED (light emitting diode) technology, although other display technologies are used in other embodiments. Touch screen 112 and display controller 156 optionally detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with touch screen 112. In an exemplary embodiment, projected mutual capacitance sensing technology is used, such as that found in the iPhone® and iPod Touch® from Apple Inc. of Cupertino, Calif.

A touch-sensitive display in some embodiments of touch screen 112 is, optionally, analogous to the multi-touch sensitive touchpads described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1, each of which is hereby incorporated by reference in its entirety. However, touch screen 112 displays visual output from device 100, whereas touch-sensitive touchpads do not provide visual output.

A touch-sensitive display in some embodiments of touch screen 112 is described in the following applications: (1) U.S. patent application Ser. No. 11/381,313, "Multipoint Touch Surface Controller," filed May 2, 2006; (2) U.S. patent application Ser. No. 10/840,862, "Multipoint Touchscreen," filed May 6, 2004; (3) U.S. patent application Ser. No. 10/903,964, "Gestures For Touch Sensitive Input Devices," filed Jul. 30, 2004; (4) U.S. patent application Ser. No. 11/048,264, "Gestures For Touch Sensitive Input Devices," filed Jan. 31, 2005; (5) U.S. patent application Ser. No. 11/038,590, "Mode-Based Graphical User Interfaces For Touch Sensitive Input Devices," filed Jan. 18, 2005; (6) U.S. patent application Ser. No. 11/228,758, "Virtual Input Device Placement On A Touch Screen User Interface," filed Sep. 16, 2005; (7) U.S. patent application Ser. No. 11/228,700, "Operation Of A Computer With A Touch Screen Interface," filed Sep. 16, 2005; (8) U.S. patent application Ser. No. 11/228,737, "Activating Virtual Keys Of A Touch-Screen Virtual Keyboard," filed Sep. 16, 2005; and (9) U.S. patent application Ser. No. 11/367,749, "Multi-Functional Hand-Held Device," filed Mar. 3, 2006. All of these applications are incorporated by reference herein in their entirety.

Touch screen 112 optionally has a video resolution in excess of 100 dpi. In some embodiments, the touch screen has a video resolution of approximately 160 dpi. The user optionally makes contact with touch screen 112 using any suitable object or appendage, such as a stylus, a finger, and so forth. In some embodiments, the user interface is designed to work primarily with finger-based contacts and gestures, which can be less precise than stylus-based input due to the larger area of contact of a finger on the touch screen. In some embodiments, the device translates the rough finger-based input into a precise pointer/cursor position or command for performing the actions desired by the user.

In some embodiments, in addition to the touch screen, device 100 optionally includes a touchpad for activating or deactivating particular functions. In some embodiments, the touchpad is a touch-sensitive area of the device that, unlike the touch screen, does not display visual output. The touchpad is, optionally, a touch-sensitive surface that is separate from touch screen 112 or an extension of the touch-sensitive surface formed by the touch screen.

Device 100 also includes power system 162 for powering the various components. Power system 162 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

Device 100 optionally also includes one or more optical sensors 164. FIG. 1A shows an optical sensor coupled to optical sensor controller 158 in I/O subsystem 106. Optical sensor 164 optionally includes charge-coupled device (CCD) or complementary metal-oxide semiconductor (CMOS) phototransistors. Optical sensor 164 receives light from the environment, projected through one or more lenses, and converts the light to data representing an image. In conjunction with imaging module 143 (also called a camera module), optical sensor 164 optionally captures still images or video. In some embodiments, an optical sensor is located on the back of device 100, opposite touch screen display 112 on the front of the device so that the touch screen display is enabled for use as a viewfinder for still and/or video image acquisition. In some embodiments, an optical sensor is located on the front of the device so that the user's image is, optionally, obtained for video conferencing while the user views the other video conference participants on the touch screen display. In some embodiments, the position of optical sensor 164 can be changed by the user (e.g., by rotating the lens and the sensor in the device housing) so that a single optical sensor 164 is used along with the touch screen display for both video conferencing and still and/or video image acquisition.

Device 100 optionally also includes one or more depth camera sensors 175. FIG. 1A shows a depth camera sensor coupled to depth camera controller 169 in I/O subsystem 106. Depth camera sensor 175 receives data from the environment to create a three dimensional model of an object (e.g., a face) within a scene from a viewpoint (e.g., a depth camera sensor). In some embodiments, in conjunction with imaging module 143 (also called a camera module), depth camera sensor 175 is optionally used to determine a depth map of different portions of an image captured by the imaging module 143. In some embodiments, a depth camera sensor is located on the front of device 100 so that the user's image with depth information is, optionally, obtained for video conferencing while the user views the other video conference participants on the touch screen display and to capture selfies with depth map data. In some embodiments, the depth camera sensor 175 is located on the back of device, or on the back and the front of the device 100. In some embodiments, the position of depth camera sensor 175 can be changed by the user (e.g., by rotating the lens and the sensor in the device housing) so that a depth camera sensor 175 is used along with the touch screen display for both video conferencing and still and/or video image acquisition.

Device 100 optionally also includes one or more contact intensity sensors 165. FIG. 1A shows a contact intensity sensor coupled to intensity sensor controller 159 in I/O subsystem 106. Contact intensity sensor 165 optionally includes one or more piezoresistive strain gauges, capacitive force sensors, electric force sensors, piezoelectric force sensors, optical force sensors, capacitive touch-sensitive surfaces, or other intensity sensors (e.g., sensors used to measure the force (or pressure) of a contact on a touch-sensitive surface). Contact intensity sensor 165 receives contact intensity information (e.g., pressure information or a proxy for pressure information) from the environment. In some embodiments, at least one contact intensity sensor is collocated with, or proximate to, a touch-sensitive surface (e.g., touch-sensitive display system 112). In some embodiments, at least one contact intensity sensor is located on the back of device 100, opposite touch screen display 112, which is located on the front of device 100.

Device 100 optionally also includes one or more proximity sensors 166. FIG. 1A shows proximity sensor 166 coupled to peripherals interface 118. Alternately, proximity sensor 166 is, optionally, coupled to input controller 160 in I/O subsystem 106. Proximity sensor 166 optionally performs as described in U.S. patent application Ser. No. 11/241,839, "Proximity Detector In Handheld Device"; Ser. No. 11/240,788, "Proximity Detector In Handheld Device"; Ser. No. 11/620,702, "Using Ambient Light Sensor To Augment Proximity Sensor Output"; Ser. No. 11/586,862, "Automated Response To And Sensing Of User Activity In Portable Devices"; and Ser. No. 11/638,251, "Methods And Systems For Automatic Configuration Of Peripherals," which are hereby incorporated by reference in their entirety. In some embodiments, the proximity sensor turns off and disables touch screen 112 when the multifunction device is placed near the user's ear (e.g., when the user is making a phone call).

Device 100 optionally also includes one or more tactile output generators 167. FIG. 1A shows a tactile output generator coupled to haptic feedback controller 161 in I/O subsystem 106. Tactile output generator 167 optionally includes one or more electroacoustic devices such as speakers or other audio components and/or electromechanical devices that convert energy into linear motion such as a motor, solenoid, electroactive polymer, piezoelectric actuator, electrostatic actuator, or other tactile output generating component (e.g., a component that converts electrical signals into tactile outputs on the device). Contact intensity sensor 165 receives tactile feedback generation instructions from haptic feedback module 133 and generates tactile outputs on device 100 that are capable of being sensed by a user of device 100. In some embodiments, at least one tactile output generator is collocated with, or proximate to, a touch-sensitive surface (e.g., touch-sensitive display system 112) and, optionally, generates a tactile output by moving the touch-sensitive surface vertically (e.g., in/out of a surface of device 100) or laterally (e.g., back and forth in the same plane as a surface of device 100). In some embodiments, at least one tactile output generator sensor is located on the back of device 100, opposite touch screen display 112, which is located on the front of device 100.

Device 100 optionally also includes one or more accelerometers 168. FIG. 1A shows accelerometer 168 coupled to peripherals interface 118. Alternately, accelerometer 168 is, optionally, coupled to an input controller 160 in I/O subsystem 106. Accelerometer 168 optionally performs as described in U.S. Patent Publication No. 20050190059, "Acceleration-based Theft Detection System for Portable Electronic Devices," and U.S. Patent Publication No. 20060017692, "Methods And Apparatuses For Operating A Portable Device Based On An Accelerometer," both of which are incorporated by reference herein in their entirety. In some embodiments, information is displayed on the touch screen display in a portrait view or a landscape view based on an analysis of data received from the one or more accelerometers. Device 100 optionally includes, in addition to accelerometer(s) 168, a magnetometer and a GPS (or GLONASS or other global navigation system) receiver for obtaining information concerning the location and orientation (e.g., portrait or landscape) of device 100.

Figure 3:
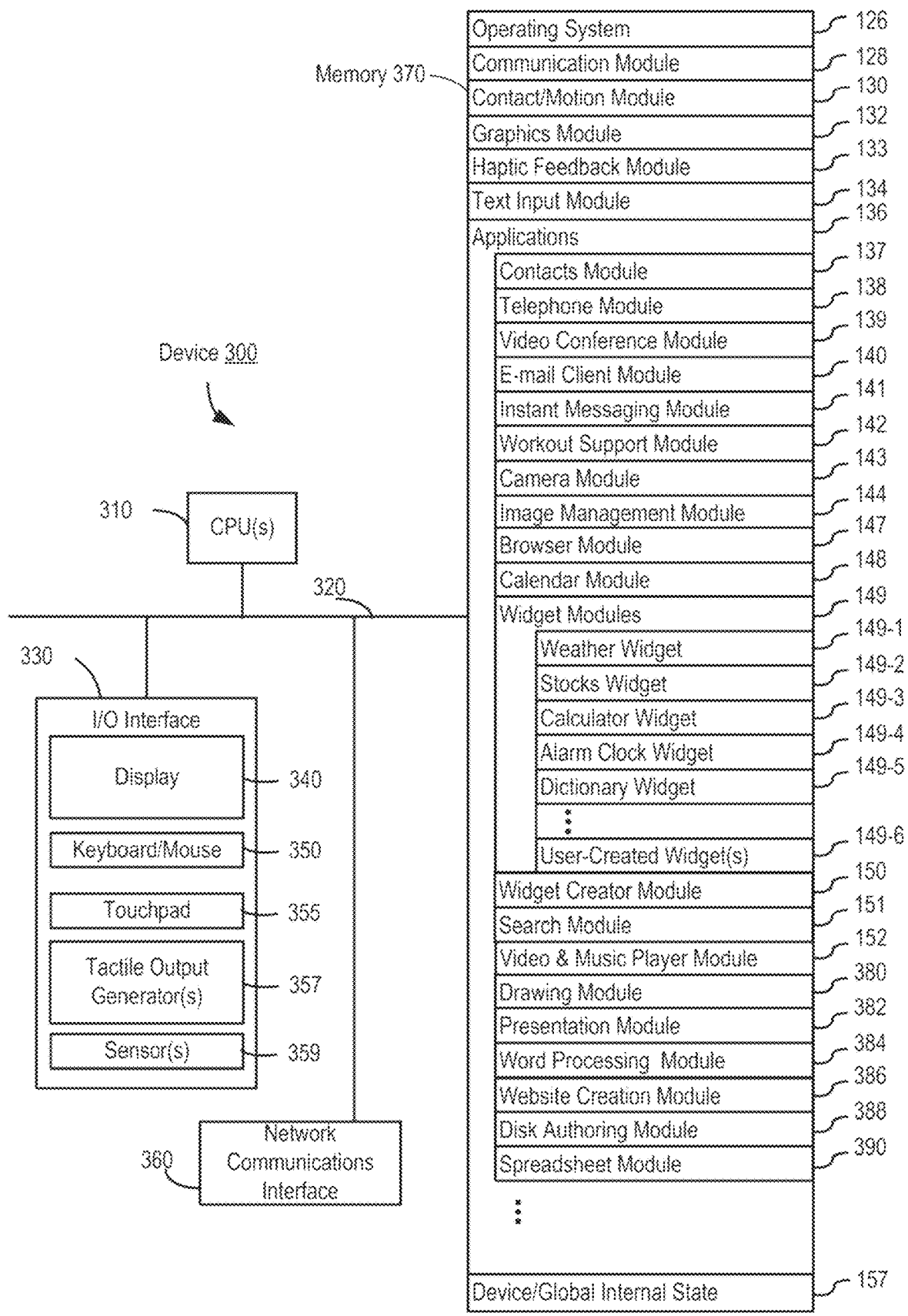
FIG. 3 is a block diagram of an exemplary multifunction device with a display and a touch-sensitive surface in accordance with some embodiments.

In some embodiments, the software components stored in memory 102 include operating system 126, communication module (or set of instructions) 128, contact/motion module (or set of instructions) 130, graphics module (or set of instructions) 132, text input module (or set of instructions) 134, Global Positioning System (GPS) module (or set of instructions) 135, and applications (or sets of instructions) 136. Furthermore, in some embodiments, memory 102 (FIG. 1A) or 370 (FIG. 3) stores device/global internal state 157, as shown in FIGS. 1A and 3. Device/global internal state 157 includes one or more of: active application state, indicating which applications, if any, are currently active; display state, indicating what applications, views or other information occupy various regions of touch screen display 112; sensor state, including information obtained from the device's various sensors and input control devices 116; and location information concerning the device's location and/or attitude.

Operating system 126 (e.g., Darwin, RTXC, LINUX, UNIX, OS X, iOS, WINDOWS, or an embedded operating system such as VxWorks) includes various software components and/or drivers for controlling and managing general system tasks (e.g., memory management, storage device control, power management, etc.) and facilitates communication between various hardware and software components.

Communication module 128 facilitates communication with other devices over one or more external ports 124 and also includes various software components for handling data received by RF circuitry 108 and/or external port 124. External port 124 (e.g., Universal Serial Bus (USB), FIREWIRE, etc.) is adapted for coupling directly to other devices or indirectly over a network (e.g., the Internet, wireless LAN, etc.). In some embodiments, the external port is a multi-pin (e.g., 30-pin) connector that is the same as, or similar to and/or compatible with, the 30-pin connector used on iPod® (trademark of Apple Inc.) devices.

Contact/motion module 130 optionally detects contact with touch screen 112 (in conjunction with display controller 156) and other touch-sensitive devices (e.g., a touchpad or physical click wheel). Contact/motion module 130 includes various software components for performing various operations related to detection of contact, such as determining if contact has occurred (e.g., detecting a finger-down event), determining an intensity of the contact (e.g., the force or pressure of the contact or a substitute for the force or pressure of the contact), determining if there is movement of the contact and tracking the movement across the touch-sensitive surface (e.g., detecting one or more finger-dragging events), and determining if the contact has ceased (e.g., detecting a finger-up event or a break in contact). Contact/motion module 130 receives contact data from the touch-sensitive surface. Determining movement of the point of contact, which is represented by a series of contact data, optionally includes determining speed (magnitude), velocity (magnitude and direction), and/or an acceleration (a change in magnitude and/or direction) of the point of contact. These operations are, optionally, applied to single contacts (e.g., one finger contacts) or to multiple simultaneous contacts (e.g., "multitouch"/multiple finger contacts). In some embodiments, contact/motion module 130 and display controller 156 detect contact on a touchpad.

In some embodiments, contact/motion module 130 uses a set of one or more intensity thresholds to determine whether an operation has been performed by a user (e.g., to determine whether a user has "clicked" on an icon). In some embodiments, at least a subset of the intensity thresholds are determined in accordance with software parameters (e.g., the intensity thresholds are not determined by the activation thresholds of particular physical actuators and can be adjusted without changing the physical hardware of device 100). For example, a mouse "click" threshold of a trackpad or touch screen display can be set to any of a large range of predefined threshold values without changing the trackpad or touch screen display hardware. Additionally, in some implementations, a user of the device is provided with software settings for adjusting one or more of the set of intensity thresholds (e.g., by adjusting individual intensity thresholds and/or by adjusting a plurality of intensity thresholds at once with a system-level click "intensity" parameter).

Contact/motion module 130 optionally detects a gesture input by a user. Different gestures on the touch-sensitive surface have different contact patterns (e.g., different motions, timings, and/or intensities of detected contacts). Thus, a gesture is, optionally, detected by detecting a particular contact pattern. For example, detecting a finger tap gesture includes detecting a finger-down event followed by detecting a finger-up (liftoff) event at the same position (or substantially the same position) as the finger-down event (e.g., at the position of an icon). As another example, detecting a finger swipe gesture on the touch-sensitive surface includes detecting a finger-down event followed by detecting one or more finger-dragging events, and subsequently followed by detecting a finger-up (liftoff) event.

Graphics module 132 includes various known software components for rendering and displaying graphics on touch screen 112 or other display, including components for changing the visual impact (e.g., brightness, transparency, saturation, contrast, or other visual property) of graphics that are displayed. As used herein, the term "graphics" includes any object that can be displayed to a user, including, without limitation, text, web pages, icons (such as user-interface objects including soft keys), digital images, videos, animations, and the like.

In some embodiments, graphics module 132 stores data representing graphics to be used. Each graphic is, optionally, assigned a corresponding code. Graphics module 132 receives, from applications etc., one or more codes specifying graphics to be displayed along with, if necessary, coordinate data and other graphic property data, and then generates screen image data to output to display controller 156.

Haptic feedback module 133 includes various software components for generating instructions used by tactile output generator(s) 167 to produce tactile outputs at one or more locations on device 100 in response to user interactions with device 100.

Text input module 134, which is, optionally, a component of graphics module 132, provides soft keyboards for entering text in various applications (e.g., contacts 137, e-mail 140, IM 141, browser 147, and any other application that needs text input).

GPS module 135 determines the location of the device and provides this information for use in various applications (e.g., to telephone 138 for use in location-based dialing; to camera 143 as picture/video metadata; and to applications that provide location-based services such as weather widgets, local yellow page widgets, and map/navigation widgets).

Applications 136 optionally include the following modules (or sets of instructions), or a subset or superset thereof:

Contacts module 137 (sometimes called an address book or contact list);
Telephone module 138;
Video conference module 139;
E-mail client module 140;
Instant messaging (IM) module 141;
Workout support module 142;
Camera module 143 for still and/or video images;
Image management module 144;
Video player module;
Music player module;
Browser module 147;
Calendar module 148;
Widget modules 149, which optionally include one or more of: weather widget 149-1, stocks widget 149-2, calculator widget 149-3, alarm clock widget 149-4, dictionary widget 149-5, and other widgets obtained by the user, as well as user-created widgets 149-6;
Widget creator module 150 for making user-created widgets 149-6;
Search module 151;
Video and music player module 152, which merges video player module and music player module;
Notes module 153;
Map module 154; and/or
Online video module 155.

Examples of other applications 136 that are, optionally, stored in memory 102 include other word processing applications, other image editing applications, drawing applications, presentation applications, JAVA-enabled applications, encryption, digital rights management, voice recognition, and voice replication.

In conjunction with touch screen 112, display controller 156, contact/motion module 130, graphics module 132, and text input module 134, contacts module 137 are, optionally, used to manage an address book or contact list (e.g., stored in application internal state 192 of contacts module 137 in memory 102 or memory 370), including: adding name(s) to the address book; deleting name(s) from the address book; associating telephone number(s), e-mail address(es), physical address(es) or other information with a name; associating an image with a name; categorizing and sorting names; providing telephone numbers or e-mail addresses to initiate and/or facilitate communications by telephone 138, video conference module 139, e-mail 140, or IM 141; and so forth.

In conjunction with RF circuitry 108, audio circuitry 110, speaker 111, microphone 113, touch screen 112, display controller 156, contact/motion module 130, graphics module 132, and text input module 134, telephone module 138 are optionally, used to enter a sequence of characters corresponding to a telephone number, access one or more telephone numbers in contacts module 137, modify a telephone number that has been entered, dial a respective telephone number, conduct a conversation, and disconnect or hang up when the conversation is completed. As noted above, the wireless communication optionally uses any of a plurality of communications standards, protocols, and technologies.

In conjunction with RF circuitry 108, audio circuitry 110, speaker 111, microphone 113, touch screen 112, display controller 156, optical sensor 164, optical sensor controller 158, contact/motion module 130, graphics module 132, text input module 134, contacts module 137, and telephone module 138, video conference module 139 includes executable instructions to initiate, conduct, and terminate a video conference between a user and one or more other participants in accordance with user instructions.

In conjunction with RF circuitry 108, touch screen 112, display controller 156, contact/motion module 130, graphics module 132, and text input module 134, e-mail client module 140 includes executable instructions to create, send, receive, and manage e-mail in response to user instructions. In conjunction with image management module 144, e-mail client module 140 makes it very easy to create and send e-mails with still or video images taken with camera module 143.

In conjunction with RF circuitry 108, touch screen 112, display controller 156, contact/motion module 130, graphics module 132, and text input module 134, the instant messaging module 141 includes executable instructions to enter a sequence of characters corresponding to an instant message, to modify previously entered characters, to transmit a respective instant message (for example, using a Short Message Service (SMS) or Multimedia Message Service (MMS) protocol for telephony-based instant messages or using XMPP, SIMPLE, or IMPS for Internet-based instant messages), to receive instant messages, and to view received instant messages. In some embodiments, transmitted and/or received instant messages optionally include graphics, photos, audio files, video files and/or other attachments as are supported in an MMS and/or an Enhanced Messaging Service (EMS). As used herein, "instant messaging" refers to both telephony-based messages (e.g., messages sent using SMS or MMS) and Internet-based messages (e.g., messages sent using XMPP, SIMPLE, or IMPS).

In conjunction with RF circuitry 108, touch screen 112, display controller 156, contact/motion module 130, graphics module 132, text input module 134, GPS module 135, map module 154, and music player module, workout support module 142 includes executable instructions to create workouts (e.g., with time, distance, and/or calorie burning goals); communicate with workout sensors (sports devices); receive workout sensor data; calibrate sensors used to monitor a workout; select and play music for a workout; and display, store, and transmit workout data.

In conjunction with touch screen 112, display controller 156, optical sensor(s) 164, optical sensor controller 158, contact/motion module 130, graphics module 132, and image management module 144, camera module 143 includes executable instructions to capture still images or video (including a video stream) and store them into memory 102, modify characteristics of a still image or video, or delete a still image or video from memory 102.

In conjunction with touch screen 112, display controller 156, contact/motion module 130, graphics module 132, text input module 134, and camera module 143, image management module 144 includes executable instructions to arrange, modify (e.g., edit), or otherwise manipulate, label, delete, present (e.g., in a digital slide show or album), and store still and/or video images.

In conjunction with RF circuitry 108, touch screen 112, display controller 156, contact/motion module 130, graphics module 132, and text input module 134, browser module 147 includes executable instructions to browse the Internet in accordance with user instructions, including searching, linking to, receiving, and displaying web pages or portions thereof, as well as attachments and other files linked to web pages.

In conjunction with RF circuitry 108, touch screen 112, display controller 156, contact/motion module 130, graphics module 132, text input module 134, e-mail client module 140, and browser module 147, calendar module 148 includes executable instructions to create, display, modify, and store calendars and data associated with calendars (e.g., calendar entries, to-do lists, etc.) in accordance with user instructions.

In conjunction with RF circuitry 108, touch screen 112, display controller 156, contact/motion module 130, graphics module 132, text input module 134, and browser module 147, widget modules 149 are mini-applications that are, optionally, downloaded and used by a user (e.g., weather widget 149-1, stocks widget 149-2, calculator widget 149-3, alarm clock widget 149-4, and dictionary widget 149-5) or created by the user (e.g., user-created widget 149-6). In some embodiments, a widget includes an HTML (Hypertext Markup Language) file, a CSS (Cascading Style Sheets) file, and a JavaScript file. In some embodiments, a widget includes an XML (Extensible Markup Language) file and a JavaScript file (e.g., Yahoo! Widgets).

In conjunction with RF circuitry 108, touch screen 112, display controller 156, contact/motion module 130, graphics module 132, text input module 134, and browser module 147, the widget creator module 150 are, optionally, used by a user to create widgets (e.g., turning a user-specified portion of a web page into a widget).

In conjunction with touch screen 112, display controller 156, contact/motion module 130, graphics module 132, and text input module 134, search module 151 includes executable instructions to search for text, music, sound, image, video, and/or other files in memory 102 that match one or more search criteria (e.g., one or more user-specified search terms) in accordance with user instructions.

In conjunction with touch screen 112, display controller 156, contact/motion module 130, graphics module 132, audio circuitry 110, speaker 111, RF circuitry 108, and browser module 147, video and music player module 152 includes executable instructions that allow the user to download and play back recorded music and other sound files stored in one or more file formats, such as MP3 or AAC files, and executable instructions to display, present, or otherwise play back videos (e.g., on touch screen 112 or on an external, connected display via external port 124). In some embodiments, device 100 optionally includes the functionality of an MP3 player, such as an iPod (trademark of Apple Inc.).

In conjunction with touch screen 112, display controller 156, contact/motion module 130, graphics module 132, and text input module 134, notes module 153 includes executable instructions to create and manage notes, to-do lists, and the like in accordance with user instructions.

In conjunction with RF circuitry 108, touch screen 112, display controller 156, contact/motion module 130, graphics module 132, text input module 134, GPS module 135, and browser module 147, map module 154 are, optionally, used to receive, display, modify, and store maps and data associated with maps (e.g., driving directions, data on stores and other points of interest at or near a particular location, and other location-based data) in accordance with user instructions.

In conjunction with touch screen 112, display controller 156, contact/motion module 130, graphics module 132, audio circuitry 110, speaker 111, RF circuitry 108, text input module 134, e-mail client module 140, and browser module 147, online video module 155 includes instructions that allow the user to access, browse, receive (e.g., by streaming and/or download), play back (e.g., on the touch screen or on an external, connected display via external port 124), send an e-mail with a link to a particular online video, and otherwise manage online videos in one or more file formats, such as H.264. In some embodiments, instant messaging module 141, rather than e-mail client module 140, is used to send a link to a particular online video. Additional description of the online video application can be found in U.S. Provisional Patent Application No. 60/936,562, "Portable Multifunction Device, Method, and Graphical User Interface for Playing Online Videos," filed Jun. 20, 2007, and U.S. patent application Ser. No. 11/968,067, "Portable Multifunction Device, Method, and Graphical User Interface for Playing Online Videos," filed Dec. 31, 2007, the contents of which are hereby incorporated by reference in their entirety.

Each of the above-identified modules and applications corresponds to a set of executable instructions for performing one or more functions described above and the methods described in this application (e.g., the computer-implemented methods and other information processing methods described herein). These modules (e.g., sets of instructions) need not be implemented as separate software programs, procedures, or modules, and thus various subsets of these modules are, optionally, combined or otherwise rearranged in various embodiments. For example, video player module is, optionally, combined with music player module into a single module (e.g., video and music player module 152, FIG. 1A). In some embodiments, memory 102 optionally stores a subset of the modules and data structures identified above. Furthermore, memory 102 optionally stores additional modules and data structures not described above.

In some embodiments, device 100 is a device where operation of a predefined set of functions on the device is performed exclusively through a touch screen and/or a touchpad. By using a touch screen and/or a touchpad as the primary input control device for operation of device 100, the number of physical input control devices (such as push buttons, dials, and the like) on device 100 is, optionally, reduced.

The predefined set of functions that are performed exclusively through a touch screen and/or a touchpad optionally include navigation between user interfaces. In some embodiments, the touchpad, when touched by the user, navigates device 100 to a main, home, or root menu from any user interface that is displayed on device 100. In such embodiments, a "menu button" is implemented using a touchpad. In some other embodiments, the menu button is a physical push button or other physical input control device instead of a touchpad.

Figure 1B:
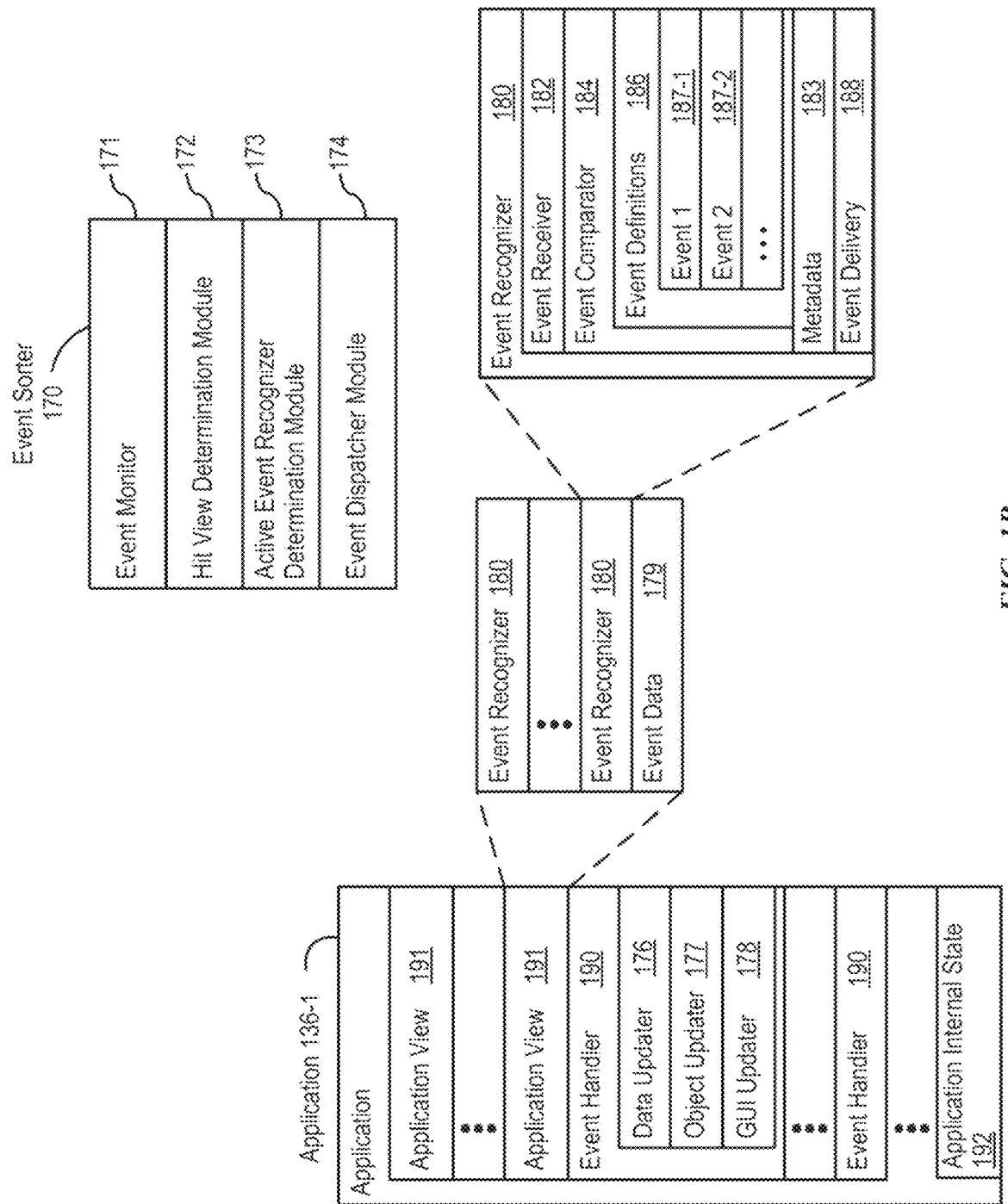
FIG. 1B is a block diagram illustrating exemplary components for event handling in accordance with some embodiments.

FIG. 1B is a block diagram illustrating exemplary components for event handling in accordance with some embodiments. In some embodiments, memory 102 (FIG. 1A) or 370 (FIG. 3) includes event sorter 170 (e.g., in operating system 126) and a respective application 136-1 (e.g., any of the aforementioned applications 137-151, 155, 380-390).

Event sorter 170 receives event information and determines the application 136-1 and application view 191 of application 136-1 to which to deliver the event information. Event sorter 170 includes event monitor 171 and event dispatcher module 174. In some embodiments, application 136-1 includes application internal state 192, which indicates the current application view(s) displayed on touch-sensitive display 112 when the application is active or executing. In some embodiments, device/global internal state 157 is used by event sorter 170 to determine which application(s) is (are) currently active, and application internal state 192 is used by event sorter 170 to determine application views 191 to which to deliver event information.

In some embodiments, application internal state 192 includes additional information, such as one or more of: resume information to be used when application 136-1 resumes execution, user interface state information that indicates information being displayed or that is ready for display by application 136-1, a state queue for enabling the user to go back to a prior state or view of application 136-1, and a redo/undo queue of previous actions taken by the user.

Event monitor 171 receives event information from peripherals interface 118. Event information includes information about a sub-event (e.g., a user touch on touch-sensitive display 112, as part of a multi-touch gesture). Peripherals interface 118 transmits information it receives from I/O subsystem 106 or a sensor, such as proximity sensor 166, accelerometer(s) 168, and/or microphone 113 (through audio circuitry 110). Information that peripherals interface 118 receives from I/O subsystem 106 includes information from touch-sensitive display 112 or a touch-sensitive surface.

In some embodiments, event monitor 171 sends requests to the peripherals interface 118 at predetermined intervals. In response, peripherals interface 118 transmits event information. In other embodiments, peripherals interface 118 transmits event information only when there is a significant event (e.g., receiving an input above a predetermined noise threshold and/or for more than a predetermined duration).

In some embodiments, event sorter 170 also includes a hit view determination module 172 and/or an active event recognizer determination module 173.

Hit view determination module 172 provides software procedures for determining where a sub-event has taken place within one or more views when touch-sensitive display 112 displays more than one view. Views are made up of controls and other elements that a user can see on the display.

Another aspect of the user interface associated with an application is a set of views, sometimes herein called application views or user interface windows, in which information is displayed and touch-based gestures occur. The application views (of a respective application) in which a touch is detected optionally correspond to programmatic levels within a programmatic or view hierarchy of the application. For example, the lowest level view in which a touch is detected is, optionally, called the hit view, and the set of events that are recognized as proper inputs are, optionally, determined based, at least in part, on the hit view of the initial touch that begins a touch-based gesture.

Hit view determination module 172 receives information related to sub-events of a touch-based gesture. When an application has multiple views organized in a hierarchy, hit view determination module 172 identifies a hit view as the lowest view in the hierarchy which should handle the sub-event. In most circumstances, the hit view is the lowest level view in which an initiating sub-event occurs (e.g., the first sub-event in the sequence of sub-events that form an event or potential event). Once the hit view is identified by the hit view determination module 172, the hit view typically receives all sub-events related to the same touch or input source for which it was identified as the hit view.

Active event recognizer determination module 173 determines which view or views within a view hierarchy should receive a particular sequence of sub-events. In some embodiments, active event recognizer determination module 173 determines that only the hit view should receive a particular sequence of sub-events. In other embodiments, active event recognizer determination module 173 determines that all views that include the physical location of a sub-event are actively involved views, and therefore determines that all actively involved views should receive a particular sequence of sub-events. In other embodiments, even if touch sub-events were entirely confined to the area associated with one particular view, views higher in the hierarchy would still remain as actively involved views.

Event dispatcher module 174 dispatches the event information to an event recognizer (e.g., event recognizer 180). In embodiments including active event recognizer determination module 173, event dispatcher module 174 delivers the event information to an event recognizer determined by active event recognizer determination module 173. In some embodiments, event dispatcher module 174 stores in an event queue the event information, which is retrieved by a respective event receiver 182.

In some embodiments, operating system 126 includes event sorter 170. Alternatively, application 136-1 includes event sorter 170. In yet other embodiments, event sorter 170 is a stand-alone module, or a part of another module stored in memory 102, such as contact/motion module 130.

In some embodiments, application 136-1 includes a plurality of event handlers 190 and one or more application views 191, each of which includes instructions for handling touch events that occur within a respective view of the application's user interface. Each application view 191 of the application 136-1 includes one or more event recognizers 180. Typically, a respective application view 191 includes a plurality of event recognizers 180. In other embodiments, one or more of event recognizers 180 are part of a separate module, such as a user interface kit or a higher level object from which application 136-1 inherits methods and other properties. In some embodiments, a respective event handler 190 includes one or more of: data updater 176, object updater 177, GUI updater 178, and/or event data 179 received from event sorter 170. Event handler 190 optionally utilizes or calls data updater 176, object updater 177, or GUI updater 178 to update the application internal state 192. Alternatively, one or more of the application views 191 include one or more respective event handlers 190. Also, in some embodiments, one or more of data updater 176, object updater 177, and GUI updater 178 are included in a respective application view 191.

A respective event recognizer 180 receives event information (e.g., event data 179) from event sorter 170 and identifies an event from the event information. Event recognizer 180 includes event receiver 182 and event comparator 184. In some embodiments, event recognizer 180 also includes at least a subset of: metadata 183, and event delivery instructions 188 (which optionally include sub-event delivery instructions).

Event receiver 182 receives event information from event sorter 170. The event information includes information about a sub-event, for example, a touch or a touch movement. Depending on the sub-event, the event information also includes additional information, such as location of the sub-event. When the sub-event concerns motion of a touch, the event information optionally also includes speed and direction of the sub-event. In some embodiments, events include rotation of the device from one orientation to another (e.g., from a portrait orientation to a landscape orientation, or vice versa), and the event information includes corresponding information about the current orientation (also called device attitude) of the device.

Event comparator 184 compares the event information to predefined event or sub-event definitions and, based on the comparison, determines an event or sub-event, or determines or updates the state of an event or sub-event. In some embodiments, event comparator 184 includes event definitions 186. Event definitions 186 contain definitions of events (e.g., predefined sequences of sub-events), for example, event 1 (187-1), event 2 (187-2), and others. In some embodiments, sub-events in an event (187) include, for example, touch begin, touch end, touch movement, touch cancellation, and multiple touching. In one example, the definition for event 1 (187-1) is a double tap on a displayed object. The double tap, for example, comprises a first touch (touch begin) on the displayed object for a predetermined phase, a first liftoff (touch end) for a predetermined phase, a second touch (touch begin) on the displayed object for a predetermined phase, and a second liftoff (touch end) for a predetermined phase. In another example, the definition for event 2 (187-2) is a dragging on a displayed object. The dragging, for example, comprises a touch (or contact) on the displayed object for a predetermined phase, a movement of the touch across touch-sensitive display 112, and liftoff of the touch (touch end). In some embodiments, the event also includes information for one or more associated event handlers 190.

In some embodiments, event definition 187 includes a definition of an event for a respective user-interface object. In some embodiments, event comparator 184 performs a hit test to determine which user-interface object is associated with a sub-event. For example, in an application view in which three user-interface objects are displayed on touch-sensitive display 112, when a touch is detected on touch-sensitive display 112, event comparator 184 performs a hit test to determine which of the three user-interface objects is associated with the touch (sub-event). If each displayed object is associated with a respective event handler 190, the event comparator uses the result of the hit test to determine which event handler 190 should be activated. For example, event comparator 184 selects an event handler associated with the sub-event and the object triggering the hit test.

In some embodiments, the definition for a respective event (187) also includes delayed actions that delay delivery of the event information until after it has been determined whether the sequence of sub-events does or does not correspond to the event recognizer's event type.

When a respective event recognizer 180 determines that the series of sub-events do not match any of the events in event definitions 186, the respective event recognizer 180 enters an event impossible, event failed, or event ended state, after which it disregards subsequent sub-events of the touch-based gesture. In this situation, other event recognizers, if any, that remain active for the hit view continue to track and process sub-events of an ongoing touch-based gesture.

In some embodiments, a respective event recognizer 180 includes metadata 183 with configurable properties, flags, and/or lists that indicate how the event delivery system should perform sub-event delivery to actively involved event recognizers. In some embodiments, metadata 183 includes configurable properties, flags, and/or lists that indicate how event recognizers interact, or are enabled to interact, with one another. In some embodiments, metadata 183 includes configurable properties, flags, and/or lists that indicate whether sub-events are delivered to varying levels in the view or programmatic hierarchy.

In some embodiments, a respective event recognizer 180 activates event handler 190 associated with an event when one or more particular sub-events of an event are recognized. In some embodiments, a respective event recognizer 180 delivers event information associated with the event to event handler 190. Activating an event handler 190 is distinct from sending (and deferred sending) sub-events to a respective hit view. In some embodiments, event recognizer 180 throws a flag associated with the recognized event, and event handler 190 associated with the flag catches the flag and performs a predefined process.

In some embodiments, event delivery instructions 188 include sub-event delivery instructions that deliver event information about a sub-event without activating an event handler. Instead, the sub-event delivery instructions deliver event information to event handlers associated with the series of sub-events or to actively involved views. Event handlers associated with the series of sub-events or with actively involved views receive the event information and perform a predetermined process.

In some embodiments, data updater 176 creates and updates data used in application 136-1. For example, data updater 176 updates the telephone number used in contacts module 137, or stores a video file used in video player module. In some embodiments, object updater 177 creates and updates objects used in application 136-1. For example, object updater 177 creates a new user-interface object or updates the position of a user-interface object. GUI updater 178 updates the GUI. For example, GUI updater 178 prepares display information and sends it to graphics module 132 for display on a touch-sensitive display.

In some embodiments, event handler(s) 190 includes or has access to data updater 176, object updater 177, and GUI updater 178. In some embodiments, data updater 176, object updater 177, and GUI updater 178 are included in a single module of a respective application 136-1 or application view 191. In other embodiments, they are included in two or more software modules.

It shall be understood that the foregoing discussion regarding event handling of user touches on touch-sensitive displays also applies to other forms of user inputs to operate multifunction devices 100 with input devices, not all of which are initiated on touch screens. For example, mouse movement and mouse button presses, optionally coordinated with single or multiple keyboard presses or holds; contact movements such as taps, drags, scrolls, etc. on touchpads; pen stylus inputs; movement of the device; oral instructions; detected eye movements; biometric inputs; and/or any combination thereof are optionally utilized as inputs corresponding to sub-events which define an event to be recognized.

Figure 2:
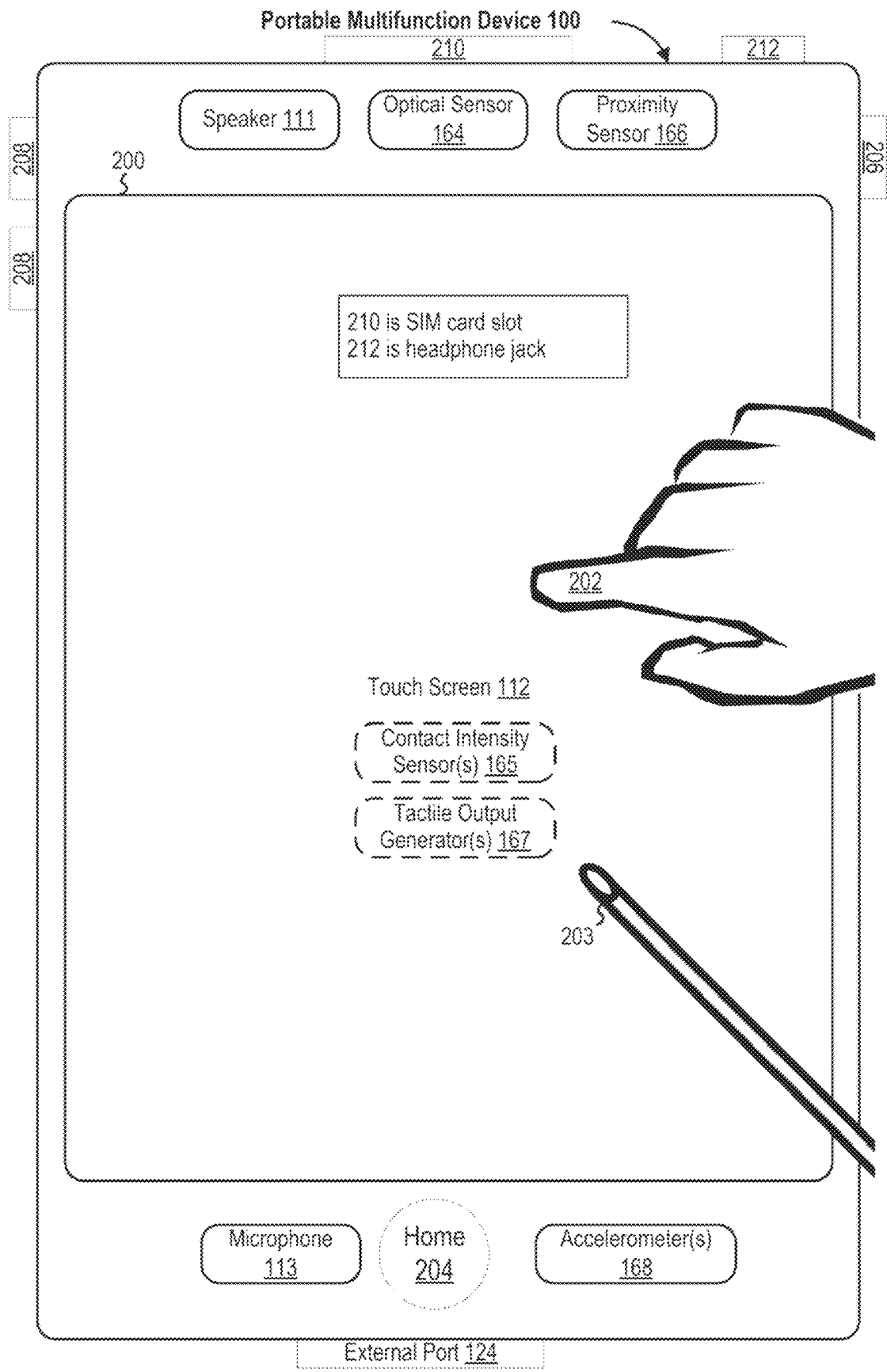
FIG. 2 illustrates a portable multifunction device having a touch screen in accordance with some embodiments.

FIG. 2 illustrates a portable multifunction device 100 having a touch screen 112 in accordance with some embodiments. The touch screen optionally displays one or more graphics within user interface (UI) 200. In this embodiment, as well as others described below, a user is enabled to select one or more of the graphics by making a gesture on the graphics, for example, with one or more fingers 202 (not drawn to scale in the figure) or one or more styluses 203 (not drawn to scale in the figure). In some embodiments, selection of one or more graphics occurs when the user breaks contact with the one or more graphics. In some embodiments, the gesture optionally includes one or more taps, one or more swipes (from left to right, right to left, upward and/or downward), and/or a rolling of a finger (from right to left, left to right, upward and/or downward) that has made contact with device 100. In some implementations or circumstances, inadvertent contact with a graphic does not select the graphic. For example, a swipe gesture that sweeps over an application icon optionally does not select the corresponding application when the gesture corresponding to selection is a tap.

Device 100 optionally also include one or more physical buttons, such as "home" or menu button 204. As described previously, menu button 204 is, optionally, used to navigate to any application 136 in a set of applications that are, optionally, executed on device 100. Alternatively, in some embodiments, the menu button is implemented as a soft key in a GUI displayed on touch screen 112.

In some embodiments, device 100 includes touch screen 112, menu button 204, push button 206 for powering the device on/off and locking the device, volume adjustment button(s) 208, subscriber identity module (SIM) card slot 210, headset jack 212, and docking/charging external port 124. Push button 206 is, optionally, used to turn the power on/off on the device by depressing the button and holding the button in the depressed state for a predefined time interval; to lock the device by depressing the button and releasing the button before the predefined time interval has elapsed; and/or to unlock the device or initiate an unlock process. In an alternative embodiment, device 100 also accepts verbal input for activation or deactivation of some functions through microphone 113. Device 100 also, optionally, includes one or more contact intensity sensors 165 for detecting intensity of contacts on touch screen 112 and/or one or more tactile output generators 167 for generating tactile outputs for a user of device 100.

FIG. 3 is a block diagram of an exemplary multifunction device with a display and a touch-sensitive surface in accordance with some embodiments. Device 300 need not be portable. In some embodiments, device 300 is a laptop computer, a desktop computer, a tablet computer, a multimedia player device, a navigation device, an educational device (such as a child's learning toy), a gaming system, or a control device (e.g., a home or industrial controller). Device 300 typically includes one or more processing units (CPUs) 310, one or more network or other communications interfaces 360, memory 370, and one or more communication buses 320 for interconnecting these components. Communication buses 320 optionally include circuitry (sometimes called a chipset) that interconnects and controls communications between system components. Device 300 includes input/output (I/O) interface 330 comprising display 340, which is typically a touch screen display. I/O interface 330 also optionally includes a keyboard and/or mouse (or other pointing device) 350 and touchpad 355, tactile output generator 357 for generating tactile outputs on device 300 (e.g., similar to tactile output generator(s) 167 described above with reference to FIG. 1A), sensors 359 (e.g., optical, acceleration, proximity, touch-sensitive, and/or contact intensity sensors similar to contact intensity sensor(s) 165 described above with reference to FIG. 1A). Memory 370 includes high-speed random access memory, such as DRAM, SRAM, DDR RAM, or other random access solid state memory devices; and optionally includes non-volatile memory, such as one or more magnetic disk storage devices, optical disk storage devices, flash memory devices, or other non-volatile solid state storage devices. Memory 370 optionally includes one or more storage devices remotely located from CPU(s) 310. In some embodiments, memory 370 stores programs, modules, and data structures analogous to the programs, modules, and data structures stored in memory 102 of portable multifunction device 100 (FIG. 1A), or a subset thereof. Furthermore, memory 370 optionally stores additional programs, modules, and data structures not present in memory 102 of portable multifunction device 100. For example, memory 370 of device 300 optionally stores drawing module 380, presentation module 382, word processing module 384, website creation module 386, disk authoring module 388, and/or spreadsheet module 390, while memory 102 of portable multifunction device 100 (FIG. 1A) optionally does not store these modules.

Each of the above-identified elements in FIG. 3 is, optionally, stored in one or more of the previously mentioned memory devices. Each of the above-identified modules corresponds to a set of instructions for performing a function described above. The above-identified modules or programs (e.g., sets of instructions) need not be implemented as separate software programs, procedures, or modules, and thus various subsets of these modules are, optionally, combined or otherwise rearranged in various embodiments. In some embodiments, memory 370 optionally stores a subset of the modules and data structures identified above. Furthermore, memory 370 optionally stores additional modules and data structures not described above.

Attention is now directed towards embodiments of user interfaces that are, optionally, implemented on, for example, portable multifunction device 100.

Figure 4A:
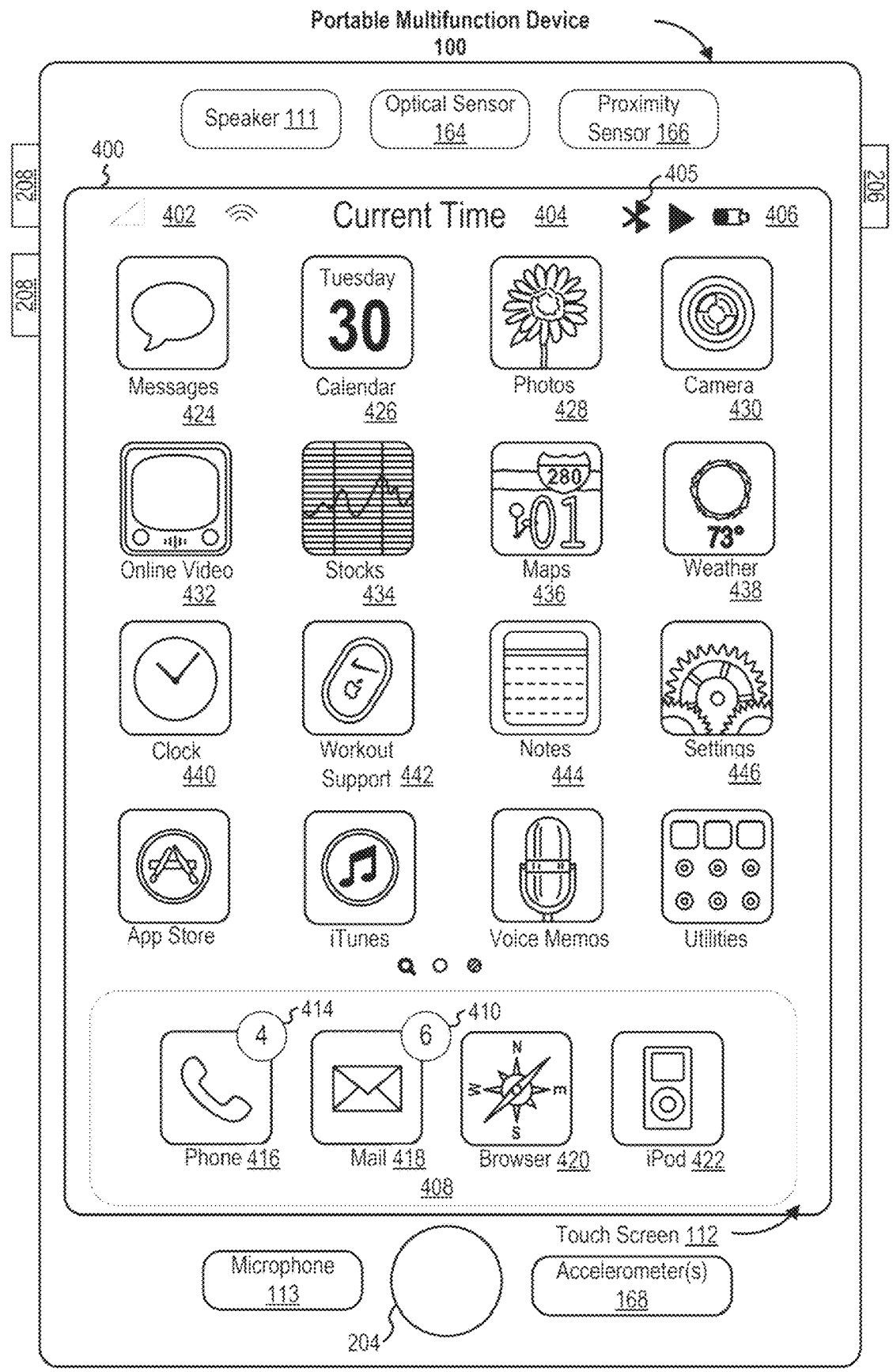
FIG. 4A illustrates an exemplary user interface for a menu of applications on a portable multifunction device in accordance with some embodiments.

FIG. 4A illustrates an exemplary user interface for a menu of applications on portable multifunction device 100 in accordance with some embodiments. Similar user interfaces are, optionally, implemented on device 300. In some embodiments, user interface 400 includes the following elements, or a subset or superset thereof:

Signal strength indicator(s) 402 for wireless communication(s), such as cellular and Wi-Fi signals;
Time 404;
Bluetooth indicator 405;
Battery status indicator 406;
Tray 408 with icons for frequently used applications, such as:
  Icon 416 for telephone module 138, labeled "Phone," which optionally includes an indicator 414 of the number of missed calls or voicemail messages;
  Icon 418 for e-mail client module 140, labeled "Mail," which optionally includes an indicator 410 of the number of unread e-mails;
  Icon 420 for browser module 147, labeled "Browser;" and
  Icon 422 for video and music player module 152, also referred to as iPod (trademark of Apple Inc.) module 152, labeled "iPod;" and
Icons for other applications, such as:
  Icon 424 for IM module 141, labeled "Messages;"
  Icon 426 for calendar module 148, labeled "Calendar;"
  Icon 428 for image management module 144, labeled "Photos;"
  Icon 430 for camera module 143, labeled "Camera;"
  Icon 432 for online video module 155, labeled "Online Video;"
  Icon 434 for stocks widget 149-2, labeled "Stocks;"
  Icon 436 for map module 154, labeled "Maps;"
  Icon 438 for weather widget 149-1, labeled "Weather;"
  Icon 440 for alarm clock widget 149-4, labeled "Clock;"
  Icon 442 for workout support module 142, labeled "Workout Support;"

Icon 444 for notes module 153, labeled "Notes;" and

Icon 446 for a settings application or module, labeled "Settings," which provides access to settings for device 100 and its various applications 136.

It should be noted that the icon labels illustrated in FIG. 4A are merely exemplary. For example, icon 422 for video and music player module 152 is labeled "Music" or "Music Player." Other labels are, optionally, used for various application icons. In some embodiments, a label for a respective application icon includes a name of an application corresponding to the respective application icon. In some embodiments, a label for a particular application icon is distinct from a name of an application corresponding to the particular application icon.

FIG. 4B illustrates an exemplary user interface on a device (e.g., device 300, FIG. 3) with a touch-sensitive surface 451 (e.g., a tablet or touchpad 355, FIG. 3) that is separate from the display 450 (e.g., touch screen display 112). Device 300 also, optionally, includes one or more contact intensity sensors (e.g., one or more of sensors 359) for detecting intensity of contacts on touch-sensitive surface 451 and/or one or more tactile output generators 357 for generating tactile outputs for a user of device 300.

Although some of the examples that follow will be given with reference to inputs on touch screen display 112 (where the touch-sensitive surface and the display are combined), in some embodiments, the device detects inputs on a touch-sensitive surface that is separate from the display, as shown in FIG. 4B. In some embodiments, the touch-sensitive surface (e.g., 451 in FIG. 4B) has a primary axis (e.g., 452 in FIG. 4B) that corresponds to a primary axis (e.g., 453 in FIG. 4B) on the display (e.g., 450). In accordance with these embodiments, the device detects contacts (e.g., 460 and 462 in FIG. 4B) with the touch-sensitive surface 451 at locations that correspond to respective locations on the display (e.g., in FIG. 4B, 460 corresponds to 468 and 462 corresponds to 470). In this way, user inputs (e.g., contacts 460 and 462, and movements thereof) detected by the device on the touch-sensitive surface (e.g., 451 in FIG. 4B) are used by the device to manipulate the user interface on the display (e.g., 450 in FIG. 4B) of the multifunction device when the touch-sensitive surface is separate from the display. It should be understood that similar methods are, optionally, used for other user interfaces described herein.

Additionally, while the following examples are given primarily with reference to finger inputs (e.g., finger contacts, finger tap gestures, finger swipe gestures), it should be understood that, in some embodiments, one or more of the finger inputs are replaced with input from another input device (e.g., a mouse-based input or stylus input). For example, a swipe gesture is, optionally, replaced with a mouse click (e.g., instead of a contact) followed by movement of the cursor along the path of the swipe (e.g., instead of movement of the contact). As another example, a tap gesture is, optionally, replaced with a mouse click while the cursor is located over the location of the tap gesture (e.g., instead of detection of the contact followed by ceasing to detect the contact). Similarly, when multiple user inputs are simultaneously detected, it should be understood that multiple computer mice are, optionally, used simultaneously, or a mouse and finger contacts are, optionally, used simultaneously.

Figure 5A:
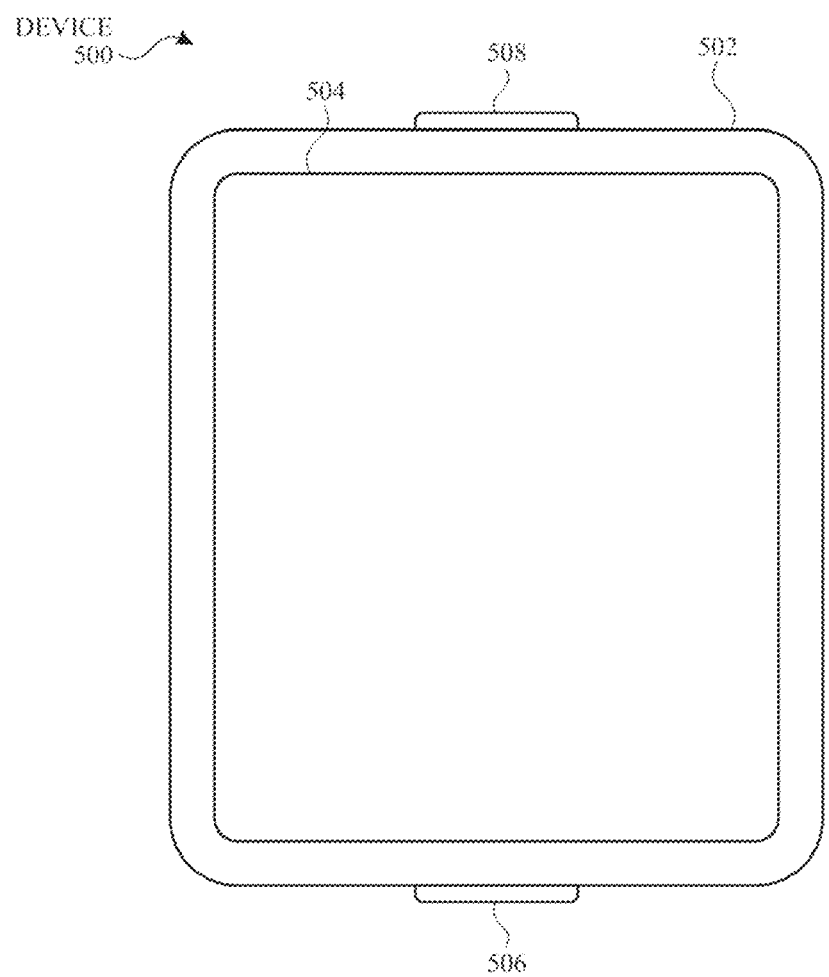
FIG. 5A illustrates a personal electronic device in accordance with some embodiments.

FIG. 5A illustrates exemplary personal electronic device 500. Device 500 includes body 502. In some embodiments, device 500 can include some or all of the features described with respect to devices 100 and 300 (e.g., FIGS. 1A-4B). In some embodiments, device 500 has touch-sensitive display screen 504, hereafter touch screen 504. Alternatively, or in addition to touch screen 504, device 500 has a display and a touch-sensitive surface. As with devices 100 and 300, in some embodiments, touch screen 504 (or the touch-sensitive surface) optionally includes one or more intensity sensors for detecting intensity of contacts (e.g., touches) being applied. The one or more intensity sensors of touch screen 504 (or the touch-sensitive surface) can provide output data that represents the intensity of touches. The user interface of device 500 can respond to touches based on their intensity, meaning that touches of different intensities can invoke different user interface operations on device 500.

Exemplary techniques for detecting and processing touch intensity are found, for example, in related applications: International Patent Application Serial No. PCT/US2013/040061, titled "Device, Method, and Graphical User Interface for Displaying User Interface Objects Corresponding to an Application," filed May 8, 2013, published as WIPO Publication No. WO/2013/169849, and International Patent Application Serial No. PCT/US2013/069483, titled "Device, Method, and Graphical User Interface for Transitioning Between Touch Input to Display Output Relationships," filed Nov. 11, 2013, published as WIPO Publication No. WO/2014/105276, each of which is hereby incorporated by reference in their entirety.

In some embodiments, device 500 has one or more input mechanisms 506 and 508. Input mechanisms 506 and 508, if included, can be physical. Examples of physical input mechanisms include push buttons and rotatable mechanisms. In some embodiments, device 500 has one or more attachment mechanisms. Such attachment mechanisms, if included, can permit attachment of device 500 with, for example, hats, eyewear, earrings, necklaces, shirts, jackets, bracelets, watch straps, chains, trousers, belts, shoes, purses, backpacks, and so forth. These attachment mechanisms permit device 500 to be worn by a user.

Figure 5B:
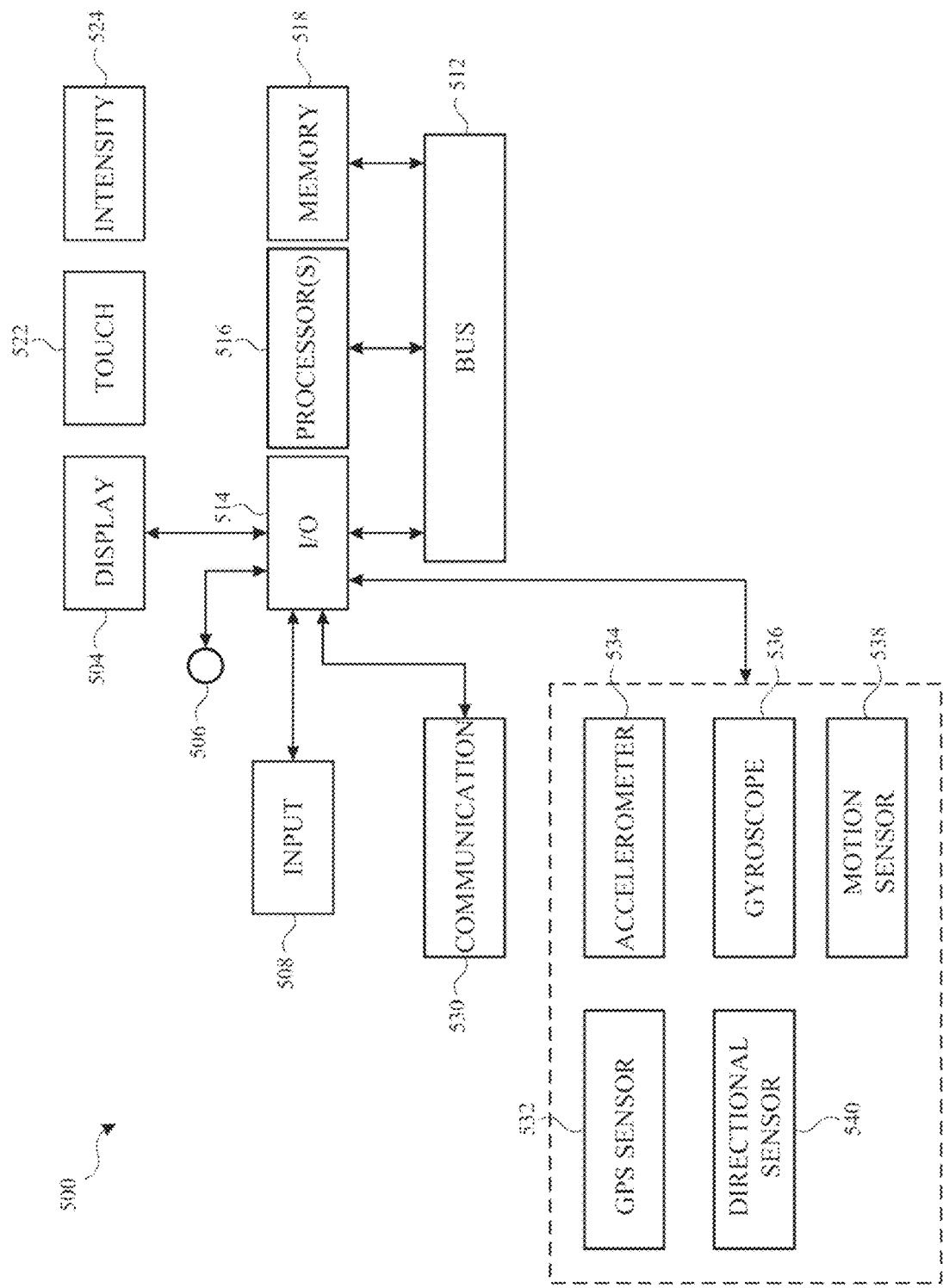
FIG. 5B is a block diagram illustrating a personal electronic device in accordance with some embodiments.

FIG. 5B depicts exemplary personal electronic device 500. In some embodiments, device 500 can include some or all of the components described with respect to FIGS. 1A, 1B, and 3. Device 500 has bus 512 that operatively couples I/O section 514 with one or more computer processors 516 and memory 518. I/O section 514 can be connected to display 504, which can have touch-sensitive component 522 and, optionally, intensity sensor 524 (e.g., contact intensity sensor). In addition, I/O section 514 can be connected with communication unit 530 for receiving application and operating system data, using Wi-Fi, Bluetooth, near field communication (NFC), cellular, and/or other wireless communication techniques. Device 500 can include input mechanisms 506 and/or 508. Input mechanism 506 is, optionally, a rotatable input device or a depressible and rotatable input device, for example. Input mechanism 508 is, optionally, a button, in some examples.

Input mechanism 508 is, optionally, a microphone, in some examples. Personal electronic device 500 optionally includes various sensors, such as GPS sensor 532, accelerometer 534, directional sensor 540 (e.g., compass), gyroscope 536, motion sensor 538, and/or a combination thereof, all of which can be operatively connected to I/O section 514.

Memory 518 of personal electronic device 500 can include one or more non-transitory computer-readable storage mediums, for storing computer-executable instructions, which, when executed by one or more computer processors 516, for example, can cause the computer processors to perform the techniques described below, including processes 700 (FIGS. 7A-7C), 900 (FIGS. 9A-9C), 1100 (FIGS. 11A-11B), 1300 (FIGS. 13A-13B), 1500 (FIGS. 15A-15B), and 1700 (FIGS. 17A-17B). A computer-readable storage medium can be any medium that can tangibly contain or store computer-executable instructions for use by or in connection with the instruction execution system, apparatus, or device. In some examples, the storage medium is a transitory computer-readable storage medium. In some examples, the storage medium is a non-transitory computer-readable storage medium. The non-transitory computer-readable storage medium can include, but is not limited to, magnetic, optical, and/or semiconductor storages. Examples of such storage include magnetic disks, optical discs based on CD, DVD, or Blu-ray technologies, as well as persistent solid-state memory such as flash, solid-state drives, and the like. Personal electronic device 500 is not limited to the components and configuration of FIG. 5B, but can include other or additional components in multiple configurations.

As used here, the term "affordance" refers to a user-interactive graphical user interface object that is, optionally, displayed on the display screen of devices 100, 300, and/or 500 (FIGS. 1A, 3, and 5A-5B). For example, an image (e.g., icon), a button, and text (e.g., hyperlink) each optionally constitute an affordance.

As used herein, the term "focus selector" refers to an input element that indicates a current part of a user interface with which a user is interacting. In some implementations that include a cursor or other location marker, the cursor acts as a "focus selector" so that when an input (e.g., a press input) is detected on a touch-sensitive surface (e.g., touchpad 355 in FIG. 3 or touch-sensitive surface 451 in FIG. 4B) while the cursor is over a particular user interface element (e.g., a button, window, slider, or other user interface element), the particular user interface element is adjusted in accordance with the detected input. In some implementations that include a touch screen display (e.g., touch-sensitive display system 112 in FIG. 1A or touch screen 112 in FIG. 4A) that enables direct interaction with user interface elements on the touch screen display, a detected contact on the touch screen acts as a "focus selector" so that when an input (e.g., a press input by the contact) is detected on the touch screen display at a location of a particular user interface element (e.g., a button, window, slider, or other user interface element), the particular user interface element is adjusted in accordance with the detected input. In some implementations, focus is moved from one region of a user interface to another region of the user interface without corresponding movement of a cursor or movement of a contact on a touch screen display (e.g., by using a tab key or arrow keys to move focus from one button to another button); in these implementations, the focus selector moves in accordance with movement of focus between different regions of the user interface. Without regard to the specific form taken by the focus selector, the focus selector is generally the user interface element (or contact on a touch screen display) that is controlled by the user so as to communicate the user's intended interaction with the user interface (e.g., by indicating, to the device, the element of the user interface with which the user is intending to interact). For example, the location of a focus selector (e.g., a cursor, a contact, or a selection box) over a respective button while a press input is detected on the touch-sensitive surface (e.g., a touchpad or touch screen) will indicate that the user is intending to activate the respective button (as opposed to other user interface elements shown on a display of the device).

As used in the specification and claims, the term "characteristic intensity" of a contact refers to a characteristic of the contact based on one or more intensities of the contact. In some embodiments, the characteristic intensity is based on multiple intensity samples. The characteristic intensity is, optionally, based on a predefined number of intensity samples, or a set of intensity samples collected during a predetermined time period (e.g., 0.05, 0.1, 0.2, 0.5, 1, 2, 5, 10 seconds) relative to a predefined event (e.g., after detecting the contact, prior to detecting liftoff of the contact, before or after detecting a start of movement of the contact, prior to detecting an end of the contact, before or after detecting an increase in intensity of the contact, and/or before or after detecting a decrease in intensity of the contact). A characteristic intensity of a contact is, optionally, based on one or more of: a maximum value of the intensities of the contact, a mean value of the intensities of the contact, an average value of the intensities of the contact, a top 10 percentile value of the intensities of the contact, a value at the half maximum of the intensities of the contact, a value at the 90 percent maximum of the intensities of the contact, or the like. In some embodiments, the duration of the contact is used in determining the characteristic intensity (e.g., when the characteristic intensity is an average of the intensity of the contact over time). In some embodiments, the characteristic intensity is compared to a set of one or more intensity thresholds to determine whether an operation has been performed by a user. For example, the set of one or more intensity thresholds optionally includes a first intensity threshold and a second intensity threshold. In this example, a contact with a characteristic intensity that does not exceed the first threshold results in a first operation, a contact with a characteristic intensity that exceeds the first intensity threshold and does not exceed the second intensity threshold results in a second operation, and a contact with a characteristic intensity that exceeds the second threshold results in a third operation. In some embodiments, a comparison between the characteristic intensity and one or more thresholds is used to determine whether or not to perform one or more operations (e.g., whether to perform a respective operation or forgo performing the respective operation), rather than being used to determine whether to perform a first operation or a second operation.

As used herein, an "installed application" refers to a software application that has been downloaded onto an electronic device (e.g., devices 100, 300, and/or 500) and is ready to be launched (e.g., become opened) on the device. In some embodiments, a downloaded application becomes an installed application by way of an installation program that extracts program portions from a downloaded package and integrates the extracted portions with the operating system of the computer system.

As used herein, the terms "open application" or "executing application" refer to a software application with retained state information (e.g., as part of device/global internal state 157 and/or application internal state 192). An open or executing application is, optionally, any one of the following types of applications:

an active application, which is currently displayed on a display screen of the device that the application is being used on;

a background application (or background processes), which is not currently displayed, but one or more processes for the application are being processed by one or more processors; and a suspended or hibernated application, which is not running, but has state information that is stored in memory (volatile and non-volatile, respectively) and that can be used to resume execution of the application.

As used herein, the term "closed application" refers to software applications without retained state information (e.g., state information for closed applications is not stored in a memory of the device). Accordingly, closing an application includes stopping and/or removing application processes for the application and removing state information for the application from the memory of the device. Generally, opening a second application while in a first application does not close the first application. When the second application is displayed and the first application ceases to be displayed, the first application becomes a background application.

Attention is now directed towards embodiments of user interfaces ("UI") and associated processes that are implemented on an electronic device, such as portable multifunction device 100, device 300, or device 500.

FIGS. 6A-6O illustrate exemplary user interfaces for managing health and safety features on an electronic device, in accordance with some embodiments. The user interfaces in these figures are used to illustrate the processes described below, including the processes in FIGS. 7A-7C.

FIG. 6A illustrates an electronic device 600A (e.g., a smartphone; a smartwatch) with a display generation component 602A (e.g., a display controller, a touch-sensitive display system; a display (e.g., integrated or connected)) and one or more input devices (e.g. gyroscope, accelerometer, microphone, a touch-sensitive surface). In some embodiments, device 600A includes one or more elements or features of device 100, 300, and 500.

In FIG. 6A, device 600A displays, via display generation component 602A, a user interface 610 of a user account page of a health application. The health application collects and presents data on device 600A for health-related functions related to the user account. The health-related functions correspond to applications (e.g., or application features) operating on, or available to operate on, device 600A or operating on, or available to operate on, an external electronic devices, such as a smartwatch that is paired with device 600A (e.g., device 600B first described below with reference to FIG. 8I) or a server. User interface 610 includes a selectable user interface element 612 that, when selected, causes display of the user interface described with reference to FIG. 6B.

In FIG. 6A, while displaying user interface 610, device 600A receives an input 601 (e.g., a touch input; a tap input) directed to selectable user interface element 612.

Figure 6B:
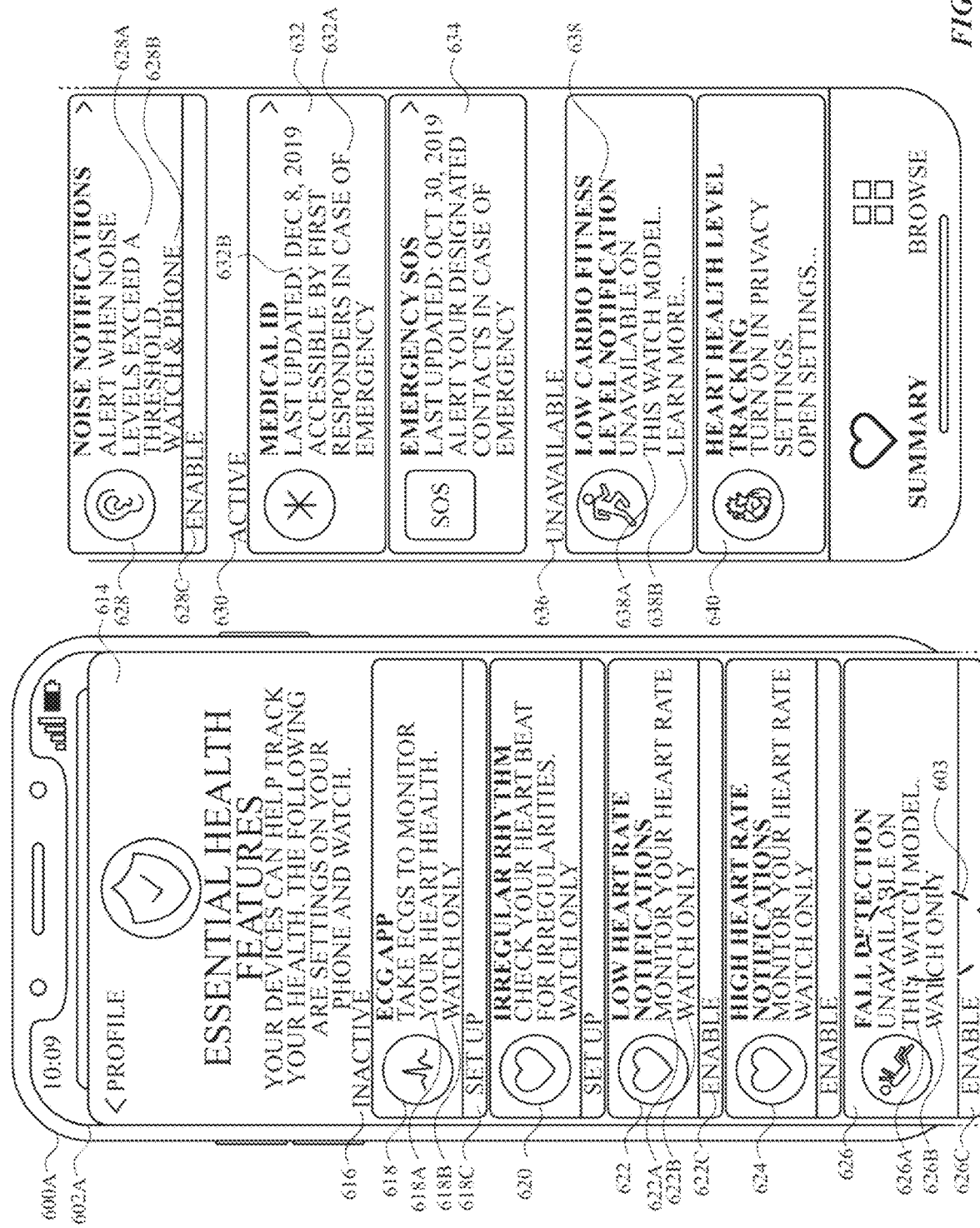

In FIG. 6B, in response to receiving input 601, device 600A displays a user interface 614. The left depiction of device 600A in FIG. 6B displaying user interface 614 corresponds to a top portion of user interface 614 and the right depiction of device 600A in FIG. 6B displaying user interface 614 corresponds to a bottom portion of user interface 614.

User interface 614 includes user interface objects, also referred to herein as platters, (e.g., 618, 620, 622, 624, 626, 628, 632, 634, 638, and 640. Each platter corresponds to a particular health-related function that is currently inactive on, active on, or unavailable to operate on device 600A or the paired smartwatch. Within user interface 614, device 600A arranges the platters based on whether a respective health-related function is inactive on, active on, or unavailable to operate on device 600A or the paired smartwatch. A respective health-related function is inactive on device 600A or the paired smartwatch if the respective health-related function is not enabled or not setup to be used by device 600A or the paired smartwatch. A respective health-related function is active on device 600A or the paired smartwatch if the respective health-related function is (e.g., automatically) being used, continuously and/or intermittently, or is enabled to (e.g., manually) be used, by device 600A or the paired smartwatch. A respective health-related function is unavailable on device 600A or the paired smartwatch if the respective health-related function cannot be enabled or setup to be used by device 600A or the paired smartwatch.

As shown in FIG. 6B, user interface 614 includes a region 616 that includes platters 618, 620, 622, 624, 626, and 628 that correspond to health-related functions that are currently inactive on device 600A and/or on the paired smartwatch. In region 616, a platter includes information about its corresponding application (e.g., information on the function of the application), an indication of the one or more devices (e.g., device 600A and/or the paired smartwatch) for which the respective application (e.g., or application feature) can be activated on, and a type of affordance (e.g., a setup affordance; an enable affordance) for activating the respective application (e.g., or application feature).

For example, platter 618 corresponding to a ECG application includes information 618A about taking ECG measurements to monitor heart health, an indication 618B that the ECG application can only be used via the paired smartwatch, and a setup affordance 618C. Setup affordance 618C, when activated, initiates a setup process for enabling the ECG application for use via the paired smartwatch.

For another example, platter 622 corresponding to a low heart rate notifications application that can measure the user's heart rate, manage the measured heart rate data, and generation low heart notifications based on the heart rate data if the measured heart rate falls below a notification threshold. Platter 622 includes information 622A about monitoring heart rate, an indication 622B that the low heart rate notifications application can be used via the paired smartwatch, and an enable affordance 622C. Affordance 622C, when activated, initiates a simplified (e.g., one-step; expedited) process for activating the low heart rate notifications application.

For another example, platter 626 corresponding to a fall detection application includes information 626A about one or more features of the fall detection application, an indication 626B that the fall detection application can be used via the paired smartwatch, and an enable affordance 626C that, when activated, initiates a simplified (e.g., one-step; expedited) process for activating the fall detection application (e.g., instead of activating a native setup process for the fall detection application).

For another example, platter 628 corresponding to a noise notifications application that can detect noise level of the surrounding environment and generation notifications if the detected noise level is determined to be higher than a noise level threshold. Platter 628 includes information 628A about one or more features of noise notifications, an indication 628A that the noise notifications application can be used via both device 600A and the paired smartwatch, and an enable affordance 628C that, when activated, initiates a simplified (e.g., one-step; expedited) process for activating the noise notifications application on both device 600A and the paired smartwatch.

As also shown in FIG. 6B, user interface 614 includes a region 630 that includes platters 632 and 636 that correspond to health-related functions that are currently active on device 600A and/or on the external device (e.g., device 600B) that is paired with device 600A. In the embodiment of FIG. 6B, region 630 includes platter 632 corresponding to a medical ID application and platter 634 corresponding to an emergency SOS application.

In region 630, a platter includes information about its respective application (e.g., or application feature) and an indication of when the respective application (e.g., or application feature) was last updated (e.g., when one or more settings of the respective application was last updated/changed; when one or more user interface stored in the respective application was last updated/changed; when a version of the respective application was last updated to a newer version).

For example, platter 632 corresponding to the medical ID application includes information 632A about how the medical ID application is used and an indication 632B of a date when the medical ID application and/or information entered by the user in the medical ID application was last updated.

As also shown in FIG. 6B, user interface 614 includes a region 636 that includes platters 638 and 640 that correspond to health-related functions that are unavailable to be operated on device 600A and/or on the paired smartwatch. Region 636 includes platter 638 corresponding to a low cardio fitness level notifications application and platter 640 corresponding to a heart health level tracking application.

In region 636, a platter includes information about why its respective application (e.g., or application feature) is unavailable and a type of affordance for viewing additional information about the application or changing a device setting (e.g., a device privilege, such as a privacy setting) of a respective device to make the application available (e.g., such that the application is available to be activated).

For example, platter 638 corresponding to the low cardio fitness level notifications application includes an indication 638A of why the low cardio fitness level notifications application is not available (e.g., on the paired smartwatch) and a learn more affordance 638B for viewing additional information about the low cardio fitness level notifications application and/or why the application is not available on (e.g., not compatible with) the paired smartwatch.

For another example, platter 640 corresponding to the heart health level tracking application includes an indication 640A that the application is not available because of a device setting (e.g., a privacy setting) and an open settings affordance 640B that, when activated, causes display of a settings user interface from which device settings (e.g., including the privacy setting) can be changed.

In FIG. 6B, while displaying user interface 614, device 600A receives an input 603 directed to enable affordance 626C of platter 626 corresponding to the fall detection application.

Figure 6C:
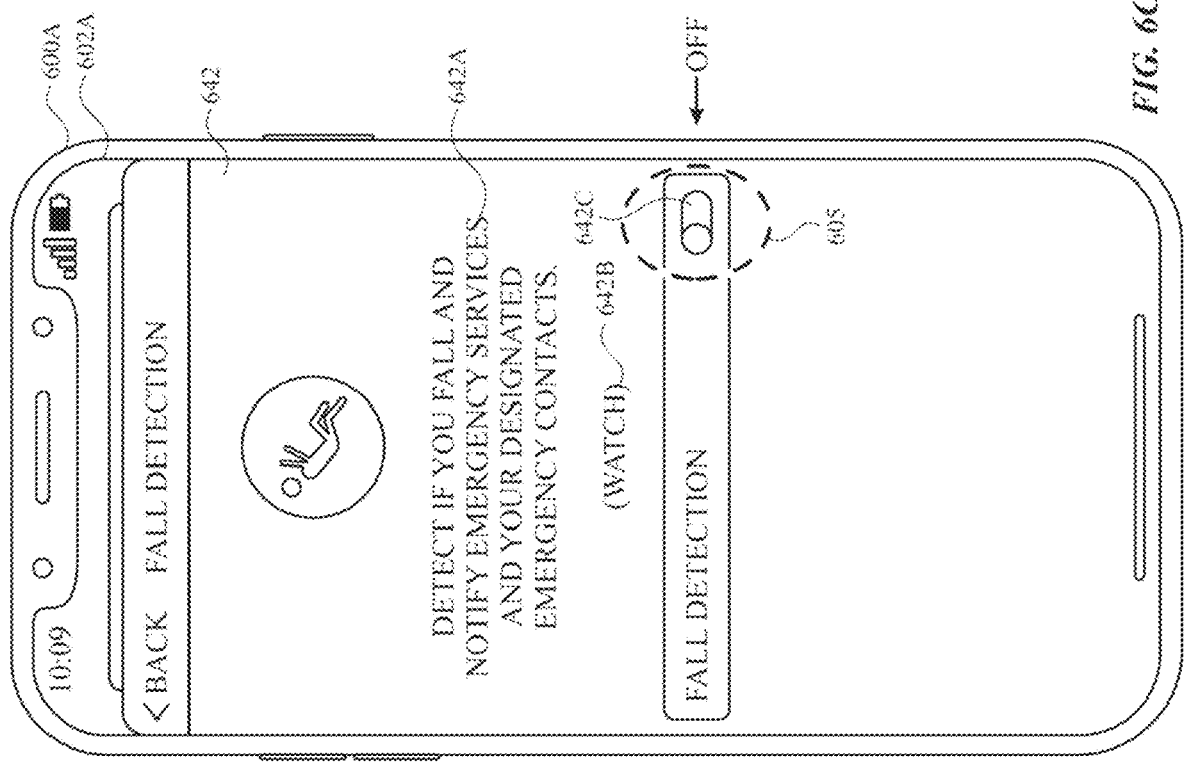

In FIG. 6C, in response to receiving input 603, device 600A displays a user interface 642 for activating the fall detection application. User interface 642 includes information 642A about one or more features of the fall detection application. User interface 642 also includes an indication 642B that the fall detection application is operated via the connected smartwatch (e.g., device 600B) that is paired with device 600A. User interface 642 also includes a selectable toggle button 642C that, when selected, toggles the fall detection application from its current inactive "off" state to an active "on" state, without requiring further inputs or steps. In the inactive "off" state, the fall detection application is not activated, and thus the fall detection feature of the application is not enabled on device 600B or on the paired smartwatch. In the active "on" state, the fall detection application is activated, and thus the fall detection feature of the application is enabled and being used by device 600B or the paired smartwatch. Thus, user interface 642 enables a one-step process for activating the fall detection application.

Also in FIG. 6C, while displaying user interface 642, device 600A receives an input 605 directed to toggle button 642C to activate the fall detection application (e.g., turning the toggle on). In response to receiving input 605 directed to activating the fall detection application, device 600A causes the fall detection application to be activated on the paired smartwatch.

Figure 6D:
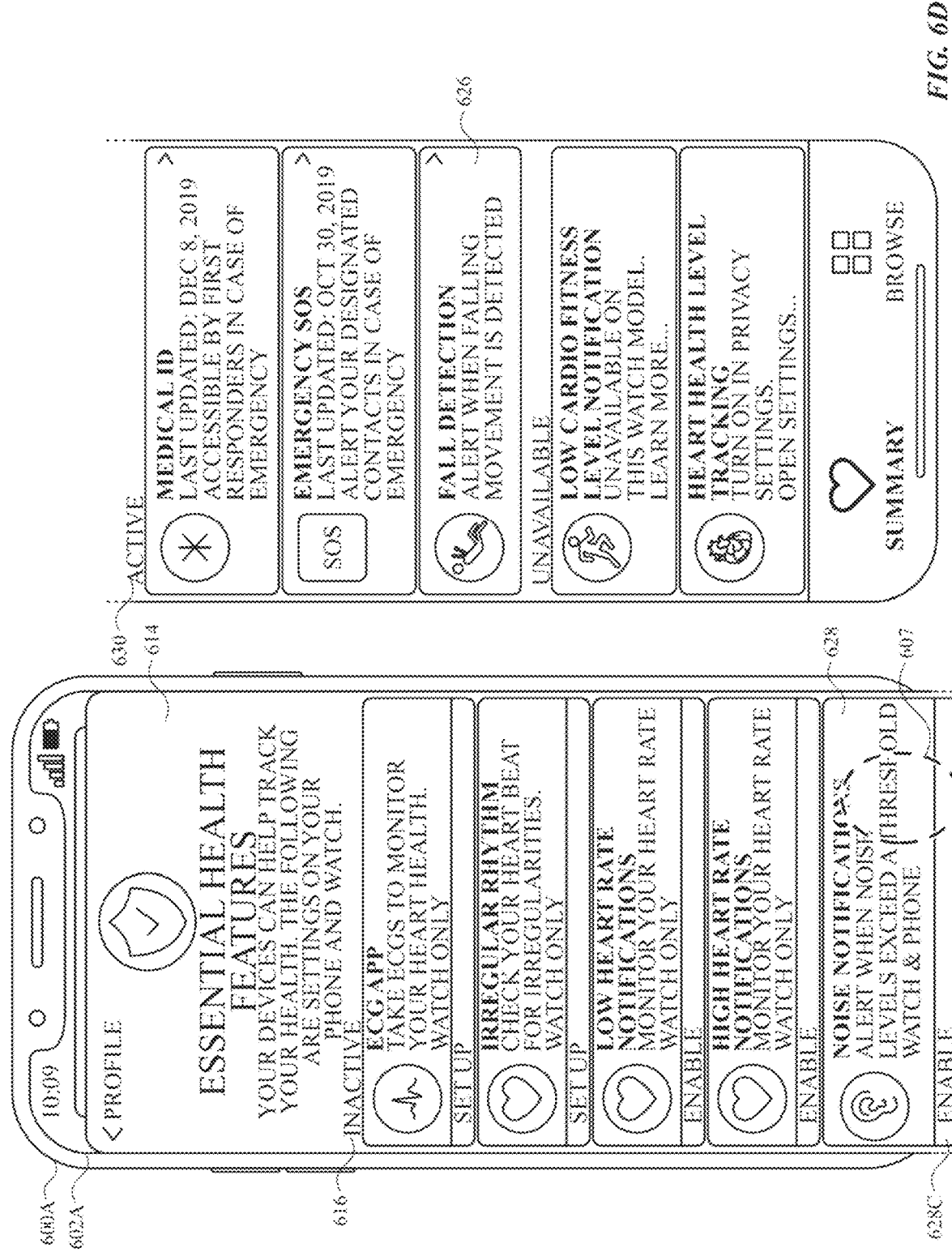

FIG. 6D illustrates device 600A displaying user interface 614 after the fall detection application has been activated via input 605. In FIG. 6D, device 600A displays platter 626 corresponding to the fall detection application in region 630 instead of in region 616, as the fall detection application has been activated.

Also in FIG. 6D, while displaying user interface 614, device 600A receives an input 607 directed to enable affordance 628C of platter 628 that corresponds to the noise notifications application.

In FIG. 6E, in response to receiving input 607, device 600A displays a user interface 644 for activating the noise notifications application. User interface 644 includes information 644A about one or more features of the noise notifications application. User interface 644 also includes an indication 644B that the noise notifications application is operated via both device 600A and the paired smartwatch. User interface 644 also includes a selectable toggle button 644C; an affordance that, when activated, toggles the noise notifications application from its current inactive "off" state to an active "on" state. User interface 644 also includes a selectable user interface object 644D that, when activated, enables a user to change a decibel threshold used to determine whether a noise notification should be triggered from the currently-selected threshold, 80 dB, to a different threshold. 80 dB is an example of a selectable decibel threshold; noise notifications application may provide multiple decibel thresholds for selection, including or not including 80 dB.

Also in FIG. 6E, while displaying user interface 644, device 600A receives an input 609 directed to toggle button 644C to activate the noise notifications application. In response to receiving input 609, device 600A causes the noise notifications application to be activated on both device 600A and on the paired smartwatch.

Figure 6F:
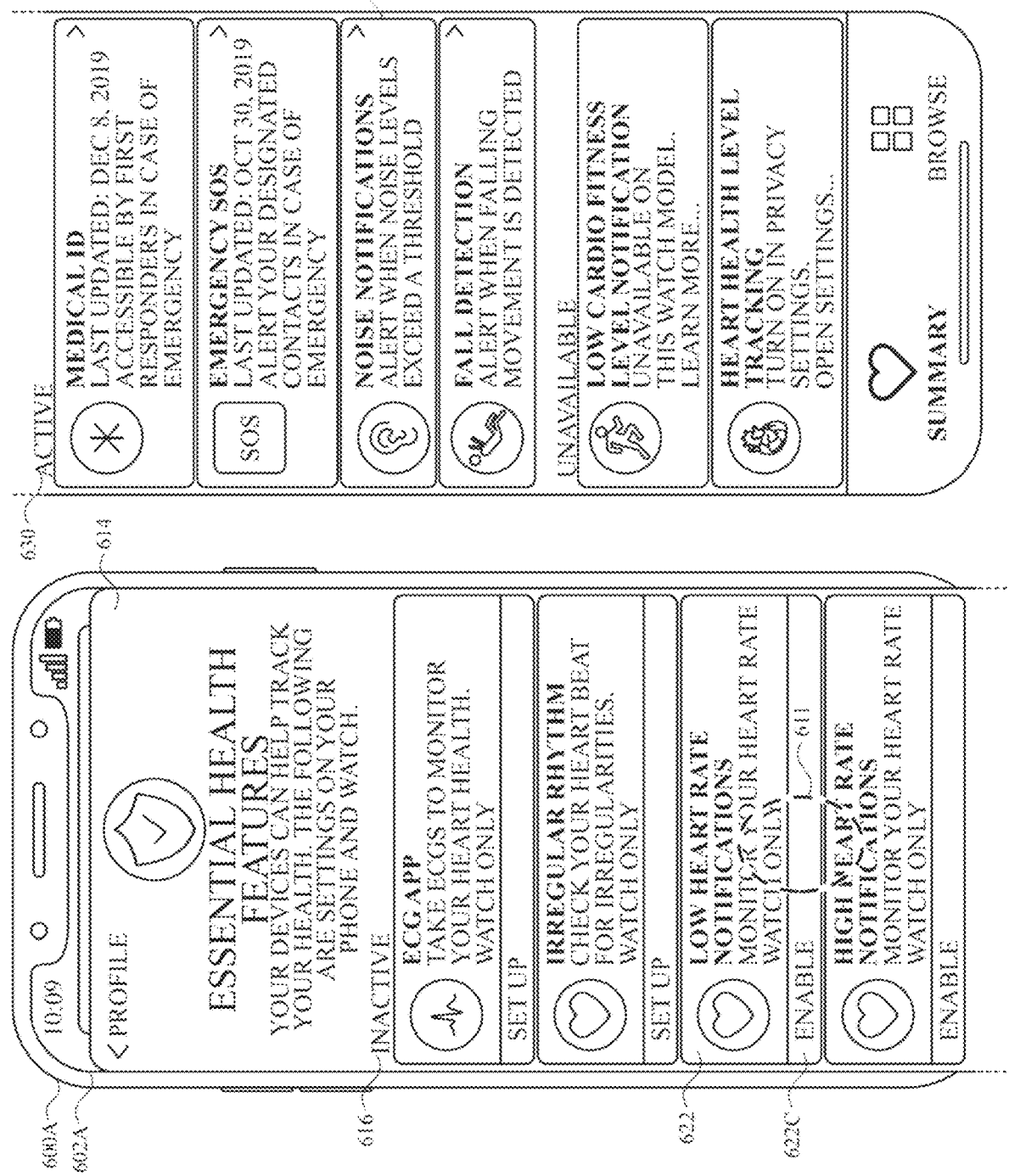

FIG. 6F illustrates device 600A displaying user interface 614 after the noise notifications application has been enabled via input 609. In FIG. 6F, device 600A displays platter 628 corresponding to the fall detection application in region 630 instead of region 616, as the noise notifications application is now activated.

In FIG. 6F, while displaying user interface 614, device 600A receives an input 611 directed to enable affordance 622C of platter 622 corresponding to the low heart rate notifications application.

In FIG. 6G, in response to receiving input 611, device 600A displays a user interface 646 for activating the low heart rate notifications feature (e.g., of a heart rate measurement/management application). User interface 646 includes information 646A about one or more features of the low heart rate notifications application, including an indication that a BPM threshold needs to be selected to activate the low heart rate notifications application. User interface 646 also includes an indication 646B that the low heart rate notifications application is operated via the paired smartwatch, and a threshold selection region 648 for selecting a heat rate threshold for which, if a measured heart rate is lower than the heart rate threshold, would trigger a low heart rate notification. Threshold selection region 648 includes multiple BPM thresholds 648A-648F, with threshold 648A corresponding to OFF (and thus notifications are not activated), threshold 648B corresponding to 55 BPM, threshold 648C corresponding to 50 BPM, threshold 648D corresponding to 45 BPM, threshold 648E corresponding to 40 BPM, and threshold 648F corresponding to 35 BPM.

Also in FIG. 6G, while displaying user interface 646, device 600A receives an input 613 directed to selecting threshold 648D (45 BPM). In response to receiving input 613 directed to selecting threshold 648D, device 600A causes the low heart rate notification application to be activated on the paired smartwatch based on the selected notification threshold of 45 BPM.

Figure 6H:
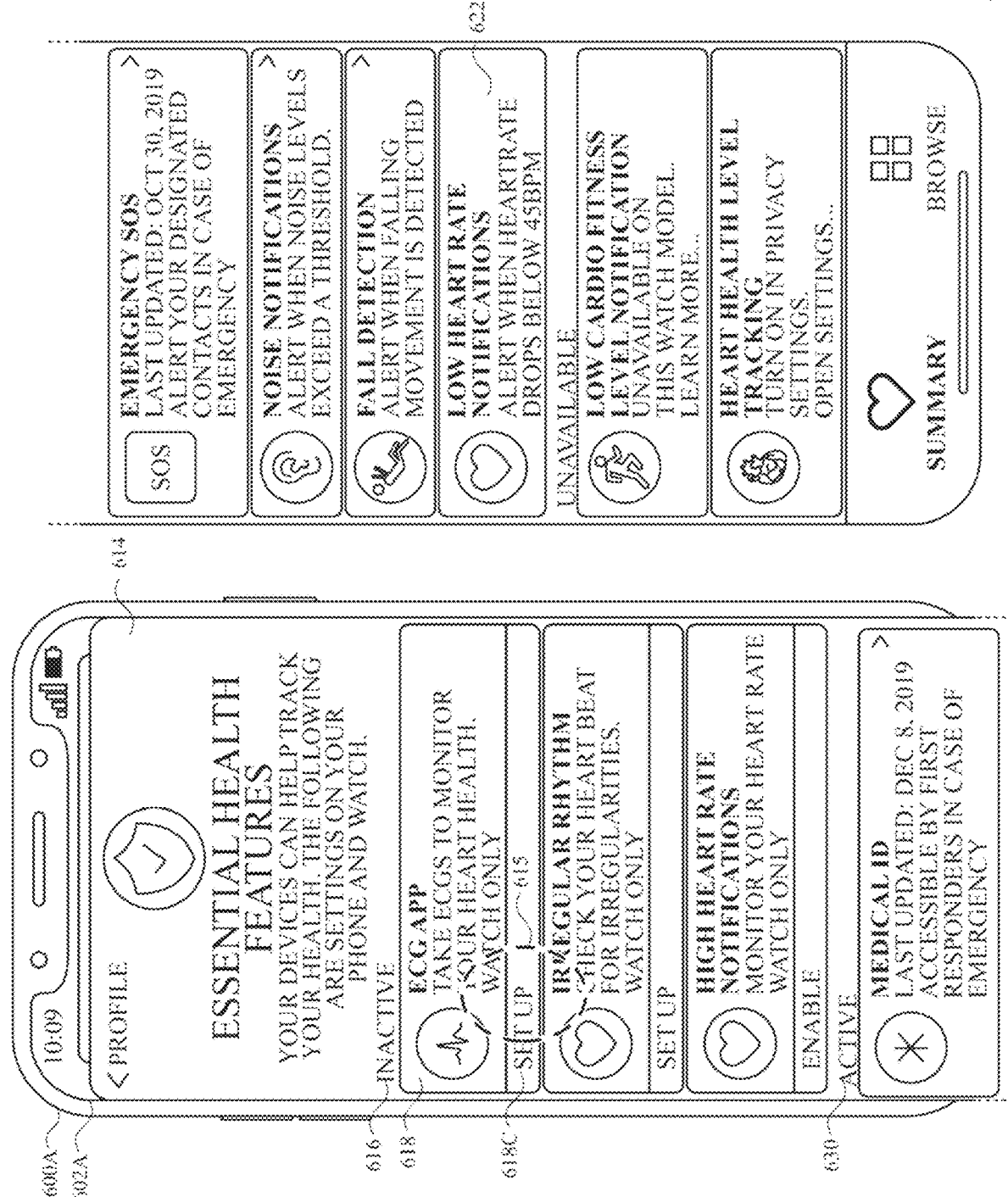

FIG. 6H illustrates device 600A displaying user interface 614 after the low hear rate notifications application has been enabled in FIG. 6G. In FIG. 6H, device 600A displays platter 622 corresponding to the low hear rate notifications application in region 630 instead of region 616, as the low hear rate notifications application is now activated.

In FIG. 6H, while displaying user interface 614, device 600A receives an input 615 directed to setup affordance 618C of platter 618 corresponding to the ECG application. In response to receiving input 615, device 600A initiates a setup process for the ECG application that corresponds to the native, multi-step setup process of the ECG application, as (e.g., partially) shown in FIGS. 6I-6K.

Figure 6I:
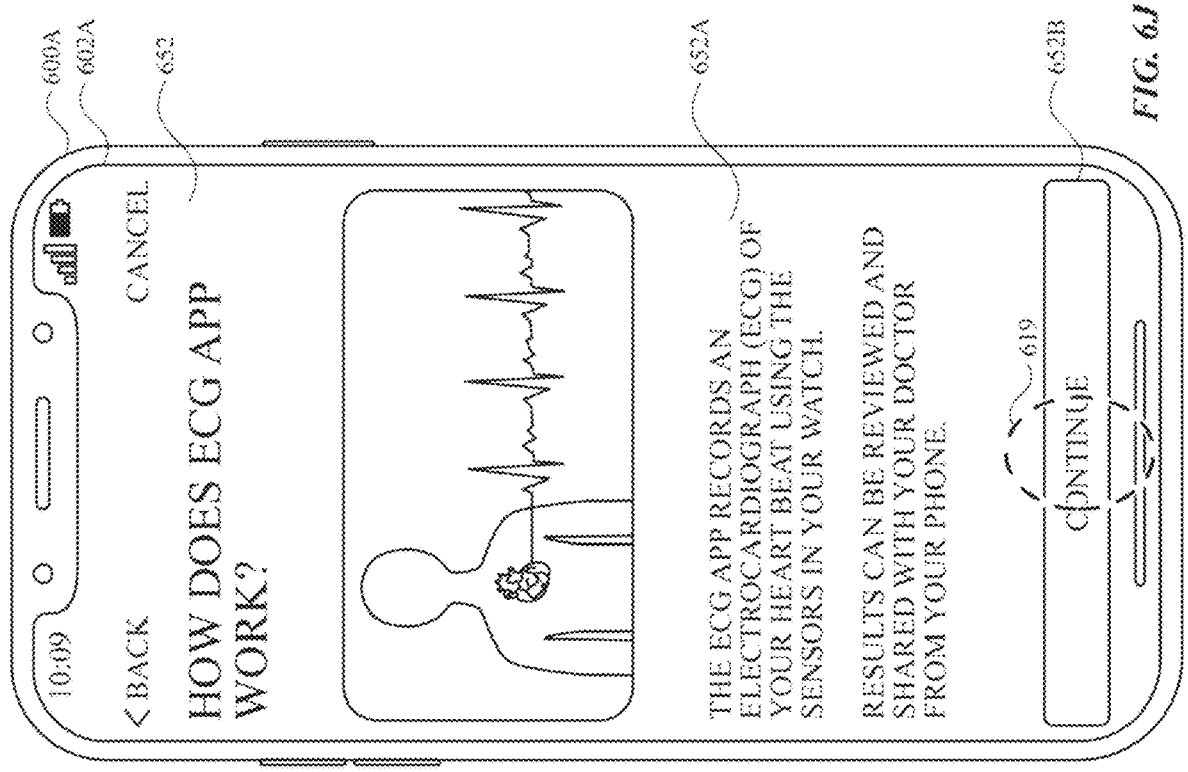

In FIG. 6I, device 600A displays a first setup user interface 650 of the setup process for the ECG application. First setup user interface 650 includes information 650A about ECG measurements, a request 650B for user information (e.g., date of birth; age), and an affordance 650C for continuing the setup process for the ECG application. Also in FIG. 6I, while displaying first setup user interface 650, device 600A receives an input 617 directed to affordance 650C.

Figure 6J:
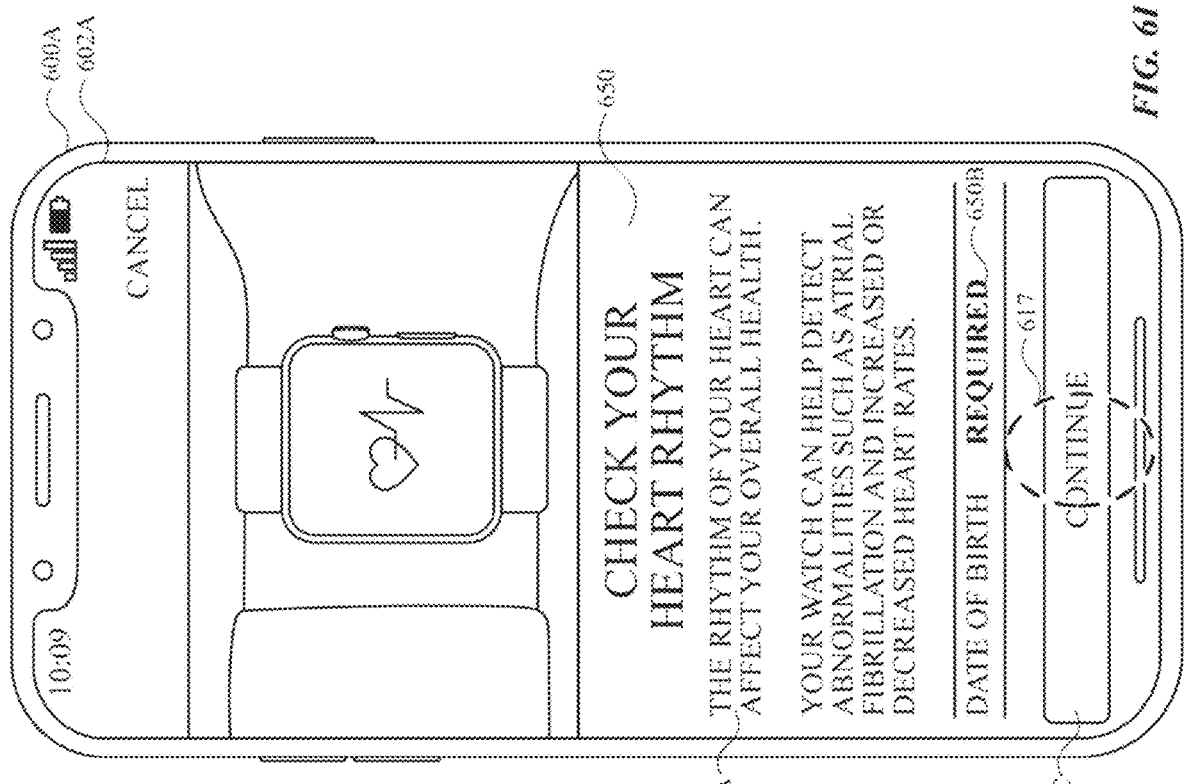

In FIG. 6J, in response to receiving input 617, device 600A displays a second setup user interface 652 of the setup process for the ECG application. Second setup user interface 652 includes detailed information 652A about ECG measurements and its relation to heart health, as well as an affordance 652B for continuing the setup process for the ECG application. Also in FIG. 6J, while displaying second setup user interface 652, device 600A receives an input 619 directed to affordance 652B.

In FIG. 6K, in response to receiving input 619 as shown in FIG. 6J, device 600A displays a third setup user interface 654 of the setup process for the ECG application. Third setup user interface 654 includes information 654A about completing the setup process by taking a ECG measurement using the paired smartwatch. In some embodiments, device 600A activates the ECG application upon detecting the completion of a successful first ECG measurement taken via the paired smartwatch.

Figure 6L:
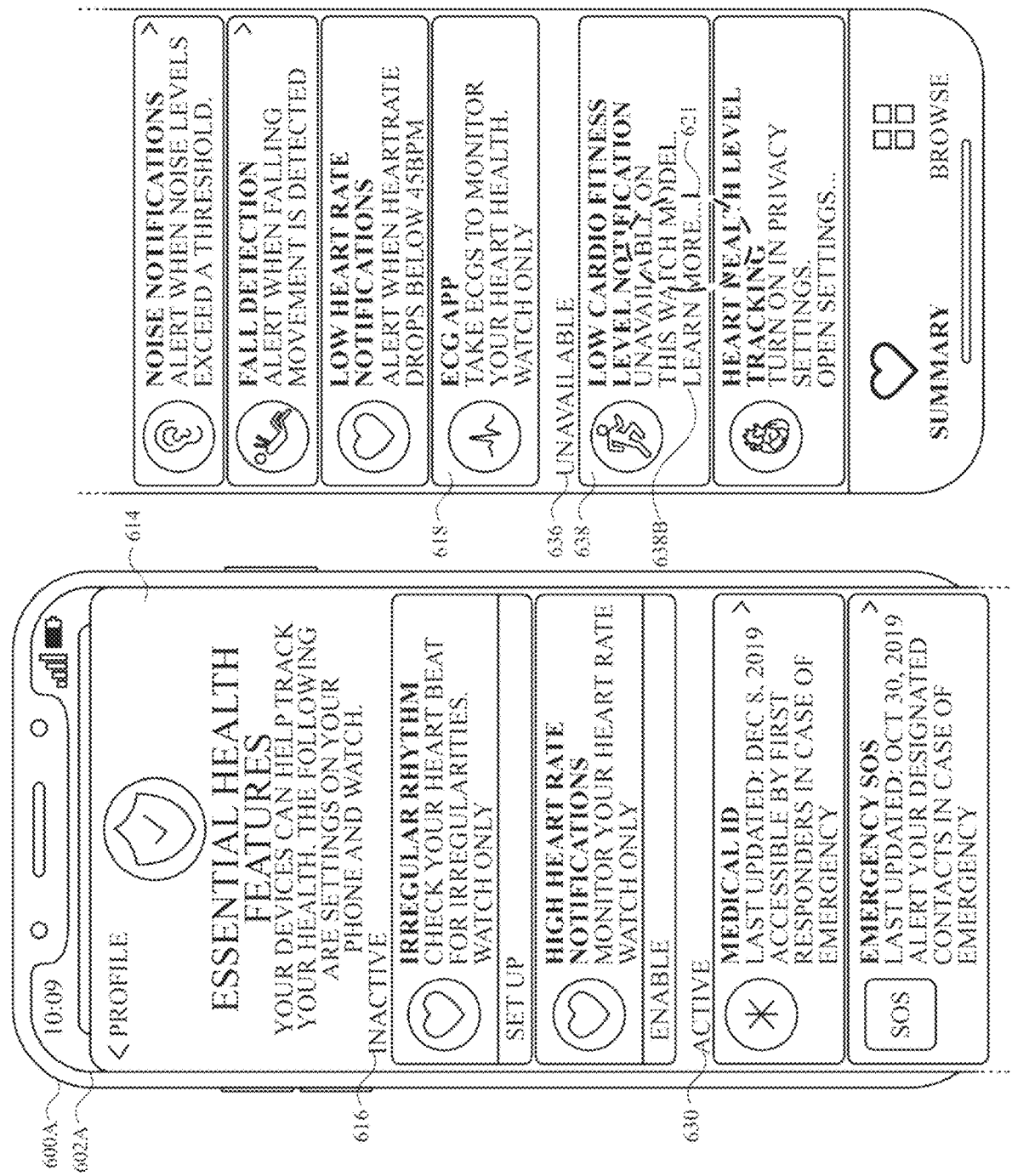
Figure 60:
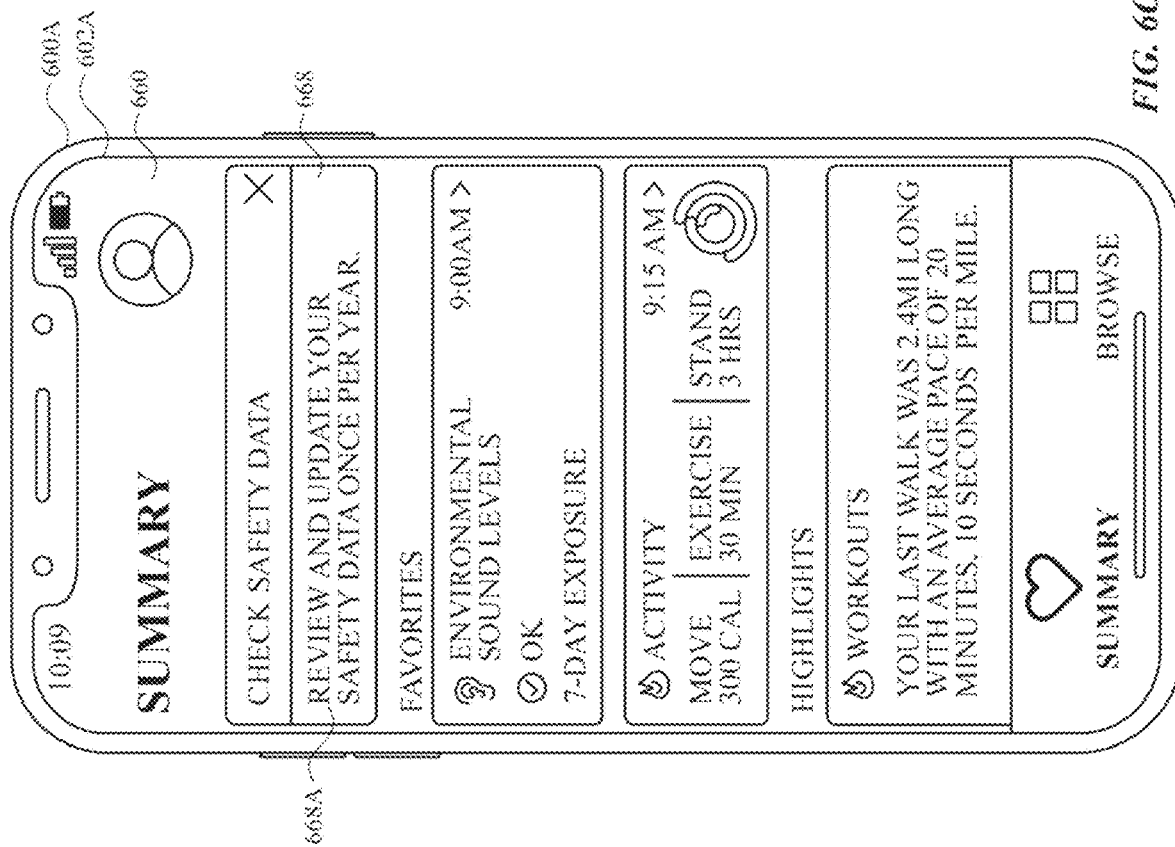

FIG. 6L illustrates device 600A displaying user interface 614 after the ECG application has been enabled in FIGS. 6I-6K. In FIG. 6L, device 600A displays platter 616 corresponding to the ECG application in region 630 instead of region 616, as the ECG application is now activated.

In FIG. 6L, while displaying user interface 614, device 600A receives an input 621 directed to learn more affordance 638B of platter 638 corresponding to the low cardio fitness level notifications application.

In FIG. 6M, in response to receiving input 621, device 600A displays a user interface 656 associated with the low cardio fitness notifications application. User interface 656 includes an indication 656A that the low cardio fitness notifications application is unavailable to be operated device 600A or on the paired smartwatch, and an indication 656B of a reason(s) why the application is unavailable.

In some embodiments, an application (e.g., or application feature) is unavailable (to be operated device 600A and/or on the paired smartwatch) because of access to data or a regulation (e.g., a government regulation) at a location (e.g., city; state; country) in which device 600A or the external device (e.g., device 600B) is being used, as described in greater detail below with reference to FIGS. 8A-8S and 10A-10V. In some embodiments, an application (e.g., or application feature) is unavailable (to be operated device 600A or on the paired smartwatch) because of a biological characteristic (e.g., age; pregnancy; pre-existing medical condition) of the user, as described in greater detail below with reference to FIGS. 8A-8S.

FIG. 6N illustrates device 600A displaying a summary user interface 660 of the health application. Summary user interface 660 includes multiple of user interface objects 662, 664, and 666 corresponding to different health-related functions corresponding to health-related applications (e.g., or application features) that are operating on device 600A and/or on the paired smartwatch. Summary user interface 660 includes a user interface object 662 corresponding to the noise level notifications application and including information associated with detected noise levels. Summary user interface 660 also includes a user interface object 664 corresponding to an activity application and including measured/detected activity-related information. Summary user interface 660 also includes a user interface object 666 corresponding to a workout application and including a past workout information.

FIG. 6O illustrates device 600A displaying, in summary user interface 600, a notification 668 (e.g., a time-based notification) related to user interface 614. Notification 668 includes an indication 668A that health-related functions listed in user interface 614 as shown in FIG. 6B should be reviewed and, as needed, updated. In some embodiments, device 600A displays notification 668 as a banner notification (e.g., over a home user interface or a user interface of a different application). In some embodiments, device 600A displays notification 668 in a wake screen of device 600A.

In some embodiments, device 600A automatically displays notification 668 annually. In some embodiments, device 600A automatically displays notification 668 monthly.

In some embodiments, in response to receiving an input directed to notification 668, device 600A displays user interface 614 such that the health-related applications (e.g., or application features) can easily and conveniently be managed by the user.

FIGS. 7A-7C are a flow diagram illustrating a method for managing health and safety features on an electronic device, in accordance with some embodiments. Method 700 is performed at a computer system (e.g., an electronic device (e.g., 100, 300, 500, 600A)) that is in communication with a display generation component (e.g., 602A) (e.g., a display controller, a touch-sensitive display system; a display (e.g., integrated or connected)) and one or more input devices (e.g. gyroscope, accelerometer, microphone, a touch-sensitive surface). Some operations in method 700 are, optionally, combined, the orders of some operations are, optionally, changed, and some operations are, optionally, omitted.

In some embodiments, the electronic device (e.g., 600A) is a computer system. The computer system is optionally in communication (e.g., wired communication, wireless communication) with the display generation component (e.g., 602A) and with the one or more input devices. The display generation component is configured to provide visual output, such as display via a CRT display, display via an LED display, or display via image projection. In some embodiments, the display generation component is integrated with the computer system. In some embodiments, the display generation component is separate from the computer system.

The one or more input devices are configured to receive input, such as a touch-sensitive surface receiving user input. In some embodiments, the one or more input devices are integrated with the computer system. In some embodiments, the one or more input devices are separate from the computer system. Thus, the computer system can transmit, via a wired or wireless connection, data (e.g., image data or video data) to an integrated or external display generation component to visually produce the content (e.g., using a display device) and can receive, a wired or wireless connection, input from the one or more input devices.

As described below, method 700 provides an intuitive way for managing and/or presenting health data. The method reduces the cognitive burden on a user for managing and/or presenting health data, thereby creating a more efficient human-machine interface. For battery-operated computing devices, enabling a user to manage and/or present health data faster and more efficiently conserves power and increases the time between battery charges.

The computer system (e.g., 600A) displays (702), via the display generation component (e.g., 602A), a user interface (e.g., 614) (e.g., a health-function listing interface) that includes a plurality of user interface objects (e.g., 618-628, 632-634, 638-640) that correspond to health-related (e.g., physical health (including physical safety), mental health) functions (e.g., applications or application features operating on, or available to operate on, the computer system or operating on, or available to operate on, external electronic devices in communication with the computer system), the plurality of user interface objects including a first user interface object that corresponds to a first health-related function (e.g., a heart-rate-tracking-related function (e.g., 620, 622, 624, 638, 640), a medical identification function (e.g., 632), an emergency contact function (e.g., 634), an ambient-noise-level-tracking function (e.g., 628)).

The first user interface object (e.g., 632, 634) includes (704), in accordance with a determination that the first health-related function is currently active (e.g., active on the computer system; active on an external electronic device in communication with the computer system; active to provide data of the first health-related function to the computer system), an indication (e.g., 632A) that the first health-related function is active (e.g., a graphical or textual indication) (706).

The first user interface object (e.g., 618, 620, 622, 624, 626, 628) includes (704), in accordance with a determination that the first health-related function is currently inactive and available for activation via a set of one or more inputs received at the computer system (e.g., 602a), an indication that the first health-related function is available for activation (e.g., a graphical or textual indication; a selectable user interface object (e.g., 618C, 626C) that, when selected, initiates a process for activation of the first health-related function) (708). In some embodiments, and an indication that the first health-related function is inactive.

The first user interface object (e.g., 638, 640) includes (704), in accordance with a determination that the first health-related function is currently inactive and not available for activation (e.g., not available for activation via the computer system; not currently available for activation (e.g., due to regulatory, hardware, or software restrictions or limitations)), an indication (e.g., 638A) that the first health-related function is not available for activation (e.g., a graphical or textual indication) (710).

Displaying the first user interface object with indications based on whether the first health-related function is active or inactive and available or inactive and unavailable for activation provides the user with feedback as to the state of the first health-related function. Providing improved visual feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently.

In some embodiments, the indication (e.g., 638A) that the first health-related function is not available for activation includes an indication that describes why the function is not available for activation.

In some embodiments, the first health-related function is not available for activation due to a first resolvable issue (e.g., a software issue resolvable through an update; a hardware issue resolvable through replacement and/or procurement of the hardware; a location-based issue resolvable by altering location), and the indication that the first health-related function is not available for activation includes (724) a selectable portion (e.g., a selectable region, an affordance) that, when selected via an input received via the one or more input devices, initiates a process (e.g., a process at the computer system; a process at an external device in communication with the computer system) to resolve the first resolvable issue and to thereby make the first health-related function available for activation (726). Providing an selectable portion of initiating a process to resolve resolvable issues preventing activation of a health-related function provides the user with more control of the device and resolve an issue without having to manually identify the cause of the issue and without having to clutter the UI with multiple options for identifying and resolving issues. Providing additional control of the computer system without cluttering the UI with additional displayed controls enhances the operability of the computer system and makes the user-device interface more efficient (e.g., by helping the user to provide proper inputs and reducing user mistakes when operating/interacting with the device) which, additionally, reduces power usage and improves battery life of the device by enabling the user to use the computer system more quickly and efficiently.

In some embodiments, the first health-related function is currently inactive and available for activation and the first user interface object (e.g., 618, 620, 622, 624, 626, 628) further includes (712) a selectable portion (e.g., a selectable region, an affordance) that when selected via an input received via the one or more input devices, initiates a process for activating the first health-related function (e.g., as shown in FIGS. 6C, 6E, 6G, and 6I-6K) (714). In some embodiments, in accordance with a determination that the first-health related function is active, the first user interface object (e.g., 632, 634) does not include the selectable portion that when selected via an input received via the one or more input devices, initiates a process for activating the first health related function.

In some embodiments, the process for activating the first health-related function (e.g., as shown in FIGS. 6C, 6E, 6G, and 6I-6K) includes (716), in accordance with a determination that the first health-related function is a function of a first type (e.g., a function having binary states (active, inactive) (e.g., emergency fall detection, emergency contacts)), a first type of activation process that requires a first minimum number of inputs (e.g., the least number of inputs that must be received) to activate the first-health related function (e.g., as shown in FIGS. 6C, 6E, and 6G) (718). In some embodiments, the first minimum number of inputs is one.

In some embodiments, the process for activating the first health-related function (e.g., as shown in FIGS. 6C, 6E, 6G, and 6I-6K) includes (716), in accordance with a determination that the first health-related function is a function of a second type (e.g., a function that requires additional information or approvals to activate), a second type of activation process, wherein the second type of activation process requires a second number of minimum inputs (e.g., the first number of minimum inputs, plus one (e.g., 2 or more minimum inputs when the first type of activation process requires a minimum of one input)) to activate the first-health related function (e.g., as shown in FIGS. 6I-6K), and wherein the second number of minimum inputs is greater than the first number of minimum inputs (722). Initiating a process for activating the first health-related function using difference types of activation processes, that require different amounts of minimum inputs, based on whether the first health-related function is of a first type or a second type, provides the system with the capability to accommodate activation of differing types of health-related functions, thereby increasing the control options available to the user via the user interface. Providing additional control options enhances the operability of the computer system and makes the user-device interface more efficient (e.g., by helping the user to provide proper inputs and reducing user mistakes when operating/interacting with the device) which, additionally, reduces power usage and improves battery life of the device by enabling the user to use the computer system more quickly and efficiently.

In some embodiments, a health-related function is a function of a first type and has binary states (e.g., active or inactive). In some embodiments, a health-related function of the first type has non-binary states (e.g., inactive, active with a first parameter; active with a second parameter) and the first type of activation process includes pre-populating at least one parameter of the function.

In some embodiments, the second type of activation process (e.g., as shown in FIGS. 6I-6K) includes providing information or selection of parameters (e.g., threshold values, frequency of activation values) affecting the function.

In some embodiments, the first type of activation process (e.g., as shown in FIGS. 6C, 6E, and 6G) includes displaying, via the display generation component (e.g., 602A), a single selectable user interface object that when selected via an input received via the one or more input devices, activates the first health-related function (e.g., the first health-related function can be activated by a single input) (720). Providing a single user interface object to activate the function enables the user to activate the function without cluttering the user interface with multiple controls. Providing additional control of the computer system without cluttering the UI with additional displayed controls enhances the operability of the computer system and makes the user-device interface more efficient (e.g., by helping the user to provide proper inputs and reducing user mistakes when operating/interacting with the device) which, additionally, reduces power usage and improves battery life of the device by enabling the user to use the computer system more quickly and efficiently.

In some embodiments, the second type of activation process (e.g., as shown in FIGS. 6I-6K) includes displaying, via the display generation component (e.g., 602A), a sequence of a plurality of user interfaces (e.g., 650, 652, 654), and receiving a plurality of user inputs, received while interfaces of the plurality of user interfaces are displayed, before activating the first health-related function. Activating a health-related function via a plurality of inputs and using a plurality of user interfaces ensures that information required to properly activate the function is received, thereby ensuring proper activation and reducing errors. Ensuring proper activation of functions and reducing errors enhances the operability of the computer system and makes the user-device interface more efficient (e.g., by helping the user to provide proper inputs and reducing user mistakes when operating/interacting with the device) which, additionally, reduces power usage and improves battery life of the device by enabling the user to use the computer system more quickly and efficiently.

In some embodiments, the indication (e.g., 618A, 626A) that the first health-related function is available for activation includes an indication that describes how to activate the function.

In some embodiments, the computer system (e.g., 600A) is associated with a first user account (e.g., an identification account, an access account, an account with information stored on a server), the first user account is associated with a first external electronic device (e.g., 600B of FIG. 8I) (e.g., a smart watch, a tablet computer), and the first health-related function, when active, includes one or more functions operating on the computer system and one or more functions operating on the first external electronic device. In some embodiments, the computer system (e.g., 600) receives a set of one or more inputs that includes an input corresponding to the first user interface object. In some embodiments, in response to receiving the set of one or more inputs that includes an input corresponding to the first user interface object, the computer system displays, via the display generation component (e.g., 602a), a feature user interface corresponding to the first health-related feature that includes a first feature user interface object that corresponds to a function of the one or more operating on the computer system, and a second feature user interface object that corresponds to a function of the one or more functions operating on the first external electronic device. In some embodiments, the first feature user interface object is selectable to modify one or more parameters of the first health-related feature on the computer system, without affecting the function of the first health-related feature on the first external electronic device. In some embodiments, the second feature user interface object is selectable to modify one or more parameters of the first health-related feature on the first external electronic device, without affecting the function of the first health-related feature on the computer system. Providing a feature user interface with separate interface objects the correspond to operation of a health-related function on the computer system and the first external electronic device provides the user with feedback, specific to the computer system or the external device, on the operation of the function. Providing improved visual feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently.

In some embodiments, the process for activating the first health-related function includes displaying a settings user interface (e.g., 644) that concurrently includes a first setting user interface object (e.g., 644D) for modifying (e.g., affects; changes; sets) a parameter of the first health-related function for the computer system, and a second setting user interface object (e.g., 644D) for modifying (e.g., affects; changes; sets) a parameter of the first health-related function for a second external electronic device (e.g., a smart watch, a tablet computer; a device that is the same as or different from the first external electronic device). Concurrently displaying setting user interface objects for a health-related function for both the computer system and an external electronic device provides the user with feedback about the settings/parameters of the function for both the computer system and the external device. Providing improved visual feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently.

In some embodiments, a settings user interface for the first health-related function is accessible from an application (e.g., the application corresponding to user interface 660 of FIG. 6N) (e.g., a health-data aggregation application) that collects and presents data for a plurality of health-related functions, including the first health-related function.

In some embodiments, the process for activating the first health-related function includes displaying a settings user interface that includes one or more prepopulated or preselected values for selectable parameters of the function (e.g., as shown in user interface 806 of FIGS. 8C-8D) and that also includes options to modify the one or more prepopulated or preselected values.

Figure 8B:
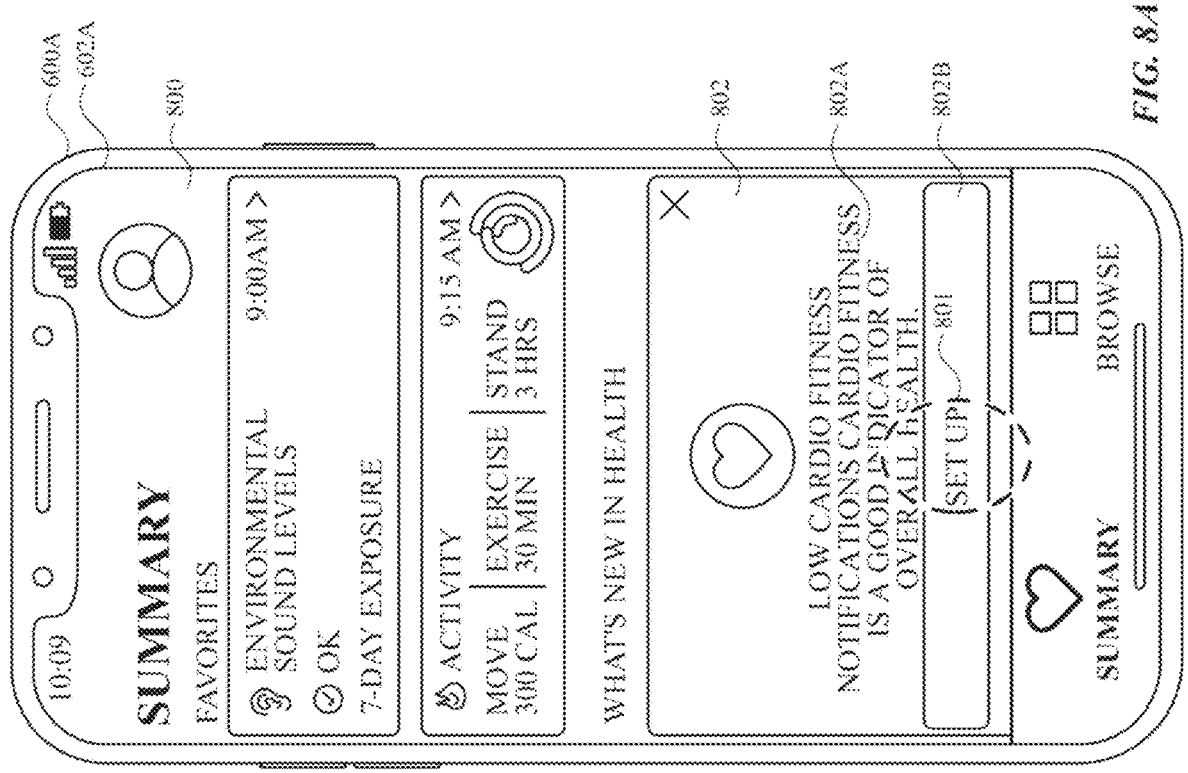
Figures 8C, 8D:
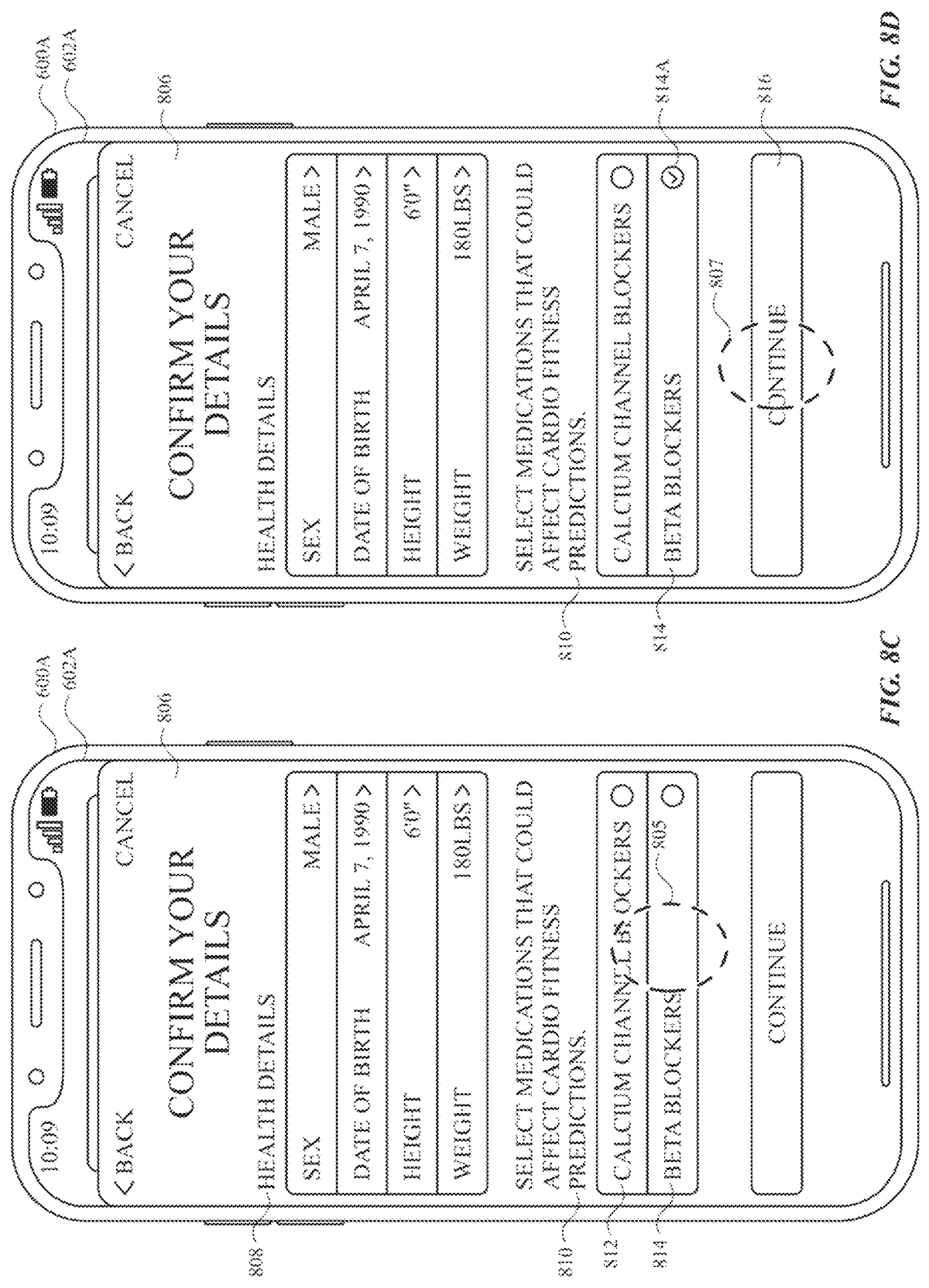
Figure 8F:
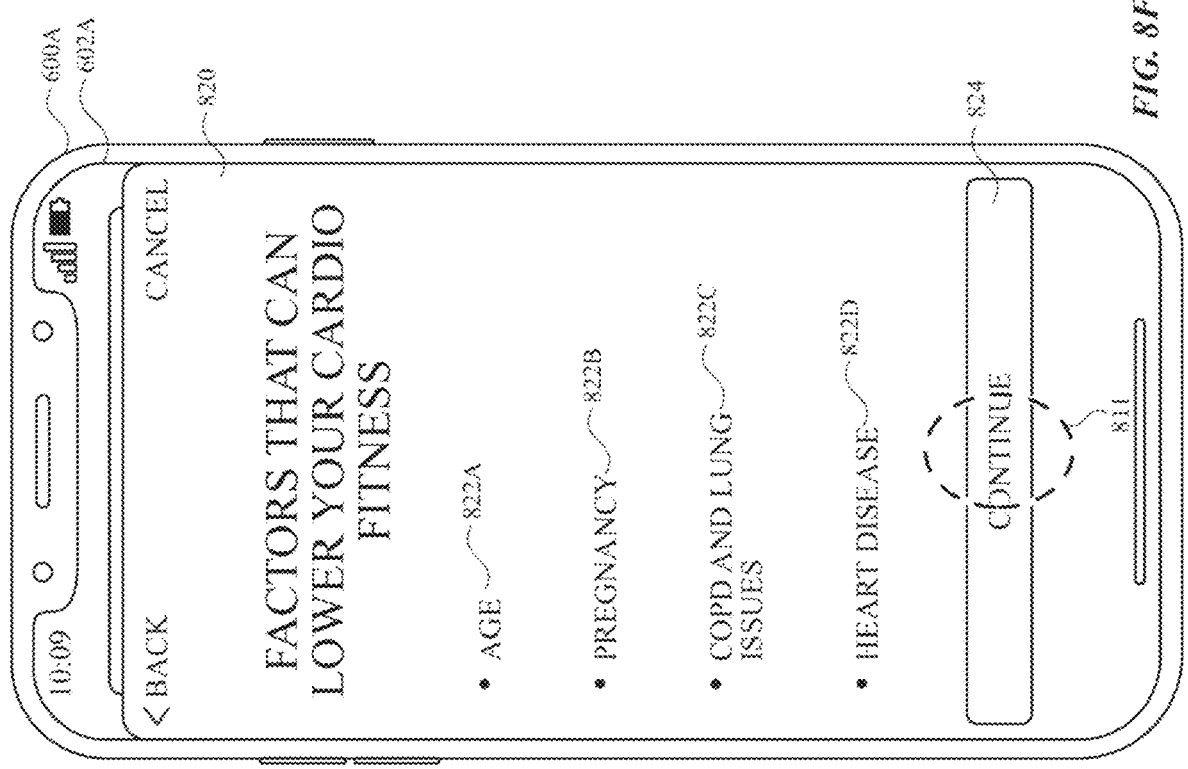
Figure 8E:
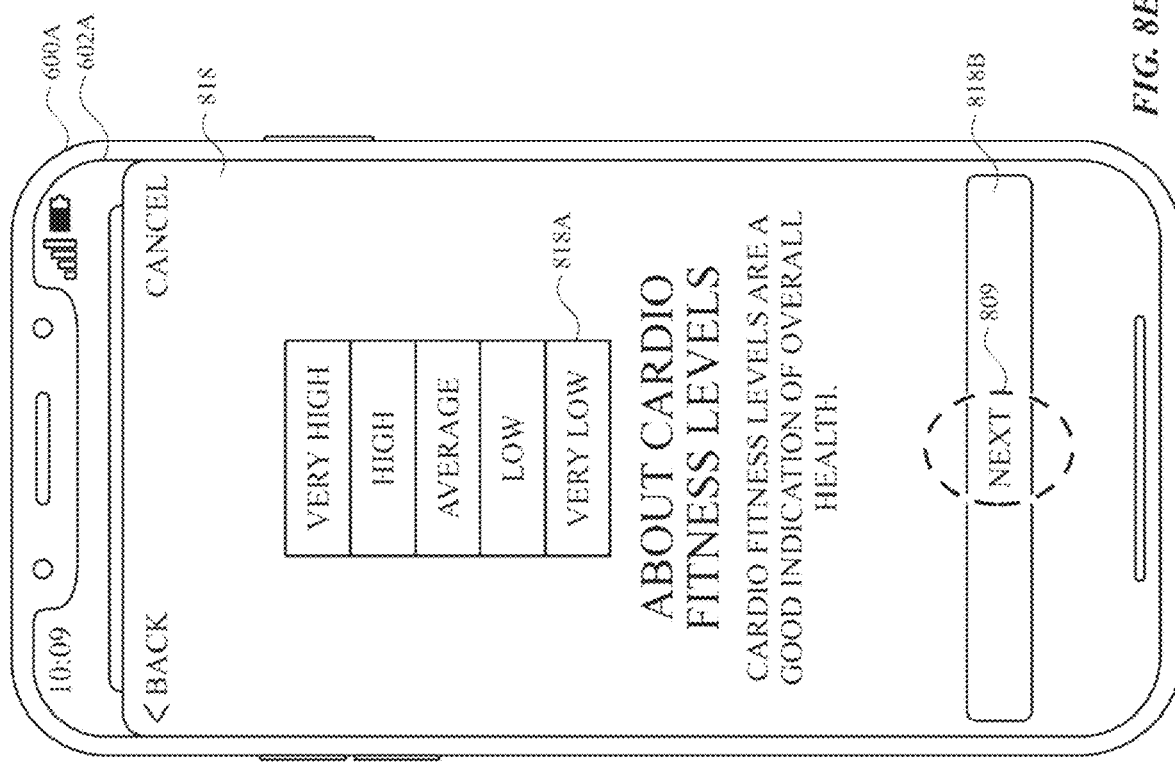
Figure 8I:
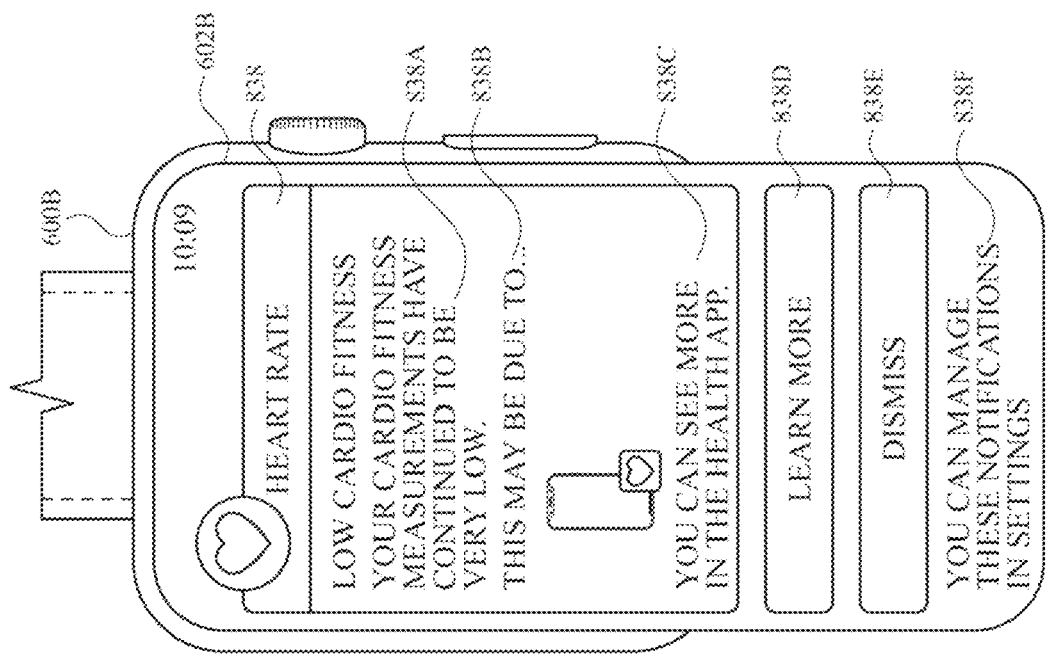

In some embodiments, the process for activating the first health-related function includes displaying a settings user interface (e.g., 644, 646) that includes one or more selectable user interface objects that control parameters for the function at the computer system (e.g., 600A) and at least one external electronic device (e.g., 600B of FIG. 8I). In some embodiments, the parameters are stored on a remote server and are accessible to multiple devices associated with a user of the computer system.

In some embodiments, the computer system (e.g., 600A) displays (e.g., at predetermined times, after predetermined time intervals (e.g., a set number of months)) a notification reminding the user to check (e.g., via a settings user interface) one or more settings of the first health-related function. In some embodiments, the notification is displayed in an application (e.g., a health-data aggregation application) that collects and presents data for a plurality of health-related functions, including the first health-related function.

In some embodiments, settings (e.g., any settings, including the activation state of the function) of the first health-related function cannot be modified from the user interface that includes the plurality of user interface objects that correspond to health-related functions (e.g., modifying settings of the function requires navigation to one or more different user interfaces). Preventing modification of settings of the first health-related function from the user interface reduces the risk of inadvertent modification of the settings and/or reduces the risk that the user will make a modification without having access to additional information and/or settings pertaining to the function. Reducing the risk of inadvertent operations making the user-device interface more efficient (e.g., by helping the user to provide proper inputs and reducing user mistakes when operating/interacting with the device) which, additionally, reduces power usage and improves battery life of the device by enabling the user to use the computer system more quickly and efficiently.

Note that details of the processes described above with respect to method 700 (e.g., FIGS. 7A-7C) are also applicable in an analogous manner to the methods described above. For example, method 900 optionally includes one or more of the characteristics of the various methods described above with reference to method 700. For example, the user interfaces for managing health and safety features described with reference to method 700 can be used to manage one or more features of the health applications described with reference to method 900. For another example, method 1100 optionally includes one or more of the characteristics of the various methods described above with reference to method 700. For example, the user interfaces for managing health and safety features described with reference to method 700 can be used to manage one or more features of the background measurement features described with reference to method 1100. For another example, method 1300 optionally includes one or more of the characteristics of the various methods described above with reference to method 700. For example, the user interfaces for managing health and safety features described with reference to method 700 can be used to manage one or more features of the application used to measure the biometric information described with reference to method 1300. For another example, method 1500 optionally includes one or more of the characteristics of the various methods described above with reference to method 700. For example, the user interfaces for managing health and safety features described with reference to method 700 can be used to manage one or more features of the health application user interfaces described with reference to method 1500. For another example, method 1700 optionally includes one or more of the characteristics of the various methods described above with reference to method 700. For example, the user interfaces for managing health and safety features described with reference to method 700 can be used to manage one or more features of the background measurement features described with reference to method 1700. For brevity, these details are not repeated below.

FIGS. 8A-8S illustrate exemplary user interfaces for managing the setup of a health feature on an electronic device, in accordance with some embodiments. The user interfaces in these figures are used to illustrate the processes described below, including the processes in FIGS. 9A-9C.

FIG. 8A illustrates device 600A displaying a summary user interface 800 of the health application (corresponding to summary user interface 660 first described above with reference to FIG. 6N). In FIG. 8A, device 600A displays, in summary user interface 660, a notification 802 that low cardio fitness notifications can be set up (e.g., enabled) on device 600A. Notification 802 includes information 802A about low cardio fitness notifications and its relation to heart health. Notification 802 also includes an affordance 802B for initiating setup of low cardio fitness notifications.

Also in FIG. 8A, while displaying summary user interface 800, device 600A receives an input 801 directed to affordance 802B.

In FIG. 8B, in response to receiving input 801, device 600A displays a setup user interface 804 corresponding to a part of a setup (e.g., onboarding) process for activating the low cardio fitness notifications application. User interface 804 includes an indication 804A that the paired smartwatch can be enabled to generate low cardio fitness notifications. User interface 804 also includes an affordance 804B for continuing the setup process for activating the low cardio fitness notifications application.

Also in FIG. 8B, while displaying user interface 804, device 600A receives an input 803 directed to affordance 804B.

In FIG. 8C, in response to receiving input 803, device 600A displays a setup user interface 806 corresponding to a part of the setup process for activating the low cardio fitness notifications application.

In the embodiment of FIG. 8C, setup user interface 806 includes a user health details region 808 for receiving information about the user's health (e.g., sex; date of birth; height; weight). In some embodiments, device 600A requests user input of the user's health information in user health details region 808. In some embodiments, device 600A automatically, without manual user input, pre-populates the user's health information based on stored user information, e.g., from the health application.

Setup user interface 806 also includes medications region 810 for receiving information regarding one or more medications that the user is currently taking. Medications region 810 includes multiple selectable user interface objects corresponding to different medications, (e.g., a user interface object 812 corresponding to calcium channel blockers, a user interface object 814 corresponding to beta blockers) that can be selected by the user.

In some embodiments, setup user interface 806 also includes a region for receiving additional information that may affect cardio fitness, such as whether the user is currently pregnant or whether the user currently has any pre-existing medical conditions.

In FIG. 8C, while displaying setup user interface 806, device 600A receives an input 805 directed to selecting user interface object 814 corresponding to beta blockers in medications region 810.

In FIG. 8D, in response to receiving input 805, device 600A displays, in user interface object 814 corresponding to beta blockers, an indication 814A (e.g., a checkmark; a visual marker) that beta blockers has been selected as a medication that is currently being taken by the user.

Also in FIG. 8D, while displaying onboarding user interface 806, device 600A receives an input 807 directed to an affordance 816 for continuing the setup process for activating the low cardio fitness notifications application.

In FIG. 8E, in response to receiving input 807 shown in FIG. 8D, device 600A displays a setup user interface 818 corresponding to a part of the setup process for activating the low cardio fitness notifications application. Setup user interface 818 includes an indication 818A (e.g., including a chart or a list) of the quintiles (e.g., very high, high, average, low, very low) into which the user's cardio fitness measurement results will be classified. The quintiles comprise very high, high, average, low, very low. Setup user interface 818 also includes an affordance 818B for continuing the setup process for activating the low cardio fitness notifications application.

Also in FIG. 8E, while displaying onboarding user interface 818, device 600A receives an input 809 directed to affordance 818B.

In FIG. 8F, in response to receiving input 809 as shown in FIG. 8E, device 600A displays a setup user interface 820 corresponding to a part of the setup process for activating the low cardio fitness notifications application. Setup user interface 820 includes an indication of (e.g., a list of) multiple factors 822A-822D that can affect (e.g., lower) the user's cardio fitness levels, including age, pregnancy, COPD and lung issues, and heart disease. Setup user interface 820 also includes an affordance 824 for continuing the setup process for activating the low cardio fitness notifications application.

Also in FIG. 8F, while displaying onboarding user interface 820, device 600A receives an input 811 directed to affordance 824.

In FIG. 8G, in response to receiving input 811, device 600A displays a setup user interface 826 that includes an affordance 826A for completing the onboarding process of the low cardio fitness notifications application and enabling low cardio fitness notifications on the paired smartwatch. Setup user interface 826 also includes an affordance 826B for exiting the onboarding process without enabling low cardio fitness notifications on the paired smartwatch.

Also in FIG. 8G, while displaying onboarding user interface 826, device 600A receives an input 813 directed to affordance 826A.

In some embodiments, prior to enabling an application (e.g., or application feature), such as enabling the low cardio fitness notifications application, device 600A determines or receives a determination as to whether the application can be operated on device 600A or on the paired smartwatch. In some embodiments, the determination is based on a regulation (e.g., a government regulation) that applies to a current location of device 600A and/or the external device (e.g., device 600B), where the current location is determined based on one or more sensors (e.g., GPS sensors) of device 600A and/or the paired smartwatch. In some embodiments, the determination is based on a characteristic (e.g., age) of the user.

In response to receiving input 813, device 600A determines whether low cardio fitness notifications can be enabled based on a current age of the user, where the current age of the user is compared with an age threshold (e.g., 50; 60) under which low cardio fitness notifications can be enabled on the external device (e.g., device 600B). In FIG. 8G, device 600A determines that the user's current age is under the age threshold.

In FIG. 8H, in response to receiving input 813 (e.g., and in accordance with the determination that the user's current age is below the threshold age), device 600A activates low cardio fitness notifications and displays a user interface 828 corresponding to the low cardio fitness notifications application.

User interface 828 includes a selectable user interface object 830 for causing display of measurement data corresponding to previous cardio fitness levels measured via the paired smartwatch. User interface 828 also includes an indication 832 that low cardio fitness notifications are currently enabled. User interface 828 also includes an information region 834 that includes multiple selectable user interface objects 834A-834D for viewing additional, more detailed information about cardio fitness. User interface 828 also includes an information region 836 that includes information (e.g., basic information) about low cardio fitness.

FIG. 8I illustrates the paired smartwatch (referred to from hereon as device 600B). Device 600B includes one or more biometric sensors (e.g., enclosed in a housing of the device) for measuring cardio fitness while the device is being worn by the user. In some embodiments, device 600B includes one or more features or elements of devices 100, 300, 500, and 600A.

In FIG. 8I, low cardio fitness notifications have been enabled on device 600B via the setup process described above with reference to FIGS. 8A-8H. In response to detecting that, based on multiple cardio fitness measurements taken via the one or more biometric sensors, one or more cardio fitness measurements (e.g., a certain number of sequence for previous cardio fitness measurements; at least a predefined number of measurements within the previous certain number of measurements) were determined to be in the very low quintile, device 600B displays a notification 838 as in FIG. 8I.

Notification 838 includes an indication 838A that previous cardio fitness measurements have been measured to be very low. Notification 838 also includes an indication 838B of potential causes of the very low measurements. Notification 838 also includes an indication 838C that additional (e.g., more detailed) information about the very low measurement can be accessed via device 600A. Notification 838 also includes an affordance 838D for causing display on device 600B of additional information about very low cardio fitness measurements. Notification 838 also includes an affordance 838E for causing device 600B to cease display of the notification. Notification 838 also includes and an indication 838F that notifications (e.g., whether to enable or disable notifications on device 600B, including notification 838) can be managed via a settings application.

Figure 8K:
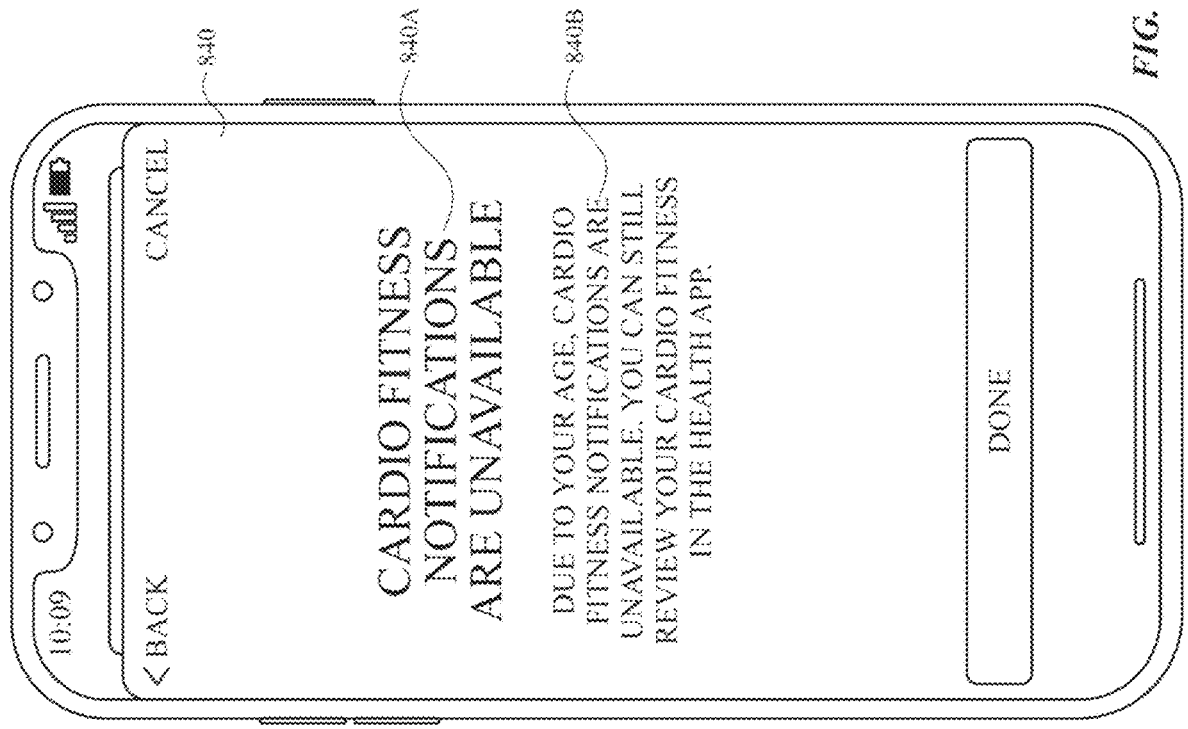
Figure 8J:
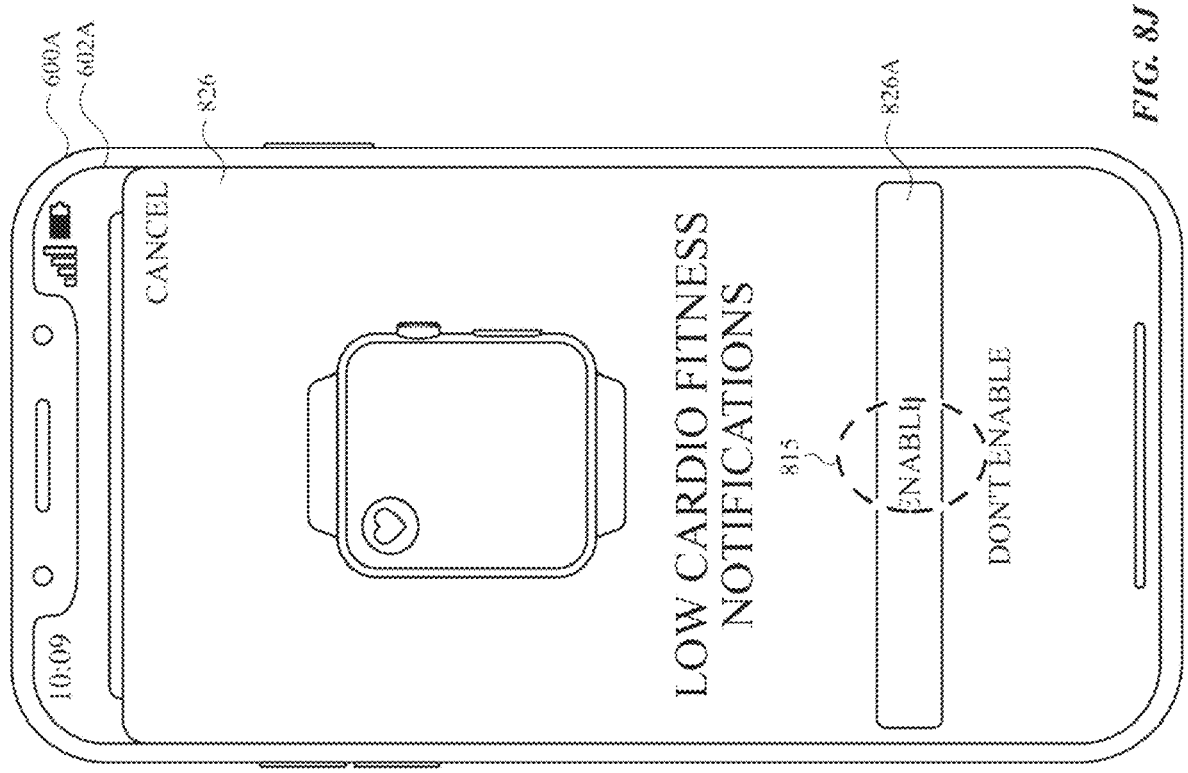

FIG. 8J illustrates device 600B displaying setup user interface 826, as first described above with reference to FIG. 8G. Unlike in FIG. 8G, however, in FIG. 8J, the user is of an age that is above the age threshold (e.g., above 50; above 60) at which low cardio fitness notifications are allowed to be used.

In FIG. 8J, while displaying onboarding user interface 826, device 600A receives an input 815 directed to affordance 826A for enabling low cardio fitness notifications on device 600B. As in FIG. 8G, in response to receiving input 815, device 600A determines whether low cardio fitness notifications can be enabled based on a current age of the user, where the current age of the user is compared with the age threshold (e.g., 50; 60) under which low cardio fitness notifications can be enabled.

In FIG. 8K, in response to receiving input 815, device 600A forgoes activating low cardio fitness notifications and displays a user interface 840. User interface 840 includes an indication 840A that low cardio fitness notifications are unavailable (e.g., that low cardio fitness notifications cannot be activated). User interface 840 also includes an indication 840B of why low cardio fitness notifications are unavailable—due to the user's age being above the age threshold for enabling low cardio fitness notifications.

Figure 8M:
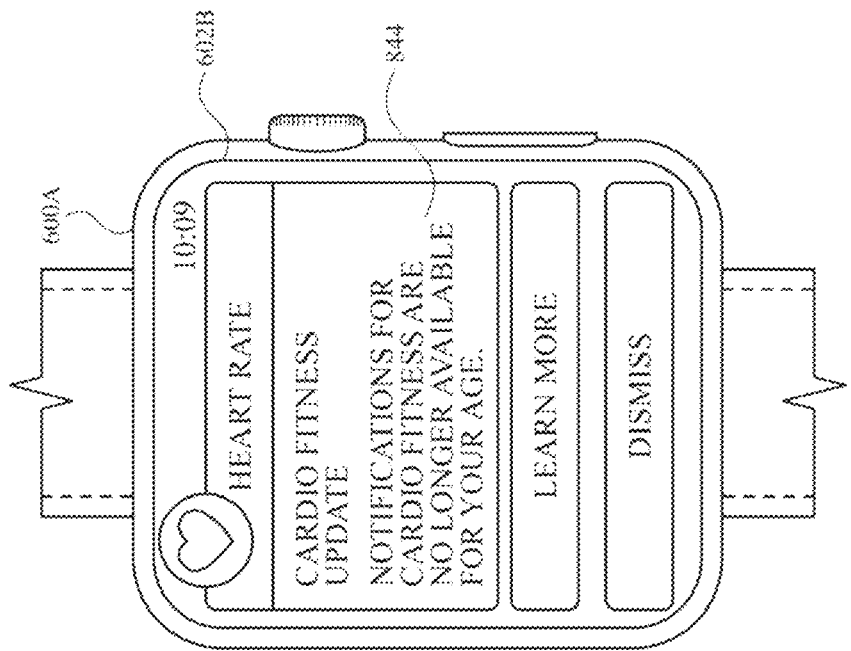
Figure 8L:
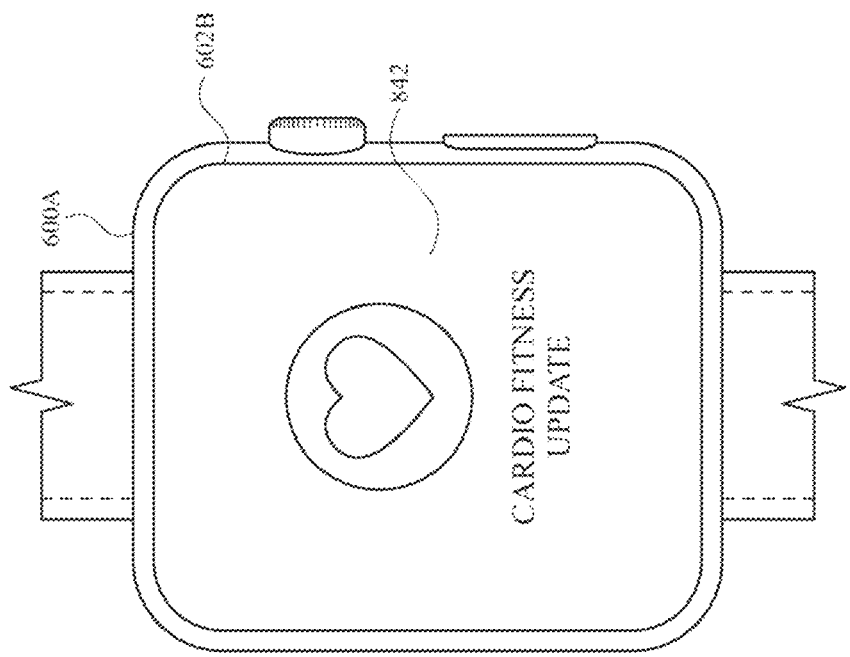

FIG. 8L illustrates device 600B displaying, via display generation component 602B, a notification 842 indicating that there is an update regarding low cardio fitness notifications. In FIG. 8L, device 600A and/or device 600B has determined that the user's age has reached the age threshold (e.g., 50; 60) at which low cardio fitness notifications are unavailable (e.g., the user has become 50 years old; the user has become 60 years old). Upon determining that the user's age has reached the age threshold, device 600A automatically, without user input, un-enrolls the user from low cardio fitness notifications and causes low cardio fitness notifications to be deactivated on device 600B.

In FIG. 8M, device 600B displays (e.g., in response to and/or in accordance with the determination that low cardio fitness notifications are no longer available, as described in FIG. 8L), via display generation component 602B, a notification 844 indicating that low cardio notifications are no longer available and thus will no longer be active on device 600B.

Figure 8N:
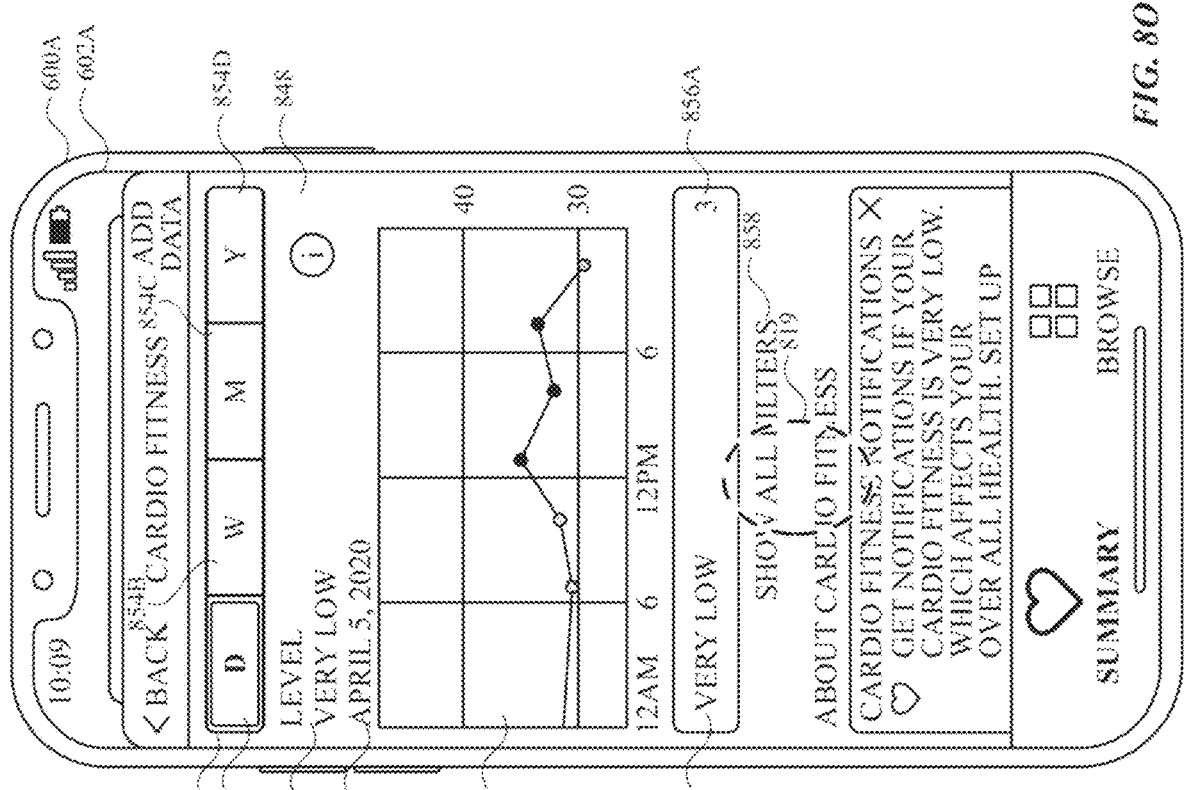

FIG. 8N illustrates device 600B displaying summary user interface 800, as first described above with reference to FIG. 8A. In FIG. 8N, low cardio fitness notifications are activated on device 600B. Summary user interface 800 includes a user interface object 846, referred to from hereon as platter 846, corresponding to low cardio fitness notifications. Platter 846 includes an indication 846A that very low cardio fitness levels have been detected via device 600B.

Also in FIG. 8N, while displaying summary user interface 800, device 600A receives an input 817 directed to platter 846.

Figure 8O:
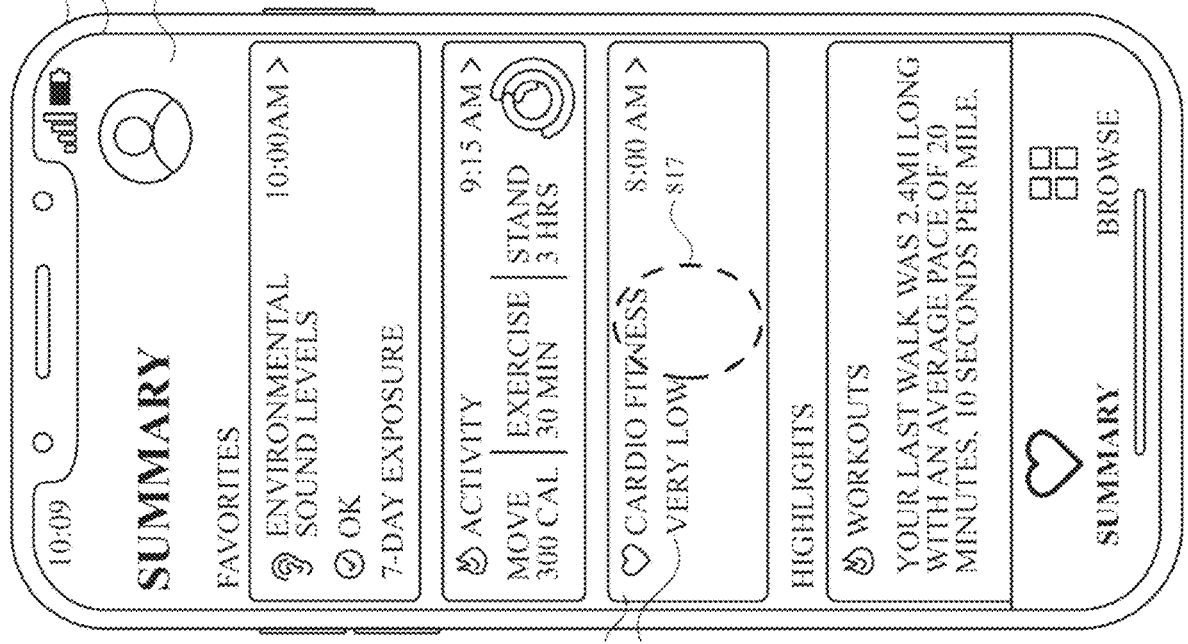

In FIG. 8O, in response to receiving input 817, device 600A displays a user interface 848 for the cardio fitness application. User interface 848 includes a graph region 852 that includes a graphical indication (e.g., via a chart graph or a point graph) of the user's previous cardio fitness measurements that fall within the currently-selected time range. In, the currently-selected time range is a current day, as indicated via time range indication 850A. Device 600A also indicates, in the graphical indication of graph region 852, the points (e.g., by visually marking or highlighting) corresponding to cardio fitness measurements that fall within the currently-selected cardio fitness level quintile filter.

User interface 848 also includes a cardio fitness level indication 850B (e.g., that includes an indication of the cardio fitness level quintile) of one or more cardio fitness measurements during the currently-selected time range (or, alternatively, of an aggregated average of the cardio fitness measurements throughout the currently-selected time range). In FIG. 8O, cardio fitness level indication 850B indicates that the cardio fitness level of the user during the current day falls in the very low quintile.

User interface 848 also includes a time range selection region 854 that includes multiple selectable time ranges, including a current day option 854A, a past week option 854B, a past month option 854C, and a past year option 854D. As mentioned above, the currently-selected time range is the current day, and time range selection region 854 includes a visual indication that current day option 854A is the currently-selected time range (e.g., by visually highlighting or marking current day option 854A).

User interface 848 also includes an indication 856 of the currently-selected cardio fitness level quintile and a numerical indication 856A of the number of cardio fitness level measurements that fall within the currently-selected cardio fitness level quintile level during the currently-selected time range. In FIG. 8O, the currently-selected cardio fitness level quintile is the very low, and number indication 856A indicates that 3 cardio fitness measurements taken during the current day fall within the very low quintile.

User interface 848 also includes an affordance 858 (e.g., stating "show all filters") that, when activated, causes display of all available cardio fitness quintiles (e.g., very high, high, average, low, very low) to apply as a filter for the currently-displayed cardio fitness data in graphical region 852. In FIG. 8O, while displaying user interface 848, device 600A receives an input 819 (e.g., a touch input; a tap input) directed to filters affordance 858.

Figure 8P:
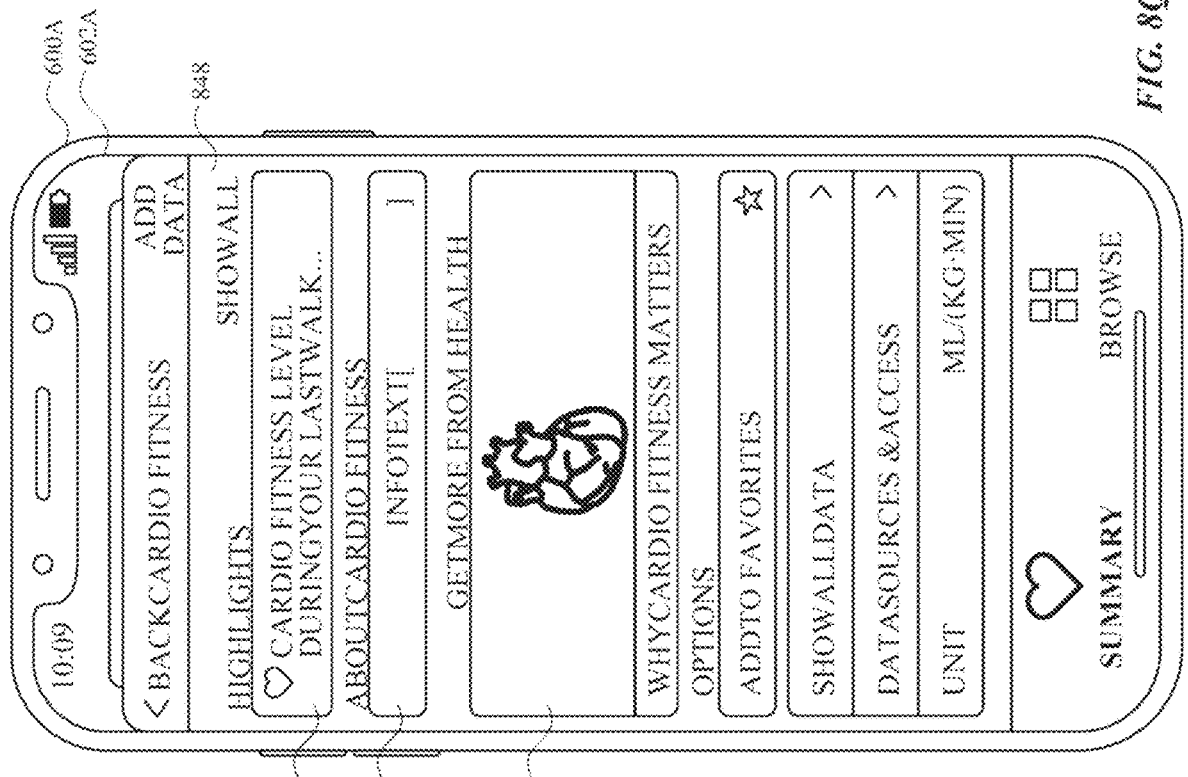

In FIG. 8P, in response to receiving input 819, device 600A displays, in user interface 848, multiple filters 860A-860E corresponding to the quintiles (very high, high, average, low, and very low), with very low filter 860E the currently-selected filter.

The cardio fitness level measurements displayed in graphical region 852 include 3 measurements that fall in the very low quintile, 1 measurement that fall within the low quintile, 2 measurements that fall within the average quintile, 0 measurements that fall within the high quintile, and 0 measurements that fall within the very high quintile. The number of measurements corresponding to each respective quintile is also indicated via filters 860A-860E.

Device 600A also visually indicates, in graph region 852, the cardio fitness level measurements that fall within the currently-selected quintile filter by indicating a zone or region of the graph (e.g., using a particular visual characteristic, such as a different background color or fill color/pattern) that corresponds to the currently-selected quintile level. In FIG. 8P, the currently-selected quintile corresponds to filter 860E (the very low quintile), and graphical region 852 includes a visual indication 852A of a region of the graph that encompasses to the very low quintile.

Also in FIG. 8P, while displaying user interface 848, device 600A receives an input 821 (e.g., a scrolling input; a swipe input) directed to scrolling the user interface.

Figure 8Q:
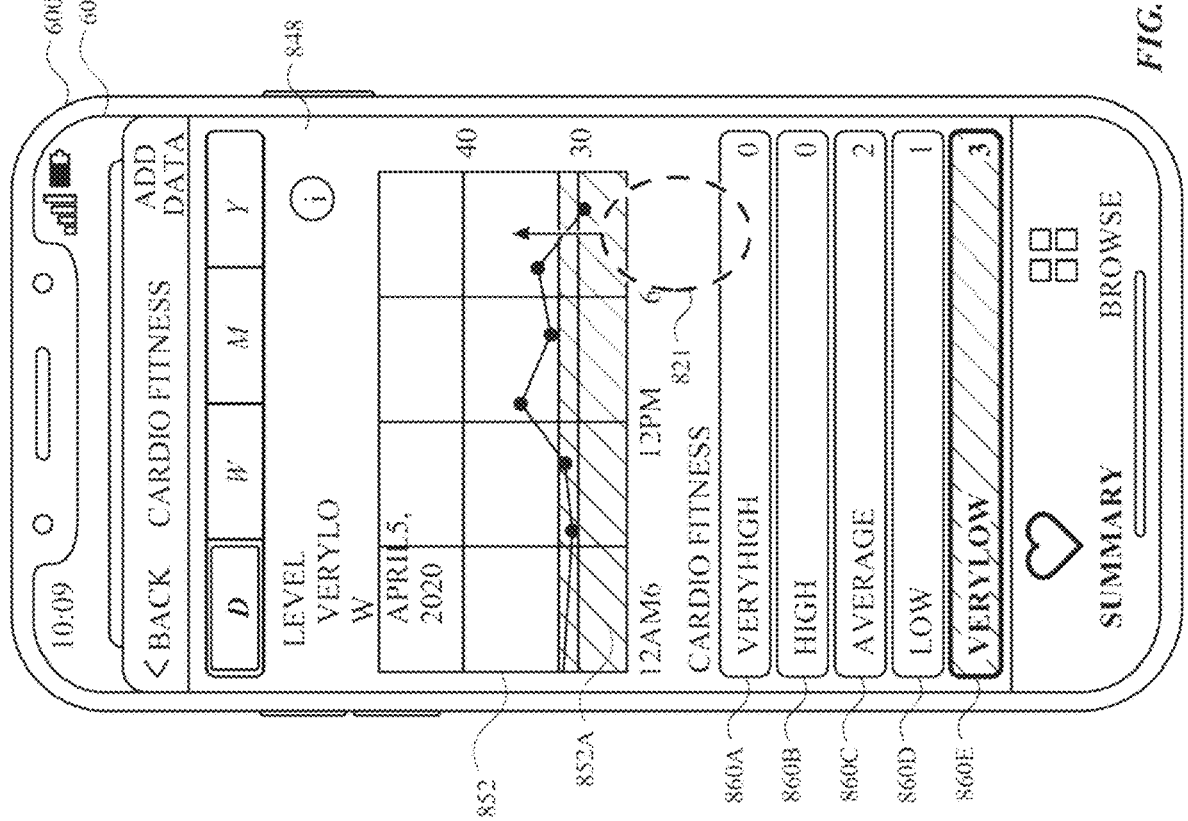

In FIG. 8Q, in response to receiving input 821, device 600A scrolls user interface 848 (e.g., downwards). As shown in FIG. 8Q, user interface 848 further includes previous cardio fitness level measurement information 862 (e.g., the measured cardio fitness level during the user's last walk). User interface 848 also includes information 864 about cardio fitness. User interface 848 also includes information 866 about how cardio fitness relates to heart health.

FIG. 8R illustrates device 600A displaying user interface 848. In FIG. 8R, low cardio fitness notifications are not enabled. Device 600A displays, in user interface 848, a cardio fitness notification 868 (e.g., displayed as a prompt or platter within the user interface) that includes an indication that cardio fitness applications can be enabled (e.g., and the benefit of monitoring cardio fitness for overall health).

In FIG. 8R, while displaying notification 868, device 600A receives an input 823 directed to notification 868. In some embodiments, if the low cardio fitness notifications application had previously been set up, device 600A enables low cardio fitness notifications in response to receiving input 823 (e.g., without requiring that the user go through the onboarding process as described above with reference to FIGS. 8A-8H). In some embodiments (e.g., if the low cardio fitness notifications application had previously been set up), device 600A displays a setup user interface that allows for quick (e.g., one-step) enabling of low cardio fitness notifications (e.g., via an input on a toggle or affordance to enable the notifications) in response to receiving input 823. In some embodiments (e.g., if the low cardio fitness notifications application had not previously been set up), device 600A initiates the onboarding process described above with reference to FIGS. 8A-8H in response to receiving input 823.

FIG. 8S illustrates device 600A displaying summary user interface 800 of the health application, as first described above with reference to FIG. 8A. In FIG. 8S, upon determining that a predetermined number of previous cardio fitness measurements fall in the very low quintile, device 600A displays, in summary user interface 870, a notification 870 indicating that the predetermined number of previous card fitness measurements were determined to fall into the very low quintile.

In FIG. 8S, notification 870 includes information 870A about the number of measurements that fell into the very low quintile. Notification 870 also includes a graphical indication 870B (e.g., a line graph or point graph mapping the measurements versus an average cardio fitness level) of the previous measurements that fell into the very low quintile.

In some embodiments, with respect to FIGS. 8A-8S, the features described regarding measuring low cardio fitness are instead directed to measuring or tracking blood oxygen level (e.g., SpO$_2$). In some embodiments, with respect to FIGS. 8A-8S, the features described regarding measuring low cardio fitness are instead directed to measuring or tracking SPO$_2$ blood oxygen levels. In some embodiments, the computer system is in communication with a blood oxygen sensor (e.g., an optical blood oxygen sensor that operates in conjunction with a light source (e.g., an LED). In some embodiments, the quintiles are based on the percentage of blood oxygen.

FIGS. 9A-9C are a flow diagram illustrating a method for managing the setup of a health feature on an electronic device, in accordance with some embodiments. Method 900 is performed at a computer system (e.g., an electronic device (e.g., 100, 300, 500, 600A, 600B)) that is in communication with a display generation component (e.g., 602A, 602B) (e.g., a display controller, a touch-sensitive display system; a display (e.g., integrated or connected)) and one or more input devices (e.g. gyroscope, accelerometer, microphone, a touch-sensitive surface). Some operations in method 900 are, optionally, combined, the orders of some operations are, optionally, changed, and some operations are, optionally, omitted.

In some embodiments, the electronic device (e.g., 600A, 600B) is a computer system. The computer system is optionally in communication (e.g., wired communication, wireless communication) with the display generation component (e.g., 602A, 602B) and with the one or more input devices. The display generation component is configured to provide visual output, such as display via a CRT display, display via an LED display, or display via image projection. In some embodiments, the display generation component is integrated with the computer system. In some embodiments, the display generation component is separate from the computer system. The one or more input devices are configured to receive input, such as a touch-sensitive surface receiving user input. In some embodiments, the one or more input devices are integrated with the computer system. In some embodiments, the one or more input devices are separate from the computer system. Thus, the computer system can transmit, via a wired or wireless connection, data (e.g., image data or video data) to an integrated or external display generation component to visually produce the content (e.g., using a display device) and can receive, a wired or wireless connection, input from the one or more input devices.

As described below, method 900 provides an intuitive way managing and/or presenting health data. The method reduces the cognitive burden on a user for managing and/or presenting health data, thereby creating a more efficient human-machine interface. For battery-operated computing devices, enabling a user to manage and/or present health data faster and more efficiently conserves power and increases the time between battery charges.

The computer system (e.g., 600A, 600B) displays (902) (e.g., in response to an automatic determination that set of display criteria are met (e.g., after a software update, at a predetermined time)), via the display generation component (e.g., 602A, 602B), a set of one or more user interfaces (e.g., as shown in FIGS. 8A-8H and 10D-10E) that corresponds to a first health-related function (e.g., an application or application feature available to operate on the computer system or available to operate on an external electronic device in communication with the computer system (e.g., a heart-rate-tracking-related function, a medical identification function, an emergency contact function, an ambient-noise-level-tracking function)), wherein the first health-related function is currently inactive (e.g., not enabled (e.g., one or more features of the function are inactive or not enabled)).

Displaying the set of one or more user interfaces (e.g., as shown in FIGS. 8A-8H and 10D-10E) that correspond to the first health-related function includes (904), in accordance with a determination that a set of activation-permissibility criteria (e.g., a set of criteria that governs whether the first health-related function is currently available for activation)

are satisfied, the set of activation-permissibility criteria including a location-based criterion that is satisfied when a current location (e.g., a location within a state, region, or country) of the computer system satisfies a set of location-based criteria, displaying a first activation user interface (e.g., 826, 828, 1004, 1008) of a set of one or more activation user interfaces, the set of one or more activation user interfaces including a first selectable user interface object (e.g., an affordance; a "done" button, an "activate" switch) that, when selected via an input received via the one or more input devices, activates the first health-related function (906).

Displaying the set of one or more user interfaces that correspond to the first health-related function includes (904), in accordance with a determination that the set of activation-permissibility criteria are not satisfied, displaying a notification interface that includes first information corresponding to (e.g., about, related to) the first health-related function (e.g., details regarding the function, information as to why the function is not available at the current location) and that does not include a selectable user interface object (e.g., that does not include any selectable user interface object for activating the first health-related function) that, when selected via an input received via the one or more input devices, activates the first health related function (908). Alternatively displaying a first activation user interface or a notification interface provides the user with feedback as to whether the set of one or more location-based criteria are currently satisfied and feedback as to whether the first health-related functions can be activated at the current location. Providing improved visual feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently.

In some embodiments, the set of location-based criteria includes a criterion that is satisfied when the current location of the computer system (e.g., 600A, 600B) matches a predetermined set of one or more locations (910) (e.g., location that is within a predetermined state, region, or country that permits (e.g., per relevant regulations) use of the first-health related function)). Alternatively displaying a first activation user interface or a notification interface based on criteria that include matching the current location to predetermined locations provides the user with feedback as to the current location corresponds to a predetermined location that permits activation of the first health-related function. Providing improved visual feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently.

In some embodiments, the first health-related function is a function for measuring or tracking SPO$_2$ blood oxygen levels.

In some embodiments, the set of one or more activation user interfaces includes a second activation user interface (e.g., an interface that is different or the same as the first activation user interface) that includes a user interface object for confirming (e.g., the user interface object is a selectable user interface object that is useable to modify the first biometric detail) a first biometric detail (e.g., age, weight, sex) of a user of the computer system (e.g., 600A, 600B) (e.g., as shown in FIGS. 8C-8D). Providing the user with an interface object for confirming a biometric detail provides the user with feedback as the current value of the detail as stored on or accessible to the computer system. Providing improved visual feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently.

In some embodiments, the first biometric detail is a detail that is associated with a health profile for the user that includes a plurality of biometric details of the user (e.g., as shown in FIGS. 8C-8D). In some embodiments, the health profile was accessible to the computer system (e.g., 600A, 600B) (e.g., via the health application corresponding to user interface 800) prior to displaying the user interface that corresponds to a first health-related function.

In some embodiments, the set of one or more activation user interfaces includes a third activation user interface (e.g., an interface that is different or the same as the first or second activation user interfaces) that includes an indication of one or more medications that can affect the first health-related function (e.g., affect heart rate when the function is a heart-related function) (e.g., as shown via 810 in FIGS. 8C-8D). Providing the user with an indication of one or more medications that can affect heart rate provides the user with feedback as factors that can affect the functionality of the first health-related system as it operates on the computer system. Providing improved visual feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently.

In some embodiments, the third activation user interface includes a selectable user interface object (e.g., 814) for providing inputs to indicate whether the user is currently taking the one or more medications.

In some embodiments, the set of one or more activation user interfaces include a fourth activation user interface (e.g., an interface that is different or the same as the first, second, or third activation user interfaces) that includes an indication of one or more physiological parameters that can affect the first health-related function (e.g., as shown in FIGS. 8C-8D).

In some embodiments, the first health-related function includes, when activated, performing one or more biometric measurements (e.g., measuring heart rate) (e.g., as shown in FIGS. 12A-12G). In some embodiments, the biometric measurement is performed automatically (e.g., without an explicit user request) in the background). In some embodiments, after completing a biometric measurement of the first health-related function, the computer system (e.g., 600A and/or 600B) issues a perceptual indication (e.g., 838) (e.g., a visual, audio, or haptic indication; an alert) corresponding to the biometric measurement. In some embodiments, the indication is a selectable user interface object that, when selected, displays a result of the measurement). Issuing a perceptual indication corresponding to the biometric measurement provide the user with feedback as to a completed biometric measurement. Providing improved visual feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently.

In some embodiments, the activation-permission criteria includes a criterion that is satisfied when the age of a user (e.g., as indicated by data available to the computer system or entered by a user) of the computer system (e.g., 600A, 600B) does not exceed a threshold age value (e.g., 50, 55, 60) (912). Including age limitations in the activation-permission criteria provides the user with feedback as to what ages are required for activation of the first health-related criteria. Providing improved visual feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently.

In some embodiments, while the first health-related function is active (e.g., after activation of the function), the computer system (e.g., 600A, 600B) detects (916) that a current age of a user exceeds (e.g., has changed to exceed) a threshold age value (e.g., 50, 55, 60). In some embodiments, in response to detecting that the current age of the user exceeds the threshold age value, the computer system deactivates (916) at least one function (e.g., one component, one function among a set of functions; all the functions of the first health-related function) of the first health-related function. Automatically deactivating a function of the first health-related function based on a user age reduces the need for user input to perform the deactivation. Performing an operation when a set of conditions are met without requiring further user input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, deactivating the at least one function of the first health-related function includes displaying, via the display generation component (e.g., 602A, 602B), an indication (e.g., 844) that the deactivated at least one function of the first health-related function is not available for reactivation (918). Displaying an indication that the first health-related function is not available for reactivation provides the user with feedback as to the state of the function. Providing improved visual feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently.

In some embodiments, the first health-related function includes, when activated, performing one or more biometric measurements (e.g., heart rate) (920). In some embodiments, the biometric measurement is performed automatically (e.g., without an explicit user request) in the background. In some embodiments, after completing a first biometric measurement of the first health-related function, the computer system (e.g., 600A, 600B) displays (922), via the display generation component (e.g., 602A, 602B), a result of the first biometric measurement, wherein the result of the biometric measurement includes an indication classifying the result into a quintile of five possible quintiles (e.g., the results is very high, high, average, low, or very low) (e.g., as shown in FIGS. 8O-8P). Displaying the result of the biometric measurement as a quintile provides the user with feedback as to the result of the measurement. Providing improved visual feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently.

In some embodiments, the first biometric measurement was classified into a first quintile (e.g., the lowest of the five possible quintile). In some embodiments, after completing the first biometric measurement, the computer system (e.g., 600A, 600B) performs a second biometric measurement. In some embodiments, after completing the second biometric measurement, the computer system displays, via the display generation component (e.g., 602A, 602B), a result of the second biometric measurement that includes, in accordance with a determination that result of the second biometric measurement is classified into the first quintile (e.g., the same quintile as the first result) an indication that the second biometric measurement is classified into the first quintile, wherein the indication classifying the result of the second biometric measurement into the first quintile differs from the indication classifying the result of the first biometric measurement into the first quintile. In some embodiments, the indication for the second biometric measurement emphasizes that the user's results continue to remain in the first quintile across multiple measurements. (e.g., "your results continue to be very low"). Displaying an indication of the results of a second biometric that is in a first quintile that differs from the indication of the results of a first biometric measurement that was also in the first quintile provides feedback to the user that at least two measurements have been in the first quintile and distinguishes the results of the two measurements, despite being in the same quintile. Providing improved visual feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently.

In some embodiments, the result of the first biometric measurement or the result of the second biometric measuring includes an indication of a length of time that biometric measurements of the first health-related function have remained in a certain quintile (e.g., in the lowest quintile).

In some embodiments, prior to displaying the set of one or more user interfaces that correspond to the first health-related function, the computer system (e.g., 600A, 600B) determines the current location of the computer system (e.g., via GPS, via cell phone tower ping, via Wi-Fi access point positioning).

In some embodiments, displaying the first activation user interface of the set of one or more activation user interfaces occurs in response to an input received while displaying a user interface of an application (e.g., the health application corresponding to user interface 800) (e.g., a health-data aggregation application) that collects and presents data for a plurality of health-related functions, including the first health-related function. Displaying the first activation user interface of a set of one or more activation user interfaces based on an input received in a health aggregation application provides the user with the ability to activate the first health-related function from an application related to health information, which surfaces relevant functionality of the computer system to the user and improves machine-human interactions. Surfacing relevant functionality and improving the machine-human interactions enhances the operability of the computer system and makes the machine-user interface more efficient and effective (e.g., effective at providing computer operations and functions to the user).

In some embodiments, the first health-related function includes, when activated, performing one or more biometric measurements (e.g., heart rate). In some embodiments, the biometric measurement is performed automatically (e.g., without an explicit user request) in the background). In some embodiments, after completing a plurality of biometric measurements of the first health-related function, the computer system (e.g., 600A, 600B) displays a data user interface (e.g., 848) that includes a graphical representation (e.g., 852) (e.g., a chart; a graph) of results of at least a subset of the plurality of biometric measurements. In some embodiments, the graphical representation corresponds to results for an adjustable period of time (e.g., day, week, month, year). Displaying a data user interface that includes a graphical representation of results of at least a subset of the plurality of biometric measurements provides the user with feedback as to measurement data accessible at the computer system. Providing improved visual feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently.

In some embodiments, the data user interface (e.g., 848) that includes graphical representation (e.g., 852) includes additional information about the first health-related function (e.g., text information) and one or more selectable user interface objects for accessing additional information corresponding to or about first health-related function.

In some embodiments, the first health-related function includes, when activated, performing one or more biometric measurements (e.g., measuring heart rate). In some embodiments, the biometric measurement is performed automatically (e.g., without an explicit user request) in the background). In some embodiments, after completing a third biometric measurement of the first health-related function, the computer system (e.g., 600A, 600B) displays, via the display generation component (e.g., 602A, 602*b*), a result of the third biometric measurement, wherein displaying the result (e.g., very high, high, average, low, or very low) of the third biometric measurement includes displaying reference measurement values from a plurality of different age ranges. In some embodiments, the result page (e.g., 848) includes averages and/or statistical ranges for the biometric measurement, by age group). Displaying the result of the user's biometric measurement along with reference measurement values from a plurality of different age ranges provides the user with feedback as to reference measurement values stored at and/or accessible from the computer system. Providing improved visual feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently.

In some embodiments, the reference measurement values from a plurality of different age ranges does not include measurement values from age ranges above a predetermined age threshold (e.g., 50, 55, 60).

In some embodiments, the reference measurement values from a plurality of different age ranges can be configured to show reference values by specific sex (e.g., male, female) or for all sexes, combined.

Note that details of the processes described above with respect to method 900 (e.g., FIGS. 9A-9C) are also applicable in an analogous manner to the methods described above and below. For example, method 700 optionally includes one or more of the characteristics of the various methods described above with reference to method 900. For example, the user interfaces for managing health and safety features described with reference to method 700 can be used to manage one or more features of the health applications described with reference to method 900. For another example, method 1100 optionally includes one or more of the characteristics of the various methods described above with reference to method 900. For example, features concerning the conditional display of a setup user interface as described with reference to method 900 can be applied to the setup process described with reference to method 1100. For another example, method 1300 optionally includes one or more of the characteristics of the various methods described above with reference to method 900. For example, features concerning the conditional display of a setup user interface as described with reference to method 900 can be applied during a process for setting up the biometric measurement application described with reference to method 1300. For another example, method 1500 optionally includes one or more of the characteristics of the various methods described above with reference to method 900. For example, health information that is presented in the user interfaces described with reference to method 1500 can at least partly be based on whether a particular type of health application or feature can be enabled or setup as described with reference to method 900. For another example, method 1700 optionally includes one or more of the characteristics of the various methods described above with reference to method 900. For example, the type of health information that is collected via background measurements as described with reference to method 1700 can at least partly be based on whether a particular type of health application or feature can be enabled or setup as described with reference to method 900. For brevity, these details are not repeated below.

FIGS. 10A-10V illustrate exemplary user interfaces for managing background health measurements on an electronic device, in accordance with some embodiments. The user interfaces in these figures are used to illustrate the processes described below, including the processes in FIGS. 11A-11B.

FIG. 10A illustrates device 600A displaying a user interface 1000 of a companion application for device 600B, where the companion application can be used to manage settings, applications, and/or application features of device 600B. In FIG. 10A, user interface 1000 includes multiple user interface objects (e.g., affordances) corresponding to applications that are installed on device 600B, including a user interface object 1002 corresponding to a heart health level tracker application.

The heart health level tracker application causes device 600B to perform automatic/background heart rate measurements using one or more biometric sensors of device 600B without requiring manual user input for the measurements. In some embodiments, the automatic/background heart rate measurements are performed at predetermined time intervals.

In FIG. 10A, while displaying user interface 1000, device 600A receives an input 1001 directed to user interface object 1002.

In FIG. 10B, in response to receiving input 1001, device 600A displays a setup user interface 1004 corresponding to a setup (e.g., onboarding) process for the heart health level tracker application. In some embodiments, setup user interface 1004 is also accessible from the health application (e.g., setup user interface 1004 is displayed as a pop-up over a user interface of the health application).

In FIG. 10B, setup user interface 1004 includes information 1004A about features of the heart health level tracker application. Setup user interface 1004 also includes an indication 1004B that location information will be used to determine whether the heart health level tracker application is available for use at the current location. Setup user interface 1004 also includes an affordance 1004C for continuing the onboarding process for the heart health level tracker application.

In FIG. 10B, device 600A is at a location (e.g., a city; a state; a country; a region) where the heart health level tracker application is not available for use (e.g., due to regulations at the respective location). While displaying onboarding user interface 1004, device 600A receives an input 1003 directed to affordance 1004C.

In FIG. 10C, in response to receiving input 1003 (e.g., and based on a determination that device 600A is at the location at which the heart health level tracker application is not available for use), device 600A displays, overlaid on setup user interface 1004, a notification 1006 that includes an indication 1006A that the heart health level tracker application is not available for use at the current location. Device 600A also forgoes enabling the heart health measurement feature.

FIG. 10D illustrates device 600A again displaying setup user interface 1004, as first described above with reference to FIG. 10B. In FIG. 10D, device 600A is at a location where the heart health level tracker application is available for use (e.g., is not prohibited for use by a regulation). While displaying onboarding user interface 1004, device 600A receives an input 1005 directed to affordance 1004C.

Figure 10E:
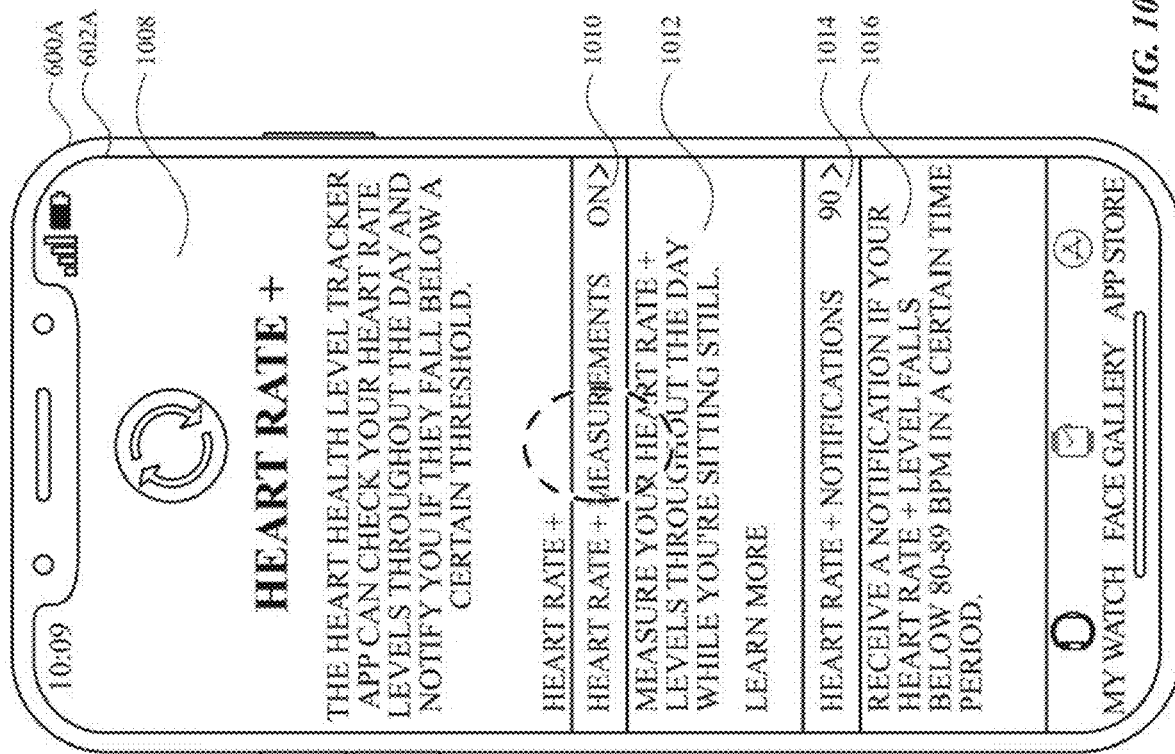
FIGS. 10A-10V illustrate exemplary user interfaces for managing background health measurements on an electronic device, in accordance with some embodiments.

In FIG. 10E, in response to receiving input 1005 (e.g., and based on a determination that device 600A is at the location at which the heart health level tracker application is available for use), device 600A displays a user interface 1008 (e.g., a settings page for the heart health level tracker application).

User interface 1008 includes a selectable user interface object 1010 that indicates that the heart health level tracker feature is activated. User interface 1008 also includes information 1012 about the heart health level tracker feature.

User interface 1008 also includes a selectable user interface object 1014 that includes an indication of a currently-selected threshold (e.g., a default threshold) for triggering notifications indicating that measured heart health level information is lower than the selected threshold. User interface 1008 also includes information 1016 about when the notifications will be triggered.

FIG. 10F illustrates device 600B displaying a user interface 1018 (e.g., a home user interface; an applications user interface) that includes an application icon 1020 corresponding to the heart health level tracker application. In FIG. 10F, the heart health level tracker application is not activated on device 600B.

In FIG. 10F, while displaying user interface 1018, device 600B receives an input 1007 directed to application icon 1020.

In FIG. 10G, in response to receiving input 1007 directed to application icon 1020, device 600B displays a notification 1022 that includes an indication 1022A that the heart health level tracker application can be activated (e.g., the setup process for the heart health level tracker application can be completed on device 600A).

In FIG. 10H, device 600A displays (e.g., while device 600B is displaying notification 1022) a notification 1024 corresponding to the heart health level tracker application. Notification 1024 includes an affordance 1024A for enabling the heart health level tracker feature on device 600B. While displaying notification 1024, device 600A receives an input 1009 directed to affordance 1024A.

In FIG. 10I, in response to receiving input 1009, device 600A displays user interface 1008 corresponding to the heart health level tracker application as first described above with reference to FIG. 10E. While displaying user interface 1008, device 600A receives an input 1011 directed to selectable user interface object 1010. In FIG. 10I, selectable user interface object 1010 indicates that the heart health level tracker feature corresponding to the heart health level tracker application is active.

In FIG. 10J, in response to receiving input 1011, device 600A displays a user interface 1026 that includes information 1026A about the heart health level tracking application (e.g., that device 600B will initiate automatic/background heart rate measurements at predetermined time intervals throughout a day).

Also in FIG. 10J, user interface 1026 includes a selectable user interface object 1028 (e.g., a toggle; an affordance) for enabling or disabling automatic/background heart rate measurements on device 600B. Selectable user interface object 1028 indicates that background heart rate measurements are currently in an ON state.

While background heart rate measurements are in the ON state, user interface 1026 enables management of automatic/background heart rate measurements based on a current device state of device 600B. In some embodiments, the device states include a sleep mode and a theater mode (e.g., a do-not-disturb mode).

With respect to sleep mode, user interface 1026 includes a selectable user interface object 1030 (e.g., a toggle; an affordance) for enabling or disabling automatic/background heart rate measurements when device 600B is in sleep mode. If selectable user interface object 1030 is in the ON state, device 600B continues to perform automatic/background heart rate measurements (e.g., at predetermined time intervals) even if device 600B is in sleep mode. If selectable user interface object 1030 is in the OFF state, device 600B forgoes performing automatic/background heart rate measurements (e.g., at predetermined time intervals) if device 600B is in sleep mode. In FIG. 10J, selectable user interface object 1030 is in the OFF state.

With respect to theater mode (e.g., do-not-disturb mode), user interface 1026 includes a selectable user interface object 1032 (e.g., a toggle; an affordance) for enabling or disabling automatic/background heart rate measurements when device 600B is in theater mode. If selectable user interface object 1032 is in the ON state, device 600B continues to perform automatic/background heart rate measurements (e.g., at predetermined time intervals) even if device 600B is in theater mode. If selectable user interface object 1032 is in the OFF state, device 600B forgoes performing automatic/background heart rate measurements (e.g., at predetermined time intervals) if device 600B is in theater mode. In FIG. 10J, selectable user interface object 1032 is in the OFF state.

In FIG. 10J, while displaying user interface 1026 with selectable user interface object 1030 corresponding to sleep mode in the OFF state, device 600A receives an input 1013 directed to selectable user interface object 1030.

In FIG. 10K, in response to receiving input 1013, device 600A indicates, via selectable user interface object 1030, that automatic/background heart rate measurements are now enabled while in sleep mode and causes background heart rate measurements on device 600B to be enabled when device 600B is in sleep mode. In FIG. 10K, automatic/background heart rate measurements are still disabled while in theater mode; thus, device 600B will perform automatic/background heart rate measurements while device 600B is not in either sleep mode or theater mode or while in sleep mode, but will not perform automatic/background heart rate measurements while device 600B is in theater mode.

Also in FIG. 10K, while displaying user interface 1026 with selectable user interface object 1032 corresponding to theater mode in the OFF state, device 600A receives an input 1015 directed to selectable user interface object 1032.

Figure 10L:
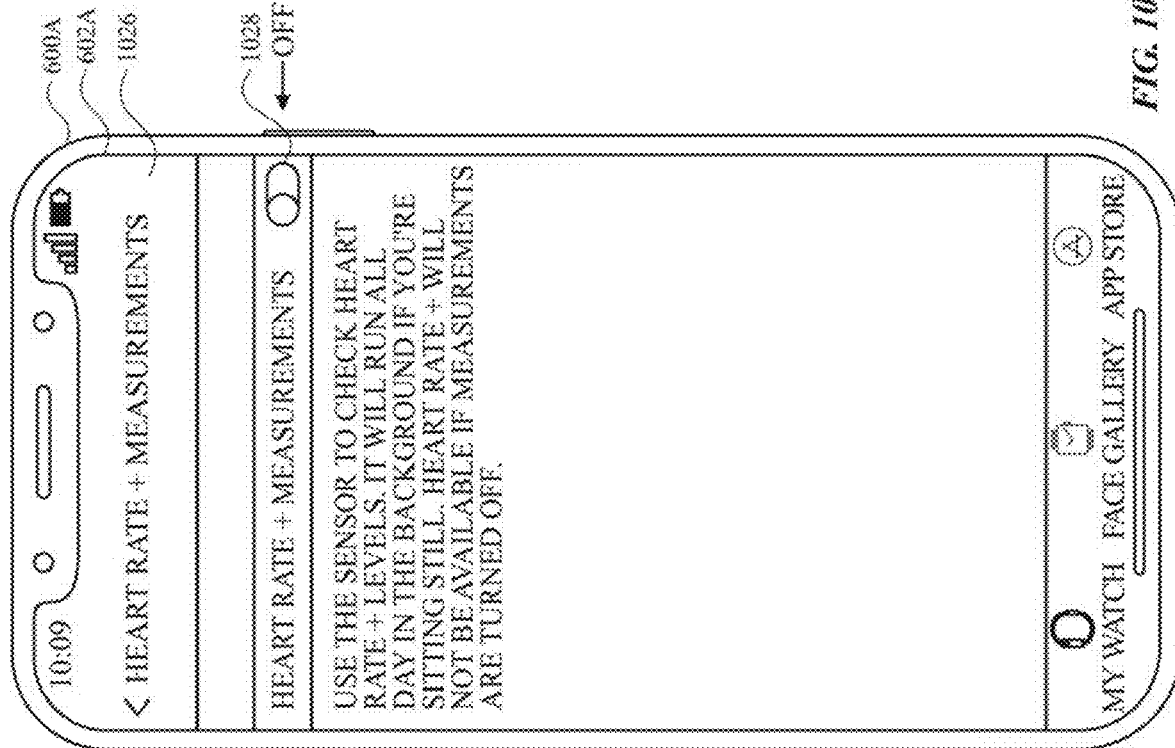

In FIG. 10L, in response to receiving input 1015, device 600A indicates, via selectable user interface object 1032, that automatic/background heart rate measurements are now enabled while in theater mode and causes automatic/background heart rate measurements on device 600B to be enabled when device 600B is in theater mode. In the embodiment of FIG. 10L, automatic/background heart rate measurements are now always enabled, whether or not device 600B is in sleep mode and/or theater mode.

Also in FIG. 10L, while displaying user interface 1026 and automatic/background heart rate measurements are enabled, device 600A receives an input 1017 directed to selectable user interface object 1028.

Figure 10M:
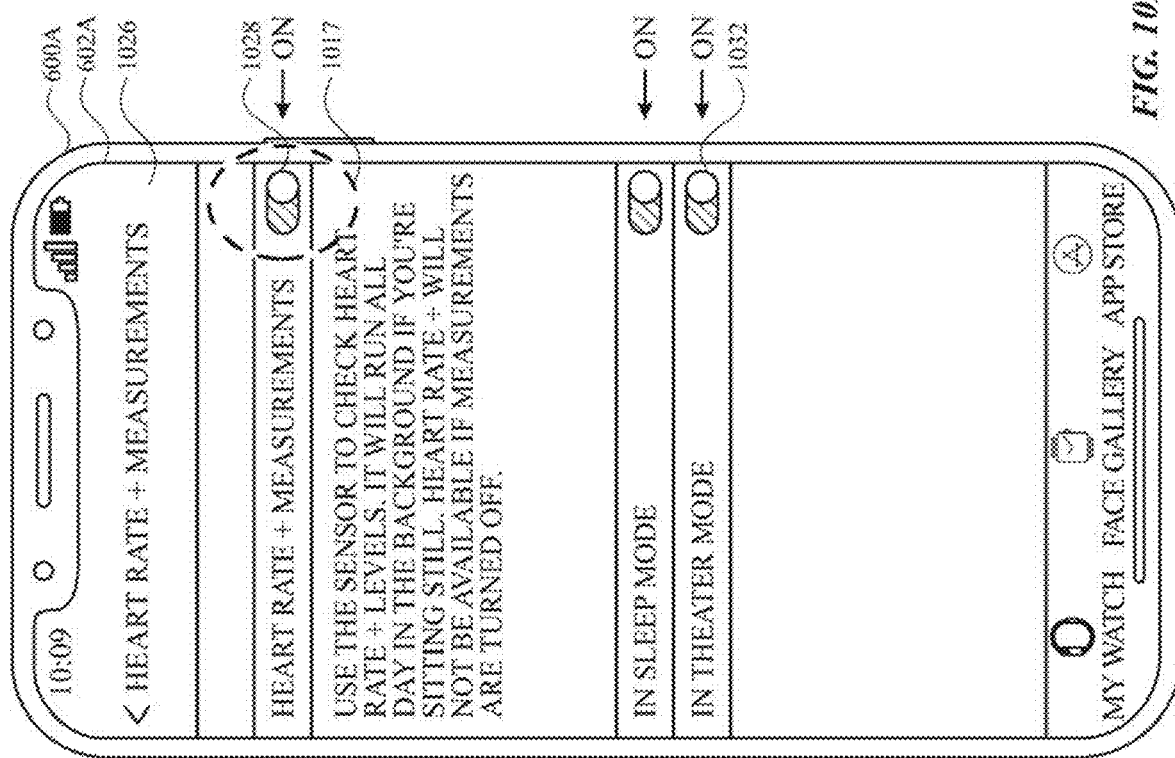

In FIG. 10M, in response to receiving input 1017, device 600A indicates, via selectable user interface object 1026, that automatic/background heart rate measurements are now disabled. Device 600A forgoes displaying selectable user interface object 1030 corresponding to sleep mode and selectable user interface object 1032 corresponding to theater mode. Device 600A also causes automatic/background heart rate measurements to be disabled on device 600B such that device 600B will not perform any automatic/background heart rate measurements.

FIGS. 10N-10P illustrate a corresponding process for enabling or disabling automatic/background heart rate measurements using device 600B (instead of using device 600A). In FIG. 10N, device 600B displays a user interface 1034 for a device settings application, where user interface 1034 includes multiple user interface objects (e.g., platters) corresponding to applications that are installed on device 600B, including user interface object 1036 corresponding to the heart health level tracker application.

Also in FIG. 10N, while displaying user interface 1034, device 600B receives an input 1019 directed to user interface object 1036.

In FIG. 10O, in response to receiving input 1019, device 600B displays a user interface 1038 of the heart health level tracker application corresponding to user interface 1008 first described above with reference to FIG. 10E. Similar to user interface 1008, user interface 1038 includes a selectable user interface object 1040 (e.g., an affordance) that indicates that the heart health level tracker feature is active on device 600B. User interface 1038 also includes a selectable user interface object 1042 that includes an indication of a currently-selected threshold (e.g., a default threshold) for triggering heart rate notifications.

Also in FIG. 10O, while displaying user interface 1038, device 600B receives an input 1021 directed to selectable user interface object 1040.

In FIG. 10P, in response to receiving input 1021, device 600B displays a user interface 1044 that corresponds to user interface 1026 first described above with reference to FIG. 10J. Similar to user interface 1026, user interface 1044 includes information 1044A about the heart health level tracking application, in particular that automatic/background heart rate measurements will be initiated by device 600B (e.g., at predetermined time intervals throughout a day).

Also similar to user interface 1026, user interface 1044 includes a selectable user interface object 1046 (e.g., a toggle; an affordance) for enabling or disabling automatic/background heart rate measurements on device 600B. In FIG. 10P, selectable user interface object 1046 indicates that automatic/background heart rate measurements are currently in an ON state (e.g., the toggle is in the ON position).

As with user interface 1026, while automatic/background heart rate measurements are in the ON state, user interface 1044 also enables management of automatic/background heart rate measurements based on a current device state of device 600B that operates the automatic/background heart rate measurements. In FIG. 10P, the device states include a sleep mode and a theater mode (e.g., a do-not-disturb mode).

With respect to sleep mode, user interface 1044 includes a selectable user interface object 1048 (e.g., a toggle; an affordance) for enabling or disabling automatic/background heart rate measurements when device 600B is in sleep mode. If selectable user interface object 1048 is in the ON state, device 600B continues to perform automatic/background heart rate measurements (e.g., at predetermined time intervals) even if device 600B is in sleep mode. If selectable user interface object 1048 is in the OFF state, device 600B forgoes performing automatic/background heart rate measurements (e.g., at predetermined time intervals) if device 600B is in sleep mode. In FIG. 10P, selectable user interface object 1048 is in the ON state.

With respect to theater mode (e.g., do-not-disturb mode), user interface 1044 includes a selectable user interface object 1050 (e.g., a toggle; an affordance) for enabling or disabling automatic/background heart rate measurements when device 600B is in theater mode. If selectable user interface object 1050 is in the ON state, device 600B continues to perform automatic/background heart rate measurements (e.g., at predetermined time intervals) even if device 600B is in theater mode. If selectable user interface object 1050 is in the OFF state, device 600B forgoes performing automatic/background heart rate measurements (e.g., at predetermined time intervals) if device 600B is in theater mode. In FIG. 10P, selectable user interface object 1050 is in the OFF state.

FIG. 10Q illustrates device 600B displaying user interface 1008 as first described above with reference to FIG. 10E. In FIG. 10Q, while displaying user interface 1008, device 600B receives an input 1023 directed to selectable user interface object 1014.

In FIG. 10R, in response to receiving input 1023, device 600B displays a user interface 1052 for changing the heart rate BPM threshold for triggering a notification, as described via information 1052A. User interface 1052 also includes information 1052B about typical, average, or normal heart rates.

User interface 1052 also includes multiple threshold options 1054A-1054E. In FIG. 10R, the threshold options include OFF option 1054A (which, if selected, would not enable notifications), first threshold option 1054B (e.g., 40 BPM), second threshold option 1054C (e.g., 45 BPM), third threshold option 1054D (e.g., 50 BPM), and fourth threshold option 1054E (e.g., 55 BPM). Also in FIG. 10R, marker 1056 indicates that third threshold option 1054D is the currently-selected heart rate threshold.

Figure 10T:
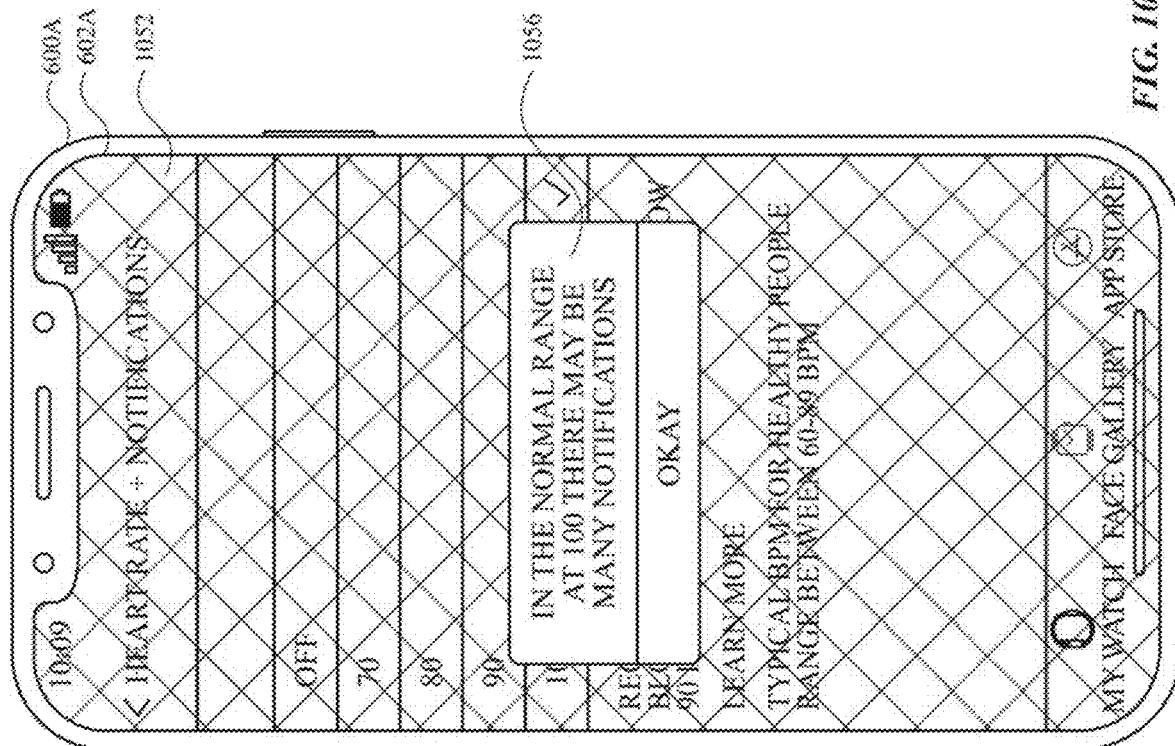
Figure 10S:
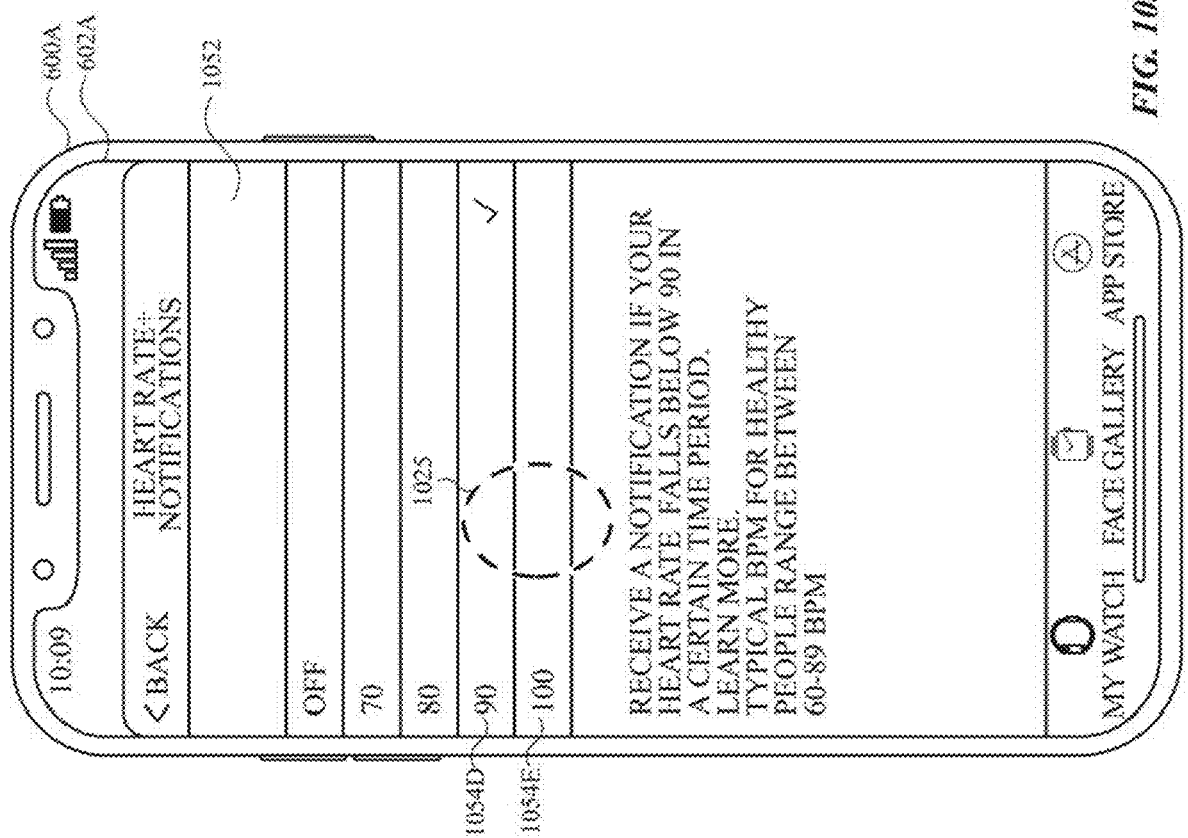

In FIG. 10S, while displaying user interface 1052 with third threshold option 1054D (e.g., 50 BPM) the currently-selected threshold, device 600A receives an input 1025 directed to fourth threshold option 1054E (e.g., 55 BPM).

In FIG. 10T, in response to receiving input 1025 directed to fourth threshold option 1054E, device 600B displays a notification 1056 indicating that the newly-selected threshold (e.g., 55 BPM) would cause frequent heart rate notifications (e.g., because if a high heart rate threshold is set, a greater number of automatic/background heart rate measurements performed by device 600B would fall under the high heart rate threshold as compared to if a low heart rate threshold is set, thus causing a greater number of notifications).

FIGS. 10U-10V illustrate corresponding user interfaces for changing the heart rate notification threshold on device 600B. In FIG. 10U, device 600B displays user interface 1038 of the heart health level tracker application as first described above with reference to FIG. 10O. While display user interface 1038, device 600B receives an input 1027 directed to selectable user interface object 1042 that includes an indication of a currently-selected threshold (e.g., a default threshold) for triggering heart rate notifications.

In FIG. 10V, in response to receiving input 1027, device 600B displays a user interface 1058, similar to user interface 1052 first described above with reference to FIG. 10R, for changing the heart rate BPM threshold. Similar to user interface 1052, user interface 1052 includes information 1052B about typical, average, or normal heart rates.

Also similar to user interface 1052, user interface 1058 includes multiple threshold options 1060A-1060E. In FIG. 10V, as in FIG. 10R, the threshold options include OFF option 1060A (which, if selected, would not enable notifications), first threshold option 1060B (e.g., 40 BPM), second threshold option 1060C (e.g., 45 BPM), third threshold option 1060D (e.g., 50 BPM), and fourth threshold option 1060E (e.g., 55 BPM). Also in FIG. 10V, marker 1062 indicates that fourth threshold option 1060E is the currently-selected heart rate threshold. As described above with reference to user interface 1052 in FIG. 10S, a different heart rate threshold for triggering heart rate notifications can be selected via user interface 1058.

In some embodiments, the heart rate level tracking function of FIGS. 10A-10V is instead a blood oxygen level tracking function. In some embodiments, the computer system is in communication with a blood oxygen sensor (e.g., an optical blood oxygen sensor that operates in conjunction with a light source (e.g., an LED). In some embodiments, the threshold is a percentage of blood oxygen. In some embodiments, the heart rate level tracking function of FIGS. 10A-10V is instead a function for measuring or tracking $VO_2$max (e.g., maximal oxygen consumption; the maximum rate of oxygen consumption measured during incremental exercise).

FIGS. 11A-11B are a flow diagram illustrating a method for managing background health measurements on an electronic device, in accordance with some embodiments. Method 1100 is performed at a computer system (e.g., an electronic device (e.g., 100, 300, 500, 600A, 600B)) that is in communication with a display generation component (e.g., 602A, 602B) (e.g., a display controller, a touch-sensitive display system; a display (e.g., integrated or connected)) and one or more input devices (e.g. gyroscope, accelerometer, microphone, a touch-sensitive surface). Some operations in method 1100 are, optionally, combined, the orders of some operations are, optionally, changed, and some operations are, optionally, omitted.

In some embodiments, the electronic device (e.g., 600A, 600B) is a computer system. The computer system is optionally in communication (e.g., wired communication, wireless communication) with the display generation component (e.g., 602A, 602B) and with the one or more input devices. The display generation component is configured to provide visual output, such as display via a CRT display, display via an LED display, or display via image projection. In some embodiments, the display generation component is integrated with the computer system. In some embodiments, the display generation component is separate from the computer system. The one or more input devices are configured to receive input, such as a touch-sensitive surface receiving user input. In some embodiments, the one or more input devices are integrated with the computer system. In some embodiments, the one or more input devices are separate from the computer system. Thus, the computer system can transmit, via a wired or wireless connection, data (e.g., image data or video data) to an integrated or external display generation component to visually produce the content (e.g., using a display device) and can receive, a wired or wireless connection, input from the one or more input devices.

As described below, method 1100 provides an intuitive way for managing and/or presenting health data. The method reduces the cognitive burden on a user for managing and/or presenting health data, thereby creating a more efficient human-machine interface. For battery-operated computing devices, enabling a user to manage and/or present health data faster and more efficiently conserves power and increases the time between battery charges.

The computer system (e.g., 600A, 600B) displays (1102), via the display generation component (e.g., 602A, 602B), a first configuration user interface of a set of one or more configuration user interfaces (e.g., 1004, 1008, 1026, 1038, 1044, 1052, 1058) for a first health-related tracking function (e.g., a tracking (e.g., data tracking, data gathering) application or application feature available to operate on the computer system or available to operate on an external electronic device in communication with the computer system (e.g., a heart-rate-tracking function, an ambient-noise-level-tracking function)), wherein the first configuration user interface includes a first selectable user interface object, and wherein the first health-related tracking function is currently configured to track (e.g., automatically track; track without requiring express user input) a first set of health-related data (e.g., heart rate data, blood pressure data, ambient noise data) while the computer system is in a first mode (e.g., a sleep mode, a locked mode; a low power mode; a mode that corresponds to a predetermined time of the day, a do-notdisturb mode (e.g., a theater DND mode)) and a second mode that is different from the first mode (e.g., a default mode; a mode that is in operation when the first mode is not in operation).

The computer system (e.g., 600A, 600B) receives (1108) a set of one or more inputs, the set of one or more inputs including an input corresponding to the first selectable user interface object (e.g., 1028, 1030, 1032) (e.g., a toggle switch, a check box, a drop-down menu).

In response to the set of one or more inputs, the computer system (e.g., 600A, 600B) configures (1110) the first health-related tracking function to not track (e.g., not automatically track (e.g., not track without user input); not track in the background) the first set of health-related data while the computer system is in the first mode (e.g., as in FIG. 10J) while continuing to track the first set of health-related data while the computer system is in the second mode. Configuring the first health-related tracking function to not track while in a first mode while continuing to track while in second mode allows the user to configure the computer system to automatically and selectively perform a tracking function, without the user having to manual activate and deactivate the function. Performing an optimized operation when a set of conditions has been met without requiring further user input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the first health-related tracking function is a heart rate tracking function.

In some embodiments, the set of one or more configuration user interfaces (e.g., 1004, 1008, 1026, 1038, 1044, 1052, 1058) for the first health-related tracking function includes a selectable affordance (e.g., 1028, 1046) for modifying (e.g., activating or deactivating) an activation state of the first health-related tracking function and information about the first health-related tracking function.

In some embodiments, the set of one or more configuration user interfaces (e.g., 1004, 1008, 1026, 1038, 1044, 1052, 1058) for the health-related tracking functions is accessible from an application for configuring one or more features of an external electronic device (e.g., 600B) (e.g., a smart watch) that is paired with the computer system (e.g., 600A).

In some embodiments, the set of one or more configuration user interfaces (e.g., 1004, 1008, 1026, 1038, 1044, 1052, 1058) for the health-related tracking functions is accessible from an application (e.g., a health-data aggregation application) that collects and presents data for a plurality of health-related functions, including the first health-related function (e.g., the health application corresponding to user interface 800 of FIG. 8A). In some embodiments, the set of one or more configuration user interfaces is displayed as a pop-up overlaid on a user interface of the application that collects and presents health data.

In some embodiments, prior to displaying the first configuration user interface of the set of one or more configuration user interfaces (e.g., 1004, 1008, 1026, 1038, 1044, 1052, 1058) for the first health-related tracking function, the computer system (e.g., 600A, 600B) receives, from an external electronic device in communication with the computer system (e.g., a smart watch paired with the computer system), data indicating that a process for configuring (e.g., a process for activating, a process for initially configuring or setting up the function) the first health-related tracking function was initiated at the external electronic device. In some embodiments, in response to receiving the data, the computer system displays a notification (e.g., 1022) indicating that the process for configuring the first health-related tracking function can be completed at the computer system. In some embodiments, selection of the notification causes display of a second configuration user interface (e.g., that is the same as or different from the first configuration user interface) of the set of one or more configuration user interfaces for a first health-related tracking function. Displaying a notification indicating that the process for configuring the first health-related tracking function can be completed at the computer system provides the user with feedback about a process that has been initiated and that can be completed using the computer system. Providing improved visual feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently.

In some embodiments, after displaying the notification (e.g., 1022) indicating that the process for configuring the first health-related tracking function can be completed at the computer system (e.g., 600A), the computer system receives a set of one or more inputs that completes the process for configuring the first health-related tracking function at the computer system (e.g., as shown in FIG. 10H), wherein the process for configuring the first health-related tracking function includes enabling (e.g., automatically) the first health-related tracking function to perform tracking operations without requiring further user input (e.g., performing automatically, background measurements). Enabling the first health-related tracking function to perform tracking operations without requiring further user input enables the user to permit the computer system to perform an operation without requiring further user input. Performing an operation without requiring further user input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the set of one or more configuration user interfaces (e.g., 1004, 1008, 1026, 1038, 1044, 1052, 1058) includes a second selectable user interface object (e.g., 1028, 1046) that, when selected, disables performance of tracking operations (e.g., measurements) of the first health-related tracking function that occur without user input (e.g., without user input manually activating the tracking function). Proving user interface object to disable performance of tracking operations of the first health-related tracking function that occur without user input provides the user with an option to disable the function and thereby conserve system resources. Conserving system resources enhances the operability of the computer system and makes the user-device interface more efficient (e.g., by limiting unwanted operations) which, additionally, reduces power usage and improves battery life of the computer system by enabling the user to use the computer system more efficiently.

In some embodiments, the first health-related tracking function is configured to perform tracking operations only in response to a user input (e.g., the first health-related tracking function does not perform automatic and/or background tracking operations). Performing tracking operations of the first health-related tracking function only on user request conserves system resources. Conserving system resources enhances the operability of the computer system and makes the user-device interface more efficient (e.g., by limiting unwanted operations) which, additionally, reduces power usage and improves battery life of the computer system by enabling the user to use the computer system more efficiently.

In some embodiments, while the first health-related tracking function is inactive, the computer system (e.g., 600A, 600B) receives a user request to activate the first health-related tracking function. In some embodiments, in response to the request, the computer system configures the first health-related tracking function to track in both the first mode (e.g., corresponding to 1030, 1048) and the second mode (e.g., corresponding to 1032, 1050).

In some embodiments, the computer system (e.g., 600A, 600B) is in the first mode (e.g., the mode in which the tracking function does not occur) when the current time corresponds to a predetermined period of time (e.g., certain hours of the day; hours of the day identified as corresponding to a sleep period) (1106). Disabling tracking during a predetermined period of the day conserves system resources. Conserving system resources enhances the operability of the computer system and makes the user-device interface more efficient (e.g., by limiting unwanted operations) which, additionally, reduces power usage and improves battery life of the computer system by enabling the user to use the computer system more efficiently.

In some embodiments, the computer system (e.g., 600A, 600B) receives (1112) an input of a first type (e.g., input detected by an accelerometer indicative of movement of the computer system that matches a predetermined movement pattern). In some embodiments, in response to receiving the input of the first type (1114), in accordance with a determination that the computer system is not in the first mode (e.g., a determination that the device is in another mode), the computer system increases (1116) the brightness of the display generation component (e.g., 602A, 602B) (e.g., including activating the component from an inactive state). In some embodiments, in response to receiving the input of the first type (1114), in accordance with a determination that the computer system is in the first mode, the computer system forgoes increasing (1118) the brightness of the display generation component. In some embodiments, the first mode is a "theater mode" in which brightening of a display screen is more limited than when the mode is not active. Selectively brightening the display generation component conserves system resources and prevents unintentional brightening. Conserving system resources enhances the operability of the computer system and makes the user-device interface more efficient (e.g., by limiting unwanted operations) which, additionally, reduces power usage and improves battery life of the computer system by enabling the user to use the computer system more efficiently.

In some embodiments, the set of one or more configuration user interfaces (e.g., 1004, 1008, 1026, 1038, 1044, 1052, 1058) include a third selectable user interface object that, when selected, configures a threshold value of the first set of health-related data (e.g., as shown in 1052 and 1058) that causes the computer system (e.g., 600A, 600B) to issue a perceptual notification (e.g., 838) when the health-related tracking function detects that the threshold value has been exceeded (1104). In some embodiments, the computer system receives (1120) a set of one or more user inputs that includes an input corresponding to the third selectable user interface object. In some embodiments, in response to receiving the set of one or more user inputs that includes an input corresponding to the third selectable user interface object (1122), in accordance with a determination that the set or one or more inputs cause the threshold value to be configured to a predetermined value (e.g., a value (e.g., one of a plurality of predetermined values) that will likely result in frequent notifications), the computer system displays (1124) an indication that frequent perceptual notifications can result. In some embodiments, in response to receiving the set of one or more user inputs that includes an input corresponding to the third selectable user interface object (1122), in accordance with a determination that the set or one or more inputs cause the threshold value to be configured to a value that is not the predetermined value, the computer system forgoes displaying (1126) the indication that frequent perceptual notifications can result. Conditionally displaying an indication that frequent perceptual notifications can result based on a setting for a threshold value provides the user with feedback as to the configuration of the first health-related tracking function. Providing improved visual feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently.

In some embodiments, the first health-related tracking function is a blood oxygen level tracking function. In some embodiments, the computer system is in communication with a blood oxygen sensor (e.g., an optical blood oxygen sensor that operates in conjunction with a light source (e.g., an LED). In some embodiments, the threshold is a percentage of blood oxygen. In some embodiments, the first health-related function is a function for measuring or tracking $VO_2$max (e.g., maximal oxygen consumption; the maximum rate of oxygen consumption measured during incremental exercise).

Note that details of the processes described above with respect to method 1100 (e.g., FIGS. 11A-11B) are also applicable in an analogous manner to the methods described above and below. For example, method 700 optionally includes one or more of the characteristics of the various methods described above with reference to method 1100. For example, the user interfaces for managing health and safety features described with reference to method 700 can be used to manage one or more features of the background measurement features described with reference to method 1100. For another example, method 900 optionally includes one or more of the characteristics of the various methods described above with reference to method 1100. For example, features concerning the conditional display of a setup user interface as described with reference to method 900 can be applied to the setup process described with reference to method 1100. For another example, method 1300 optionally includes one or more of the characteristics of the various methods described above with reference to method 1100. For example, the setup user interfaces described with reference to method 1100 can be used to setup the health application used for the biometric measurement as described with reference to method 1300. For another example, method 1500 optionally includes one or more of the characteristics of the various methods described above with reference to method 1100. For example, health information that is presented in the user interfaces described with reference to method 1500 can at least partly be based on health measurements from an application that has been setup via the setup user interfaces described with reference to method 1100. For another example, method 1700 optionally includes one or more of the characteristics of the various methods described above with reference to method 1100. For example, the background health measurements described with reference to method 1700 can be enabled via a health application that has been setup via the setup user interfaces described with reference to method 1100. For brevity, these details are not repeated below.

FIGS. 12A-12N and 12Q-12AG illustrate exemplary user interfaces for managing a biometric measurement taken using an electronic device, in accordance with some embodiments. FIGS. 120 and 12P are flow diagrams illustrating methods for managing prompts and measurements based on position and movement data, respectively, in accordance with some embodiments. The user interfaces in these figures are used to illustrate the processes described below, including the processes in FIG. 13.

FIG. 12A illustrates device 600B displaying a home user interface 1200. In some embodiments, device 600B includes a set of one or more biometric sensors (e.g., a maximum oxygen consumption level sensor; a heart rate sensor). In some embodiments, device 600B includes a set of one or more sensors (e.g., gyroscope; accelerometer; microphone; location sensor; GPS sensor).

In FIG. 12A, the heart rate tracker application, first described above with reference to FIG. 8A, is installed on device 600B. User interface 1200 includes an application icon 1202 corresponding to the heart rate tracker application. While displaying application icon 1202, device 600B receives an input 1201 directed to application icon 1202.

In FIG. 12B, in response to receiving input 1201, device 600B displays a measurement user interface 1204 for the heart rate tracker application prior to a heart rate measurement being initiated.

Prior to initiating a heart rate measurement, device 600B displays, in measurement user interface 1204, measurement instructions 1206 indicating (e.g., explaining; coaching) to the user how the heart rate measurement should be taken on device 600B. In FIG. 12B, measurement instructions 1206 informs the user to "hold as still as you can during the measurement." In the embodiment of FIGS. 12A-12P, the hearth rate measurement is most accurate when the user minimizes movement of their arm (and device 600B) and maintains an ideal arm orientation with the user's wrist facing down and display generation component 602B of device 600B facing up.

Prior to initiating a heart rate measurement, device 600B also displays, in measurement user interface 1204, at least a portion of a measurement animation 1208 that animates the measurement process. As illustrated in FIGS. 12C to 12E, measurement animation 1208 comprises multiple shapes (e.g., ripples; lines), where the multiple shapes initially have a first visual characteristic (e.g., a first color) and an increasing portion of the multiple shapes transition to having a second visual characteristic (e.g., a second color) different from the first visual characteristic as the measurement progresses until all of the multiple shapes have the second visual characteristic when the measurement has been completed.

In FIG. 12B, measurement user interface 1204 also includes an affordance 1210 for initiating a heart rate measurement. While displaying measurement user interface 1204 with affordance 1210, device 600 receives an input 1203 directed to affordance 1210 for initiating a heart rate measurement on device 600B.

FIGS. 12C-12E illustrate device 600B displaying measurement user interface 1204 while a heart rate measurement is being performed via device 600B. In some embodiments, the heart rate measurement process includes collecting heart rate data (e.g., multiple, discrete sets (e.g., samples) of heart rate data) over a predetermined period of time (e.g., 10 seconds; 15 seconds; 30 seconds). In FIGS. 12C-12E, the predetermined period of time for completing a heart rate measurement is 15 seconds.

Device 600B displays measurement user interface 1204, as in FIG. 12C, in response to receiving input 1210 for initiating the heart rate measurement. In some embodiments, while a heart rate measurement is being performed, device 600B displays, in measurement user interface 1204, a time counter 1212 that indicates the amount of time remaining to complete the current heart rate measurement.

In FIG. 12C, the remaining time is 15 seconds (as the measurement has just been initiated). Also in FIG. 12C, measurement animation 1208 comprises the first visual characteristic (e.g., the first color), as the measurement has just been initiated.

In FIG. 12D, the remaining time is 10 seconds (as the measurement has been progressing). Also in FIG. 12D, measurement animation 1208 partially comprises the first visual characteristic (e.g., the first color) and partially comprises the second visual characteristic (e.g., the second color), as a portion of the multiple shapes of measurement animation 1208 has transitioned from the first visual characteristic to the second visual characteristic while the measurement has progressed.

In FIG. 12E, the remaining time is 3 seconds (as the measurement has been progressing and is now close to being completed). Also in FIG. 12E, a greater portion of measurement animation 1208 comprises the second visual characteristic (e.g., the second color) than the first visual characteristic (e.g., the first color) and partially comprises the second visual characteristic (e.g., the second color), as the measurement is now close to being completed and a majority of the multiple shapes of measurement animation 1208 has transitioned from the first visual characteristic to the second visual characteristic.

FIG. 12F illustrates device 600B displaying a result user interface 1214 upon detecting (e.g., determining) that the heart rate measurement depicted in FIGS. 12C-12E has been successfully completed.

Result user interface 1214 includes a result indication 1216. In FIG. 12F, result indication 1216 indicates that the measured heart rate was 87 BPM. Result user interface 1214 also includes an affordance 1220 for causing device 600B to cease display of result user interface 1214. Result user interface 1214 also includes an indication 1218 that more detailed information about the measurement can be viewed via the health application on device 600A (e.g., via user interface 660 of the health application first described above with reference to FIG. 6N).

FIG. 12G illustrates device 600B displaying, upon detecting (e.g., determining) that the heart rate measurement depicted in FIGS. 12C-12E has been successfully completed, result user interface 1214 for the completed heart rate measurement, where the completed heart rate measurement was performed in an unusual condition, such as a high elevation environment. In some embodiments, device 600B detects (e.g., determines) the presence of an unusual condition (e.g., high elevation) via the set of one or more sensors (e.g., location sensor; GPS sensor).

In FIG. 12G, because the heart rate measurement was taken in a high elevation environment, device 600B displays, in result user interface 1214, an indication 1222 informing the user that the measurement taken in the high elevation environment. In FIG. 12G, indication 1222 states "measurement taken in a high elevation environment."

FIGS. 12H-12K illustrate device 600B displaying measurement user interface 1204 while another heart rate measurement is being performed via device 600B.

In FIG. 12H, device 600B displays measurement user interface 1204, where the measurement has just been initiated. Thus, time counter 1212 indicates that there are 15 second remaining to complete the current heart rate measurement.

In FIG. 12I, as the heart rate measurement is progressing, time counter 1212 now indicates that there are 12 seconds remaining to complete the current heart rate measurement.

While the heart rate measurement is progressing, device 600B detects (e.g., determines), via the set of one or more sensors (e.g., gyroscope, accelerometer), one or more sets of sensor data. In some embodiments, the one or more sets of sensor data include a first set of sensor data (e.g., accelerometer and/or gyroscope data) that is indicative of a movement and/or a change in orientation of device 600B. In some embodiments, the one or more sets of sensor data include a second set of sensor data (e.g., accelerometer and/or gyroscope data) that is indicative of a change in position (e.g., change in spatial position and/or spatial orientation) of device 600B or movement (e.g., change in position or a rate of change) of device 600B causing the change in position. As noted above, the hearth rate measurement is most accurate when the user minimizes movement of his or her arm (and of device 600B) and maintains an ideal arm position (e.g., arm orientation) with the user's wrist facing down and display generation component 602B of device 600B facing up.

In FIG. 12I, in accordance with determining (e.g., using the detected position of device 600B and/or the detected movement of device 600B) that sensor data (e.g., data indicative of position) satisfies a set of prompting criteria, device 600B displays, in measurement user interface 1204, a prompt 1224 (e.g., an instructions prompt; a coaching prompt) indicating to the user that user action is required (e.g., change in position of device 600B and/or decreasing/ceasing movement of device 600B) in order to complete the measurement process. Specifically, in FIG. 12I, device 600B has detected that the position of the device is in a non-ideal position (e.g., a predetermined position that causes the prompting criteria to be met) and issues an position-related prompt. In FIG. 12I, prompt 1224 indicates to the user to "keep your wrist flat and your watch facing up."

FIG. 12J illustrates device 600B displaying, in measurement user interface 1204, a different type of prompt (e.g., a different version of the prompt) than prompt 1224 described above with reference to FIG. 12I.

In FIG. 12J, as the heart rate measurement is progressing, time counter 1212 indicates that there are 10 seconds remaining to complete the current heart rate measurement. In FIG. 12J, in accordance with determining that sensor data (e.g., data indicative of movement) satisfies the set of prompting criteria, device 600B displays, in measurement user interface 1204, a prompt 1226 indicating to the user that user action is required (e.g., change in position of device 600B and/or decreasing/ceasing movement of device 600B) in order to complete the measurement process. Specifically, in FIG. 12J, device 600B has detected that the device is being moved by a non-ideal amount (e.g., an amount that exceeds a threshold) and issues a movement-related prompt. In FIG. 12J, prompt 1226 indicates to the user to "try not to move."

In some embodiments, after detecting that the second set of sensor data satisfies the set of prompting criteria as in FIG. 12I or 12J, in response to detecting (e.g., within a predetermined time period (e.g., within 0.5 seconds; within 1 second)) that the sensor data (e.g., position data and/or movement data) no longer satisfies the set of prompting criteria (e.g., because the user has corrected device 600B's position and/or decreased/ceased the movement of the device), device 600B continues the heart rate measurement process, without interruption.

In some embodiments, as shown in FIG. 12K, device 600B displays, in measurement user interface 1204, a second prompt in accordance with again determining (e.g., based on the detected (e.g., determined) position of device 600B and/or the detected (e.g., determined) movement of device 600B) that sensor data satisfies the set of prompting criteria. Specifically, in FIG. 12K, prompt 1228 indicates to the user to "keep your wrist flat." In some embodiments, device 600B issues different prompts if the same non-ideal condition (e.g., non-ideal position or movement) persists for longer than a predetermined time to provide the user better feedback that the condition persists. In some embodiments, device 600B issues different prompts only if different conditions occur, such as a position condition followed by a movement condition.

In some embodiments, while the heart rate measurement is progressing, device 600B detects (e.g., determines) that the first set of sensor data (e.g., accelerometer and/or gyroscope data that is indicative of the movement and/or a change in position) satisfies a first set of cessation criteria (e.g., criteria for causing device 600B to cease the measurement process).

In FIG. 12L, in accordance with detecting that the first set of sensor data satisfies the first set of cessation criteria, device 600B forgoes displaying measurement user interface 1204 without completing the measurement. Specifically, device 600B has detected that the non-ideal position and non-ideal degree of movement of the device during the heart rate measurement of FIGS. 12H-12K has persisted and aborts the measurement prior to completion. Device 600B ceases the measurement without displaying results and, instead, displays a user interface 1230 (e.g., a notification; a prompt).

User interface 1230 includes an indication 1232 that the measurement was unsuccessful and could not be completed. User interface 1230 also includes an indication 1234 of the reason(s) for the unsuccessful measurement (e.g., one or more causes that triggered device 600B to cease the measurement process without completing the measurement process). User interface 1230 also includes an affordance 1236 for causing device 600B to cease display of user interface 1230.

Also in FIG. 12L, while displaying user interface 1230, device 600B receives an input 1205 directed to affordance 1205. In some embodiments, in response to receiving input 1205, device 600B displays measurement user interface 1204 of FIG. 12B.

As mentioned, after displaying a prompt (e.g., prompt 1224; prompt 1226; prompt 1228) during a heart rate measurement (because the second set of sensor data satisfied the set of prompting criteria during the measurement), in response to detecting (e.g., determining) (e.g., within a predetermined time period (e.g., within 0.5 seconds; within 1 second)) that the second set of sensor data no longer satisfies the set of prompting criteria, device 600B continues the heart rate measurement process.

As described with reference to FIG. 12L, the set of cessation criteria is satisfied when at least a first number of (e.g., $M_M$) discrete sets of data of the first set of sensor data, out of a sampling window of discrete sets of data (e.g., $N_M$), exceeds a threshold value. In some embodiments, the first set of sensor data is accelerometer data, and the set of cessation criteria is satisfied when at least 5 discrete windows of accelerometer data, out of the sampling window of discrete sets of data, exceeds the threshold value (e.g., 5 discrete sets out of a sampling window of 5 discrete sets).

In some embodiments, device 600B analyzes accelerometer data over 3 axes in the x, y, and z directions. In some embodiments, if the maximum value of any of the 3 axes from the accelerometer data exceeds the threshold value within a given sampling window (e.g., 1 second), device 600B generates a prompt (e.g., prompt 1224 of FIG. 12I, prompt 1226 of FIG. 12J, prompt 1228 of FIG. 12K). In some embodiments, each sampling window (e.g., of 1 second) is spaced apart by less than the length of the sampling window (e.g., spaced apart by 0.5 seconds) so that the sampling windows overlap.

In some embodiments, if device 600B detects (e.g., determines) that a predetermined number (e.g., 5) of samples, within a predetermined set of samples (e.g., 5) have exceeded the threshold values (e.g., 5 samples out of a predetermined set of 5 samples), device 600B automatically aborts a current heart rate measurement sessions. In some embodiments, this corresponds to device 600B having generated the predetermined number (e.g., 5) of prompts (e.g., prompt 1224 of FIG. 12I, prompt 1226 of FIG. 12J, and/or prompt 1228 of FIG. 12K). Upon aborting the heart rate measurement session, device 600B displays user interface 1230 as shown in FIG. 12L.

In some embodiments, device 600B aborts a current heart rate measurement session if (e.g., only if) at least the predetermined number of detected samples that exceed the threshold value are from consecutive sampling windows. In some embodiments, device 600B does not abort the heart rate measurement session if at least the predetermined number of detected samples that exceed the threshold value are detected, but they are not from consecutive sampling windows.

In some embodiments, device 600B tracks 2 channels of sampling data—one directed to movement of device 600B and the other directed to a position of device 600B. In some embodiments, the 2 channels of sampling data are evaluated independently from one another. That is, device 600B does not aggregate sampling data based on movement of device 600B and sampling data based on position of device 600B when detecting (e.g., determining) whether the predetermined number (e.g., 5) of prompts have been generated to cause a current heart rate measurement session to abort (e.g., 2 movement-based samples that exceed the threshold value and 3 position-based samples that exceed the threshold value are not aggregated, and thus do not cause the current session to abort).

In some embodiments, if the heart rate measurement depicted in FIGS. 12H-12L is successfully completed, device 600B displays the measurement results in a result user interface similar to result user interface 1214 of FIG. 12G.

Flowchart 1201A in FIG. 12O depicts a process for determining whether to continue (and eventually complete) or abort a heart rate measurement, as described above with respect to FIG. 12L. Flowchart 1201A particularly depicts whether a heart rate measurement process should be continued or aborted based on position data.

At step 1203 A, device 600B initiates the heart rate measurement (e.g., as described with reference to FIG. 12B). At step 1205A, device 600B detects (e.g., via the accelerometer) position data corresponding to a current position of device 600B.

At step 1207A, device 600B determines whether the detected position data satisfies position criteria (e.g., device 600B determines, based on position data from the accelerometer, whether or not it is in an acceptable position for the measurement). If device 600B determines that the detected position satisfies the position criteria, device 600B determines, at step 1209A, whether a prompt criterion is satisfied (e.g., based on a number of prompts that has already been generated during the current measurement). If device 600B determines that the detected position does not satisfy the position criteria, device 600B determines, at step 1211A, whether there is remaining time in the current measurement (e.g., whether there is sufficient time for another sampling window in the current measurement).

At step 1209A, if device 600B determines that the prompt criteria is satisfied, device 600B, at step 1212, generates a prompt (e.g., prompts 1224, 1226, or 1228 described above with respect to FIGS. 12I-12K, respectively). At step 1209A, if device 600B determines that the prompt criterion is not (is no longer) satisfied, device 600B forgoes generating the prompt.

At step 1211A, if device 600B determines that there is remaining time in the current measurement, device 600B returns to step 1205A and again detects for position data while continuing the heart rate measurement. At step 1211A, if device 600B determines that there is no remaining time, device 600B, at step 1215A, successfully completes the current measurement.

After (or in response to) generating the prompt at step 1213A, at step 1217A, device 600B determines whether measurement cessation criteria has been satisfied (e.g., whether at least a predetermined number of prompts have been generated; whether at least a predetermined number of occurrences of position criteria being satisfied have been detected). At step 1217A, if device 600B determines that the cessation criteria have been satisfied, device 600B moves on to step 1219A, where it aborts the current heart rate measurement without completing the measurement. At step 1217A, if device 600B determines that the cessation criteria have not be satisfied, device 600B returns to step 1205A, where it and again detects for position data while continuing the heart rate measurement.

Similarly, flowchart 1221A in FIG. 12P depicts a process for determining whether to continue (and eventually complete) or abort a heart rate measurement, as described above with respect to FIG. 12L. Flowchart 1201A particularly depicts whether a heart rate measurement process should be continued or aborted based on movement data.

At step 1223A, device 600B initiates the heart rate measurement (e.g., as described with reference to FIG. 12B). At step 1225A, device 600B detects (e.g., via the accelerometer) movement data corresponding to detected movement of device 600B (e.g., from one position in the 3D space to a different position in the 3D space).

At step 1227A, device 600B determines whether the detected movement data satisfies movement criteria (e.g., device 600B determines, based on movement data from the accelerometer, whether or not it has been moved beyond a movement threshold). If device 600B determines that the detected movement satisfies the movement criteria, device 600B determines, at step 1229A, whether a prompt criterion is satisfied (e.g., based on a number of prompts that has already been generated during the current measurement). If device 600B determines that the detected movement does not satisfy the movement criteria, device 600B determines, at step 1231A, whether there is remaining time in the current measurement (e.g., whether there is sufficient time for another sampling window in the current measurement).

At step 1229A, if device 600B determines that the prompt criterion is satisfied, device 600B, at step 1233A, generates a prompt (e.g., prompts 1224, 1226, or 1228 described above with respect to FIGS. 12I-12K, respectively). At step 1229A, if device 600B determines that the prompt criterion is not (is no longer) satisfied, device 600B forgoes generating the prompt.

At step 1231A, if device 600B determines that there is remaining time in the current measurement, device 600B returns to step 1225A and again detects for movement data while continuing the heart rate measurement. At step 1231A, if device 600B determines that there is no remaining time, device 600B, at step 1235A, successfully completes the current measurement.

After (or in response to) generating the prompt at step 1233A, at step 1237A, device 600B determines whether measurement cessation criteria has been satisfied (e.g., whether at least a predetermined number of prompts have been generated; whether at least a predetermined number of occurrences of movement criteria being satisfied have been detected). At step 1237A, if device 600B determines that the cessation criteria have been satisfied, device 600B moves on to step 1239A, where it aborts the current heart rate measurement without completing the measurement. At step 1237A, if device 600B determines that the cessation criteria have not be satisfied, device 600B returns to step 1225A, where it and again detects for movement data while continuing the heart rate measurement.

Figure 12M:
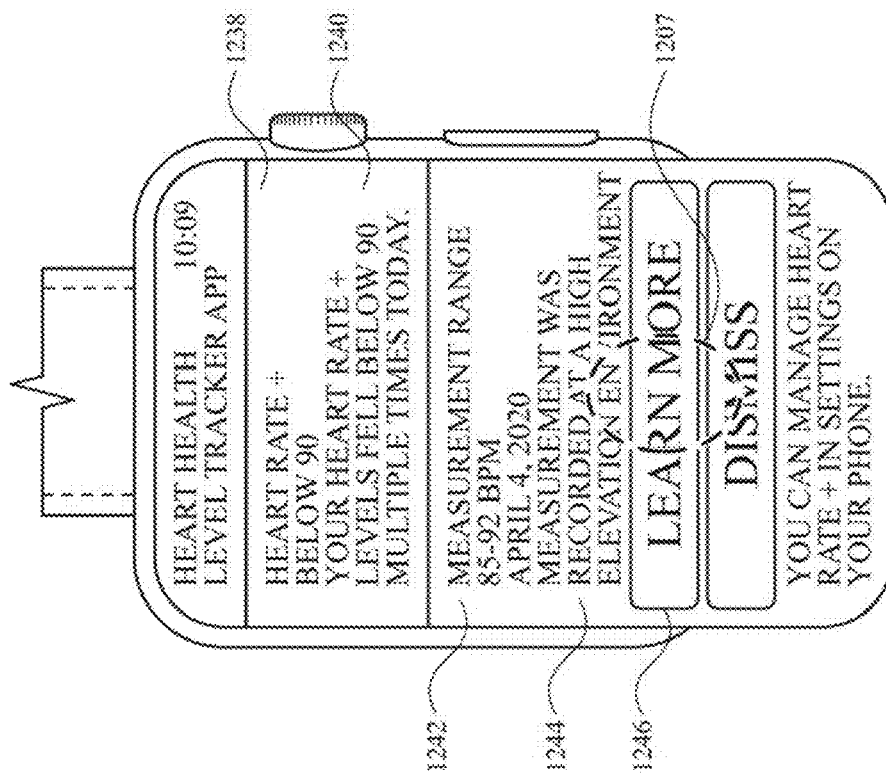
Figure 12O:
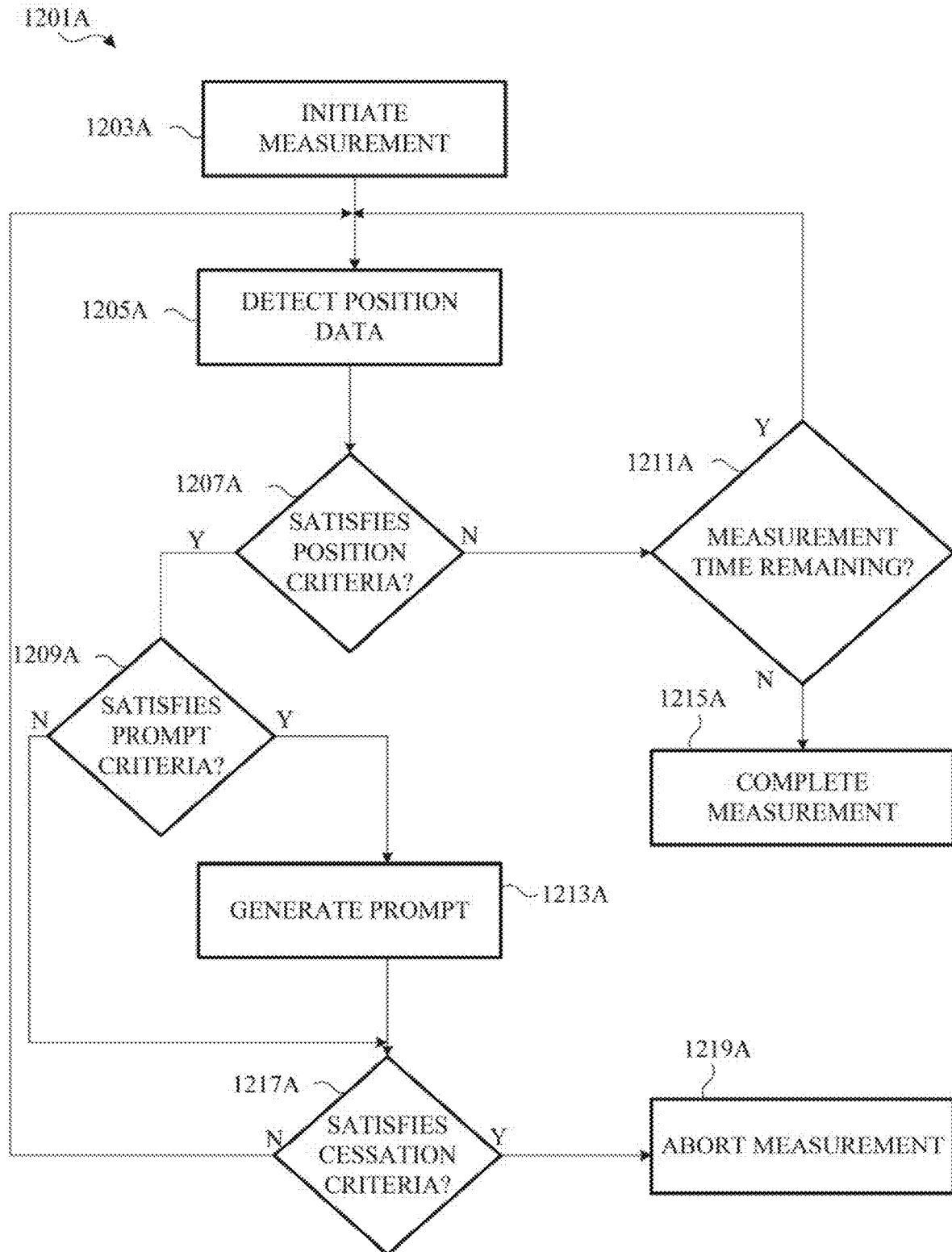
Figure 12P:
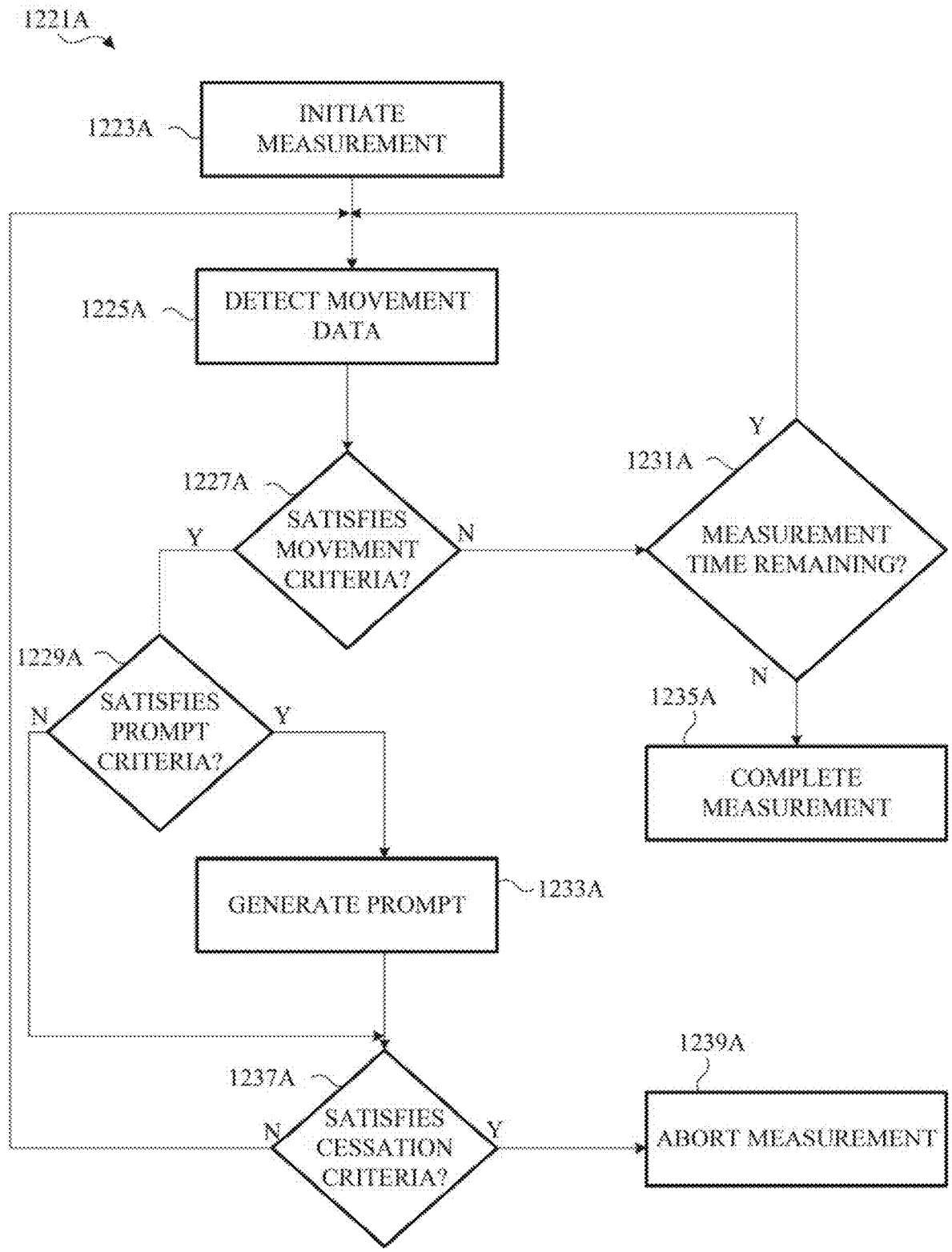
Figure 12Q:
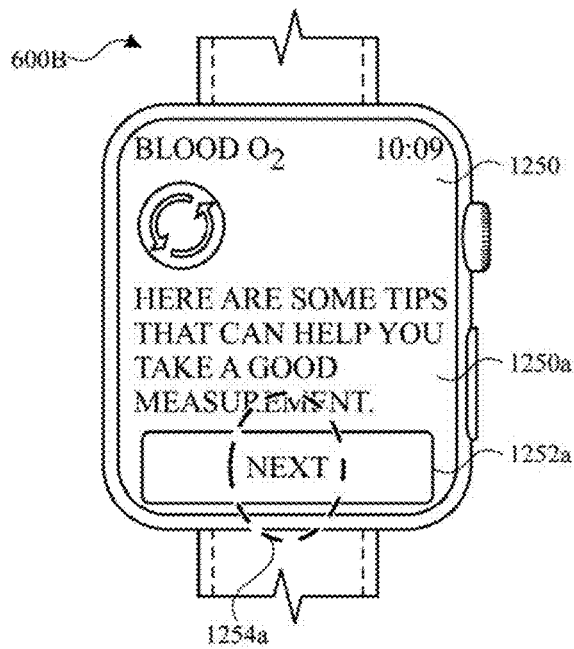

FIG. 12M illustrates device 600B displaying a user interface 1238. User interface 1238 includes information about multiple heart rate measurements (e.g., background, automatic measurements and/or manual measurements as described above with reference to FIGS. 12A-12L) that were performed during a predetermined time period, the current day.

User interface 1238 includes an indication 1240 of the number of times the user's heart rate was measured to fall below a threshold value during the predetermined time period. In FIG. 12M, indication 1240 shows that the user's heart rate was measured to fall below a threshold 90 BPM several times during the current day.

User interface 1238 includes an indication 1242 of the range of heart rates that were measured during the predetermined time period. In FIG. 12M, indication 1242 shows that the user's heart rates during the current day were measured to be within 80-92 BPM.

If one or more measurements were taken in an unusual condition (e.g., a high elevation environment), user interface 1238 includes an indication 1244 that one or more measurements during the predetermined time period were taken in the unusual condition. In FIG. 12M, indication 1244 shows that a measurement was recorded at a high elevation environment.

Also in FIG. 12M, user interface 1238 includes an affordance 1246 for causing display of additional information about heart rate measurements. While displaying user interface 1238, device 600B receives an input 1207 directed to affordance 1246.

In FIG. 12N, in response to receiving input 1207, device 600B displays a user interface 1248 that includes information (e.g., text information) about heart rate measurements and/or the heart rate tracker application (e.g., what a measured heart rate represents; how heart rate measurements works on device 600B; information about one or more application features of the heart rate tracker application).

In some embodiments, the heart rate measurement described in FIGS. 12A-12O is instead a blood oxygen level measurement (e.g., $SpO_2$). In some embodiments, the set of one or more biometric sensors include a blood oxygen sensor (e.g., an optical blood oxygen sensor that operates in conjunction with a light source (e.g., an LED). In some embodiments, the threshold is a percentage of blood oxygen. In some embodiments, the heart rate measurement described in FIGS. 12A-12P is instead measuring or tracking $VO_2$max (e.g., maximal oxygen consumption; the maximum rate of oxygen consumption measured during incremental exercise).

FIGS. 12Q-12AG illustrate exemplary user interfaces of an application for blood oxygen level measurement using an embodiment of device 600B that includes a blood oxygen sensor (e.g., an optical blood oxygen sensor that operates in conjunction with a light source (e.g., an LED). In some embodiments, the user interfaces of FIGS. 12Q-12AG are generated by a blood oxygen tracker application that includes one or more features of the heart rate tracker application first described above with reference to FIG. 8A. For example, the blood oxygen tracker application implements the processes for determining whether to continue (and eventually complete) or abort a biometric measurement described with reference to FIGS. 12O-12P. For ease of understanding, elements in the user interfaces of the blood oxygen tracking application that are similar to elements in the user interfaces of the heart rate tracker application are described using similar reference numerals; it is understood that similar elements can include one or more features of the corresponding element. For example, measurement interface 1204a of the blood oxygen tracker application (described in more detail below) can include one or more features described with reference to measurement interface 1204 of the heart rate tracker application, with the difference being that the measurement performed using interface 1204a is for blood oxygen, rather than heart rate. For the sake of brevity, these similarities will be evident from the use of the similar reference number (with the "a" or other letter appended).

Figure 12R:
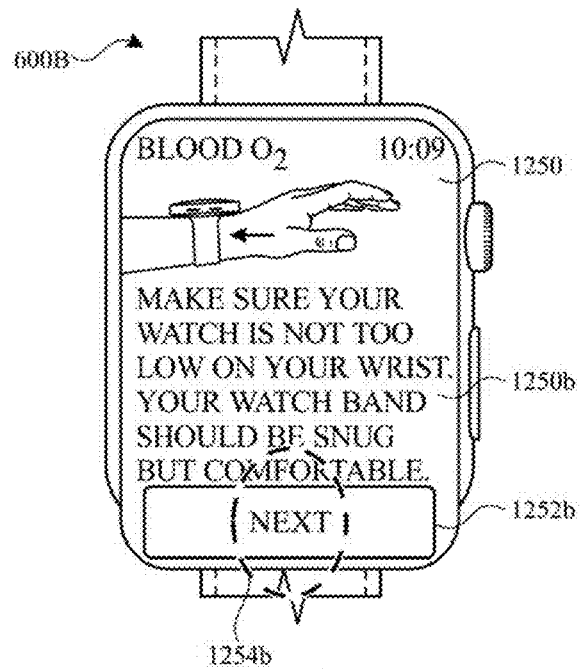
Figure 12S:
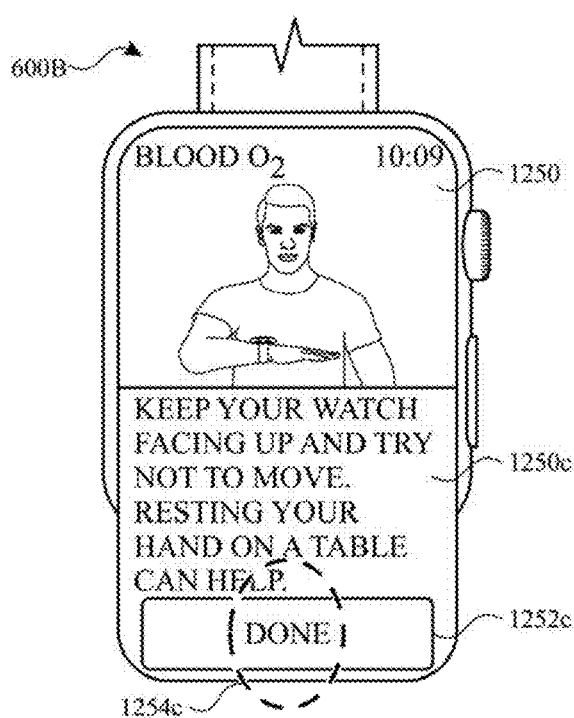

FIGS. 12Q-12S illustrate device 600B displaying introduction user interface 1250 on display 602B. In some embodiments, introduction user interface 1250 is only displayed on initial (e.g., first time) launch of the blood oxygen application. In some embodiments, introduction user interface 1250 is displayed each time that the application is launched, until a successful blood oxygen measurement is performed using the application.

In FIG. 12Q, introduction user interface 1250 includes introductory text 1250a and next button 1252a. In FIG. 12Q, device 600B receives input 1254a on next button 1252a.

In FIG. 12R, in response to receiving input 1254a, device 600B displays a second screen of introduction user interface 1250 that includes guidance text 1252b and next button 1252b. Guidance text 1252b provides suggestions on proper positioning of device 600B on the user's wrist. In FIG. 12R, device 600B receives input 1254b on next button 1252b.

In FIG. 12S, in response to receiving input 1254b, device 600B displays a third screen of introduction user interface 1250 that includes guidance text 1252c and next button 1252c. Guidance text 1252c provides suggestions on properly orienting and positioning of device 600B during the blood oxygen measurement. In FIG. 12S, device 600B receives input 1254c on next button 1252c.

Figure 12T:
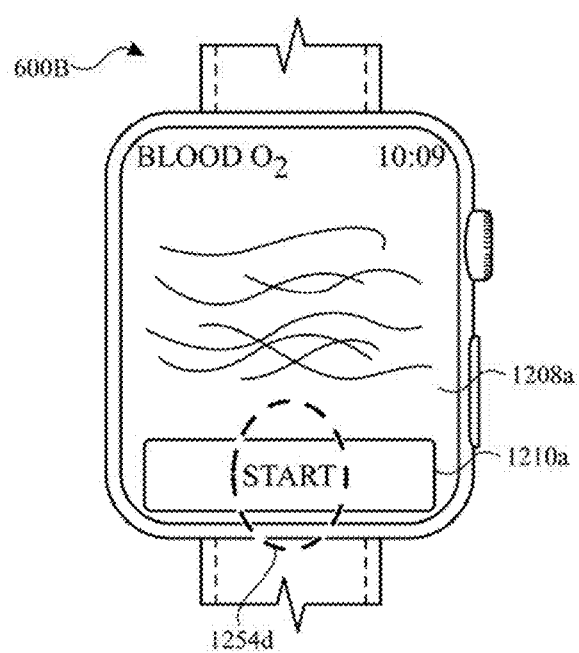

In FIG. 12T, in response to receiving input 1254c, device 600B displays blood oxygen measurement interface 1204a. In some embodiments, blood oxygen measurement interface 1204a is displayed on launch of the blood oxygen tracker function, without first displaying introduction user interface 1250, other than on first-time launch of the application. Blood oxygen measurement interface 1204a includes measurement animation 1208a, similar to measurement animation 1208 described above, and a start button 1210a. In some embodiments, prior to starting a blood oxygen measurement process, blood oxygen measurement interface 1204a can include different content, depending on the outcome of a previous blood oxygen measurement process, as described in more detail, below. In FIG. 12T, device 600B receives input 1254d on start button 1210a.

Figure 12U:
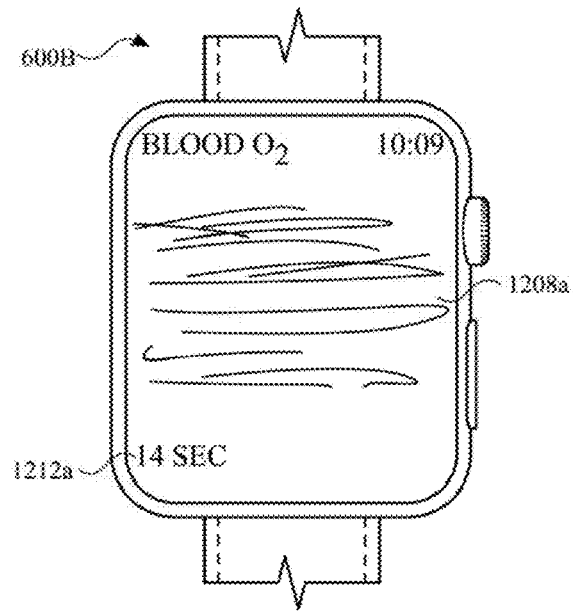

In FIG. 12U, device 600B has started a blood oxygen measurement process, in response to receiving input 1254d. In the embodiment of FIG. 12U, the measurement nominally takes 15 seconds to complete, with 1 second of the nominal time having already elapsed, as indicated by time counter 1212. As noted above, the blood oxygen measurement process implemented by the blood oxygen tracker application can implement the processes depicted in FIGS. 12O-12P and therefore can provide one or more prompts, or abort the measurement operation, as discussed in more detail with respect to FIGS. 12O-12P.

Figure 12V:
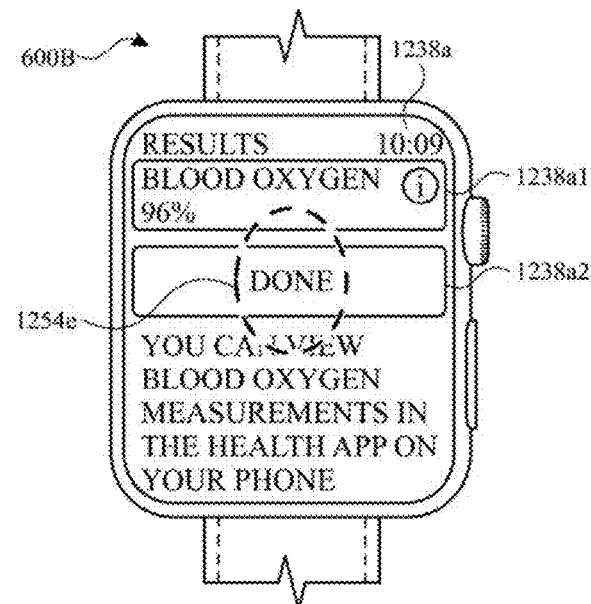

In FIG. 12V, the blood oxygen measurement process shown in FIG. 12U has successfully completed, and device 600B displays a results interface 1238a. Results interface 1238a includes blood oxygen measurement result 1238a1 that indicates the user's measured blood oxygen level as 96% SpO₂. Results interface 1238a also includes done button 1238a2 for dismissing the result. In FIG. 12V, device 600b receives input 1254e on done button 1238a2.

Figure 12W:
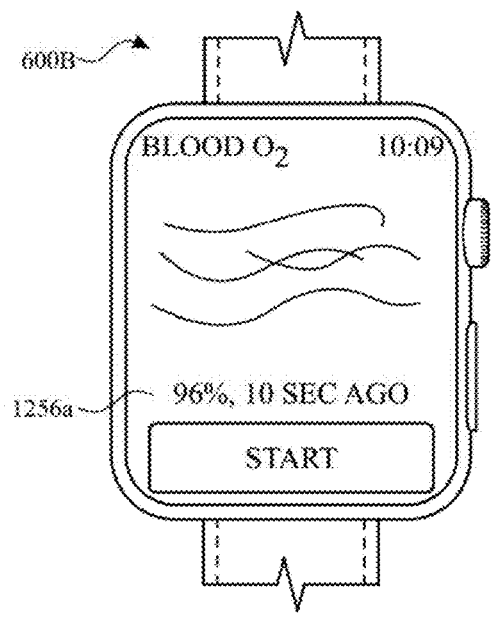

In FIG. 12W, device 600B re-displays blood oxygen measurement interface 1204a in response to input 1254e. Blood oxygen measurement interface 1204 includes indication 1256a, which provides an indication of the outcome of the last blood oxygen measurement. In FIG. 12W, indication 1256a shows that the last measurement had a result of 96% SPO₂, which was received 10 seconds ago.

Figure 12X:
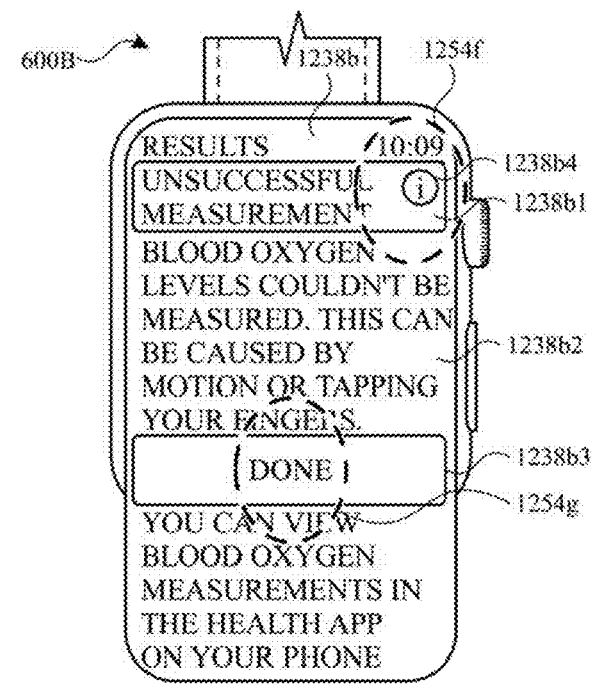
Figure 12Y:
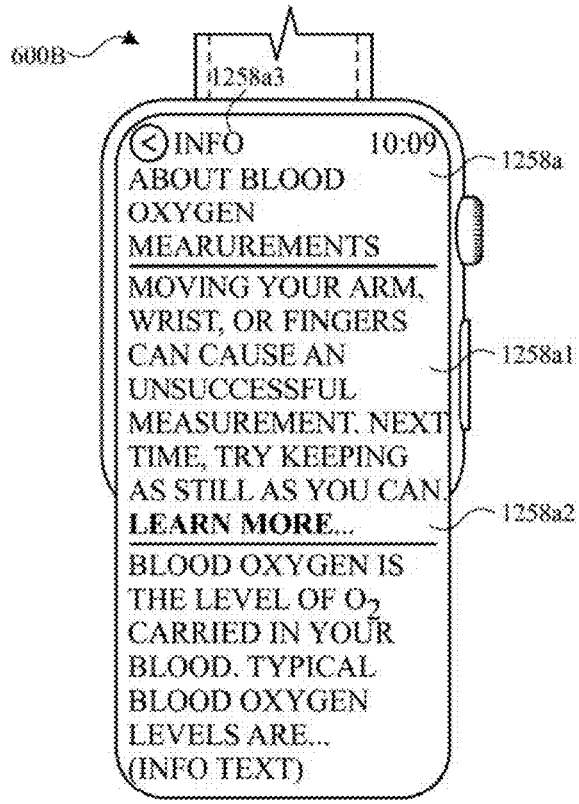
Figure 12Z:
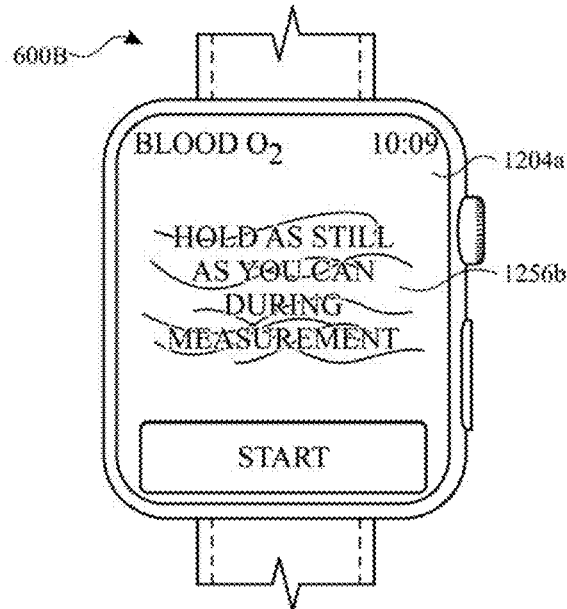
Figure 12A:
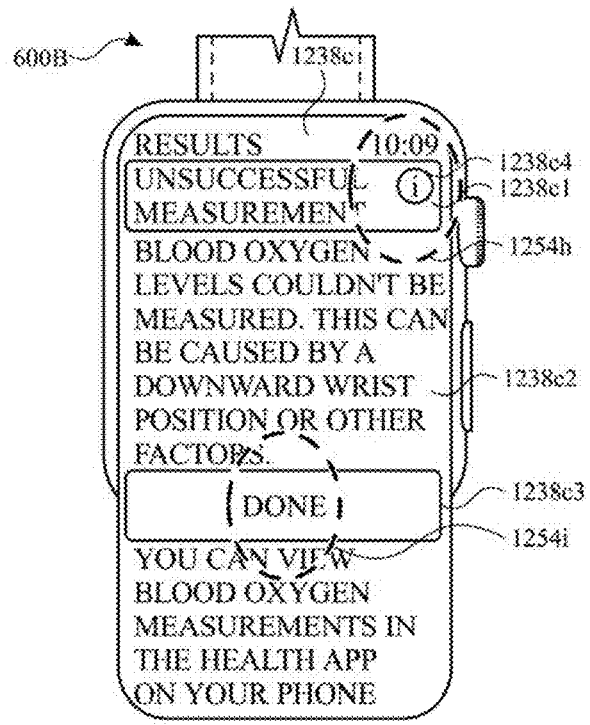
Figure 12A:
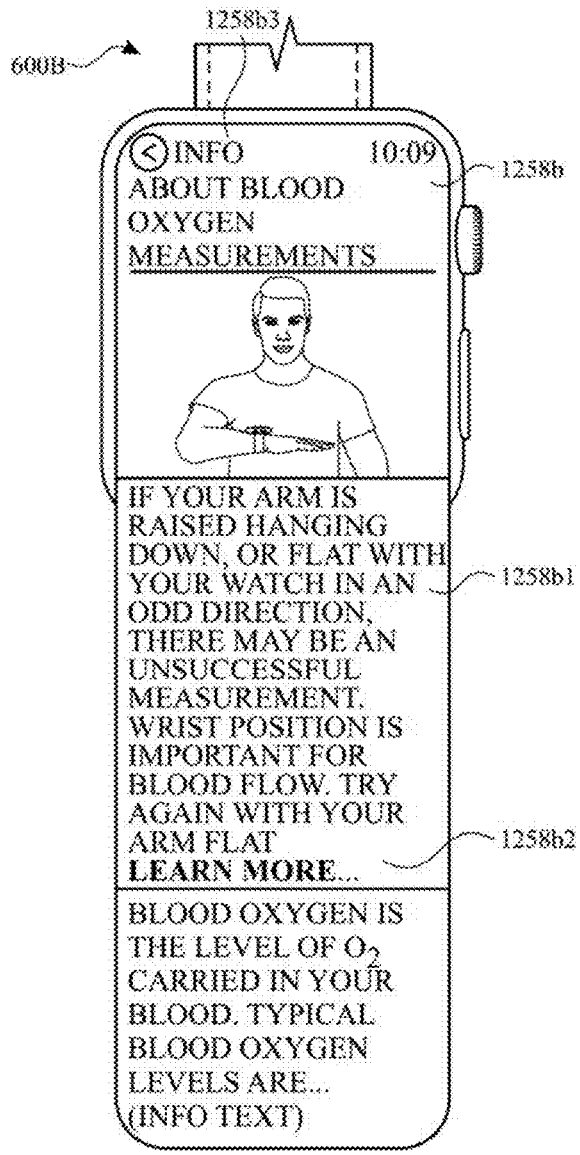
Figure 12A:
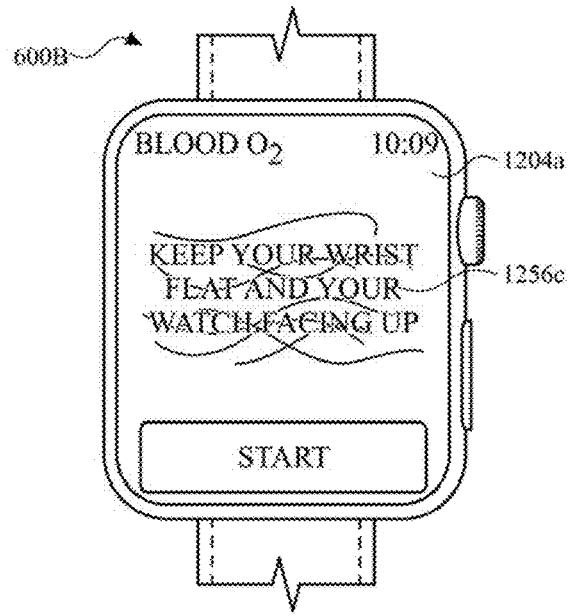
Figure 12A:
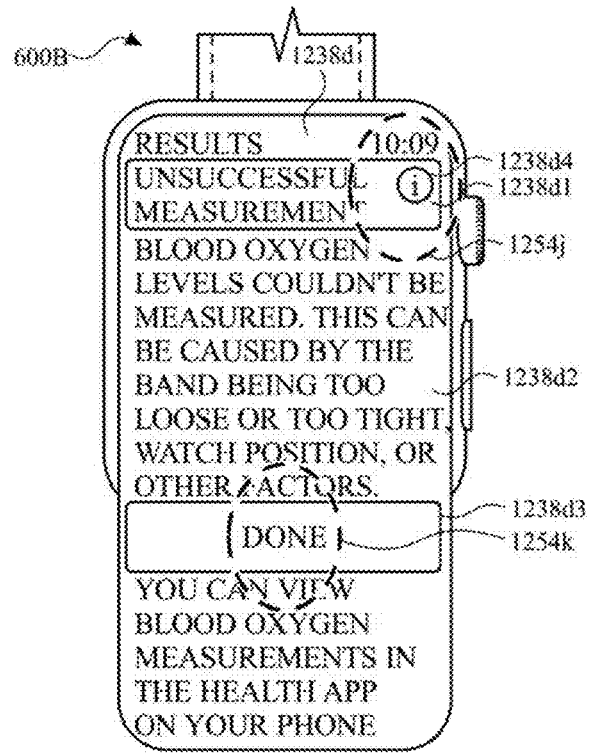
Figure 12A:
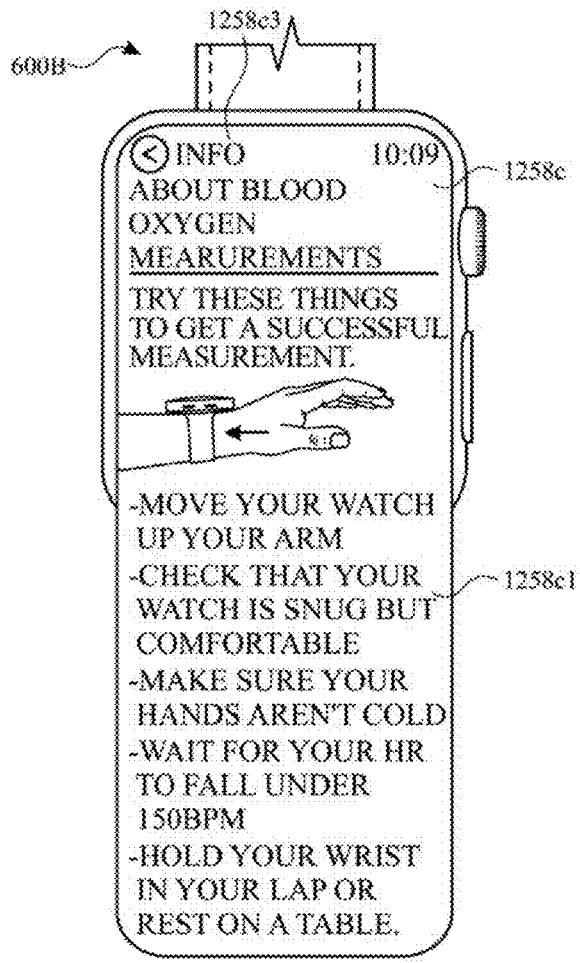
Figure 12A:
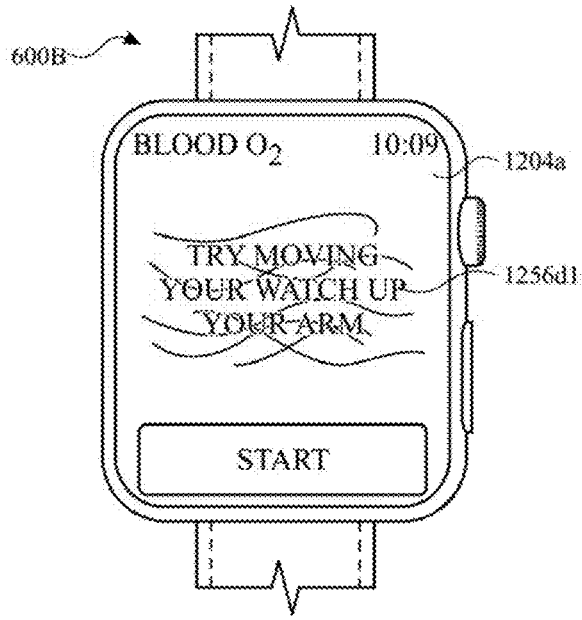
Figure 12A:
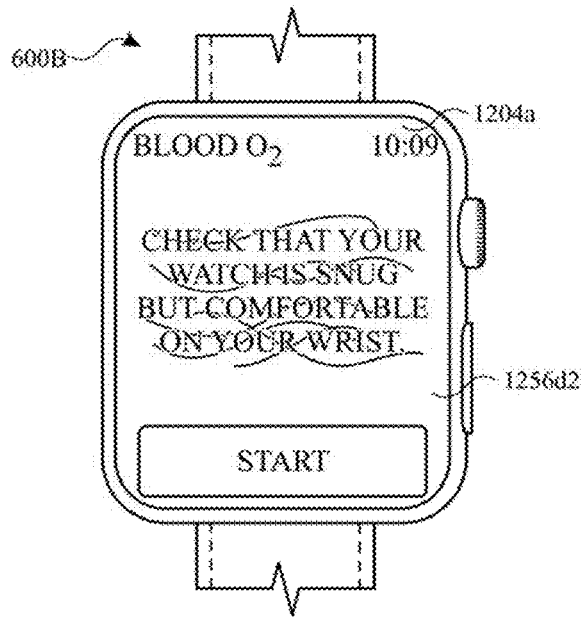

FIGS. 12X-12Z illustrate interfaces that are shown if the blood oxygen measurement process initiated by input 1254d did not successfully complete due to detected excessive movement. In FIG. 12X, rather than displaying a result (e.g., in results interface 1238a), device 600B displays result interface 1238b. Results interface 1238b includes outcome 1238b1 that indicates that the blood oxygen measurement was unsuccessful and text 1238b2 that explains that movement could be the cause of the unsuccessful measurement. Results interface 1238b also includes a done button 1238b3 for dismissing results interface 1238b and an information button 1238b4 to display further information on the unsuccessful measurement. In FIG. 12X, device 600B receives input 1254f on information button 1238b4 and input 1254g on done button 1238b3.

In FIG. 12Y, device 600B displays information user interface 1258a that provides additional information about the unsuccessful outcome reported in results interface 1238b. information user interface 1258a includes guidance text 1258a1 that provides additional guidance on how to reduce movement to reduce the risk of an unsuccessful measurement for a subsequent measurement process. Guidance text 1258a1 includes learn more text 1258a2 that can be selected to display additional information and/or guidance on the error. Back button 1258a3 can be selected to return to results interface 1238b.

In FIG. 12Z, device 600B re-displays blood oxygen measurement interface 1204a in response to input 1254g. Blood oxygen measurement interface 1204 includes indication 1256b, which is based on the outcome of the last blood oxygen measurement. In FIG. 12Z, indication 1256b provides guidance on holding still, since the last measurement failed to complete due to excessive detected movement.

FIGS. 12AA-12AC illustrate interfaces that are shown if the blood oxygen measurement process initiated by input 1254d did not successfully complete due to improper positioning. In FIG. 12AA, rather than displaying a result (e.g., in results interface 1238a), device 600B displays result interface 1238c. Results interface 1238c includes outcome 1238c1 that indicates that the blood oxygen measurement was unsuccessful and text 1238c2 that explains that improper positioning/orientation of device 600B could be the cause of the unsuccessful measurement. Results interface 1238c also includes a done button 1238c3 for dismissing results interface 1238c and an information button 1238c4 to display further information on the unsuccessful measurement. In FIG. 12AA, device 600B receives input 1254h on information button 1238c4 and input 1254i on done button 1238c3.

In FIG. 12AB, device 600B displays information user interface 1258b that provides additional information about the unsuccessful outcome reported in results interface 1238c. information user interface 1258b includes guidance text 1258b1 that provides additional guidance on how to position device 600B to reduce the risk of an unsuccessful measurement for a subsequent measurement process. Guidance text 1258b1 includes learn more text 1258b2 that can be selected to display additional information and/or guidance on the error. Back button 1258b3 can be selected to return to results interface 1238c.

In FIG. 12AC, device 600B re-displays blood oxygen measurement interface 1204a in response to input 1254i. Blood oxygen measurement interface 1204 includes indication 1256c, which is based on the outcome of the last blood oxygen measurement. In FIG. 12AC, indication 1256c provides guidance on positioning of device 600B, since the last measurement failed to complete due to excessive detected movement.

FIGS. 12AD-12AG illustrate interfaces that are shown if the blood oxygen measurement process initiated by input 1254d did not successfully complete due to improper certain factors. In FIG. 12AD, rather than displaying a result (e.g., in results interface 1238a), device 600B displays result interface 1238d. Results interface 1238d includes outcome 1238d1 that indicates that the blood oxygen measurement was unsuccessful and text 1238d2 that explains that certain factors could be the cause of the unsuccessful measurement. In some embodiments, the factors can be based on abnormal blood oxygen signal data that is indicative of atypical blood oxygen sensor data. In some embodiments, the factors can be based on a combination of abnormal blood oxygen signal data coupled with an absence of excessive movement or improper positioning data. In some embodiments, blood oxygen data is collected for the nominal period (e.g., 15 seconds) and an unsuccessful measurement outcome is determined by post-processing of the data. Results interface 1238*d* also includes a done button 1238*d*3 for dismissing results interface 1238*d* and an information button 1238*d*4 to display further information on the unsuccessful measurement. In FIG. 12AD, device 600B receives input 1254*j* on information button 1238*d*4 and input 1254*k* on done button 1238*d*3.

In FIG. 12AE, device 600B displays information user interface 1258*c* that provides additional information about the unsuccessful outcome reported in results interface 1238*d*. information user interface 1258*c* includes guidance text 1258*c*1 that provides additional guidance on how to reduce the risk of an unsuccessful measurement for a subsequent measurement process. Back button 1258*c*3 can be selected to return to results interface 1238*d*.

In FIG. 12AF, device 600B re-displays blood oxygen measurement interface 1204*a* in response to input 1254*k*. Blood oxygen measurement interface 1204 includes indication 1256*d*1, which is based on the outcome of the last blood oxygen measurement. In FIG. 12AF, indication 1256*d*1 provides guidance on positioning of device 600B on the user's arm, since the last measurement failed to complete due to certain factors that can include improper positioning of device 600B on the user's arm.

In FIG. 12AG, device 600B displays blood oxygen measurement interface 1204 with indication 1256*d*2, which is based on the outcome of the last blood oxygen measurement. In FIG. 12AG, indication 1256*d*2 provides guidance on securing device 600B on the user's arm, since the last measurement failed to complete due to certain factors that can include improper securing of device 600B on the user's arm. In some embodiments, the interface of FIG. 12AG is automatically displayed after displaying the interface of FIG. 12AF for a predetermined time. In some embodiments, the interface of FIG. 12AG is displayed in response to an input (e.g., a tap or a swipe) received while displaying the interface of FIG. 12AF. In some embodiments, the interface of FIG. 12AG is displayed in response to input 1254*k*.

FIGS. 13A-13B are a flow diagram illustrating a method for managing a biometric measurement taken using an electronic device, in accordance with some embodiments. Method 1300 is performed at a computer system (e.g., an electronic device (e.g., 100, 300, 500, 600A, 600B)) that is in communication with a display generation component (e.g., 602A, 602B) (e.g., a display controller, a touch-sensitive display system; a display (e.g., integrated or connected)), a set of one or more biometric sensors (e.g., a maximum oxygen consumption level sensor; a heart rate sensor), and a set of one or more sensors (e.g. gyroscope, accelerometer, microphone) that are different from the set of one or more biometric sensors. Some operations in method 1300 are, optionally, combined, the orders of some operations are, optionally, changed, and some operations are, optionally, omitted.

In some embodiments, the electronic device (e.g., 600A; 600B) is a computer system. The computer system is optionally in communication (e.g., wired communication, wireless communication) with the display generation component (e.g., 602A, 602B), the set of one or more biometric sensors, and the set of one or more sensors. The display generation component is configured to provide visual output, such as display via a CRT display, display via an LED display, or display via image projection. In some embodiments, the display generation component is integrated with the computer system. In some embodiments, the display generation component is separate from the computer system. In some embodiments, the one or more biometric sensors include a maximum oxygen consumption level sensor. In some embodiments, the set of one or more biometric sensors include a heart rate sensor.

As described below, method 1300 provides an intuitive way for managing and/or presenting health data. The method reduces the cognitive burden on a user for managing and/or presenting health data, thereby creating a more efficient human-machine interface. For battery-operated computing devices, enabling a user to manage and/or present health data faster and more efficiently conserves power and increases the time between battery charges.

The computer system (e.g., 600A; 600B) initiates (1302) a biometric analysis process (e.g., the process that is depicted in FIGS. 12B-12L) that includes detecting, via the one or more biometric sensors, first biometric data. In some embodiments, the biometric analysis process includes collecting biometric data (e.g., multiple, discrete sets (e.g., samples) of biometric data) over a predetermined period of time. In some embodiments, the biometric analysis process includes measuring one or more biometric parameters (e.g., maximum oxygen consumption level, heart rate) of a user.

During the biometric analysis process (1306), the computer system (e.g., 600A; 600B) detects (1308), via the set of one or more sensors, a first set of sensor data (e.g., accelerometer and/or gyroscope data that is indicative of the movement and/or a change in orientation).

During the biometric analysis process (1306), in response to detecting the first set of sensor data (1310), in accordance with a determination that the first set of sensor data satisfies a first set of cessation criteria, the computer system (e.g., 600A, 600B) ceases (1312) (e.g., terminates; ends) the biometric analysis process (e.g., ceasing to collect biometric data that is used in the biometric process). In some embodiments, the computer system also displays, via the display generation component (e.g., 602A, 602B), an indication (e.g., notification 1230 of FIG. 12L) that the biometric analysis process has been ceased/terminated). In some embodiments, in response to detecting the first set of sensor data and in accordance with a determination that the first set of sensor data does not satisfy the first set of cessation criteria, the computer system continues with the biometric analysis process. Ceasing the biometric analysis process when a first set of cessation criteria are met, without the user having to manual cease the process, optimizes the analysis process and reduces the risk of erroneous biometric results. Performing an optimized operation when a set of conditions has been met without requiring further user input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the set of one or more sensors include at least a first sensor (e.g., an accelerometer, a gyroscope, a GPS sensor) configured to detect a position (e.g., location (e.g., a GPS location; a location relative to a starting location); orientation) or movement (e.g., a change in position or a rate of change in position)) of the computer system (e.g., 600A, 600B) (!304).

In some embodiments, during the biometric analysis process (e.g., the process that is depicted in FIGS. 12B-12L), the computer system (e.g., 600A, 600B) detects (1314), via the set of one or more sensors, a second set of sensor data (e.g., accelerometer and/or gyroscope data that is indicative of the movement and/or a change in orientation) indicative of a position (e.g., spatial position and/or spatial orientation) of the computer system or movement (e.g., change in position or a rate of change) of the computer system. In some embodiments, during the biometric analysis process, in response to detecting the second set of sensor data (1316), in accordance with a determination that the second set of sensor data satisfies a first set of prompting criteria, the computer system displays (1318), via the display generation component (e.g., 602A, 602B), a first prompt (e.g., 1224, 1226, 1228) to change a position (e.g., from an improper positon to a proper position) of the computer system or to limit (e.g., eliminate) changes in position (e.g., movement) of the computer system. In some embodiments, the prompt includes an indication of whether the data indicated a movement of the computer system and/or the data indicated excessive movement/changes in position (1320). In some embodiments, the second set of sensor data is indicative of a position or a movement of a user's hand. Displaying a prompt to change a position of the computer system or to limit (e.g., eliminate) changes in position of the computer system provides the user with feedback that the computer system has detected sensor data that satisfies the prompting criteria. Providing improved visual feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently.

In some embodiments, after displaying the first prompt (e.g., 1224, 1226, 1228) (1328), the computer system (e.g., 600A, 600B) continues (1330) with the biometric analysis process (e.g., the process that is depicted in FIGS. 12B-12L). In some embodiments, while displaying the first prompt, the computer system detects that data from the set of one or more sensors no longer satisfies the first set of prompting criteria and in response, ceases to display the first prompt.

In some embodiments, during the biometric analysis process (e.g., the process that is depicted in FIGS. 12B-12L) and after displaying the first prompt (e.g., 1224, 1226, 1228), the computer system (e.g., 600A, 600B) detects (1332), via the set of one or more sensors, a third set of sensor data (e.g., accelerometer and/or gyroscope data that is indicative of the user's hand moving above a predetermined threshold level of movement) indicative of a position (e.g., spatial position and/or spatial orientation) of the computer system or a movement (e.g., a change in position or a rate of change) of the computer system that satisfies the first set of criteria (e.g., continued movement that exceeds a threshold). In some embodiments, in response to detecting the third set of sensor data, the computer system replaces (1334) the first prompt (e.g., 1226) with a second prompt (e.g., 1228) to change a position of the computer system or to limit changes in position of the computer system, wherein the second prompt is different from the first prompt. Replacing the first prompt with a different second prompt provides the user with feedback that indicates that the computer system has detected further sensor data that satisfies the first set of criteria. Providing improved visual feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently.

In some embodiments, the first prompt (e.g., 1224, 1226, 1228) includes guidance on how to have a proper position of the computer system (e.g., 600A, 600B) or limit motion of the computer system (e.g., "keep your wrist flat and your watch facing up"). Providing guidance on how to limit changes in position of the computer system provides the user with a prompt to modify the user's interactions with the computer system (e.g., modify interactions so as to not cause a disruption of the biometric measurement and provides feedback as to the ongoing state of the computer system. Providing prompts for improved system-user interactions and providing improved visual feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently.

In some embodiments, displaying the first prompt (e.g., 1224, 1226, 1228) to change a position of the computer system (e.g., 600A, 600B) or to limit changes in position of the computer system includes (1322), in accordance with a determination that the second set of sensor data satisfies a first set of position criteria, the first set of position criteria including a criterion that is satisfied when the position of the computer system matches a first predetermined position of a set of one or more predetermined positions (e.g., a set of one or more predetermined positions (e.g., a range of orientations that cause prompting; a range of improper orientations; a range of orientations that negatively affect the biometric analysis process)), a prompt to change the position of the computer system (e.g., a prompt to adopt a proper position or a prompt to adopt a proper orientation (e.g., "place your hand palm or wrist down") (1324). In some embodiments, displaying the first prompt to change a position of the computer system or to limit changes in position of the computer system includes (1322), in accordance with a determination that the second set of sensor data satisfies a first set of movement criteria, the first set of movement criteria including a criterion that is satisfied when a degree of movement of the computer system (e.g., movement speed; amount of movement; acceleration) exceeds a threshold value, a prompt to limit movement of the computer system (e.g., "keep your hand still") (1326). Displaying different prompts based on different criteria being met provides the user with feedback as to the type of sensor data detected and the proper corrective action to take. Providing improved visual feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently.

In some embodiments, the first biometric data is heart rate data.

In some embodiments, the process of collecting the biometric measurement (e.g., the process that is depicted in FIGS. 12B-12L) is initiated at the computer system (e.g., 600A, 600B). In some embodiments, the process of collecting the biometric measurement is initiated at an external electronic device (e.g., 600B) (e.g., a smart watch) that is in communication with the computer system.

In some embodiments, prior to initiating the process for collecting the biometric measurement (e.g., the process that is depicted in FIGS. 12B-12L), the computer system (e.g., 600A, 600B) displays a prompt (e.g., 1224, 1226, 1228) to limit changes in location of the computer system and a selectable user interface object that, when selected, initiates the process for collecting the biometric measurement.

In some embodiments, after completing the biometric analysis process (e.g., the process that is depicted in FIGS. 12B-12L), the computer system (e.g., 600A, 600B) displays a first result user interface (e.g., 1238) that includes information corresponding to the biometric analysis process (e.g., a result of the collection operation; an indication that the collection operation was not completed (e.g., due to an interruption; due to an error)), wherein the first result user interface includes a first dismissal selectable user interface object (e.g., as shown below affordance 1246 in FIG. 12M). In some embodiments, the computer system receives a user input corresponding to the first dismissal selectable user interface object. In some embodiments, in response to receiving the user input corresponding to the first dismissal selectable user interface object, the computer system displays a first user interface of a set of one or more biometric analysis process initiation user interfaces, wherein the set of one or more biometric analysis process initiation user interfaces includes (e.g., includes in the first user interface of the set or a different user interface of the set) a first initiation selectable user interface object that, when selected, initiates a second biometric analysis process via the set of one or more biometric sensors (e.g., the process that is depicted in FIGS. 12B-12L). Providing a selectable user interface object to initiate a second biometric analysis process helps to sustain the machine-user interaction. Providing a user interface that helps to sustain machine-user interacts enhances the operability of the computer system and makes the user-device interface more efficient (e.g., by helping the user to provide proper inputs) which, enables the user to use the computer system more quickly and efficiently.

In some embodiments, during the biometric analysis process (e.g., the process that is depicted in FIGS. 12B-12L), the computer system (e.g., 600A, 600B) displays a graphical indication (e.g., 1208) (e.g., a status bar) that collection of biometric data is progressing, wherein displaying the graphical indication that collection of biometric data is progressing includes displaying a first graphical object (e.g., an icon; an image) that has a first visual characteristic (e.g., color, brightness, size) transitioning to a second graphical object that has a second visual characteristic, different from the first visual characteristic. In some embodiments, the graphical indication is a status bar that transitions from having the first visual characteristic (e.g., a first color, brightness, size) to the second visual characteristic (e.g., a second color, brightness, size). Displaying an indication that collection of the biometric data is progressing provides the user with feedback as to the state of the biometric measurement. Providing improved visual feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently.

In some embodiments, while the computer system (e.g., 600A, 600B) is collecting the biometric measurement (e.g., via the process that is depicted in FIGS. 12B-12L), the computer system displays an indication of the time (e.g., 1212) remaining in the collection operation (e.g., the time required to complete the biometric measurement).

In some embodiments, after completion of the biometric analysis process (e.g., the process that is depicted in FIGS. 12B-12L), the computer system (e.g., 600A, 600B) displays a second result user interface (e.g., 1214 of FIG. 12G) that includes a result (e.g., a quantitative or qualitative of the measured data) of the biometric analysis process, and in accordance with a determination that the biometric analysis process was conducted under one or more conditions (e.g., environmental conditions (e.g., an elevation, an ambient atmospheric pressure) of a first type (e.g., the one or more conditions satisfy a set of one or more condition criteria; the one or more conditions exceed (e.g., are greater than or less than) a threshold value (e.g., a threshold elevation, a threshold atmospheric pressure)), an indication (e.g., 1222) (e.g., a text indication, a graphical indication) that the biometric analysis process was conducted under one or more conditions of the first type. In some embodiments, in accordance with a determination that the biometric analysis process was not conducted under the one or more conditions of the first type, the result user interface (e.g., 1214 of FIG. 12F) does not include the indication that the biometric analysis process was conducted under one or more conditions of the first type. Conditionally including an indication that the biometric analysis process was conducted under one or more conditions of the first type provides the user feedback as to conditions under which the biometric analysis process was conducted. Providing improved visual feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently.

In some embodiments, the second result user interface (e.g., 1214 of FIG. 12G) includes a selectable user interface object that, when selected, causes display of additional information about the biometric measurement.

In some embodiments, the first set of cessation criteria is satisfied when a first detected value corresponding to the first set of sensor data (e.g., a value derived from the sensor data; the raw sensor data) exceeds an expected value (e.g., a predetermined threshold value).

In some embodiments, the first set of cessation criteria is satisfied when at least a first number of (e.g., $M_M$) discrete sets (e.g., windows) of data (e.g., accelerometer data) of the first set of sensor data, out of a sampling window of discrete sets of data (e.g., $N_M$), exceeds a threshold value (e.g., 5 discrete sets out of a sampling window of 5 discrete sets). Using cessation criteria that requires that at least a first number of discrete sets (e.g., windows) of data of the first set of sensor data, out of a sampling window of discrete sets of data, exceeds a threshold value reduces the susceptibility of the criteria to noisy date. Reducing the susceptibility to noise enhances the operability of the computer system and makes the system more efficient (e.g., by reducing errors) which, additionally, reduces power usage and improves battery life of the computer system by enabling the user to use the computer system more quickly and efficiently.

In some embodiments, the sampling window of discrete sets of data includes a plurality of discrete sets of data (e.g., $N_M>1$) and the at least a first number of discrete sets of data is a plurality of consecutive sets of data (e.g., $M_M>1$ (e.g., 2 consecutive discrete sets of data that exceed the threshold out of a window of 5 sets of data; 5 consecutive discrete sets of data that exceed the threshold out of a window of 5 sets of data).

In some embodiments, the at least a first number of discrete sets of data is a plurality of sets of data that each are collected over the same predetermined time period (e.g., 1 second, 0.5 seconds).

In some embodiments, at least two of the plurality of sets of data of the at least a first number of discrete sets of data overlap in time (e.g., each discrete set of data is 1 second long and a first and second sets of data overlap by 0.5 seconds of their respective 1 second durations (e.g., first set runs from 0 to 1 seconds and second set runs from 0.5 seconds to 1.5 seconds)).

In some embodiments, the first set of sensor data is detected at a first time during the biometric analysis process (e.g., the process that is depicted in FIGS. 12B-12L). In some embodiments, at a second time during the biometric analysis process that is after the first, the computer system (e.g., 600A, 600B) detects, via the set of one or more sensors, a fourth set of sensor data (e.g., accelerometer and/or gyroscope data that is indicative of the movement and/or a change in orientation). In some embodiments, in response to detecting the fourth set of sensor data, in accordance with a determination that the fourth set of sensor data satisfies a second set of cessation criteria, different from the first set of cessation criteria, the computer system ceases the biometric analysis process. In some embodiments, the cessation criteria (e.g., threshold criteria) varies over the duration of the biometric analysis process. In some embodiments, the criteria become more restrictive as the process continues (e.g., less movement is permitted as the process progresses). Using different criteria for cessation at different points in time for the biometric analysis process provides the system with more refined criteria for determining whether to cease the process. Employing more refined criteria enhances the operability of the computer system and makes the system more efficient (e.g., by reducing false negatives that can result from rigid criteria) which, additionally, reduces power usage and improves battery life of the computer system by enabling the user to use the computer system more quickly and efficiently.

In some embodiments, the first set of sensor data includes data indicative of a position of the computer system (e.g., 600A, 600B) (e.g., GPS coordinates; a street address).

In some embodiments, the first set of sensor data includes data indicative of motion (e.g., movement from a first location to a second location) of the computer system (e.g., 600A, 600B).

In some embodiments, the first set of sensor data includes data indicative of a position of the computer system and data indicative of motion of the computer system (e.g., 600A, 600B).

In some embodiments, the first set of sensor data satisfies a first set of cessation criteria and/or the first set of prompting criteria are empirically derived from clinical data obtained during clinical measurements of the first biometric data.

In some embodiments, the computer system is a wearable device (e.g., a smart watch) and the set of one or more sensors includes an accelerometer that is used to measure movement of the wearable device.

In some embodiments, the first set of sensor data includes a plurality of discrete channels of data (e.g., movement data corresponding to x, y, and z axes) and the first set of cessation criteria can be satisfied by data of any channel (e.g., when the criteria is a threshold movement value, the maximum value of any one channel of the plurality of channels can be used to determine if the threshold movement value has been exceeded).

In some embodiments, the first biometric data is a blood oxygen level measurement (e.g., $SpO_2$). In some embodiments, the set of one or more biometric sensors includes a blood oxygen sensor (e.g., an optical blood oxygen sensor that operates in conjunction with a light source (e.g., an LED). In some embodiments, threshold is a percentage of blood oxygen. In some embodiments, the first health-related function is a function for measuring or tracking $VO_2$max (e.g., maximal oxygen consumption; the maximum rate of oxygen consumption measured during incremental exercise).

In some embodiments, the computer system, after ceasing the biometric analysis process and in accordance with a determination that the biometric data and/or the first set of sensor data satisfies a first set of cessation type criteria, displays a first cessation user interface (e.g., an interface that does not include a quantitative result of the biometric analysis; an interface that includes one or more indications of one or more criterion of the first set of cessation type criteria) (e.g., 1238*b*, 1238*c*, 1238*d*). In some embodiments, the computer system, after ceasing the biometric analysis process and in accordance with a determination that the biometric data and/or the first set of sensor data satisfies a second set of cessation type criteria different from the first set of cessation type criteria, displays a second cessation user interface that is different from the first cessation user interface (e.g., an interface that does not include a quantitative result of the biometric analysis; an interface that includes one or more indications of one or more criterion of the second set of cessation type criteria). Displaying different cessation user interfaces based on different sets of cessation criteria being satisfied provides the user with feedback as to why cessation of the biometric analysis process occurred. Providing improved visual feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently.

In some embodiments, the first set of cessation type criteria includes a criterion that is satisfied when the first set of sensor data indicates movement of the computer system that satisfies a first set of movement cessation type criteria (e.g., a set of criteria that is satisfied when the biometric analysis process is terminated due to excessive movement); and the first cessation user interface includes guidance (e.g., 1238*b*2, 1258*a*1) on reducing movement of the computer system (e.g., reducing during a subsequent biometric analysis process). Displaying a cessation user interface that includes guidance on reducing movement provides the user with feedback as to the cause of cessation and, further, prompts the user to continue to interact further (and in an improved manner) with the computer system. Providing improved visual feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently; prompting the user to interact further with the system improves and sustains the user-system interaction.

In some embodiments, the second set of cessation type criteria includes a criterion that is satisfied when the first set of sensor data indicates a position of the computer system that satisfies a first set of position cessation type criteria (e.g., a set of criteria that is satisfied when the biometric analysis process is terminated due to improper positioning of the computer system during the biometric analysis process); and the second cessation user interface includes guidance (e.g., 1238c2, 1258b1) on positioning of the computer system (e.g., positioning during a subsequent biometric analysis process). Displaying a cessation user interface that includes guidance on positioning of the system provides the user with feedback as to the cause of cessation and, further, prompts the user to continue to interact further (and in an improved manner) with the computer system. Providing improved visual feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently; prompting the user to interact further with the system improves and sustains the user-system interaction.

In some embodiments, the computer system, after ceasing the biometric analysis process: displays a user interface (e.g., 1204a of FIG. 12Z, 1204a of FIG. 12AC, 1204a of FIGS. 12AF and 12AG) for initiating a second biometric analysis process that includes: an selectable user interface object that, when selected, initiates the second biometric analysis process (e.g., a process that includes detecting, via the one or more biometric sensors, second biometric data). In some embodiments, the user interface includes, in accordance with a determination that the first set of cessation criteria was satisfied by the first set of sensor data corresponding to a first type of cessation condition (e.g., excessive movement), guidance (e.g., 1256b, 1256c, 1256d1, 1256d2) corresponding to the first type of cessation condition (e.g., guidance on how to address, mitigate, and/or avoid the first type of cessation condition). In some embodiments, the user interface includes, in accordance with a determination that the first set of cessation criteria was satisfied by the first set of sensor data corresponding to a second type of cessation condition (e.g., excessive movement), guidance (e.g., 1256b, 1256c, 1256d1, 1256d2) corresponding to the second type of cessation condition (e.g., guidance on how to address, mitigate, and/or avoid the second type of cessation condition). Displaying a user interface for initiating a second biometric analysis process that includes different guidance based on the cause of cessation of a previous analysis process provides the user with feedback as to the cause of cessation and, further, prompts the user to continue to interact further (and in an improved manner) with the computer system. Providing improved visual feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently; prompting the user to interact further with the system improves and sustains the user-system interaction.

In some embodiments, the computer system, during the biometric analysis process (e.g., at any point prior to displaying the results of the biometric analysis process (e.g., quantitative results)) and in accordance with a determination that the first biometric data satisfies a second set of cessation criteria (e.g., criteria that are satisfied when the data indicates one or more abnormalities in the biometric data indicative of an error) different from the first set of cessation criteria, ceases the biometric analysis process (e.g., as discussed with reference to FIG. 12AD). Ceasing the biometric analysis process when a second set of cessation criteria are met, without the user having to manual cease the process, optimizes the analysis process and reduces the risk of erroneous biometric results. Performing an optimized operation when a set of conditions has been met without requiring further user input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the computer system, after ceasing the biometric analysis process in accordance with a determination that the first biometric data satisfied the second set of cessation criteria, displays a third cessation user interface (e.g., 1238d) that is different from the first cessation user interface and the second cessation user interface. Displaying different cessation user interfaces based on different sets of cessation criteria being satisfied provides the user with feedback as to why cessation of the biometric analysis process occurred. Providing improved visual feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently.

In some embodiments, the computer system is a wearable electronic device (e.g., a smart watch); and the third cessation user interface includes guidance (e.g., 1238d2, 1258c1) on adjusting the manner in which the wearable electronic device is worn (e.g., worn during a subsequent biometric analysis process; worn with respect to the user's body (e.g., positioning on a wrist/arm of the user)). Displaying a cessation user interface that includes guidance on the manner in which the wearable electronic device is worn provides the user with feedback as to the cause of cessation and, further, prompts the user to continue to interact further (and in an improved manner) with the computer system. Providing improved visual feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently; prompting the user to interact further with the system improves and sustains the user-system interaction.

In some embodiments, ceasing the biometric analysis process includes detecting a predetermined quantity of biometric data (e.g., a quantity based on detecting for a predetermined amount of time (e.g., an amount of time required for a valid biometric analysis process) and/or a quantity based on a predetermined amount of valid sampling points); and forgoing displaying a result indicative of a biometric parameter corresponding to the biometric data (e.g., forgoing to display of a quantitative result; displaying an indication that the analysis was not completed without otherwise displaying a result of the analysis (e.g., as seen FIG. 12AD). In some embodiments, the amount of biometric data gathered for a complete biometric analysis process and a ceased/terminated biometric analysis is the same; the difference being that a completed biometric analysis includes displaying a result (e.g., a quantitative result; a result that reports a value of a biometric parameter (e.g., blood oxygen level)) whereas the ceased/terminated biometric analysis process does not include display of the result.

Note that details of the processes described above with respect to method 1300 (e.g., FIGS. 13A-13B) are also applicable in an analogous manner to the methods described above and below. For example, method 700 optionally includes one or more of the characteristics of the various methods described above with reference to method 1300. For example, the user interfaces for managing health and safety features described with reference to method 700 can be used to manage one or more features of the application used to measure the biometric information described with reference to method 1300. For another example, method 900 optionally includes one or more of the characteristics of the various methods described above with reference to method 1300. For example, features concerning the conditional display of a setup user interface as described with reference to method 900 can be applied during a process for setting up the biometric measurement application described with reference to method 1300. For another example, method 1100 optionally includes one or more of the characteristics of the various methods described above with reference to method 1300. For example, the setup user interfaces described with reference to method 1100 can be used to setup the health application used for the biometric measurement as described with reference to method 1300. For another example, method 1500 optionally includes one or more of the characteristics of the various methods described above with reference to method 1300. For example, health information that is captured via the biometric measurement described with reference to method 1300 can be presented to a user via the user interfaces described with reference to method 1500. For another example, method 1700 optionally includes one or more of the characteristics of the various methods described above with reference to method 1300. For example, the biometric measurement features of the health application as described with reference to method 1300 can also enable the background measurement features described with reference to method 1700. For brevity, these details are not repeated below.

FIGS. 14A-14I illustrate exemplary user interfaces for providing results for captured health information on an electronic device, in accordance with some embodiments. The user interfaces in these figures are used to illustrate the processes described below, including the processes in FIGS. 15A-15B.

FIG. 14A illustrates device 600A displaying a summary user interface 1400 of the health application. Summary user interface 1400 corresponds to summary user interface 660 first described above with reference to FIG. 6N.

In FIG. 14A, device 600A displays, in user interface 1400, a notification 1402 that includes an indication 1402A that multiple background heart rate measurements have been detected (e.g., determined) to be below the low heart rate notification threshold (e.g., the low heart rate notification threshold first describe above with reference to FIGS. 10Q-10T) within a certain measurement time period (e.g., the past 6 hours; the past 24 hours; during the current day). Notification 1402 also includes a graphical indication 1402B of the previous background heart rate measurements that have been detected to be below the notification threshold. In FIG. 14A, 3 previous background heart rate measurements, measuring 87, 88, and 89 BPM, were detected to be below the low heart rate notification threshold during the current day.

Also in FIG. 14A, while displaying notification 1402, device 600A receives an input 1401 directed to notification 1402.

In FIG. 14B, in response to receiving input 1401, device 600A displays a user interface 1404 for the heart rate level tracker application. User interface 1404 includes more detailed information about background heart rate measurements made during a currently-selected measurement time range. User interface 1404 also includes a time range selection region 1410 that includes different time ranges 1410A-1410E—a current hour time range 1410A, a current day time range 1410B, a current week time range 1410C, a current month time range 1410D, and a current year time range 1410E. In FIG. 14B, the currently-selected time range is the current day, as indicated by the visual highlighting of current day time range 1410B.

User interface 1404 also includes an indication 1406 of the heart rate measurement range during the currently-selected measurement time rage. In FIG. 14B, user interface 1404 indicates, via indication 1406, that the heart rates measured during the current day ranged from 82-95 BPM.

User interface 1404 also includes a graph region 1408 (e.g., of a point graph or a chart graph) that includes markers 1408A-1408J (e.g., points) corresponding to and indicating heart rates measured during the current day. Markers 1408A-1408J include their corresponding respective BPM value. Markers 1408H-1408J corresponding to measurements that fall below the low heart rate notification threshold (below 90 BPM in the embodiment of FIG. 14B) are visually distinguished from markers 1408A-1408G corresponding to measurements that do not fall below the low heart rate notification threshold.

User interface 1404 also includes an affordance 1416 for causing display of additional information about each measurement displayed in graph region 1408. While displaying affordance 1416, device 600A receives an input 1403 directed to affordance 1416.

Figure 14C:
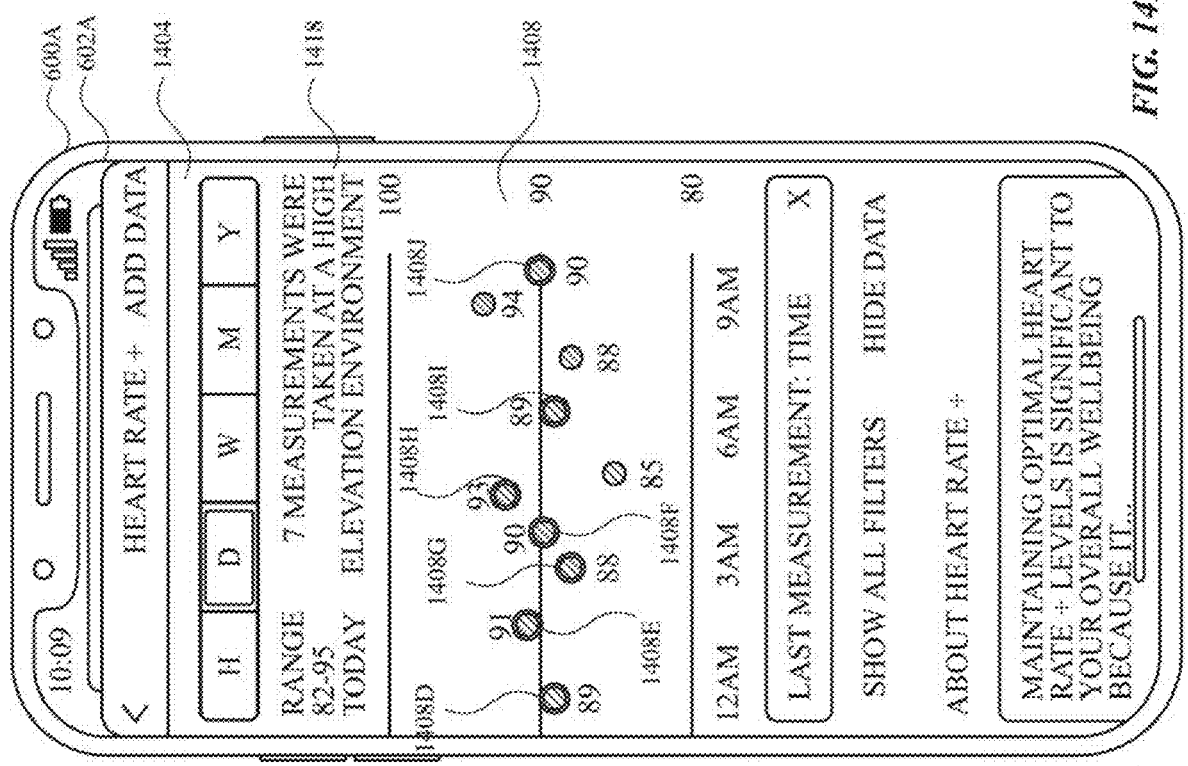

In FIG. 14C, in response to receiving input 1403, device 600A displays, for each of markers 1408A-1408J in graph region 1408, additional information. In some embodiments, the additional information includes information 1418 indicating that multiple displayed measurements were taken in an unusual circumstance. In FIG. 14C, the unusual circumstance is a high elevation environment, and information 1418 indicates that 7 (of the 10) measurements were taken in the high elevation environment. In some embodiments, the additional information includes ambient pressure information for each of markers 1408A-1408J (e.g., shown beneath, adjacent to, or proximate to each marker).

Figure 14D:
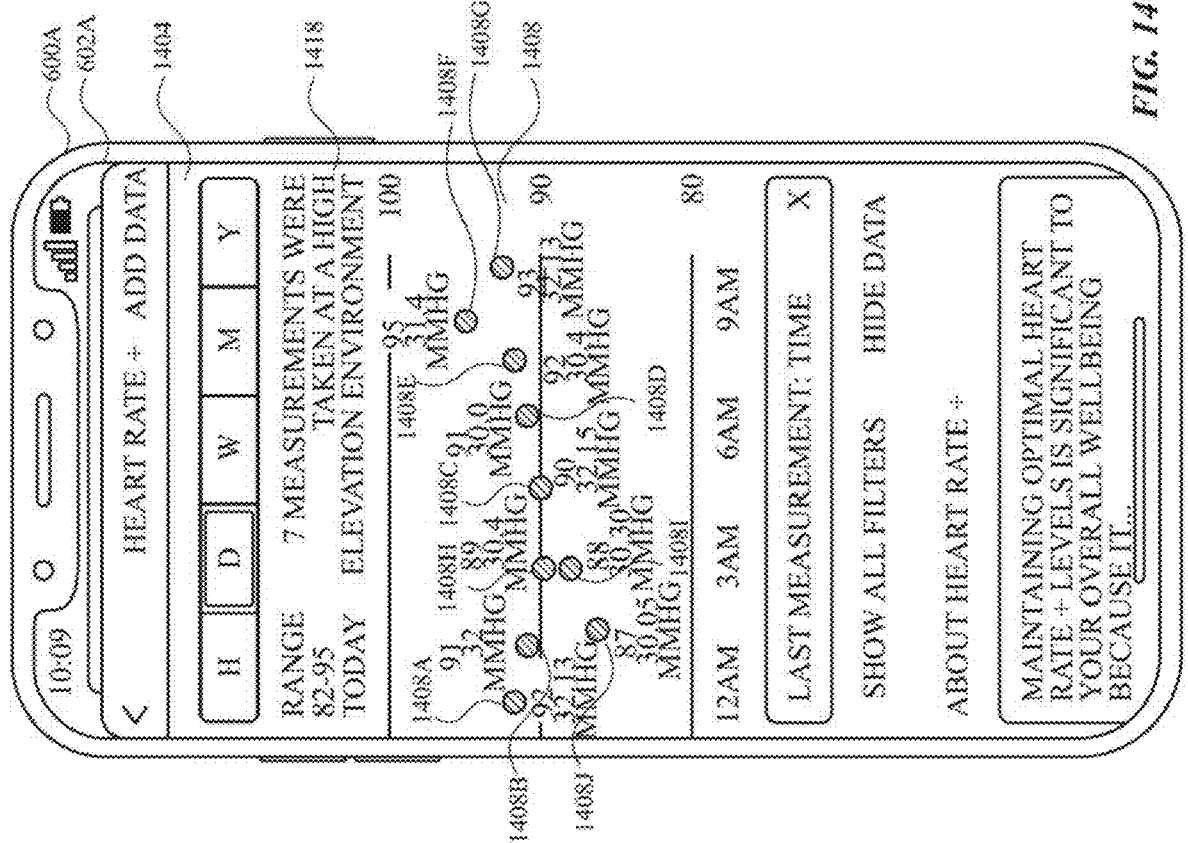

In FIG. 14D, user interface 1404 includes information 1418 that multiple displayed measurements were taken in an unusual circumstance. Device 600A visually distinguishes (e.g., highlights; uses different colors; uses different sizes) markers corresponding to measurements that were taken in the unusual circumstance with markers that were not taken in the unusual circumstance. In FIG. 14D, the unusual circumstance is a high elevation environment, with markers 1408D-1408J corresponding to measurements taken in the high elevation environment.

FIG. 14E illustrates device 600A displaying summary user interface 1400 of the health application, as described above with reference to FIG. 14A.

In FIG. 14E, device 600A displays, in user interface 1400, a notification 1420. Notification 1420 includes an indication 1420A (e.g., a text description) that multiple heart rates were measured (e.g., as a background operation on device 600B) to be below the low heart rate notification threshold (e.g., the low heart rate notification threshold first describe above with reference to FIGS. 10Q-10T) within a certain measurement time period (e.g., the past 6 hours; the past 24 hours; during the current day). Notification 1420 also includes a graphical indication 1420B of the previous background heart rate measurements that have been detected to be below the notification threshold. In FIG. 14E, 5 previous background heart rate measurements, measuring 89, 88, 85, 88, and 89 BPM, were detected to be below the low heart rate notification threshold during the past 6 hours.

Also in FIG. 14E, while displaying notification 1420, device 600A receives an input 1405 directed to notification 1420.

Figures 14F1, 14F2:
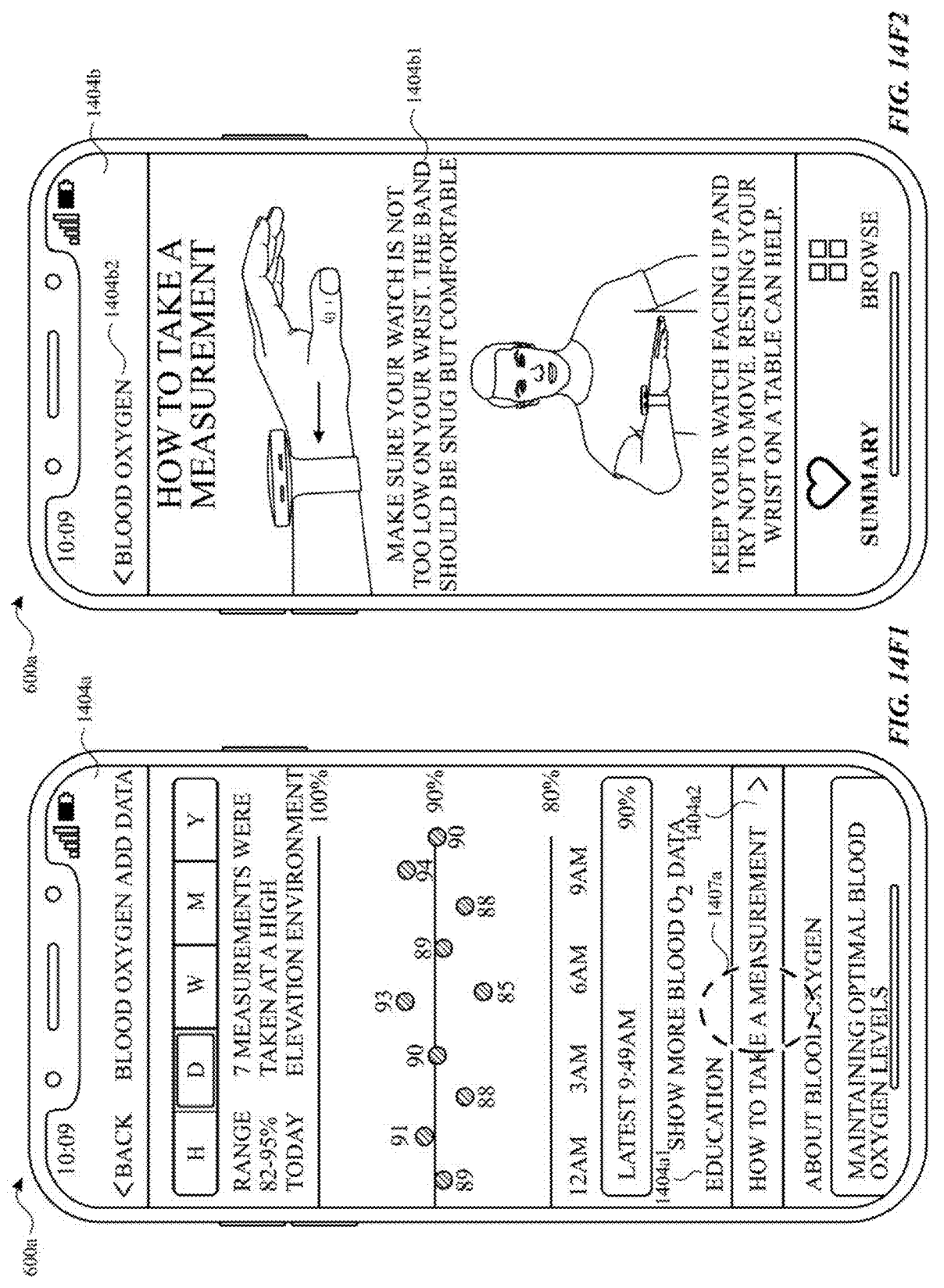

In FIG. 14F, in response to receiving input 1405, device 600A displays user interface 1404. User interface 1404 includes time range region 1410. User interface 1404 includes indication 1406 of the heart rate measurement range during the currently-selected measurement time range. User interface 1404 includes graph region 1408 (e.g., of a point graph or a chart graph) that includes markers 1408A-1408J (e.g., points) corresponding to and indicating heart rates measured during the currently-selected measurement time range, as first described above with reference to FIG. 14B.

As mentioned, in FIG. 14F, the currently-selected measurement time range is the current day, as indicated via currently day time range 1410B. While the selected time range is the current day, device 600A receives an input 1407 directed to current week time range 1410C.

In FIG. 14F1, device 600A displays a user interface 1404a that reports blood oxygen measurement data in a format similar to that of 1404 for reporting heart rate measurement data. In some embodiments, interface 1404a is displayed in response to an input on a notification relating to blood oxygen measurements in interface 1400. In some embodiments, user interface 1404a includes one or more features discussed with respect to user interface 1404 with the difference being that the reported data relates to blood oxygen, rather than heart rate. In FIG. 14F1, user interface 1404a includes an education section 1404a1 that includes tutorial affordance 1404a2. In some embodiments, education section 1404a2 includes additional affordances that provide access to further information on blood oxygen measurements. In FIG. 14F1, device 600A receives input 1407a directed to tutorial affordance 1404a2.

In FIG. 14F2, device 600A displays tutorial user interface 1404b that includes text 1404b1 with information on how to take a blood oxygen measurement and how to reduce the risk of an unsuccessful measurement. In some embodiments, tutorial user interface 1404b includes videos and/or animations demonstrating how to perform a measurement. Tutorial user interface 1404b also includes back affordance 1404b2 for returning to user interface 1404a.

Figure 14G:
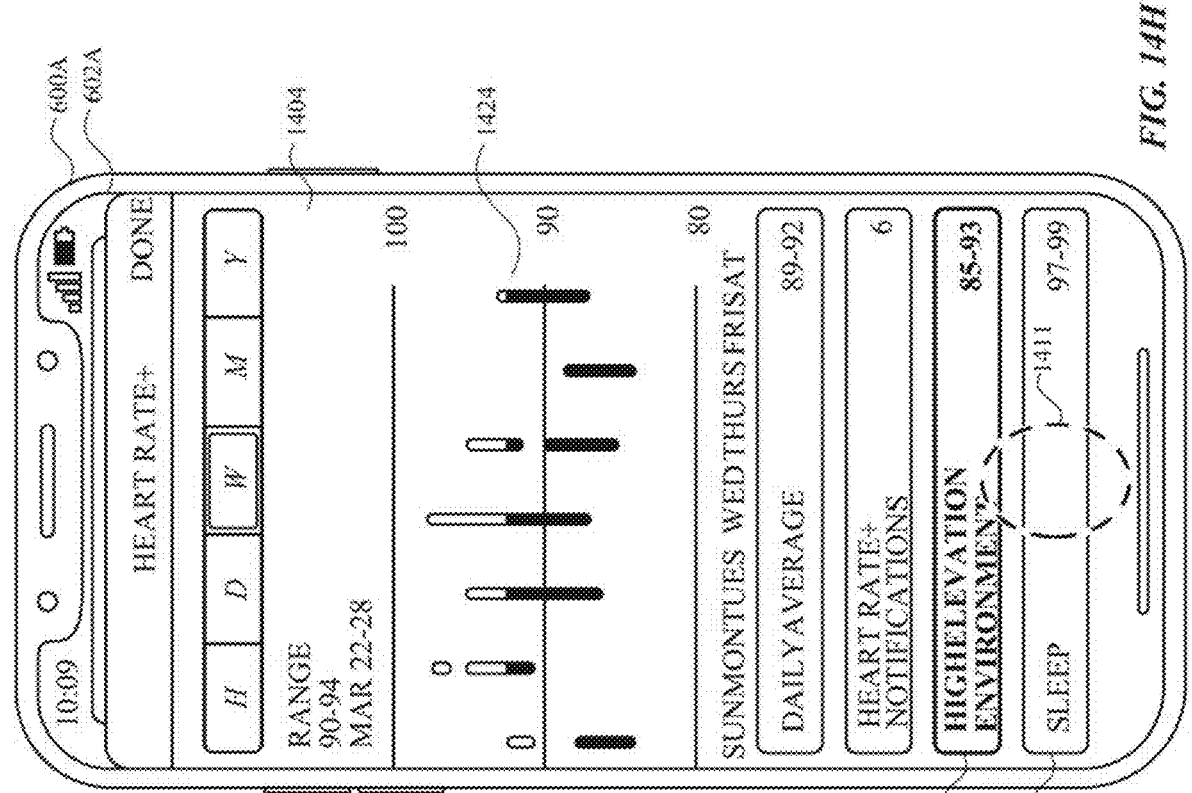

In FIG. 14G, in response to receiving input 1407 directed to current week time range 1410C of FIG. 14F, device 600A updates display of graph region 1408 to instead include markers 1424A-1424G corresponding to heart rates measured during the current week. In some embodiments, multiple heart rate measurements from a single day are aggregated (e.g., as one or more bars) to indicate one or more range of measurements during the respective day, as shown in FIG. 14G.

Also in FIG. 14G, device 600 displays, in user interface 1404, multiple information regions 1426-1432. User interface 1404 includes a first information region 1426 that indicates the daily average measured heart rate information. In FIG. 14G, first information region 1426 indicates a 89-92 daily average BPM.

In some embodiments, user interface 1404 includes a second information region 1428 that indicates notification information (e.g., a number of notifications concerning low heart rate measurements that were generated during the currently-selected time period). In FIG. 14G, second information region 1428 indicates that 6 notifications concerning low heart rate measurements were generated during the current week, and is currently selected (e.g., as indicated via visual highlighting of second information region 1428). As also shown in FIG. 14G, each of markers 1424A-1424G indicates portions corresponding to measurements that fall below the low heart rate notification threshold (in the embodiment of FIG. 14G, 90 BPM), thus causing device 600A to generate a notification(s), with a first visual characteristic (e.g., a first color) and indicates the remaining portions corresponding to measurements that do not fall below the low heart rate notification threshold with a second visual characteristic (e.g., a second color) that is different from the first visual characteristic.

In some embodiments, user interface 1404 includes a third information region 1430 that indicates information about heart rate measurements that were taken in an unusual condition (e.g., a high elevation environment). In FIG. 14G, third information region 1430 indicates that heart rate measurements taken during the current week in a high elevation environment measured between 85-93 BPM.

In some embodiments, user interface 1404 includes a fourth information region 1432 that indicates information about heart rate measurements that were taken during sleep hours (e.g., during nighttime hours; while the user is determined to be asleep; while the measuring device (e.g., device 600B) is in sleep mode). In FIG. 14G, fourth information region 1432 indicates that heart rate measurements taken during the current week during sleep hours measured between 97-99 BPM.

Also in FIG. 14G, while displaying information regions 1426-1432 in user interface 1404, device 600A receives an input 1409 directed to third information region 1430.

Figure 14H:
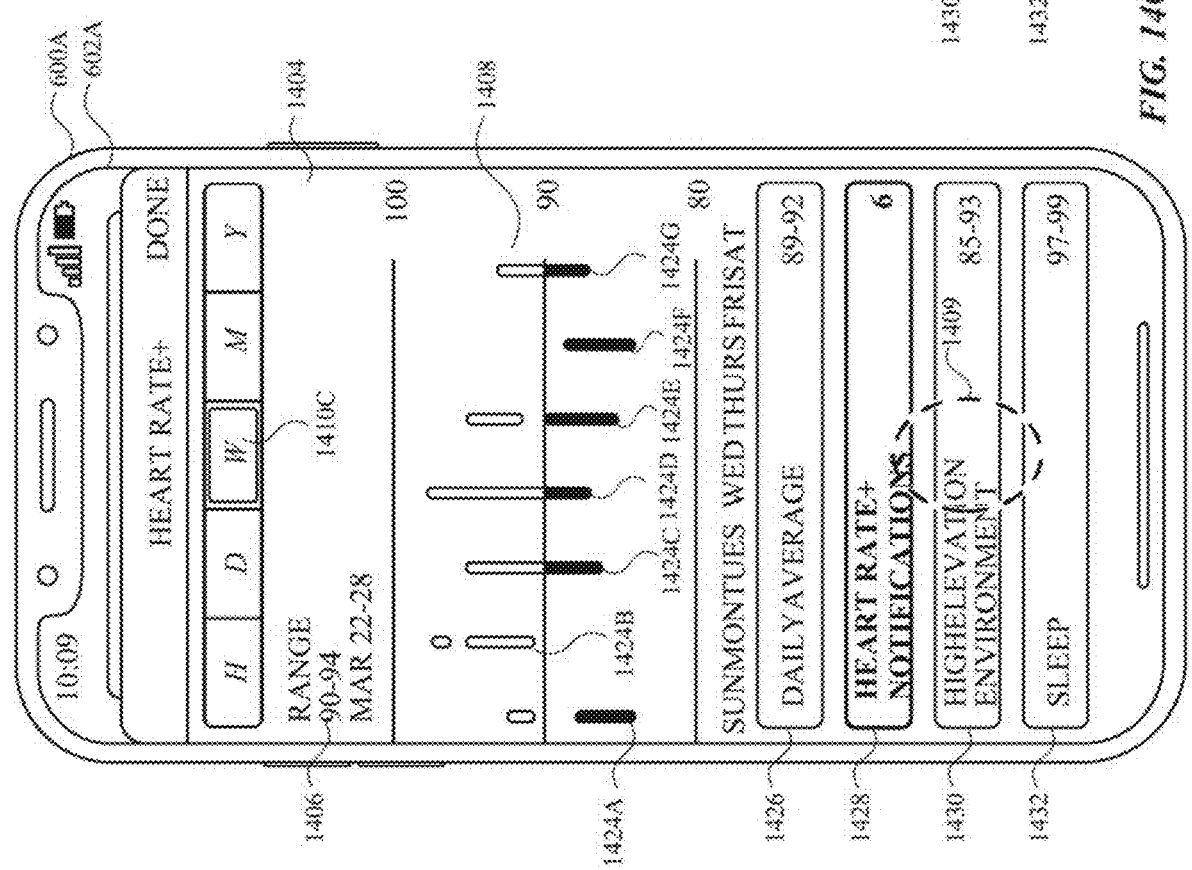

In FIG. 14H, in response to receiving input 1409 directed to third information region 1430, device 600A indicates that third information region 1430 corresponding to heart rate measurements taken in a high elevation environment is currently selected. While third information region 1430 is selected, each of markers 1424A-1424G indicates portions corresponding to measurements that fall within the range indicated via third information region 1430 (in FIG. 14G, 85-93 BPM) with a first visual characteristic (e.g., a first color) and indicates the remaining portions corresponding to measurements that do not fall thin the range indicated via third information region 1430 with a second visual characteristic (e.g., a second color) that is different from the first visual characteristic.

Also in FIG. 14H, while displaying information regions 1426-1432 in user interface 1404, device 600A receives an input 1411 directed to third information region 1430.

Figure 14I:
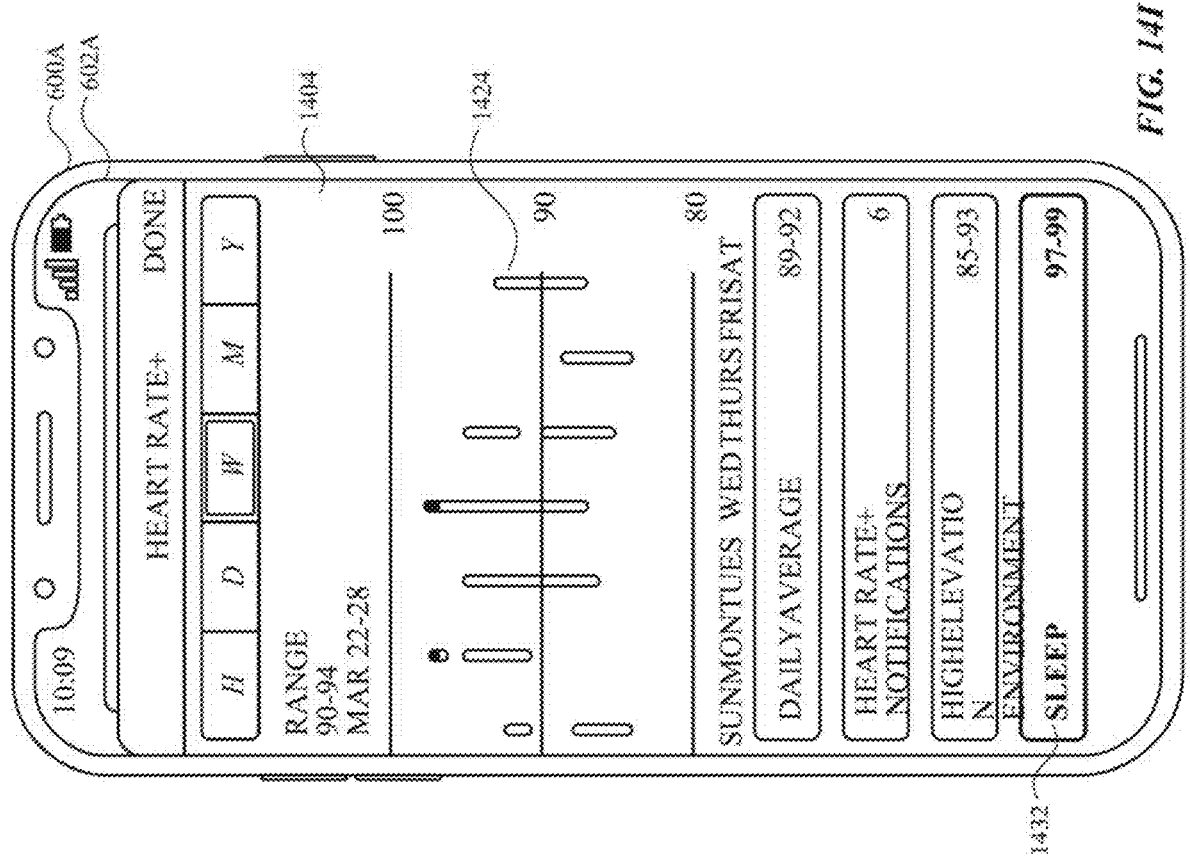

In FIG. 14I, in response to receiving input 1411 directed to fourth information region 1432, device 600A indicates that fourth information region 1430 corresponding to heart rate measurements taken during sleep hours (e.g., during nighttime hours; while the user is determined to be asleep; while the measuring device (e.g., device 600B) is in sleep mode) is currently selected (e.g., by visually highlighting fourth information region 1432). While fourth information region 1432 is selected, each of markers 1424A-1424G indicates portions corresponding to measurements that fall within the range indicated via fourth information region 1432 (in FIG. 14G, 97-99 BPM) with a first visual characteristic (e.g., a first color) and indicates the remaining portions corresponding to measurements that do not fall within the range indicated via fourth information region 1432 with a second visual characteristic (e.g., a second color) that is different from the first visual characteristic.

In some embodiments, the heart rate measurement results described in FIGS. 14A-14I are instead blood oxygen level tracking and measurement results. In some embodiments, the computer system is in communication with a blood oxygen sensor (e.g., an optical blood oxygen sensor that operates in conjunction with a light source (e.g., an LED)). In some embodiments, threshold is a percentage of blood oxygen. In some embodiments, the heart rate measurement results described in FIGS. 14A-14I are instead $VO_2max$ level tracking and measurement data (e.g., maximal oxygen consumption; the maximum rate of oxygen consumption measured during incremental exercise).

FIGS. 15A-15B are a flow diagram illustrating a method for providing results for captured health information on an electronic device, in accordance with some embodiments. Method 1500 is performed at a computer system (e.g., an electronic device (e.g., 100, 300, 500, 600A, 600B)) that is in communication with a display generation component (e.g., 602A, 602B) (e.g., a display controller, a touch-sensitive display system; a display (e.g., integrated or connected)) and one or more input devices (e.g. gyroscope, accelerometer, microphone, a touch-sensitive surface). Some operations in method 1500 are, optionally, combined, the orders of some operations are, optionally, changed, and some operations are, optionally, omitted.

In some embodiments, the electronic device (e.g., 600A) is a computer system. The computer system is optionally in communication (e.g., wired communication, wireless communication) with the display generation component (e.g., 602A, 602B) and with the one or more input devices. The display generation component is configured to provide visual output, such as display via a CRT display, display via an LED display, or display via image projection. In some embodiments, the display generation component is integrated with the computer system. In some embodiments, the display generation component is separate from the computer system. The one or more input devices are configured to receive input, such as a touch-sensitive surface receiving user input. In some embodiments, the one or more input devices are integrated with the computer system. In some embodiments, the one or more input devices are separate from the computer system. Thus, the computer system can transmit, via a wired or wireless connection, data (e.g., image data or video data) to an integrated or external display generation component to visually produce the content (e.g., using a display device) and can receive, a wired or wireless connection, input from the one or more input devices.

As described below, method 700 provides an intuitive way for managing and/or presenting health data. The method reduces the cognitive burden on a user for managing and/or presenting health data, thereby creating a more efficient human-machine interface. For battery-operated computing devices, enabling a user to manage and/or present health data faster and more efficiently conserves power and increases the time between battery charges.

The computer system (e.g., 600A, 600B) displays (1502), via the display generation component (e.g., 602A, 602B), a summary user interface (e.g., 1400, 1404) of a first health-related tracking function (e.g., a tracking (e.g., data tracking, data gathering) application or application feature available to operate on the computer system or available to operate on an external electronic device in communication with the computer system (e.g., a heart-rate tracking function, an ambient-noise-level-tracking function)).

The summary user interface (e.g., 1400, 1404) includes a set of one or more user interface objects (e.g., 1402; platters shown in summary user interface 1400 of FIG. 14A) (e.g., data points of a graph) that correspond to tracking data gathered by the first health-related tracking function (e.g., gathered at the computer system, gathered at an external device and transmitted to the computer system) (1504).

The set of one or more user interface objects includes (1506) a first user interface object (e.g., 1402, 1408, 1420) that corresponds to first datum gathered via the first health-related tracking function (1508), and displaying the summary user interface (e.g., 1400, 1404) includes (1512), in accordance with a determination that the first datum was gathered (e.g., gathered by the computer system or an external electronic device that provided data to the computer system) under one or more conditions (e.g., environmental conditions (e.g., an elevation, an ambient atmospheric pressure) of a first type (e.g., the one or more conditions satisfy a set of one or more condition criteria; the one or more conditions exceed (e.g., are greater than or less than) a threshold value (e.g., a threshold elevation, a threshold atmospheric pressure)), displaying the first user interface object with an indication (e.g., 1418, 1420B) (e.g., a text indication, a graphical indication) that indicates that at least some of the tracking data gathered by the first health-related tracking function was gathered under the one or more conditions of the first type (1514). In some embodiments, the indication indicates (e.g., specifically or precisely indicates) that the first user interface object corresponding to the first datum was gathered under the one or more conditions of the first type).

In some embodiments, in accordance with a determination that the first datum was not gathered under one or more conditions of the first type, displaying the first user object (e.g., 1402, 1408, 1420) without the indication that the first datum was gathered under the one or more conditions of the first type. Conditionally including an that indicates that at least some of the tracking data gathered by the first health-related tracking function was gathered under the one or more conditions of the first type provides the user feedback as to conditions under which the tracking data was gathered. Providing improved visual feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently.

In some embodiments, displaying the summary user interface (e.g., 1400, 1404) includes, in accordance with a determination that the tracking data gathered by the first health-related tracking function that corresponds to the displayed one or more user interface objects was not gathered under one or more conditions of the first type, displaying the set of one or more user interface objects (e.g., 1402, 1408, 1420) without the indication that at least some of the tracking data gathered by the first health-related tracking function was gathered under the one or more conditions of the first type. Displaying the set of one or more user interface objects without the indication that at least some of the tracking data gathered by the first health-related tracking function was gathered under the one or more conditions of the first type provides the user with feedback indicating that the data was not gathered under conditions of the first type. Providing improved visual feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently.

In some embodiments, the one or more conditions of the first type includes an altitude (e.g., elevation) that exceeds a threshold value (e.g., greater than 5000 feet above sea level; greater than 8000 feet above sea level) (1516).

In some embodiments, the tracking data is heart rate tracking data.

In some embodiments, the set of one or more user interface objects that correspond to tracking data gathered by the first health-related tracking function includes a plurality of user interface objects that correspond to tracking data gathered by the first health-related tracking function (1510) (e.g., as shown in FIG. 14A-14I). In some embodiments, a second user interface object (e.g., 1402B, 1408, 1420C, 1424) of the plurality of user interface objects corresponds to multiple measurements made by the first health-related tracking function (e.g., the second user interface object aggregates a predetermined plurality of measurements). Displaying a plurality of user interface objects that correspond to tracking data gathered by the first health-related tracking function provides the user with feedback as to the measurements stored at or accessible to the computer system. Providing improved visual feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently.

In some embodiments, displaying the summary user interface (e.g., 1400, 1404) includes (1518), in accordance with a determination that the tracking data gathered by the first health-related tracking function indicates that a biometric parameter (e.g., heart rate) of a user of the computer system has been below a threshold value (e.g., 60 beats per minute, 50 beats per minute) for at least a predetermined period of time (e.g., 1 hour, 6 hours, 1 day), displaying an indication (e.g., 1402A, 1420A) that the biometric parameter of the user has been below the threshold value for at least the predetermined period of time (1520). Conditionally displaying an indication that the biometric parameter of the user has been below the threshold value for at least the predetermined period of time provides the user with feedback as to tracking data gathered by the first health-related tracking function. Providing improved visual feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently.

In some embodiments, displaying the summary user interface (e.g., 1400, 1404) includes, in accordance with a determination that the first datum was gathered under one or more conditions of a first type, displaying the first user interface object (e.g., 1402, 1408, 1420) with an indication that the first datum (e.g., an indication specific to the first datum) was gathered under one or more conditions of the first type. Displaying the first user interface object with an indication that the first datum (e.g., an indication specific to the first datum) was gathered under one or more conditions of the first type provides the user with feedback that is specific to the first datum. Providing improved visual feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently.

In some embodiments, the one or more conditions of the first type includes a sleep period (e.g., a period when the user is asleep (e.g., detected as being asleep or predicted (e.g., based on time) that the user is asleep)). In some embodiments, data gathered while the user is asleep is marked to indicate such.

In some embodiments, the first health-related tracking function is configured to perform tracking operations without requiring further user input (e.g., performing automatic tracking operations, performing background measurements). Enabling the first health-related tracking function to perform tracking operations without requiring further user input enables the user to permit the computer system to perform an operation without requiring further user input. Performing an operation without requiring further user input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the summary user interface (e.g., 1400, 1404) includes a detail selectable user interface object (e.g., 1414) (e.g., a "show data" affordance) that, when selected, provides additional information about one or more conditions (e.g., altitude conditions; atmospheric pressure conditions) under which at least a portion of the tracking data was gathered. Providing a selectable user interface object for accessing additional condition data provides the user with additional data without cluttering the summary user interface with the additional data. Providing additional control of the device without cluttering the UI with additional displayed controls enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the indication (e.g., 1418, 1420B) that indicates that at least some of the tracking data gathered by the first health-related tracking function was gathered under the one or more conditions of the first type includes an indication (e.g., a text indication, a graphical indication) of a number of discrete (e.g., separate, distinguishable) measurements made by the first health-related tracking function under the one or more conditions of the first type. Providing an indication of a number of discrete (e.g., separate, distinguishable) measurements made by the first health-related tracking function under the one or more conditions of the first type provides the user with feedback as to how frequently the function made measurements under the conditions of the first type. The method of any one of claims 1-9, wherein the indication that indicates that at least some of the tracking data gathered by the first health-related tracking function was gathered under the one or more conditions of the first type includes an indication (e.g., a text indication, a graphical indication) of a number of discrete (e.g., separate, distinguishable) measurements made by the first health-related tracking function under the one or more conditions of the first type. Providing improved visual feedback to the user enhances the operability of the computer system and makes the user-device interface more efficient (e.g., by helping the user to provide proper inputs and reducing user mistakes when operating/interacting with the device) which, additionally, reduces power usage and improves battery life of the computer system by enabling the user to use the computer system more quickly and efficiently.

In some embodiments, the summary user interface (e.g., 1400, 1404) includes a set of one or more filtering user interface objects (e.g., 1410A-1410E, 1426-1432) that includes a first filtering user interface object that, when selected, filters the set of one or more user interface objects based on a first filter parameter (e.g., based on a condition under which the data was gathered; based on when the data was gathered). Providing a set of one or more filtering user interface objects provides the user with the ability to selectively filter data shown in the summary user interface which provides the user with control options for controlling the density of data which reduces clutter in the user interface. Reducing clutter in the user interface enhances the operability of the computer system and makes the user-device interface more efficient (e.g., by helping the user to provide proper inputs and reducing user mistakes when operating/ interacting with the device) which, additionally, reduces power usage and improves battery life of the computer system by enabling the user to use the computer system more quickly and efficiently.

In some embodiments, the summary user interface (e.g., 1400, 1404) includes information (e.g., information accessible via scrolling the interface) about what is being tracked by the tracking function, and its importance to health.

In some embodiments, the tracking data is blood oxygen level tracking data. In some embodiments, the computer system is in communication with a blood oxygen sensor (e.g., an optical blood oxygen sensor that operates in conjunction with a light source (e.g., an LED)). In some embodiments, threshold is a percentage of blood oxygen. In some embodiments, the tracking data is VO$_2$max level tracking data (e.g., maximal oxygen consumption; the maximum rate of oxygen consumption measured during incremental exercise).

Note that details of the processes described above with respect to method 1500 (e.g., FIGS. 15A-15B) are also applicable in an analogous manner to the methods described above and below. For example, method 700 optionally includes one or more of the characteristics of the various methods described above with reference to method 1500. For example, the user interfaces for managing health and safety features described with reference to method 700 can be used to manage one or more features of the health application user interfaces described with reference to method 1500. For another example, method 900 optionally includes one or more of the characteristics of the various methods described above with reference to method 1500. For example, health information that is presented in the user interfaces described with reference to method 1500 can at least partly be based on whether a particular type of health application or feature can be enabled or setup as described with reference to method 900. For another example, method 1100 optionally includes one or more of the characteristics of the various methods described above with reference to method 1500. For example, health information that is presented in the user interfaces described with reference to method 1500 can at least partly be based on health measurements from an application that has been setup via the setup user interfaces described with reference to method 1100. For another example, method 1300 optionally includes one or more of the characteristics of the various methods described above with reference to method 1500. For example, health information that is captured via the biometric measurement described with reference to method 1300 can be presented to a user via the user interfaces described with reference to method 1500. For another example, method 1700 optionally includes one or more of the characteristics of the various methods described above with reference to method 1500. For example, health information that is captured via the background measurements described with reference to method 1700 can be presented to a user via the user interfaces described with reference to method 1500. For brevity, these details are not repeated below.

FIGS. 16A-16C illustrate exemplary user interfaces for managing background health measurements on an electronic device, in accordance with some embodiments. The user interfaces in these figures are used to illustrate the processes described below, including the processes in FIGS. 17A-17B.

FIG. 16A illustrates device 600B, where device 600B includes a set of one or more biometric sensors (e.g., a heart rate sensor) and an outer housing 604B (e.g., a case; a frame). In some embodiments, the set of one or more biometric sensors are at least partially integrated with a housing of device 600B. Device 600B measures (e.g., periodically), via the set of one or more biometric sensors, the user's heart rate, where the measurements are automatically performed by device 600B (e.g., in the background, without manual input from the user to proceed with the measurements).

Device 600B can be in a first mode (e.g., a normal operating mode; an unlocked mode) or a second mode (e.g., a sleep mode, a locked mode; a low power mode; a mode that corresponds to a predetermined time of the day; a do-not-disturb mode (e.g., a theater DND mode); a mode that is manually selected and set by the user as a mode in which measurements of a biometric parameter (e.g., heart rate) are not to be taken without express user input). In some embodiments, display generation component 602B of device 600B is OFF while device 600B is in the first mode. In some embodiments, display generation component 602B is ON while device 600B is in the first mode.

In FIG. 16B, while device 600B is in the first mode (e.g., a normal operating mode; an unlocked mode), device 600B measures, using the set of one or more biometric sensors, the heart rate in BPM. As mentioned, device 600B includes outer housing 604B. While measuring the heart rate, device 600B activates a sensor (e.g., an optical sensor) that is visible on the outside of device 600B (e.g., from the side of device 600B). In some embodiments, the sensor is an optical sensor positioned to sense light coming from outside the outer housing of device 600B.

In FIG. 16B, device 600B includes a light generation component (e.g., an LED) that is configured to illuminate a space (e.g., adjacent to one side of outer housing 604B) outside outer housing 604B, as shown in FIG. 16B. In some embodiments, while measuring the heart rate, device 600B activates the light generation component, thus increasing the brightness of the space outside outer housing 604B (e.g., the space that is adjacent to one side of outer housing 604B). In some embodiments, the light generation component is positioned within device 600B to emit light in a direction where the emitted light can reflect from nearby objects (e.g., if device 600B is worn by the user, a portion of the user's wrist that is adjacent to device 600B). In the embodiment of FIGS. 16A-16C, the light generation component generates light of a predetermined intensity and frequency that is detected by the biometric sensors of device 600B, after that light is reflected from and affected by the user's body, thereby providing a biometric measurement (e.g., heart rate).

In some embodiments, while device 600B is in the second mode, device 600B does not measure (e.g., forgoes measuring) the heart rate. Even if background heart rate measurements are scheduled to be performed periodically (e.g., every half-hour; every hour; every 2 hours), device 600B still forgoes performing the measurement if it is in the second mode. In some embodiments, the second mode includes a sleep mode, a locked mode, a low power mode, a mode that corresponds to a predetermined time of the day, a theater mode, a do-not-disturb mode, and/or a mode that is manually selected and set by the user as a mode in which heart rate measurements are not to be taken without express user input.

As explained above, the second mode is a mode of device 600B that has been identified, via a set of one or more user inputs that were previously received by device 600B, as a mode during which measuring the heart rate does not occur without user input to initiate the measurement (e.g., a mode during which automatic/background measurements are not performed by device 600B). In some embodiments, while device 600B is in the second mode, device 600B still enables heart rate measurements via one or more express user inputs, as described above with reference FIGS. 12A-12P. That is, even while device 600B is in the second mode, manual measurements can still be performed on device 600B.

FIG. 16C illustrates a table 1600 that depicts whether an automatic/background heart rate measurement has been performed by device 600B at predetermined times (e.g., based on a set periodic time interval for performing the automatic/background measurements). In FIG. 16C, the set periodic time interval for performing the automatic/background measurements is every hour during the day.

In FIG. 16C, device 600A is in the first mode (e.g., a normal operating mode; an unlocked mode) at 8:00 am, 9:00 am, 10:00 am, 12:00 pm, 1:00 pm, 5:00 pm, 6:00 pm, 7:00 pm, 8:00 pm, and 9:00 pm.

Also in FIG. 16C, device 600B is in theater mode, a type of second mode, at 11:00 am, 2:00 pm, 3:00 pm, and 4:00 pm and in sleep mode, another type of second mode, at 10:00 pm-6:00 am.

As shown by table 1600 in FIG. 16C, while in the first mode, device 600B performs the automatic/background heart rate measurements at the predetermined time intervals (in the embodiment of FIG. 16C, every hour). As also shown by table 1600 in FIG. 16C, while in the second mode (whether the first type of the second mode or the second type of the second mode), device 600B forgoes performing the automatic/background heart rate measurements at the predetermined time intervals.

In some embodiments, the heart rate measurements described in FIGS. 16A-16C are instead blood oxygen level measurements. In some embodiments, the computer system is in communication with a blood oxygen sensor (e.g., an optical blood oxygen sensor that operates in conjunction with a light source (e.g., an LED). In some embodiments, threshold is a percentage of blood oxygen. In some embodiments, the heart rate measurements described in FIGS. 16A-16C are instead VO$_2$max level measurements (e.g., maximal oxygen consumption; the maximum rate of oxygen consumption measured during incremental exercise).

FIGS. 17A-17B are a flow diagram illustrating a method for managing background health measurements on an electronic device, in accordance with some embodiments. Method 1700 is performed at a computer system (e.g., an electronic device (e.g., 100, 300, 500, 600B)) that is in communication with a set of one or more biometric sensors (e.g., a maximum oxygen consumption level sensor; a heart rate sensor; blood pressure sensor; a sensor integrated into the computer system; a sensor integrated into an external device in communication with the computer system). Some operations in method 1700 are, optionally, combined, the orders of some operations are, optionally, changed, and some operations are, optionally, omitted.

In some embodiments, the electronic device (e.g., 600B) is a computer system. The computer system is optionally in communication (e.g., wired communication, wireless communication) with the set of one or more biometric sensors. In some embodiments, the set of one or more biometric sensors include a maximum oxygen consumption level sensor. In some embodiments, the set of one or more biometric sensors include a heart rate sensor. In some embodiments, the set of one or more biometric sensors include a blood pressure sensor. In some embodiments, the set of one or more biometric sensors are integrated into the computer system and/or are integrated into an external device in communication with the computer system.

As described below, method 1700 provides an intuitive way for managing and/or presenting health data. The method reduces the cognitive burden on a user for managing and/or presenting health data, thereby creating a more efficient human-machine interface. For battery-operated computing devices, enabling a user to manage and/or present health data faster and more efficiently conserves power and increases the time between battery charges.

The computer system (e.g., 600B) detects (1702) that a first set of health measurement criteria are satisfied (e.g., automatic or background measurement criteria). In some embodiments, the first set of health measurement criteria do not require a user input to be satisfied; the criteria include only criterion that do not require user input to be met. In some embodiments, the criteria include one or more criteria selected from the group consisting of: a predetermined time of day, a predetermined duration of time since the last health measurement, and availability of a predetermined amount of system resources (e.g., processor capacity, memory, battery power)).

In response to detecting that the set of health measurement criteria are satisfied (1710), in accordance with a determination that the computer system (e.g., 600B) is in a first mode (e.g., a normal operating mode; an unlocked mode), the computer system measures (1712) (e.g., via a first health-related tracking function (e.g., a tracking (e.g., data tracking, data gathering) application or application feature available to operate on the computer system or available to operate on an external electronic device in communication with the computer system (e.g., a heart-rate tracking function, a blood pressure tracking function)), via the set of one or more biometric sensors, a value (e.g., a data value; a plurality of data values) of a biometric parameter (e.g., heart rate, blood pressure, a maximum oxygen consumption level) (e.g., as shown in FIG. 16B). In some embodiments, a determination that an external device in communication with the computer system is in the first mode. In some embodiments, and a determination that a second set of measurement criteria are satisfied (e.g., a mode-specific set of criteria. In some embodiments, the second set of measurement criteria include a criterion that is satisfied when the first mode has not been identified (e.g., not manually identified) as a mode for which measurements are suppressed.

In response to detecting that the set of health measurement criteria are satisfied (1710), in accordance with a determination that the computer system (e.g., 600B) is in a second mode (e.g., a sleep mode, a locked mode; a low power mode; a mode that corresponds to a predetermined time of the day; a do-not-disturb mode (e.g., a theater do-not-disturb mode); a mode that was manually selected by the user as a mode in which measurements of the biometric parameter are not to be taken without express user input), different from the first mode, the computer system (e.g., 600) forgoes measuring (1718) the biometric parameter (e.g., as shown in FIG. 16A). In some embodiments, the computer system forgoes measuring any biometric parameters. Selectively performing a measurement of a biometric parameter when certain conditions are met enables the computer system to perform or not perform the measurement, without requiring further user input. Selectively performing an operation when a set of conditions has been met without requiring further user input enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the computer system (e.g., 600B) includes (1704) an outer housing (e.g., 604B) (e.g., a case; a frame) (1706), wherein measuring the value of the biometric parameter includes activating a sensor that is visible from a viewing perspective outside the outer housing (e.g., the sensor is visible on the outside of the computer system/ device) (1714). In some embodiments, the sensor is an optical sensor positioned to sense light coming from outside the outer housing of the system.

In some embodiments, the computer system (e.g., 600B) includes (1704) an outer housing (e.g., 604B) (e.g., a case; a frame) (1706) and a light generation component (e.g., an LED) configured to illuminate a volume outside the outer housing (e.g., a space adjacent to one side of the housing) (1708). In some embodiments, measuring the value of the biometric parameter includes activating the light generation component and increasing the brightness of the volume outside the outer housing (1716). In some embodiments, the sensor is an optical sensor positioned to sense light coming from outside the outer housing of the system and the system includes a light generation component positioned to emit light in a direction that can reflect from nearby objects (e.g., a portion of the user that is adjacent to the system (e.g., the system is a worn on the user (e.g., a watch)) to be measured by the optical sensor.

In some embodiments, the second mode corresponds to a mode of the computer system (e.g., 600B) that has been identified, via a set of one or more user inputs that were previously received, as a mode during which measuring the biometric parameter does not occur without user input initiating the measurement (e.g., a mode during which automatic or background measurements do not occur) (1720). In some embodiments, while the computer system is in the second mode, the computer system receives (1722) a set of one or more inputs corresponding to a request to measure the biometric parameter (e.g., as described with reference to FIGS. 12A-12L). In some embodiments, in response to receiving the set of one or more inputs corresponding to a request to measure the biometric parameter, the computer system measures (1724), via the set of one or more biometric sensors, a value of the biometric parameter. Providing the user with the ability to disable automatic or background measurements in a second mode, while still providing the ability to manually make measurements while in the second mode, provides the user with improved control over the functionality of the system. Providing a user interface for improved control of the system enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some embodiments, the computer system (e.g., 600B) receives an input of a first type (e.g., input detected by an accelerometer indicative of movement of the computer system that matches a predetermined movement pattern). In some embodiments, in response to receiving the input of the first type, in accordance with a determination that the computer system is not in the second mode (e.g., a determination that the device is in another mode (e.g., the first mode)), the computer system increases the brightness of a display generation component (e.g., 602B) (e.g., including activing the component from an inactive state) that is in communication with the computer system. In some embodiments, in response to receiving the input of the first type, in accordance with a determination that the computer system is in the second mode, the computer system forgoes increasing the brightness of the display generation component. In some embodiments, receive a notification, if not in the first mode issue an audible output, if in the 1st mode forgo issuing the audible output. In some embodiments, the second mode is a "theater mode" in which brightening of a display screen is more limited than when the mode is not active. Selectively brightening the display generation component conserves system resources and prevents unintentional brightening. Conserving system resources enhances the operability of the computer system and makes the user-device interface more efficient (e.g., by limiting unwanted operations) which, additionally, reduces power usage and improves battery life of the computer system by enabling the user to use the computer system more efficiently.

In some embodiments, the computer system (e.g., 600B) is in the second mode (e.g., the mode in which the measurement does not occur) when the current time corresponds to a predetermined period of time (e.g., certain hours of the day; hours of the day identified as corresponding to a sleep period). Disabling measurements during a predetermined period of the day conserves system resources. Conserving system resources enhances the operability of the computer system and makes the user-device interface more efficient (e.g., by limiting unwanted operations) which, additionally, reduces power usage and improves battery life of the computer system by enabling the user to use the computer system more efficiently.

In some embodiments, the biometric parameter is heart rate.

In some embodiments, the biometric parameter is a blood oxygen level. In some embodiments, the computer system is in communication with a blood oxygen sensor (e.g., an optical blood oxygen sensor that operates in conjunction with a light source (e.g., an LED). In some embodiments, the threshold is a percentage of blood oxygen. In some embodiments, the biometric parameter is $VO_2$max (e.g., maximal oxygen consumption; the maximum rate of oxygen consumption measured during incremental exercise).

Note that details of the processes described above with respect to method 1700 (e.g., FIGS. 17A-17B) are also applicable in an analogous manner to the methods described above. For example, method 700 optionally includes one or more of the characteristics of the various methods described above with reference to method 1700. For example, the user interfaces for managing health and safety features described with reference to method 700 can be used to manage one or more features of the background measurement features described with reference to method 1700. For another example, method 900 optionally includes one or more of the characteristics of the various methods described above with reference to method 1700. For example, the type of health information that is collected via background measurements as described with reference to method 1700 can at least partly be based on whether a particular type of health application or feature can be enabled or setup as described with reference to method 900. For another example, method 1100 optionally includes one or more of the characteristics of the various methods described above with reference to method 1700. For example, the background health measurements described with reference to method 1700 can be enabled via a health application that has been setup via the setup user interfaces described with reference to method 1100. For another example, method 1300 optionally includes one or more of the characteristics of the various methods described above with reference to method 1700. For example, the biometric measurement features of the health application as described with reference to method 1300 can also enable the background measurement features described with reference to method 1700. For another example, method 1500 optionally includes one or more of the characteristics of the various methods described above with reference to method 1700. For example, health information that is captured via the background measurements described with reference to method 1700 can be presented to a user via the user interfaces described with reference to method 1500. For brevity, these details are not repeated below.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the claims.

As described above, one aspect of the present technology is the gathering and use of data available from various sources to improve the measurement and presentation of health information and management of health and safety features. The present disclosure contemplates that in some instances, this gathered data may include personal information data that uniquely identifies or can be used to contact or locate a specific person. Such personal information data can include demographic data, location-based data, telephone numbers, email addresses, twitter IDs, home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For example, the personal information data can be used to present a more efficient and effective method for a user to measure, view, and manage health information. Accordingly, use of such personal information data (e.g., health information data) enables users to better assess and monitor their health information, thereby raising awareness to the users of their current health status. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of captured biometric information, the present technology can be configured to allow users to select to "opt in" or "opt out" of participation in the collection of personal information data during registration for services or anytime thereafter. In another example, users can select to limit the length of time captured biometric information is maintained on another electronic device or entirely prohibit the storing of captured biometric information on another electronic device. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, captured biometric information can be maintained entirely on a user's electronic device and access to data corresponding to the captured biometric information by another device (e.g., a server) can be prohibited without the user's express consent.

What is claimed is:

1. A computer system, comprising:
 a display generation component;
 one or more input devices;
 one or more processors; and
 memory storing one or more programs configured to be executed by the one or more processors, the one or more programs including instructions for:
  displaying, via the display generation component, a summary user interface of a first health-related tracking function, wherein:
   the summary user interface includes a time range selection region, wherein the time range selection region includes a plurality of affordances corresponding to a plurality of distinct time ranges, a set of one or more user interface objects that correspond to tracking data gathered by the first health-related tracking function over a first time range corresponding to a first affordance from the plurality of affordances, and an information affordance,
   the set of one or more user interface objects includes a first user interface object that corresponds to first datum gathered via the first health-related tracking function over the first time range, and
   displaying the summary user interface includes:
    in accordance with a determination that the information affordance has been selected and in accordance with a determination that the first datum was gathered under one or more conditions of a first type, wherein the one or more conditions of the first type includes an altitude at a first location that exceeds a threshold value, displaying the first user interface object with an indication that indicates that at least a plurality of the tracking data gathered by the first health-related tracking function was gathered under the one or more conditions of the first type over the first time range; and
    in accordance with a determination that the first datum was gathered under one or more conditions of a second type, wherein the one or more conditions of the second type includes an altitude at a second location, different from the first location, that does not exceed the threshold value, displaying the set of one or more user interface objects without the indication that indicates that at least a plurality of the tracking data gathered by the first health-related tracking function was gathered under the one or more conditions of the first type over the first time range.

2. The computer system of claim 1, wherein the tracking data is heart rate tracking data.

3. The computer system of claim 1, wherein the set of one or more user interface objects that correspond to tracking data gathered by the first health-related tracking function includes a plurality of user interface objects that correspond to tracking data gathered by the first health-related tracking function.

4. The computer system of claim 1, wherein displaying the summary user interface includes:
 in accordance with a determination that the tracking data gathered by the first health-related tracking function indicates that a biometric parameter of a user of the computer system has been below a threshold value for at least a predetermined period of time, displaying an indication that the biometric parameter of the user has been below the threshold value for at least the predetermined period of time.

5. The computer system of claim 1, wherein displaying the summary user interface includes:
 in accordance with a determination that the first datum was gathered under one or more conditions of a first type, displaying the first user interface object with an indication that the first datum was gathered under one or more conditions of the first type.

6. The computer system of claim 5, wherein the one or more conditions of the first type includes a sleep period.

7. The computer system of claim 1, wherein the first health-related tracking function is configured to perform tracking operations without requiring further user input.

8. The computer system of claim 1, wherein the summary user interface includes a detail selectable user interface object that, when selected, provides additional information about one or more conditions under which at least a portion of the tracking data was gathered.

9. The computer system of claim 8, wherein the indication that indicates that at least a plurality of the tracking data gathered by the first health-related tracking function was gathered under the one or more conditions of the first type includes an indication of a number of discrete measurements made by the first health-related tracking function under the one or more conditions of the first type.

10. The computer system of claim 1, wherein the summary user interface includes a set of one or more filtering user interface objects that includes a first filtering user interface object that, when selected, filters the set of one or more user interface objects based on a first filter parameter.

11. The computer system of claim 1, wherein the tracking data is blood oxygen level tracking data.

12. The computer system of claim 1, the one or more programs further including instructions for:
while displaying the summary user interface, receiving an input corresponding to a second affordance from the plurality of affordances, wherein the second affordance corresponds to a second time range different from the first time range;
in response to receiving the input displaying the tracking data gathered by the first health-related tracking function over the second time range;
wherein displaying the summary user interface includes:
in accordance with a determination that the first datum was gathered under one or more conditions of the first type, wherein the one or more conditions of the first type includes the altitude at the first location that exceeds the threshold value, displaying the first user interface object with the indication that indicates that at least a plurality of the tracking data gathered by the first health-related tracking function was gathered under the one or more conditions of the first type over the second time range; and
in accordance with a determination that the first datum was gathered under one or more conditions of the first type, wherein the one or more conditions of the first type includes the altitude the second location, different from the first location, that does not exceed the threshold value, forgoing displaying the first user interface object with the indication that indicates that at least a plurality of the tracking data gathered by the first health-related tracking function was gathered under the one or more conditions of the first type over the second time range.

13. The computer system of claim 1, wherein the set of one or more user interface object further includes a second user interface object that corresponds to second datum gathered via the first health-related tracking function over the first time range.

14. The computer system of claim 13, wherein further in accordance with the determination that the information affordance has been selected and further in accordance with the determination that the first datum was gathered under one or more conditions of a first type, wherein the one or more conditions of the first type includes an altitude at a first location that exceeds a threshold value:
displaying the second user interface object that corresponds to the second datum, wherein the second datum was gathered at an altitude at a third location, different from the first location, that does not exceed the threshold value.

15. A non-transitory computer-readable storage medium storing one or more programs configured to be executed by one or more processors of a computer system that is in communication with a display generation component and one or more input devices, the one or more programs including instructions for:
displaying, via the display generation component, a summary user interface of a first health-related tracking function, wherein:
the summary user interface includes a time range selection region, wherein the time range selection region includes a plurality of affordances corresponding to a plurality of distinct time ranges, a set of one or more user interface objects that correspond to tracking data gathered by the first health-related tracking function over a first time range corresponding to a first affordance from the plurality of affordances, and an information affordance,
the set of one or more user interface objects includes a first user interface object that corresponds to first datum gathered via the first health-related tracking function over the first time range, and
displaying the summary user interface includes:
in accordance with a determination that the information affordance has been selected and in accordance with a determination that the first datum was gathered under one or more conditions of a first type, wherein the one or more conditions of the first type includes an altitude at a first location that exceeds a threshold value, displaying the first user interface object with an indication that indicates that at least a plurality of the tracking data gathered by the first health-related tracking function was gathered under the one or more conditions of the first type over the first time range; and
in accordance with a determination that the first datum was gathered under one or more conditions of a second type, wherein the one or more conditions of the second type includes an altitude at a second location, different from the first location, that does not exceed the threshold value, displaying the set of one or more user interface objects without the indication that indicates that at least a plurality of the tracking data gathered by the first health-related tracking function was gathered under the one or more conditions of the first type over the first time range.

16. The non-transitory computer-readable storage medium of claim 15, wherein the tracking data is heart rate tracking data.

17. The non-transitory computer-readable storage medium of claim 15, wherein the set of one or more user interface objects that correspond to tracking data gathered by the first health-related tracking function includes a plurality of user interface objects that correspond to tracking data gathered by the first health-related tracking function.

18. The non-transitory computer-readable storage medium of claim 15, wherein displaying the summary user interface includes:
in accordance with a determination that the tracking data gathered by the first health-related tracking function indicates that a biometric parameter of a user of the computer system has been below a threshold value for at least a predetermined period of time, displaying an indication that the biometric parameter of the user has been below the threshold value for at least the predetermined period of time.

19. The non-transitory computer-readable storage medium of claim 15, wherein displaying the summary user interface includes:
in accordance with a determination that the first datum was gathered under one or more conditions of a first type, displaying the first user interface object with an indication that the first datum was gathered under one or more conditions of the first type.

20. The non-transitory computer-readable storage medium of claim 19, wherein the one or more conditions of the first type includes a sleep period.

21. The non-transitory computer-readable storage medium of claim 15, wherein the first health-related tracking function is configured to perform tracking operations without requiring further user input.

22. The non-transitory computer-readable storage medium of claim 15, wherein the summary user interface includes a detail selectable user interface object that, when selected, provides additional information about one or more conditions under which at least a portion of the tracking data was gathered.

23. The non-transitory computer-readable storage medium of claim 22, wherein the indication that indicates that at least a plurality of the tracking data gathered by the first health-related tracking function was gathered under the one or more conditions of the first type includes an indication of a number of discrete measurements made by the first health-related tracking function under the one or more conditions of the first type.

24. The non-transitory computer-readable storage medium of claim 15, wherein the summary user interface includes a set of one or more filtering user interface objects that includes a first filtering user interface object that, when selected, filters the set of one or more user interface objects based on a first filter parameter.

25. The non-transitory computer-readable storage medium of claim 15, wherein the tracking data is blood oxygen level tracking data.

26. The non-transitory computer-readable storage medium of claim 15, the one or more programs further including instructions for:
while displaying the summary user interface, receiving an input corresponding to a second affordance from the plurality of affordances, wherein the second affordance corresponds to a second time range different from the first time range;
in response to receiving the input displaying the tracking data gathered by the first health-related tracking function over the second time range;
wherein displaying the summary user interface includes:
in accordance with a determination that the first datum was gathered under one or more conditions of the first type, wherein the one or more conditions of the first type includes the altitude at the first location that exceeds the threshold value, displaying the first user interface object with the indication that indicates that at least a plurality of the tracking data gathered by the first health-related tracking function was gathered under the one or more conditions of the first type over the second time range; and
in accordance with a determination that the first datum was gathered under one or more conditions of the first type, wherein the one or more conditions of the first type includes the altitude the second location, different from the first location, that does not exceed the threshold value, forgoing displaying the first user interface object with the indication that indicates that at least a plurality of the tracking data gathered by the first health-related tracking function was gathered under the one or more conditions of the first type over the second time range.

27. The non-transitory computer-readable storage medium of claim 15, wherein the set of one or more user interface object further includes a second user interface object that corresponds to second datum gathered via the first health-related tracking function over the first time range.

28. The non-transitory computer-readable storage medium of claim 27, wherein further in accordance with the determination that the information affordance has been selected and further in accordance with the determination that the first datum was gathered under one or more conditions of a first type, wherein the one or more conditions of the first type includes an altitude at a first location that exceeds a threshold value:
displaying the second user interface object that corresponds to the second datum, wherein the second datum was gathered at an altitude at a third location, different from the first location, that does not exceed the threshold value.

29. A method, comprising:
at a computer system that is in communication with a display generation component and one or more input devices:
displaying, via the display generation component, a summary user interface of a first health-related tracking function, wherein:
the summary user interface includes a time range selection region, wherein the time range selection region includes a plurality of affordances corresponding to a plurality of distinct time ranges, a set of one or more user interface objects that correspond to tracking data gathered by the first health-related tracking function over a first time range corresponding to a first affordance from the plurality of affordances, and an information affordance,
the set of one or more user interface objects includes a first user interface object that corresponds to first datum gathered via the first health-related tracking function over the first time range, and
displaying the summary user interface includes:
in accordance with a determination that the information affordance has been selected and in accordance with a determination that the first datum was gathered under one or more conditions of a first type, wherein the one or more conditions of the first type includes an altitude at a first location that exceeds a threshold value, displaying the first user interface object with an indication that indicates that at least a plurality of the tracking data gathered by the first health-related tracking function was gathered under the one or more conditions of the first type over the first time range; and
in accordance with a determination that the first datum was gathered under one or more conditions of a second type, wherein the one or more conditions of the second type includes an altitude at a second location, different from the first location, that does not exceed the threshold value, displaying the set of one or more user interface objects without the indication that indicates that at least a plurality of the tracking data gathered by the first health-related tracking function was gathered under the one or more conditions of the first type over the first time range.

30. The method of claim 29, wherein the tracking data is heart rate tracking data.

31. The method of claim 29, wherein the set of one or more user interface objects that correspond to tracking data gathered by the first health-related tracking function includes a plurality of user interface objects that correspond to tracking data gathered by the first health-related tracking function.

32. The method of claim 29, wherein displaying the summary user interface includes:
   in accordance with a determination that the tracking data gathered by the first health-related tracking function indicates that a biometric parameter of a user of the computer system has been below a threshold value for at least a predetermined period of time, displaying an indication that the biometric parameter of the user has been below the threshold value for at least the predetermined period of time.

33. The method of claim 29, wherein displaying the summary user interface includes:
   in accordance with a determination that the first datum was gathered under one or more conditions of a first type, displaying the first user interface object with an indication that the first datum was gathered under one or more conditions of the first type.

34. The method of claim 33, wherein the one or more conditions of the first type includes a sleep period.

35. The method of claim 29, wherein the first health-related tracking function is configured to perform tracking operations without requiring further user input.

36. The method of claim 29, wherein the summary user interface includes a detail selectable user interface object that, when selected, provides additional information about one or more conditions under which at least a portion of the tracking data was gathered.

37. The method of claim 36, wherein the indication that indicates that at least a plurality of the tracking data gathered by the first health-related tracking function was gathered under the one or more conditions of the first type includes an indication of a number of discrete measurements made by the first health-related tracking function under the one or more conditions of the first type.

38. The method of claim 29, wherein the summary user interface includes a set of one or more filtering user interface objects that includes a first filtering user interface object that, when selected, filters the set of one or more user interface objects based on a first filter parameter.

39. The method of claim 29, wherein the tracking data is blood oxygen level tracking data.

40. The method of claim 29, the method further comprising for:
   while displaying the summary user interface, receiving an input corresponding to a second affordance from the plurality of affordances, wherein the second affordance corresponds to a second time range different from the first time range;
   in response to receiving the input displaying the tracking data gathered by the first health-related tracking function over the second time range;
      wherein displaying the summary user interface includes:
         in accordance with a determination that the first datum was gathered under one or more conditions of the first type, wherein the one or more conditions of the first type includes the altitude at the first location that exceeds the threshold value, displaying the first user interface object with the indication that indicates that at least a plurality of the tracking data gathered by the first health-related tracking function was gathered under the one or more conditions of the first type over the second time range; and
         in accordance with a determination that the first datum was gathered under one or more conditions of the first type, wherein the one or more conditions of the first type includes the altitude the second location, different from the first location, that does not exceed the threshold value, forgoing displaying the first user interface object with the indication that indicates that at least a plurality of the tracking data gathered by the first health-related tracking function was gathered under the one or more conditions of the first type over the second time range.

41. The method of claim 29, wherein the set of one or more user interface object further includes a second user interface object that corresponds to second datum gathered via the first health-related tracking function over the first time range.

42. The method of claim 41, wherein further in accordance with the determination that the information affordance has been selected and further in accordance with the determination that the first datum was gathered under one or more conditions of a first type, wherein the one or more conditions of the first type includes an altitude at a first location that exceeds a threshold value:
   displaying the second user interface object that corresponds to the second datum, wherein the second datum was gathered at an altitude at a third location, different from the first location, that does not exceed the threshold value.

* * * * *